(12) United States Patent
Chun et al.

(10) Patent No.: US 9,150,686 B2
(45) Date of Patent: Oct. 6, 2015

(54) EPOXY COMPOUND HAVING ALKOXYSILYL GROUP, METHOD OF PREPARING THE SAME, COMPOSITION AND CURED PRODUCT COMPRISING THE SAME, AND USES THEREOF

(71) Applicant: KOREA INSTITUTE OF INDUSTRIAL TECHNOLOGY, Cheonan-si (KR)

(72) Inventors: Hyun-Aee Chun, Seongnam-si (KR); Sang-Yong Tak, Busan (KR); Su-Jin Park, Ansan-si (KR); Yun-Ju Kim, Seoul (KR); Sung-Hwan Park, Gunpo-si (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 0 days.

(21) Appl. No.: 14/190,043

(22) Filed: Feb. 25, 2014

(65) Prior Publication Data

US 2014/0179836 A1 Jun. 26, 2014

Related U.S. Application Data

(63) Continuation of application No. PCT/KR2012/006832, filed on Aug. 27, 2012.

(30) Foreign Application Priority Data

| Aug. 25, 2011 | (KR) | 10-2011-0085340 |
| Jun. 1, 2012 | (KR) | 10-2012-0059437 |
| Jul. 6, 2012 | (KR) | 10-2012-0074197 |
| Aug. 24, 2012 | (KR) | 10-2012-0093320 |

(51) Int. Cl.

| B32B 27/38 | (2006.01) |
| B32B 27/04 | (2006.01) |
| C08G 59/14 | (2006.01) |
| C08G 59/30 | (2006.01) |
| C08L 63/00 | (2006.01) |
| H05K 1/03 | (2006.01) |
| C07D 303/02 | (2006.01) |
| C08K 7/14 | (2006.01) |
| C07F 7/18 | (2006.01) |
| C07D 407/12 | (2006.01) |
| C07D 303/12 | (2006.01) |
| C08J 5/24 | (2006.01) |

(52) U.S. Cl.
CPC ............ *C08G 59/306* (2013.01); *C07D 303/12* (2013.01); *C07D 407/12* (2013.01); *C07F 7/1836* (2013.01); *C08J 5/24* (2013.01); *C08K 7/14* (2013.01); *C08J 2363/00* (2013.01)

(58) Field of Classification Search
None
See application file for complete search history.

(56) References Cited

U.S. PATENT DOCUMENTS

| 5,336,786 A * | 8/1994 | Shiobara et al. ............... 549/215 |
| 6,001,907 A | 12/1999 | Huang et al. |
| 6,087,513 A | 7/2000 | Liao et al. |
| 6,525,160 B1 | 2/2003 | Goda et al. |
| 6,534,601 B1 | 3/2003 | Park et al. |
| 7,034,089 B2 | 4/2006 | Herr et al. |
| 7,696,286 B2 | 4/2010 | Endo et al. |
| 8,168,731 B2 | 5/2012 | Satou et al. |
| 2005/0119381 A1 | 6/2005 | Tanaka et al. |
| 2007/0100043 A1 | 5/2007 | Shiono |
| 2008/0221238 A1 | 9/2008 | Su et al. |
| 2011/0319589 A1 | 12/2011 | Takeyama et al. |
| 2012/0041102 A1 | 2/2012 | Chun et al. |
| 2012/0292487 A1 | 11/2012 | Yukawa et al. |
| 2012/0295199 A1 | 11/2012 | Takeyama et al. |
| 2012/0315765 A1 | 12/2012 | Nakajima et al. |

FOREIGN PATENT DOCUMENTS

| CN | 1303382 A | 7/2001 |
| CN | 101701058 A | 5/2010 |
| EP | 1 114 834 A1 | 7/2001 |
| EP | 1 137 328 A2 | 9/2001 |
| JP | 06-345847 A | 12/1994 |
| JP | 08-193091 A | 7/1996 |
| JP | 3077695 B1 | 6/2000 |
| JP | 2003-040970 A | 2/2003 |
| JP | 2003141933 A * | 5/2003 ............... H01B 3/40 |

(Continued)

OTHER PUBLICATIONS

Machine translation of JP 2003141933 A, provided by the JPO website (no date).*

(Continued)

*Primary Examiner* — Michael J Feely

(57) ABSTRACT

Disclosed are an epoxy compound having an alkoxysilyl group, a composite of which exhibits good heat resistant properties and/or a cured product of which exhibits good flame retardant properties, a method of preparing the same, a composition comprising the same, and a cured product and a use of the composition. An alkoxysilylated epoxy compound comprising at least one of Chemical Formula S1 substituent and at least two epoxy groups in a core, a method of preparing the epoxy compound by an allylation, a claisen rearrangement, an epoxidation and an alkoxysilylation, an epoxy composition comprising the epoxy compound, and a cured product and a use of the composition are provided. The composite of the disclosed exhibits improved chemical bonding, good heat resistant properties, a low CTE, a high glass transition temperature or Tg-less. The cured product of the composition exhibits good flame retardant properties.

13 Claims, 12 Drawing Sheets

(56) References Cited

FOREIGN PATENT DOCUMENTS

| | | |
|---|---|---|
| JP | 2006-012784 A | 1/2006 |
| JP | 2006-511664 A | 4/2006 |
| JP | 2006-137800 A | 6/2006 |
| JP | 2006-169368 A | 6/2006 |
| JP | 2007-126496 A | 5/2007 |
| JP | 2010-003897 A | 1/2010 |
| JP | 2010-065161 A | 3/2010 |
| JP | 2010-520952 A | 6/2010 |
| JP | 2011-001483 A | 1/2011 |
| JP | 2011-057755 A | 3/2011 |
| JP | 2011-208120 A | 10/2011 |
| JP | 2012-246422 A | 12/2012 |
| JP | 2012-246425 A | 12/2012 |
| KR | 10-1999-0063076 A | 7/1999 |
| KR | 10-2000-0038717 A | 7/2000 |
| KR | 10-2001-0096438 A | 11/2001 |
| KR | 10-2003-0034854 A | 5/2003 |
| KR | 10-2004-0061557 A | 7/2004 |
| KR | 10-2008-0108408 A | 12/2008 |
| KR | 10-0929380 B1 | 12/2009 |
| KR | 10-2010-0117543 A | 11/2010 |
| KR | 10-2011-0043719 A | 4/2011 |
| KR | 10-2011-0104918 A | 9/2011 |
| KR | 10-2012-0100506 A | 9/2012 |
| WO | WO 99/62894 A2 | 12/1999 |
| WO | WO 2010/092947 A1 | 8/2010 |
| WO | WO 2011/093188 A1 | 8/2011 |
| WO | WO 2011/093236 A1 | 8/2011 |
| WO | WO 2011/102470 A1 | 8/2011 |
| WO | WO 2012/070637 A1 | 5/2012 |
| WO | WO 2013/180375 A1 | 12/2013 |

OTHER PUBLICATIONS

Zhang et al. "Characterization of Siliconized Diallyl Bisphenol A Type Epoxy Resin and Study on Its Curing Properties"; Chemistry and Adhesion; vol. 28, No. 6, pp. 369-371 & 375; Jun. 2006.*

CAPLUS Abstract of Zhang et al., provided by STN (no date).*

Translation of Zhang et al., provided by USPTO translations (no date).*

International Search Report for PCT/KR2012/006832 filed on Aug. 27, 2012.

Lei Xue et al., "Precise Synthesis of Poly(silphenylenesiloxane)s with Epoxy Side Functional Groups by Tris(pentafluorophenyl)borane as a Catalyst", Polymer Journal, 2007, pp. 379-388, vol. 39, No. 4, The Society of Polymer Science, Japan.

Chinese office action for Application No. 201280052291.8 dated Feb. 28, 2015.

Chinese Office Action for CN Application No. 201280053687.4, dated May 20, 2015.

* cited by examiner

EPOXY COMPOUND HAVING ALKOXYSILYL GROUP, METHOD OF PREPARING THE SAME, COMPOSITION AND CURED PRODUCT COMPRISING THE SAME, AND USES THEREOF

This is a continuation application of PCT/KR2012/006832 (filed Aug. 27, 2012), which claims foreign priority to Korean application Nos. 10-2011-0085340 (filed Aug. 25, 2011), 10-2012-0059437 (filed Jun. 1, 2012), 10-2012-0074197 (filed Jul. 6, 2012), and 10-2012-0093320 (filed Aug. 24, 2012).

TECHNICAL FIELD

The present invention relates to an epoxy compound having an alkoxysilyl group (hereinafter 'alkoxysilylated epoxy compound'), a composite of which exhibits good heat resistant properties and/or a cured product of which exhibits good flame retardant property, a method of preparing the same, a composition comprising the same, a cured product of the composition, and a use of the composition. More particularly, the present invention relates to an alkoxysilylated epoxy compound, a composite of which exhibits good heat resistant properties, particularly exhibits low coefficient of thermal expansion (CTE) and a high glass transition temperature (including Tg-less, which means that the material does not exhibit the glass transition temperature) and/or a cured product of which exhibits good flame retardant property and does not require a additional coupling agent, a method of preparing the same, a composition comprising the same, a cured product comprising the composition, and a use of the composition.

BACKGROUND ART

The coefficient of thermal expansion (CTE) of a polymer material—specifically, a cured epoxy resin compound is about 50 to 80 ppm/° C., which is very high, several to tens of times larger than the CTE of a inorganic material, such as ceramic material or a metal (for example, the CTE of silicon is 3 to 5 ppm/° C., and the CTE of copper is 17 ppm/° C.). Thus, when the polymer material is used along with the inorganic material or the metal in a semiconductor, a display, or the like, the performance and processing of the polymer materials would be remarkably limited due to the different CTEs of the polymer material and the inorganic material or the metal. In addition, during semiconductor packaging in which a silicon wafer and a polymer substrate are used side by side, or during a coating process in which an inorganic shielding layer is coated on a polymer film to impart gas barrier properties, product defects such as the crack formations in an inorganic layer, the warpage of a substrate, the peeling-off of a coating layer, the failure of a substrate, and the like, may be generated due to a large CTE-mismatch between constituent materials during processing and/or service temperatures.

Because of the large CTE of the polymer material and the resultant dimensional change of the polymer material, the development of next-generation technologies in the fields of semiconductor substrates, printed circuit boards (PCBs), packaging, organic thin film transistors (OTFTs), and flexible display substrates, and the like may be limited. Particularly, the semiconductor and PCB industries have been challenged in the design of next generation parts requiring a higher integration and miniaturization, flexibility, superior performance, and the like, and securing processability and reliability of the parts due to the polymer material having a very higher CTE compared with metal/ceramic materials. In other words, due to the high thermal expansion properties of the polymer material at processing temperatures, defects may be generated, processing may be limited, and the design, processability and reliability of the parts may become objects of concern. Accordingly, improved thermal expansion properties or the dimensional stability of the polymer material are necessary in order to secure processability and reliability of electronic parts.

In general, in order to improve the thermal expansion properties—i.e., to obtain a low CTE of a polymer material such as an epoxy compound, (1) a method of making a composite of the epoxy compound with inorganic particles (inorganic filler) and/or a fiber or (2) a method of designing a novel epoxy compound having a decreased CTE have been used.

When the epoxy filler composite, which is a composite of epoxy compound and inorganic particles is formed in order to improve thermal expansion property, a large amount of silica particles of about 2 to 30 μm is required to decrease the CTE sufficiently. However, due to the addition of the large amount of inorganic particles, the processability and the physical properties of the parts may be deteriorated. That is, the large amount of inorganic particles may decrease fluidity, and voids may be generated due to the insufficient filling of narrow spaces. In addition, the viscosity of the material may increase exponentially due to the addition of the inorganic particles. Further, the size of the inorganic particles tends to decrease due to semiconductor structure miniaturization. When a filler of 1 μm or less is used, the decrease in fluidity (viscosity decrease) may become even more serious. When inorganic particles having a larger size (average particle diameter) are used, the insufficient filling of the filler composite occurs more frequently. While the CTE of an organic resin may be largely decreased by making glass fiber composite, the CTE however, may still be high when compared to a silicon chip or the like.

As described above, the manufacturing of highly integrated and high performance electronic parts for next generation semiconductor substrates, PCBs, and the like may be limited due to the limitations of composite technology for epoxy compounds. Thus, the development of polymer composite having improved heat resistant properties,—namely, a low CTE and a high glass transition temperature—is required to overcome the challenge of a lack of heat resistant properties due to a high CTE and processability of a common thermosetting polymer composite.

DISCLOSURE

Technical Problem

An aspect of the present invention provides an alkoxysilylated epoxy compound, a composite of which exhibits good heat resistant properties, particularly low CTE and high glass transition temperature properties and/or a cured product of which exhibits good flame retardant properties.

Another aspect of the present invention provides a method of preparing an alkoxysilylated epoxy compound, a composite of which exhibits good heat resistant properties, particularly low CTE and high glass transition temperature properties and/or a cured product of which exhibits good flame retardant properties.

Another aspect of the present invention also provides an epoxy composition comprising an alkoxysilylated epoxy compound, a composite of which exhibits good heat resistant properties, particularly low CTE and high glass transition temperature properties and/or a cured product of which exhibits good flame retardant properties.

Further another aspect of the present invention provides a cured product of an epoxy composition in accordance with an example embodiment, comprising an alkoxysilylated epoxy compound, a composite of which exhibits good heat resistant properties, particularly low CTE and high glass transition temperature properties and/or a cured product of which exhibits good flame retardant properties.

In addition, another aspect of the present invention discloses a use of an epoxy composition in accordance with an example embodiment.

Technical Solution

According to the first aspect of the present invention, there is provided an epoxy compound having an alkoxysilyl group comprising at least one substituent of the following Chemical Formula S1 and two epoxy groups at a core of the epoxy compound.

   [Chemical Formula S1]

In Chemical Formula S1, each of $R_a$, $R_b$ and $R_c$ is independently H or an alkyl group having 1 to 6 carbon atoms, at least one of $R_1$ to $R_3$ is an alkoxy group having 1 to 6 carbon atoms, and the remainder of $R_1$ to $R_3$ is an alkyl group having 1 to 10 carbon atoms, and the alkyl group and the alkoxy group may be a linear chain or a branched chain, may be cyclic or acyclic, and may or may not contain an N, O, S or P heteroatom. The epoxy compound having benzene core and one of S1, in which all of $R_a$, $R_b$ and $R_c$ are hydrogen, and all of $R_1$ to $R_3$ are the alkoxy group having 1 to 6 carbon atoms is excluded.

According to the second aspect of the present invention, the epoxy compound having an alkoxysilyl group of the first aspect, in which the epoxy group comprises the following Chemical Formula S2, may be provided.

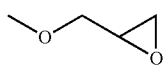   [Chemical Formula S2]

According to the third aspect of the present invention, the epoxy compound having an alkoxysilyl group of the first aspect, further comprising a substituent of the following Chemical Formula S3, may be provided.

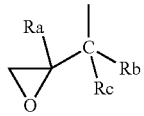   [Chemical Formula S3]

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

According to the fourth aspect of the present invention, the epoxy compound having an alkoxysilyl group of the first aspect, in which the core is at least one aromatic core selected from the group consisting of the following Chemical Formulae A' to K', may be provided.

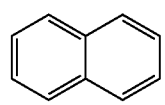   (A')

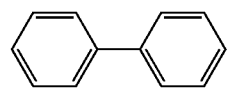   (B')

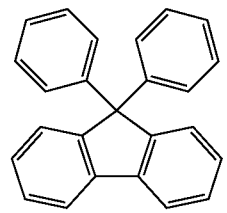   (C')

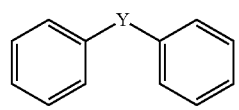   (D')

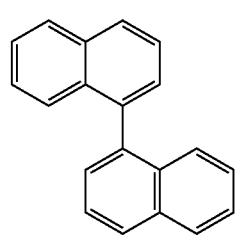   (E')

   (F')

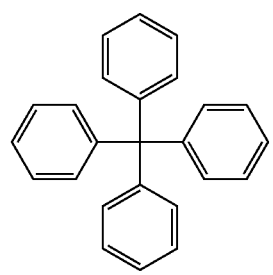   (G')

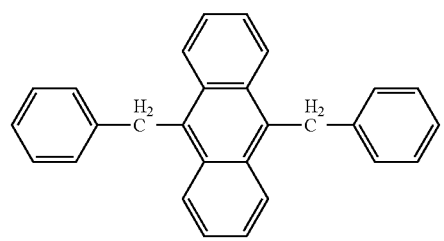   (H')

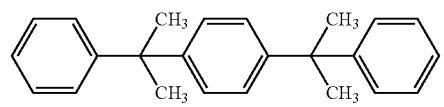   (I')

(J')

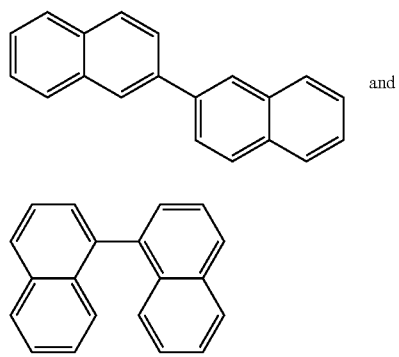

and (K')

In Chemical Formula D', Y is —CH$_2$—, —C(CH$_3$)$_2$—, —C(CF$_3$)$_2$—, —S— or —SO$_2$—.

According to the fifth aspect of the present invention, the epoxy compound having an alkoxysilyl group of the first aspect, in which the epoxy compound having the alkoxysilyl group is at least one selected from the group consisting of the following Chemical Formulae AI to KI, may be provided.

(AI)

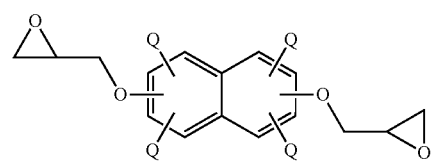

(BI)

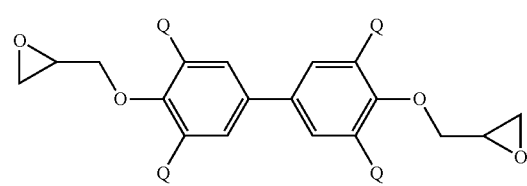

(CI)

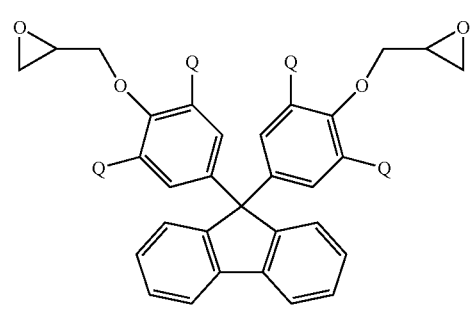

(DI)

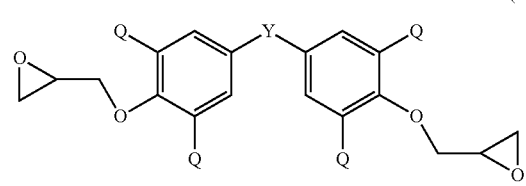

(EI)

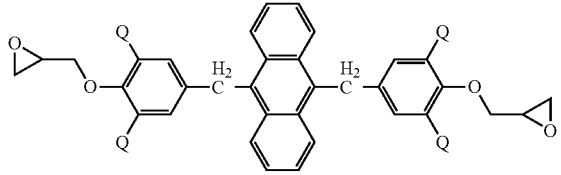

(FI)

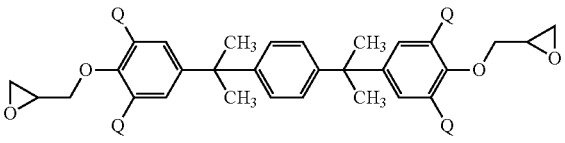

(GI)

(HI)

(II)

(JI)

and (KI)

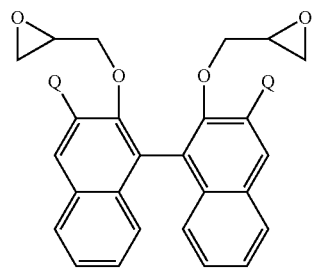

In Chemical Formulae (AI) to (KI), at least one of a plurality of Q is Chemical Formula S1, and each of the remainder of the plurality of Q is independently selected from the group consisting of the following Chemical Formula S3, hydrogen and —$CR_bR_c$—$CHR_a$=$CH_2$ (each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.), and in Chemical Formula DI, Y is —$CH_2$—, —$C(CH_3)_2$—, —$C(CF_3)_2$—, —S— or —$SO_2$—.

[Chemical Formula S1]

—$CR_bR_c$—$CHR_a$—$CH_2$—$SiR_1R_2R_3$

In Chemical Formula S1, each of $R_a$, $R_b$ and $R_c$ is independently H or an alkyl group having 1 to 6 carbon atoms, at least one of $R_1$ to $R_3$ is an alkoxy group having 1 to 6 carbon atoms, and the remainder of $R_1$ to $R_3$ is an alkyl group having 1 to 10 carbon atoms, and the alkyl group and the alkoxy group may be a linear chain or a branched chain, may be cyclic or acyclic, and may or may not contain an N, O, S or P heteroatom. The epoxy compound of Chemical Formula FI having one of S1, in which all of $R_a$, $R_b$ and $R_c$ are hydrogen, and all of $R_1$ to $R_3$ are the alkoxy group having 1 to 6 carbon atoms is excluded.

[Chemical Formula S3]

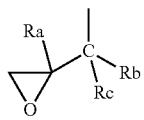

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

According to the sixth aspect of the present invention, the epoxy compound having an alkoxysilyl group of the fifth aspect, in which at least one of the plurality of Q is Chemical Formula S3 above, may be provided.

According to the seventh aspect of the present invention, the epoxy compound having an alkoxysilyl group of the fifth aspect, in which at least one of the plurality of Q is Chemical Formula S1 above, and the remainder of plurality of Q is Chemical Formula S3 above, may be provided.

According to the eighth aspect of the present invention, the epoxy compound having an alkoxysilyl group of the fifth aspect, in which $R_1$ to $R_3$ are ethoxy groups, may be provided.

According to the ninth aspect of the present invention, the epoxy compound having an alkoxysilyl group of the fifth aspect, in which the epoxy compound having the alkoxysilyl group is at least one selected from the group consisting of Chemical Formulae AI to DI above, may be provided.

According to the tenth aspect of the present invention, the epoxy compound having an alkoxysilyl group of the ninth aspect, in which the epoxy compound having the alkoxysilyl group is Chemical Formula DI above, may be provided.

According to the eleventh aspect of the present invention, the epoxy compound having an alkoxysilyl group of the tenth aspect, in which the epoxy compound having the alkoxysilyl group is Chemical Formula DI above, and Y is —$C(CH_3)_2$—, may be provided.

According to the twelfth aspect of the present invention, the epoxy compound having an alkoxysilyl group of the fifth aspect, in which the epoxy compound having the alkoxysilyl group is at least one compound having the following Chemical Formula M, may be provided.

[Chemical Formula M]

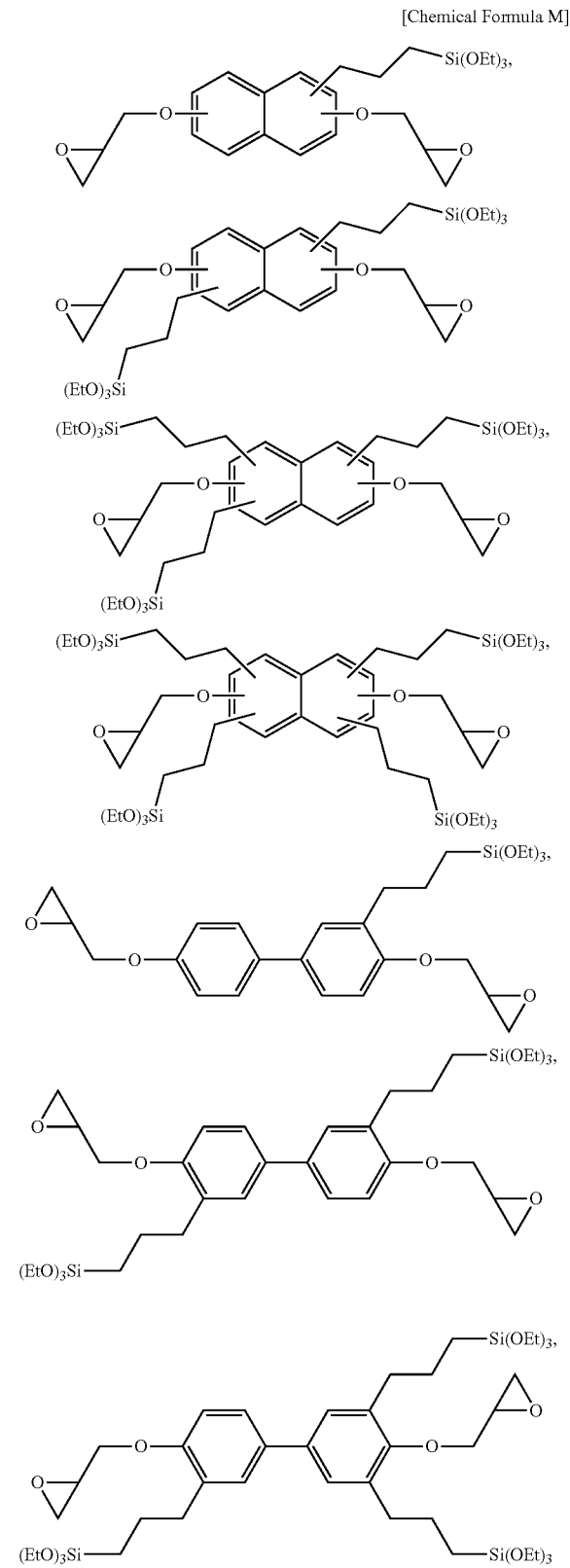

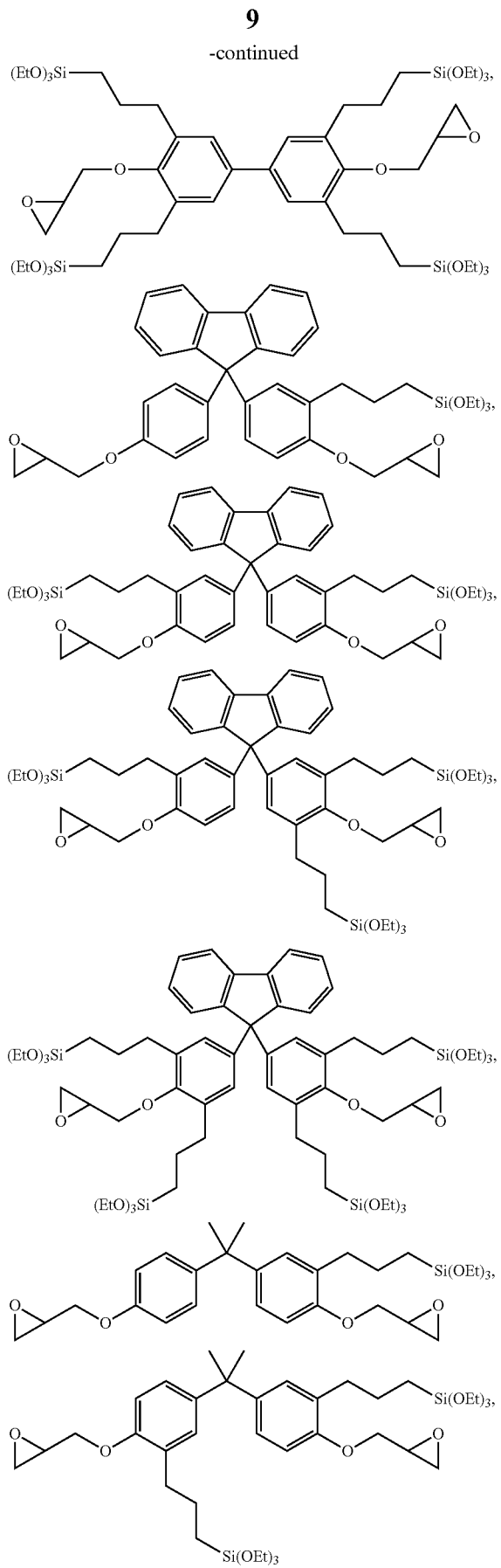
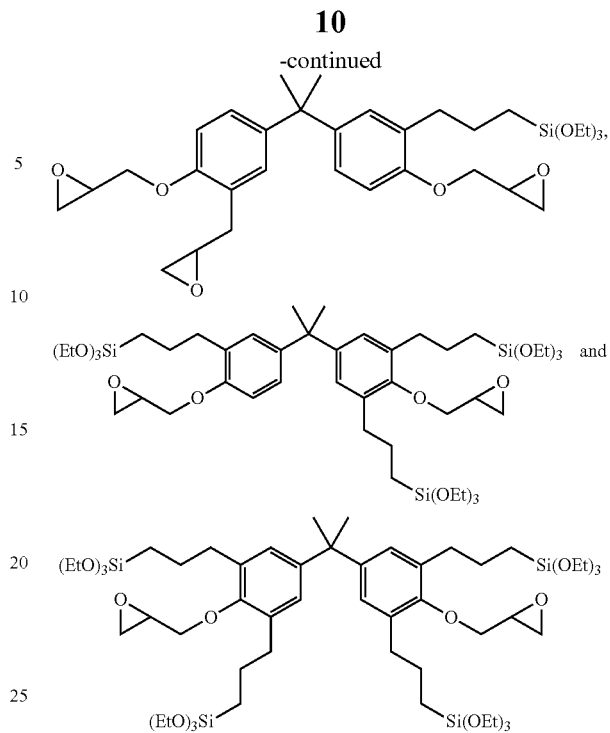
According to the thirteenth aspect of the present invention, there is provided at least one compound selected from the group consisting of the following Chemical Formulae (A11) to (K11).
(A11)
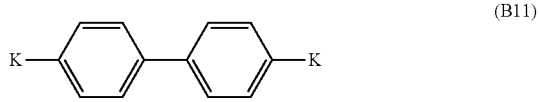
(B11)
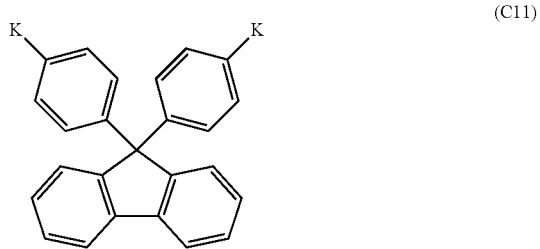
(C11)
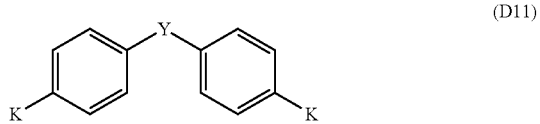
(D11)
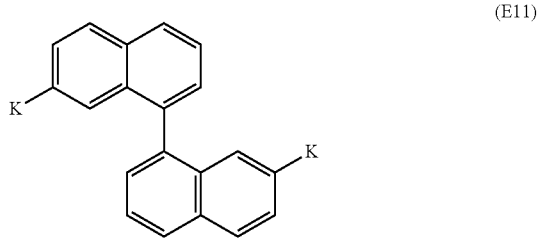
(E11)

(F11)

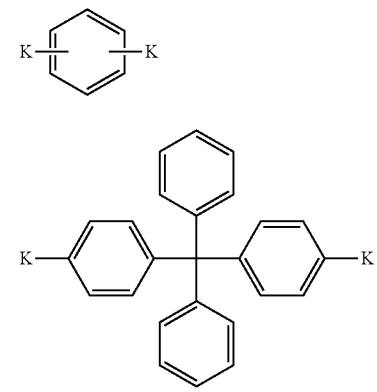

(G11)

(H11)

(I11)

(J11)

(K11)

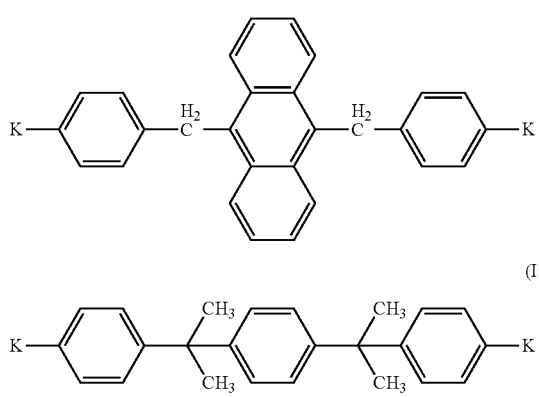

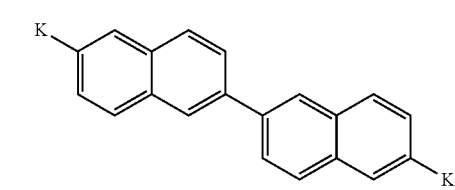

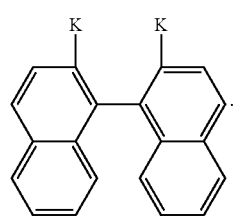

[Chemical Formulae S(11)]

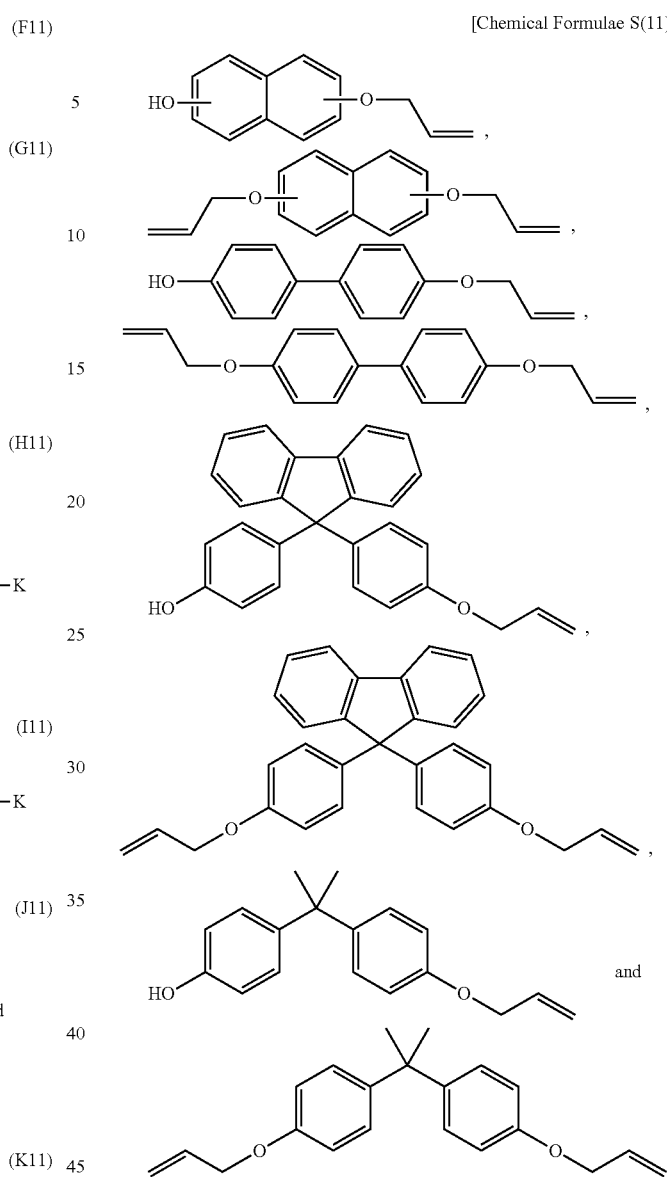

In Chemical Formulae A11 to K11, at least one of K is —O—$CH_2$—$CR_a$=$CR_bR_c$ (each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), the remainder of K is a hydroxyl group, and in Chemical Formula D11 above, Y is —$CH_2$—, —$C(CH_3)_2$—, —$C(CF_3)_2$—, —S— or —$SO_2$—.

According to the fourteenth aspect of the present invention, the compound of the thirteenth aspect, in which the compound is at least one of the following Chemical Formulae S(11), may be provided.

According to the fifteenth aspect of the present invention, there is provided at least one compound selected from the group consisting of the following Chemical Formulae (A12) to (K12).

-continued

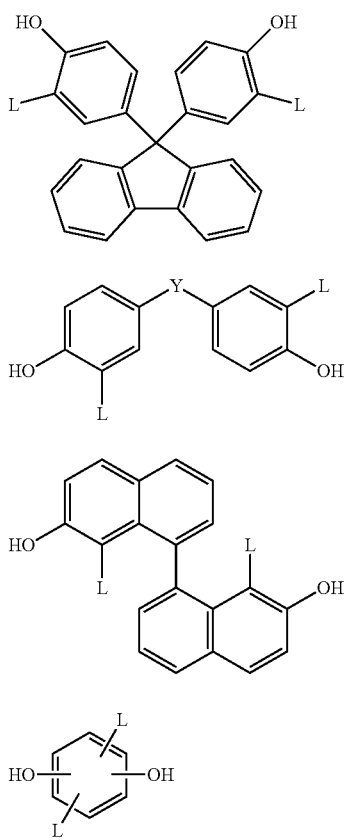

(C12)

(D12)

(E12)

(F12)

(G12)

(H12)

(I12)

-continued

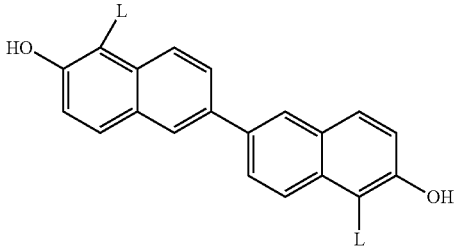

(J12)

and

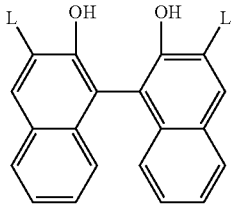

(K12)

In Chemical Formulae A12 to K12, at least one of L is —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), the remainder of L is hydrogen, and in Chemical Formula D12 above, Y is —$CH_2$—, —$C(CH_3)_2$—, —$C(CF_3)_2$—, —S— or —$SO_2$—.

According to the sixteenth aspect of the present invention, the compound of the fifteenth aspect, in which the compound is at least one of the following Chemical Formulae S(12), may be provided.

[Chemical Formulae S(12)]

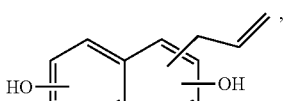

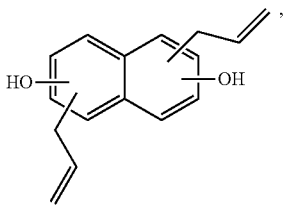

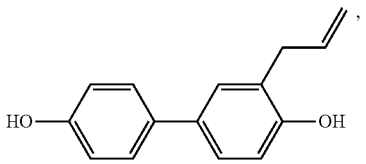

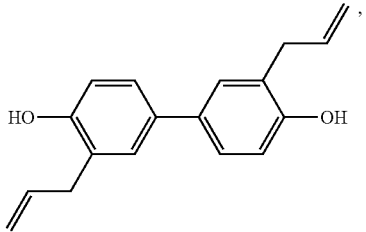

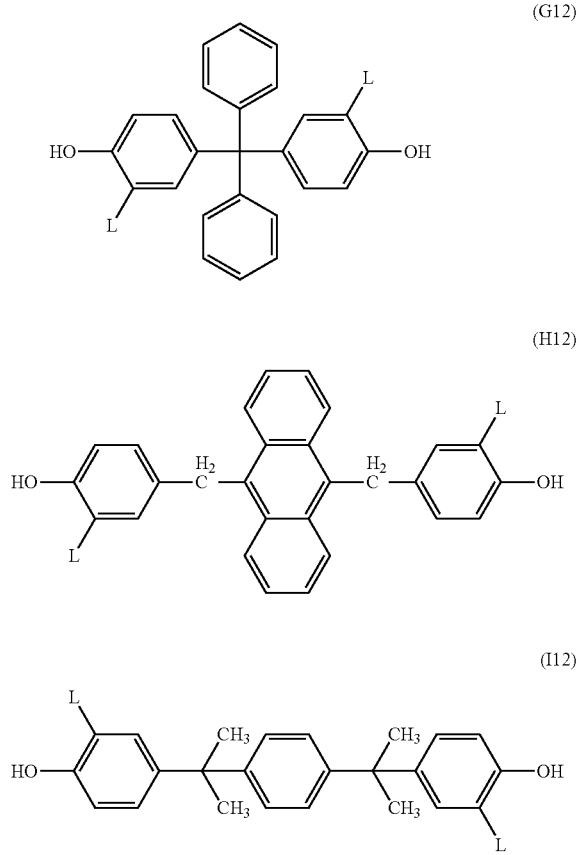

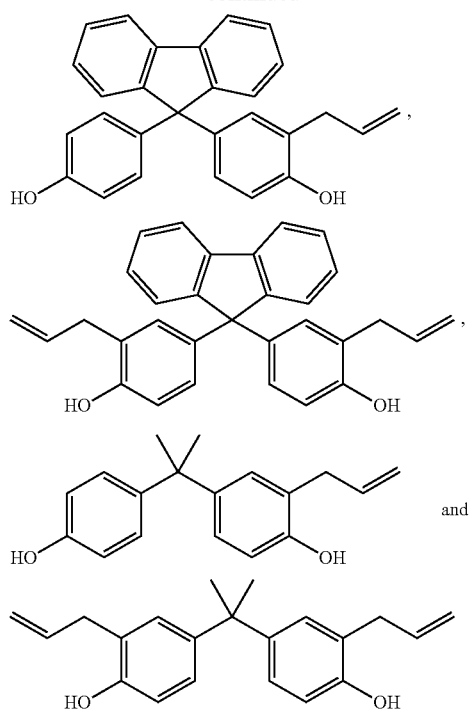
According to the seventeenth aspect of the present invention, there is provided at least one compound selected from the group consisting of the following Chemical Formulae (A13) to (K13).
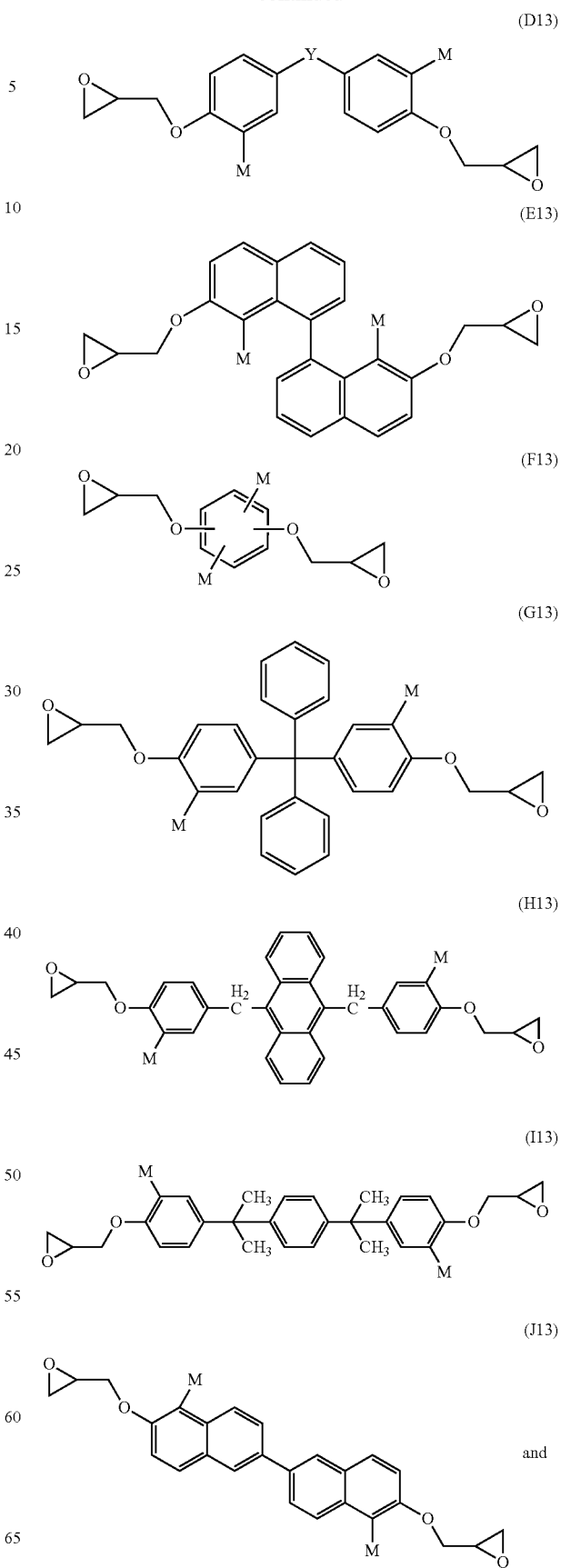

(K13)

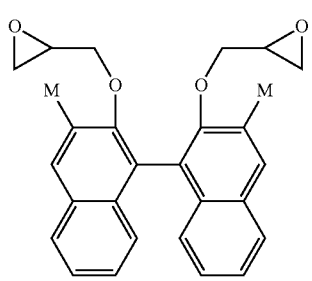

In Chemical Formulae A13 to K13, at least one of M is —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the remainder of M is hydrogen, and in Chemical Formula D13 above, Y is —CH$_2$—, —C(CH$_3$)$_2$—, —C(CF$_3$)$_2$—, —S— or —SO$_2$—.

According to the eighteenth aspect of the present invention, the compound of the seventeenth aspect, in which the compound is at least one of the following Chemical Formulae S(13), may be provided.

[Chemical Formulae S(13)]

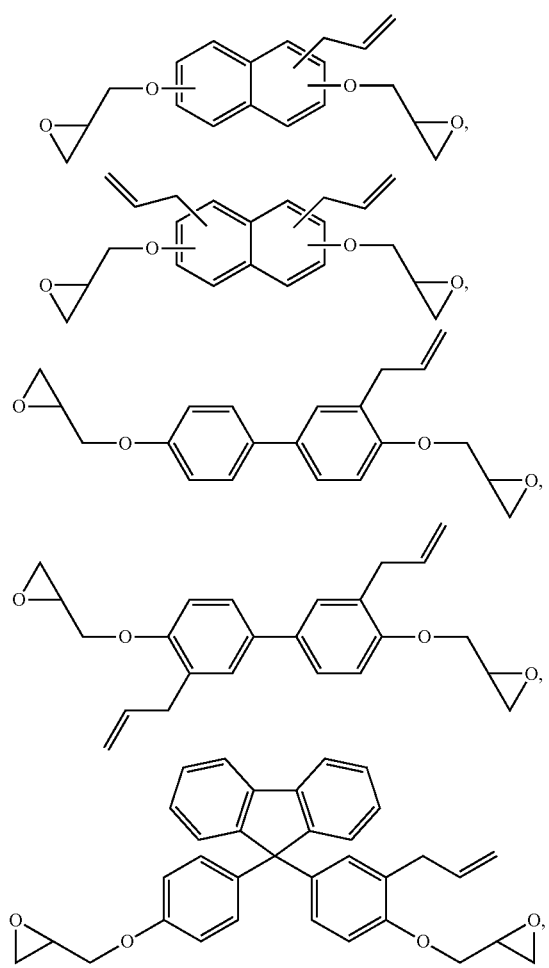

-continued

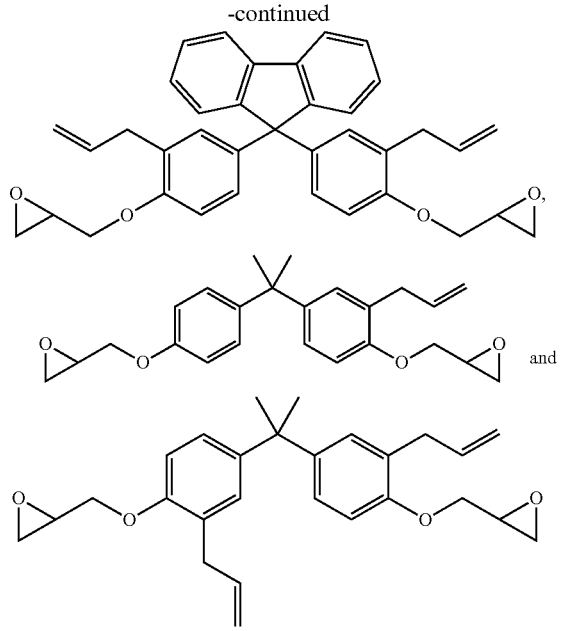

and

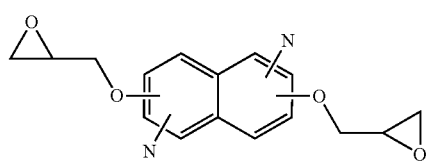

According to the nineteenth aspect of the present invention, there is provided at least one compound selected from the group consisting of the following Chemical Formulae (A13') to (K13').

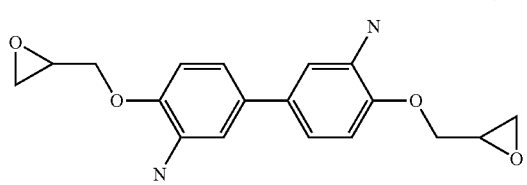

(A13')

(B13')

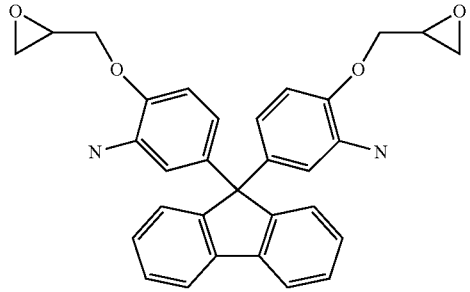

(C13')

(D13')

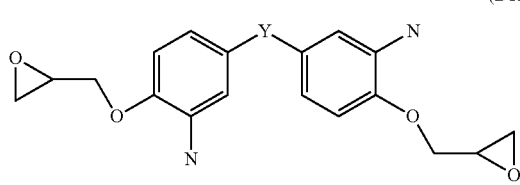

-continued

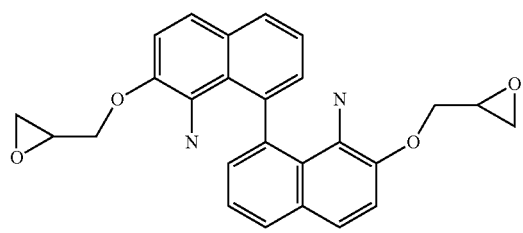
(E13')

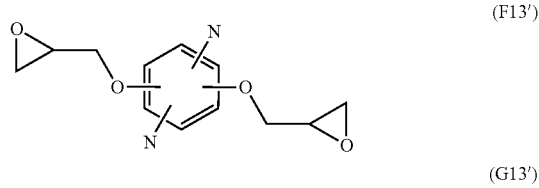
(F13')

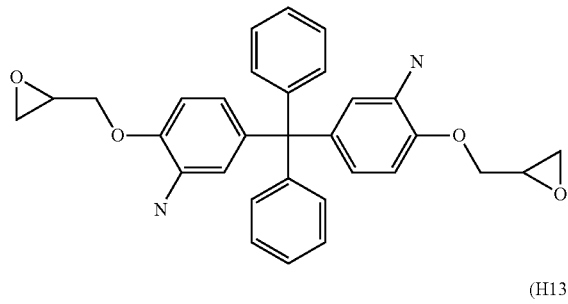
(G13')

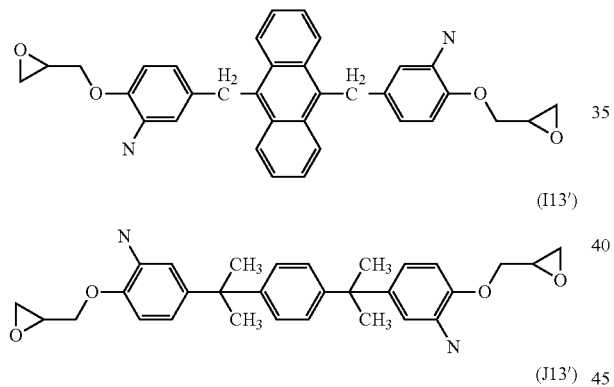
(H13')

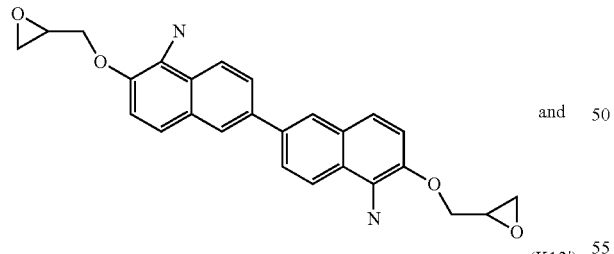
(I13')

and

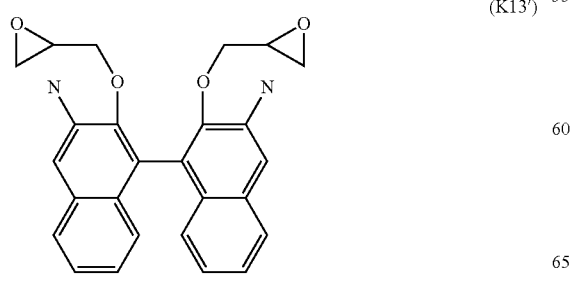
(J13')

(K13')

In Chemical Formulae A13' to K13', one of N is —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the other N is Chemical Formula S3, and in Chemical Formula D13' above, Y is —CH$_2$—, —C(CH$_3$)$_2$—, —C(CF$_3$)$_2$—, —S— or —SO$_2$—.

[Chemical Formula S3]

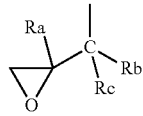

In Chemical Formula S3, each of R$_a$, R$_b$ and R$_c$ is independently H or an alkyl group having 1 to 6 carbon atoms, and the alkyl group may be a linear chain or a branched chain, may be cyclic or acyclic, and may or may not contain an N, O, S or P heteroatom.

According to the twentieth aspect of the present invention, the compound of the nineteenth aspect, in which the compound has the following Chemical Formula S(13'), may be provided.

[Chemical Formula S(13')]

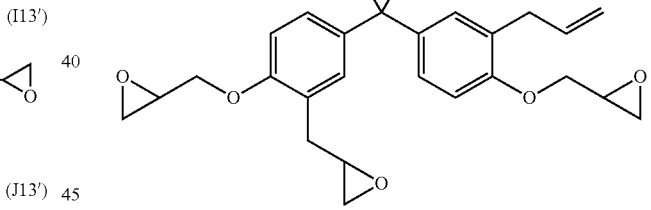

According to the twenty-first aspect of the present invention, there is provided at least one compound selected from the group consisting of the following Chemical Formulae (A23) to (J23).

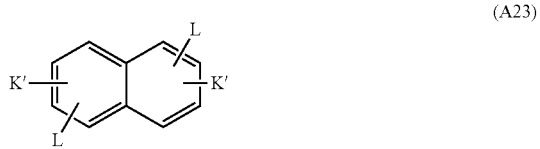
(A23)

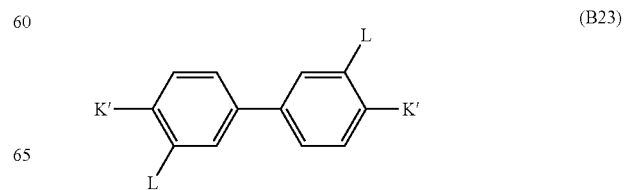
(B23)

(C23)

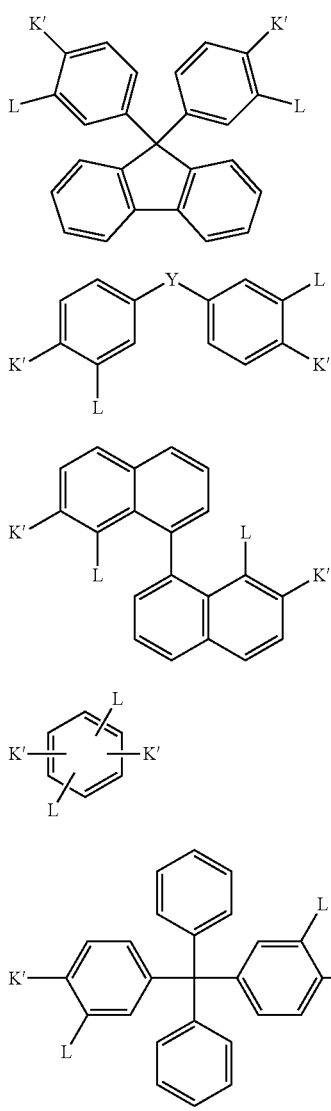

(D23)

(E23)

(F23)

(G23)

(H23)

(I23) and

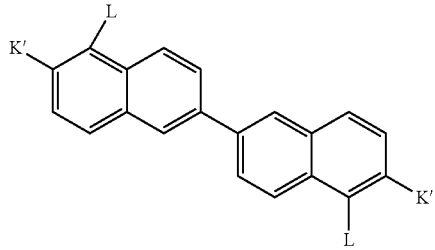
(J23)

In Chemical Formulae A23 to J23, at least one of K' is —O—$CH_2$—$CR_a$=$CR_bR_c$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), the remainder of K' is a hydroxyl group, at least one of L is —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain N, O, S, or P heteroatom), the remainder of L is hydrogen, and in Chemical Formula D23 above, Y is —$CH_2$—, —$C(CH_3)_2$—, —$C(CF_2)_2$—, —S— or —$SO_2$—.

According to the twenty-second aspect of the present invention, the compound of the twenty-first aspect, in which the compound is at least one of the following Chemical Formulae S(23), may be provided.

[Chemical Formulae S(23)]

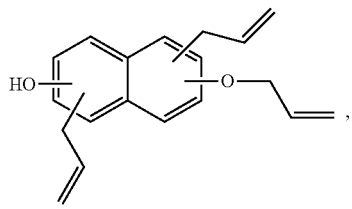

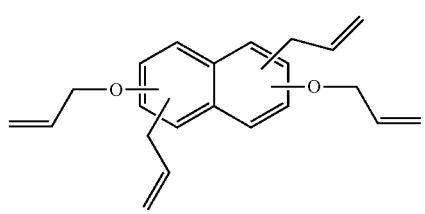

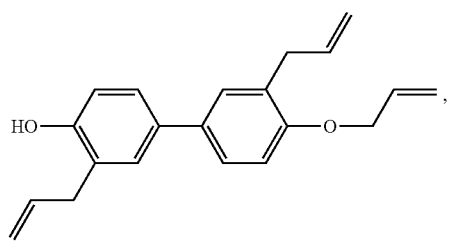

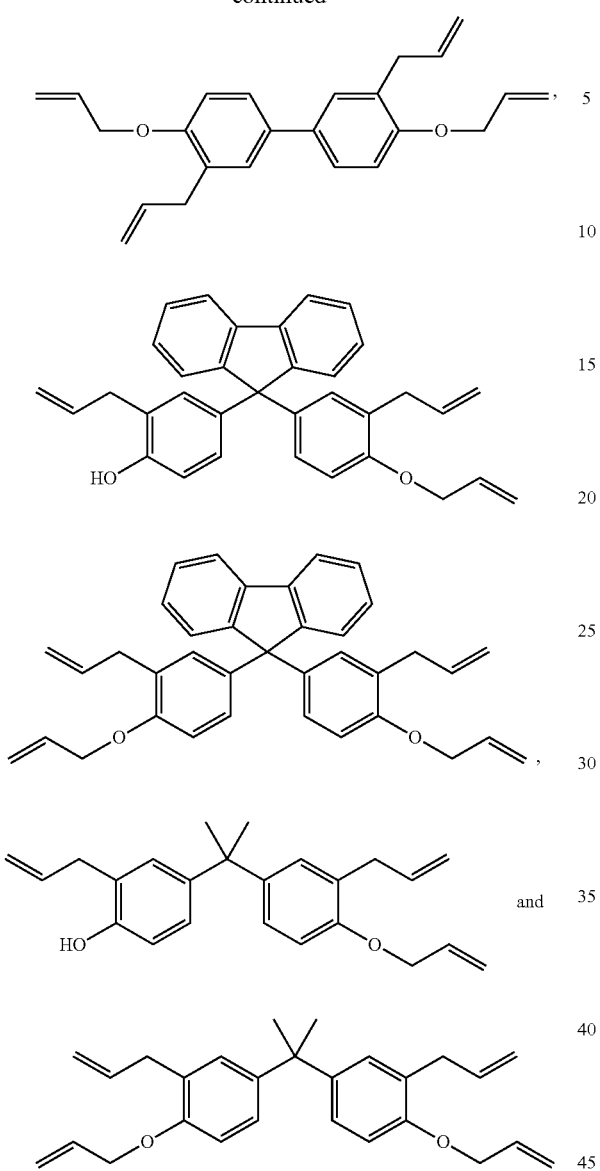
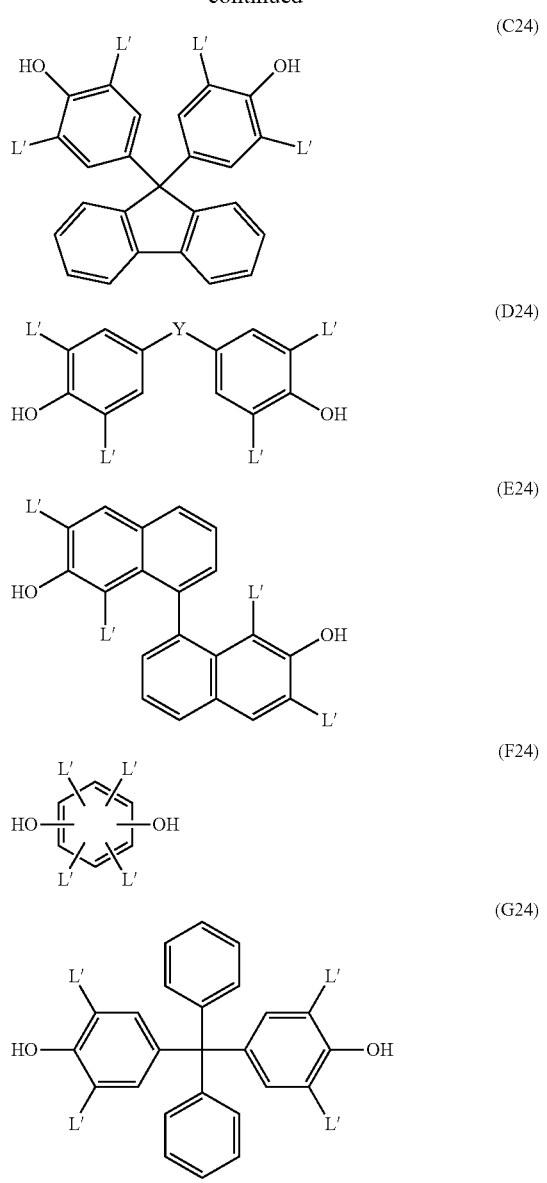
According to the twenty-third aspect of the present invention, there is provided at least one compound selected from the group consisting of the following Chemical Formulae (A24) to (J24).
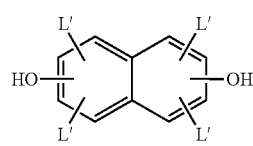
(A24)
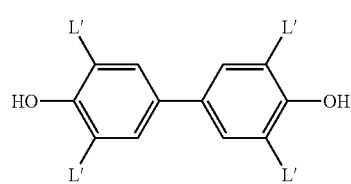
(B24)
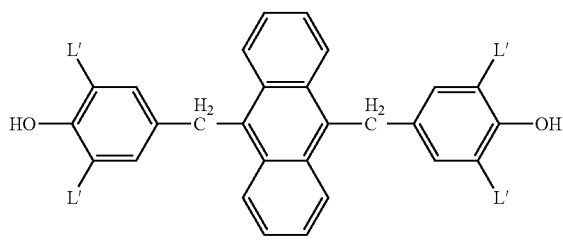
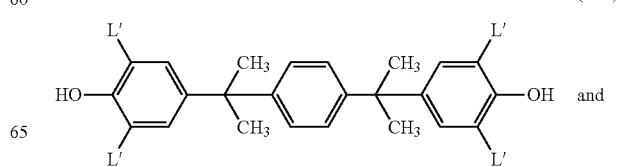
and -continued

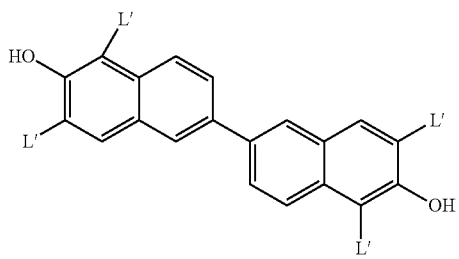
(J24)

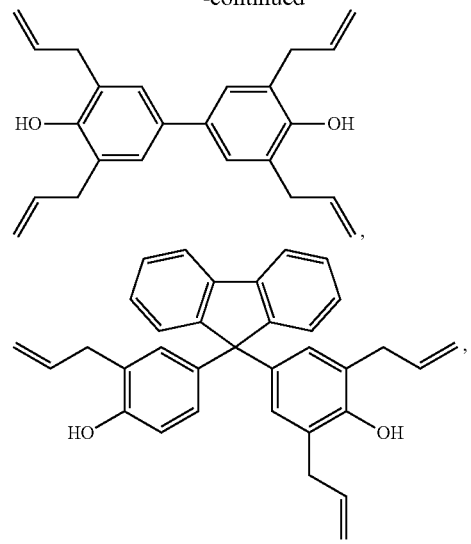

In Chemical Formulae A24 to J24, at least two of a plurality of L' are —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the remainder of L' is hydrogen, and in Chemical Formula D24 above, Y is —CH$_2$—, —C(CH$_3$)$_2$—, C(CF$_3$)$_2$—, —S— or —SO$_2$—.

According to the twenty-fourth aspect of the present invention, the compound of the twenty-third aspect, in which the compound is at least one compound from the following Chemical Formulae S(24), may be provided.

[Chemical Formulae S(24)]

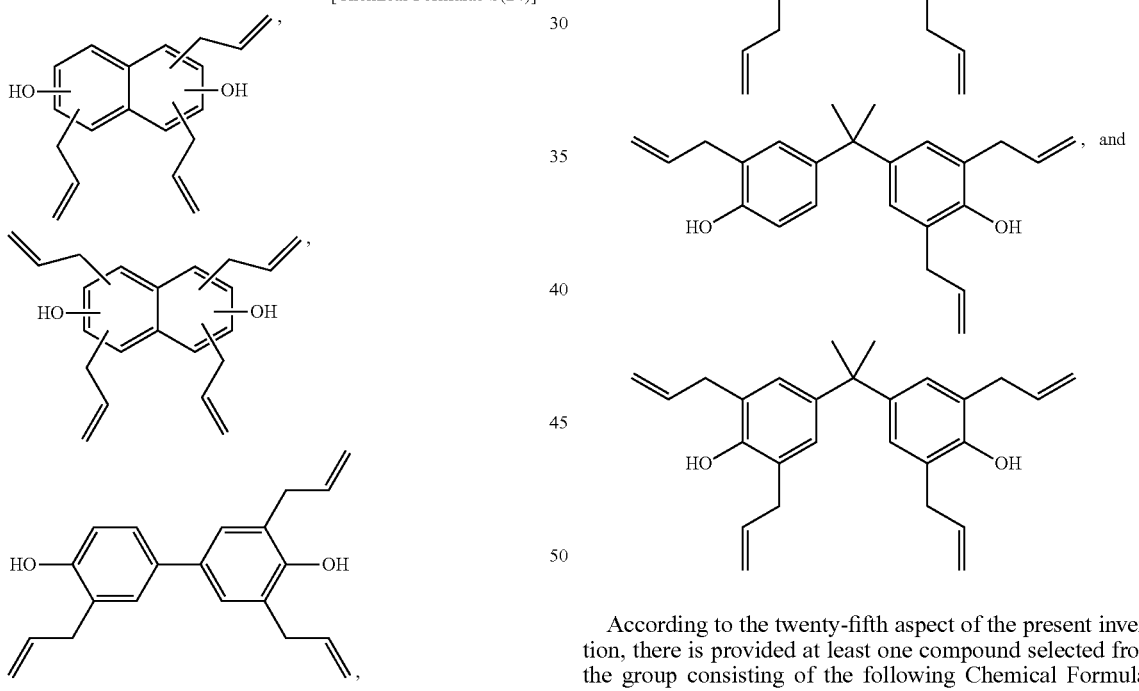

According to the twenty-fifth aspect of the present invention, there is provided at least one compound selected from the group consisting of the following Chemical Formulae (A25) to (J25).

(A25)

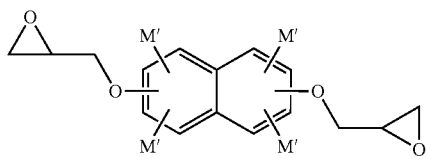

(B25)

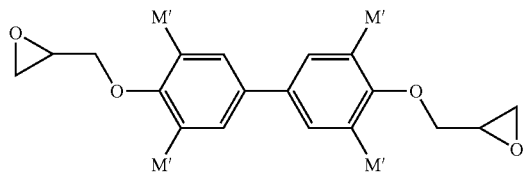

-continued

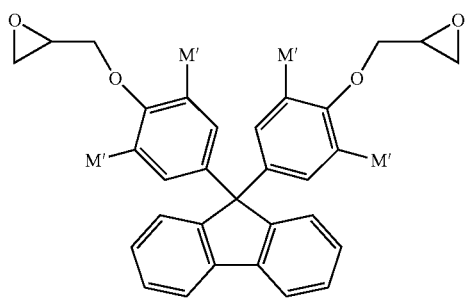 (C25)

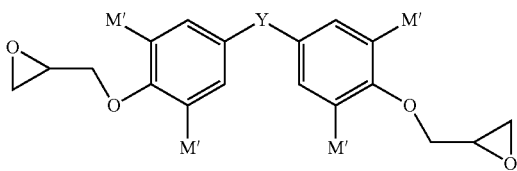 (D25)

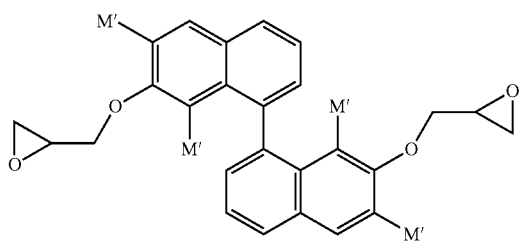 (E25)

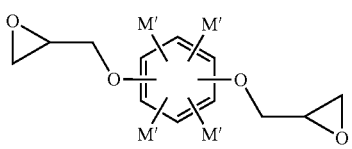 (F25)

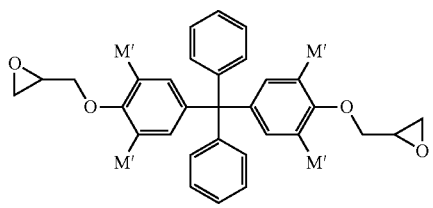 (G25)

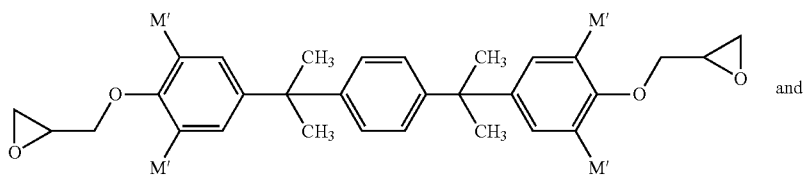 (H25)

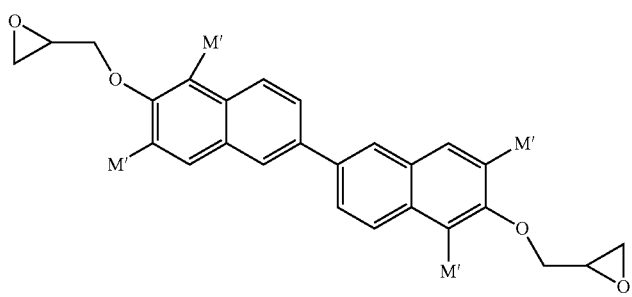 (I25)

and (J25)

In Chemical Formulae A25 to J25, at least two of a plurality of M' are —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom.), the remainder of M' is hydrogen, and in Chemical Formula D25 above, Y is —CH$_2$—, —C(CH$_3$)$_2$—, —C(CF$_3$)$_2$—, —S— or —SO$_2$—.

According to the twenty-sixth aspect of the present invention, the compound of the twenty-fifth aspect, in which the compound is at least one compound from the following Chemical Formulae S(25), may be provided.

[Chemical Formulae S(25)]

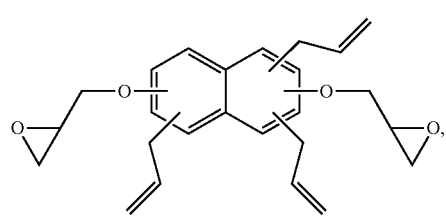

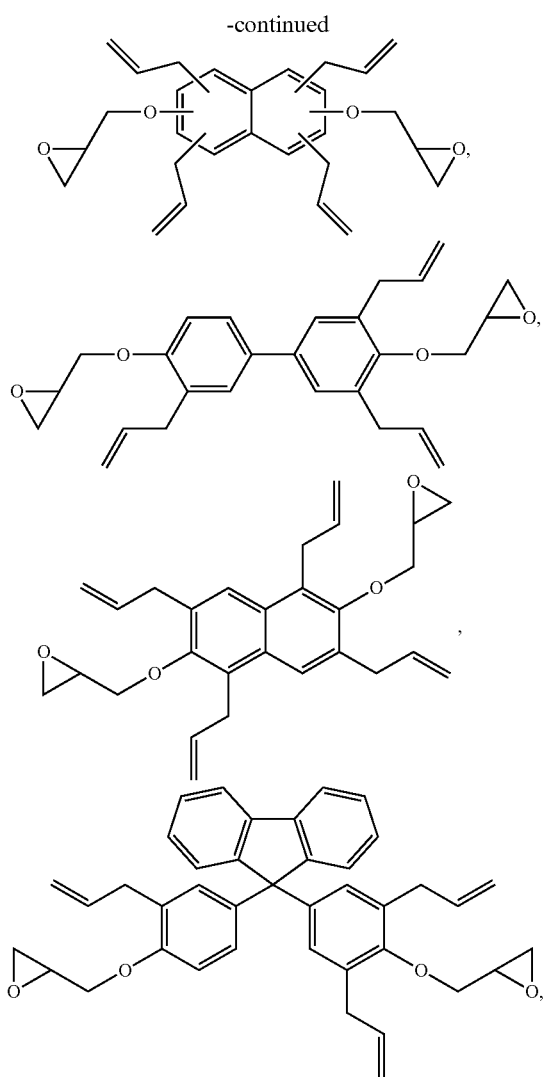
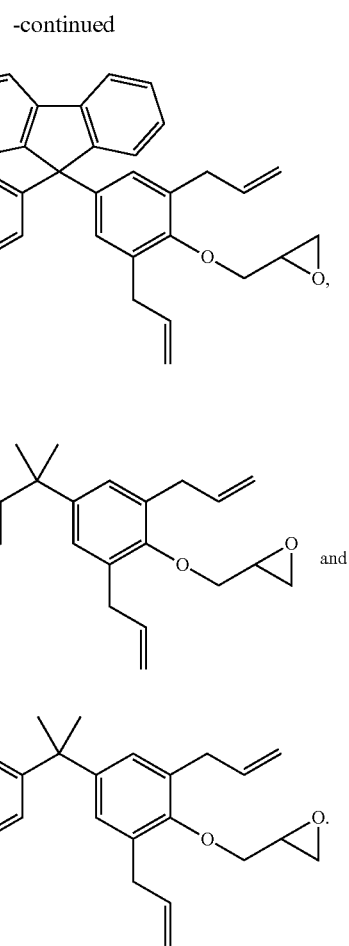
According to the twenty-seventh aspect of the present invention, there is provided at least one compound selected from the group consisting of the following Chemical Formulae (A25') to (J25').
(A25') 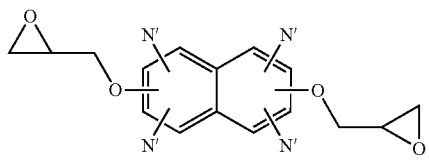
(B25') 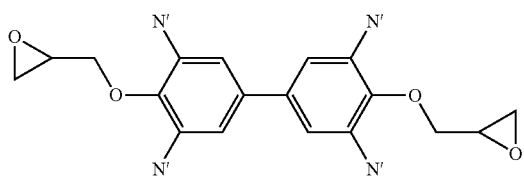
(C25') 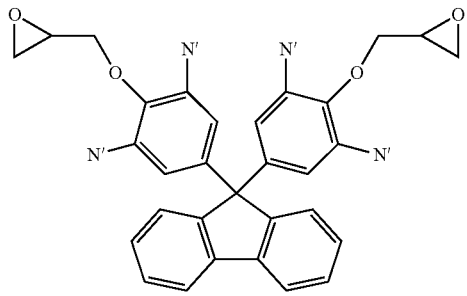
(D25') 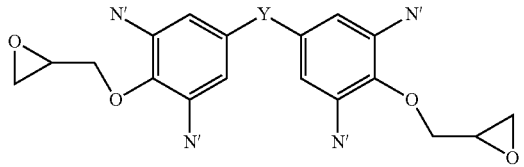

-continued

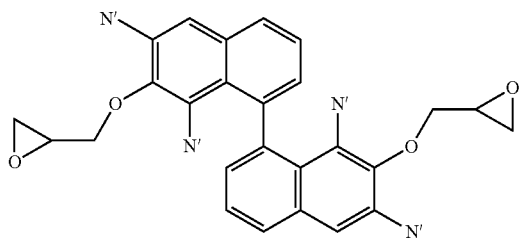
(E25')

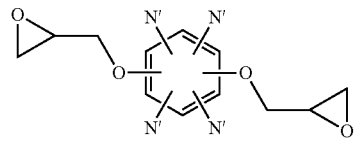
(F25')

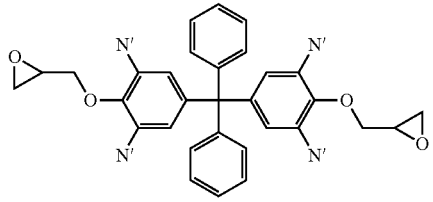
(G25')

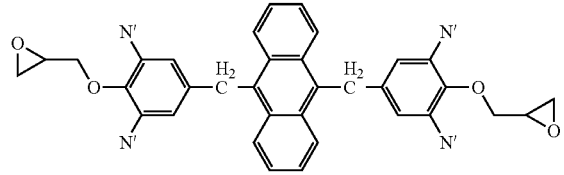
(H25')

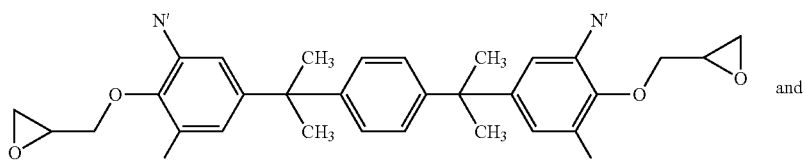
(I25')

and

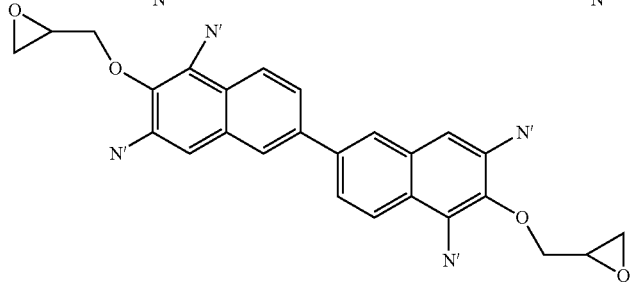
(J25')

In Chemical Formulae A25' to J25', one to three of a plurality of N' are —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), one to three of the N' are the following Chemical Formula S3, and the remainder of N' is hydrogen, and in Chemical Formula D25' above, Y is —$CH_2$—, —$C(CH_3)_2$—, —$C(CF_3)_2$—, —S— or —$SO_2$—.

[Chemical Formula S3]

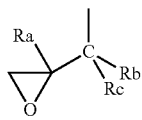

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

According to the twenty-eighth aspect of the present invention, there is provided an epoxy polymer having an alkoxysilyl group which is at least one selected from the group consisting of the following Chemical Formulae AP to KP.

[Chemical Formula AP]

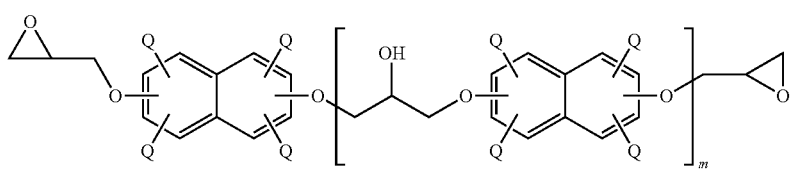

[Chemical Formula BP]
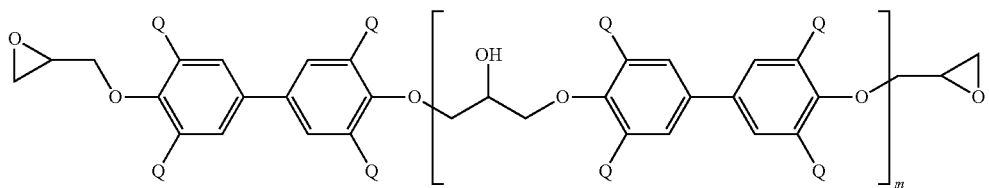
[Chemical Formula CP]
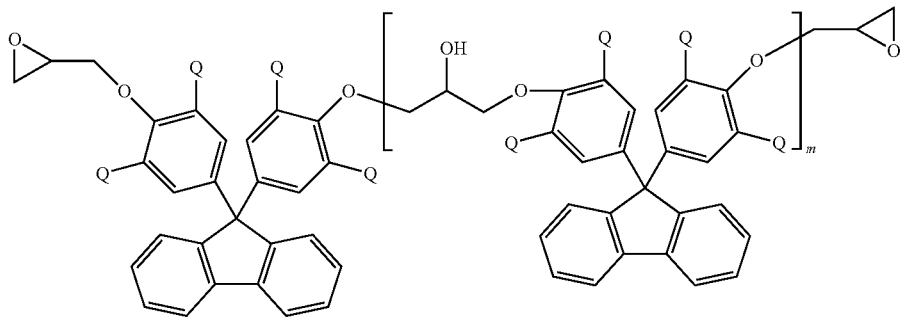
[Chemical Formula DP]
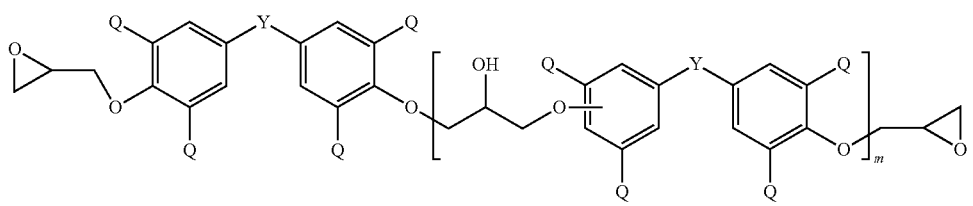
[Chemical Formula EP]
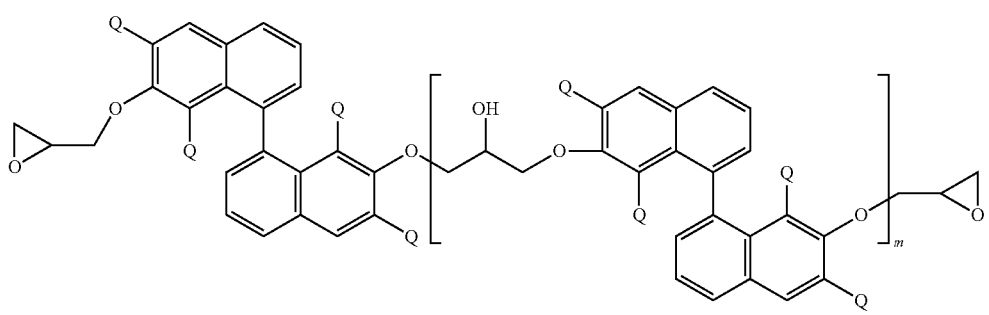
[Chemical Formula FP]
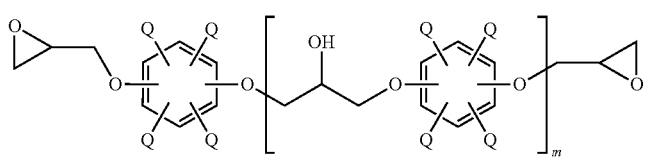
[Chemical Formula GP]
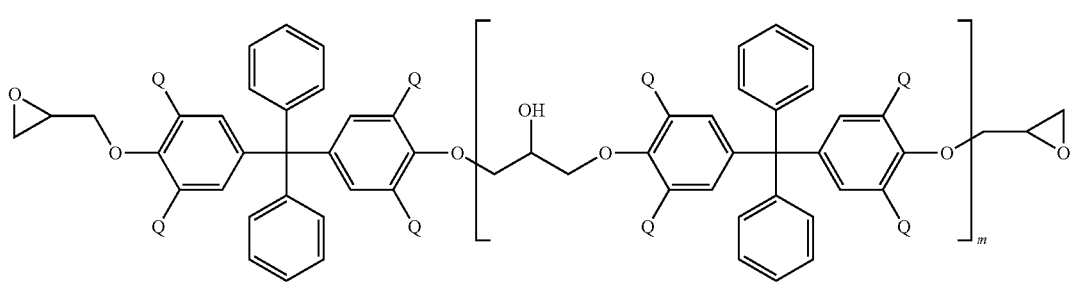

-continued

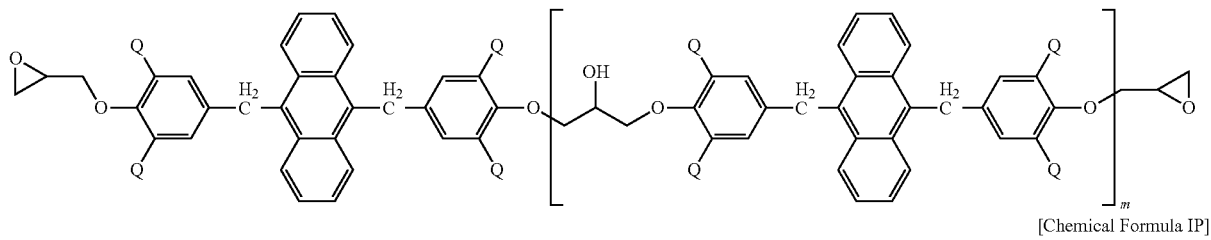
[Chemical Formula HP]

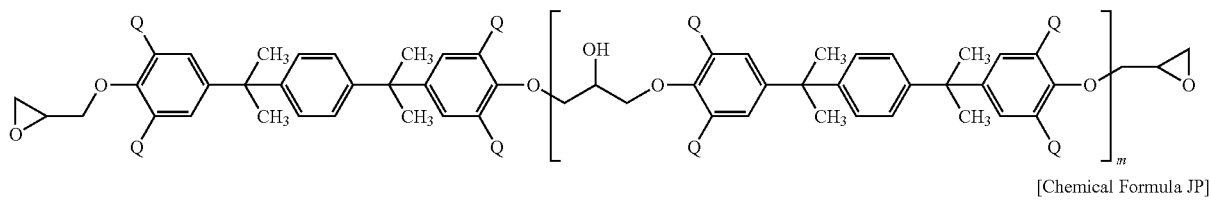
[Chemical Formula IP]

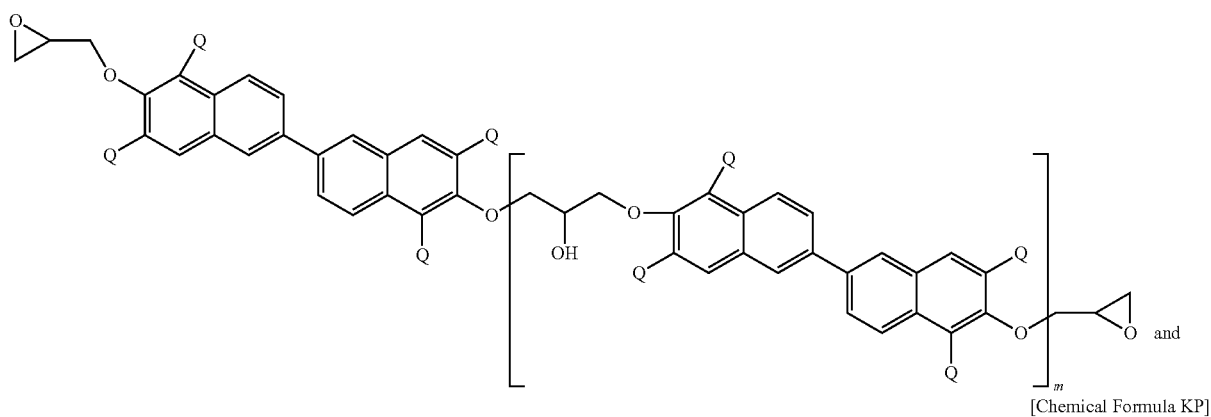
[Chemical Formula JP]

and

[Chemical Formula KP]

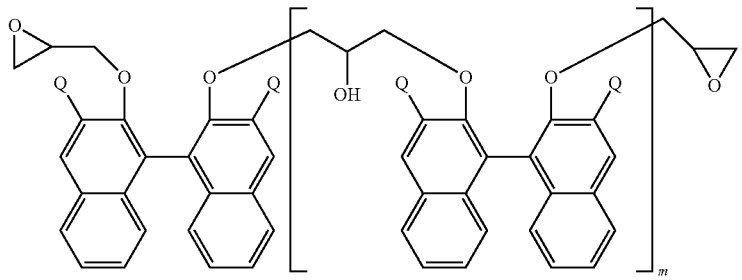

In Chemical Formulae AP to KP, at least one of a plurality of Q is Chemical Formula S1, each of the remainder of Q is independently selected from the group consisting of the following Chemical Formula S3, hydrogen and —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), m is an integer of 1 to 100, and in Chemical Formula DP above, Y is —$CH_2$—, —$C(CH_3)_2$—, —$C(CF_3)_2$—, —S— or —$SO_2$—.

—$CR_bR_c$—$CHR_a$—$CH_2$—$SiR_1R_2R_2$   [Chemical Formula S1]

In Chemical Formula S1, each of $R_a$, $R_b$ and $R_c$ is independently H or an alkyl group having 1 to 6 carbon atoms, at least one of $R_1$ to $R_3$ is an alkoxy group having 1 to 6 carbon atoms, and the remainder of $R_1$ to $R_3$ is an alkyl group having 1 to 10 carbon atoms, and the alkyl group and the alkoxy group may be a linear chain or a branched chain, may be cyclic or acyclic, and may or may not contain an N, O, S or P heteroatom.

[Chemical Formula S3]

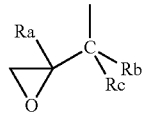

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

According to the twenty-ninth aspect of the present invention, the epoxy polymer of the twenty-eighth aspect, in which $R_1$ to $R_3$ are ethoxy groups, may be provided.

According to the thirtieth aspect of the present invention, there is provided a method of preparing an epoxy compound having an alkoxysilyl group of Chemical Formulae A(14) to K(14), comprising:

a $1^{st}$ step of preparing one intermediate product (11) from the following Chemical Formulae (A11) to (K11) by reacting one starting material from the following Chemical Formulae (AS) to (KS) with an allyl compound of the following Chemical Formula B1 in a presence of a base and an optional solvent;

a $2^{nd}$ step of preparing one intermediate product (12) from the following Chemical Formulae (A12) to (K12) by heating one of the intermediate product (11) in a presence of an optional solvent;

a $3^{rd}$ step of preparing one intermediate product (13) from the following Chemical Formulae (A13) to (K13) by reacting one of the intermediate product (12) with epichlorohydrin in a presence of a base and an optional solvent;

an optional 3-1-th step of preparing one intermediate product (13') from the following Chemical Formulae (A13') to (K13') by reacting one of the intermediate product (13) with a peroxide compound in a presence of an optional base and an optional solvent; and a $4^{th}$ step of reacting one of the intermediate product (13) or one of the intermediate product (13') with an alkoxysilane of the following Chemical Formula B2 in a presence of a metal catalyst and an optional solvent.

[Chemical Formulae (AS) to (KS)]

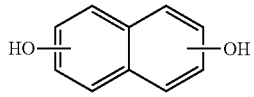
(AS)

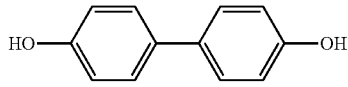
(BS)

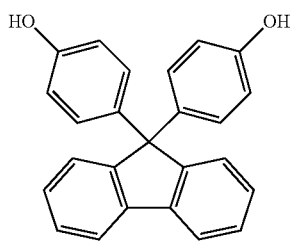
(CS)

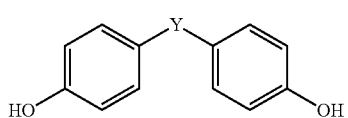
(DS)

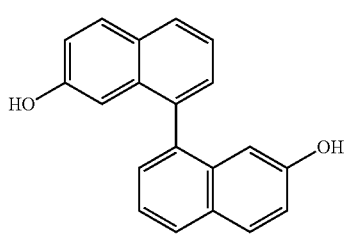
(ES)

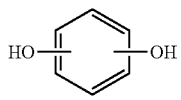
(FS)

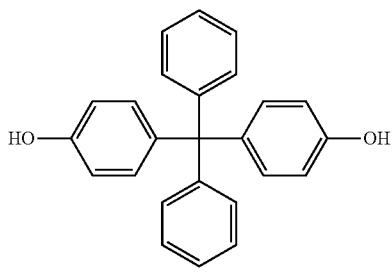
(GS)

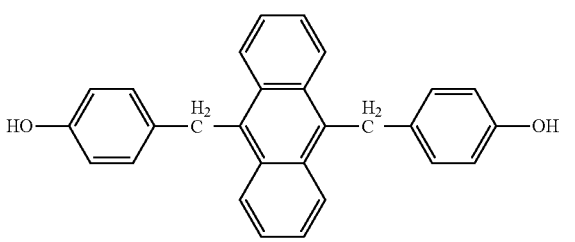
(HS)

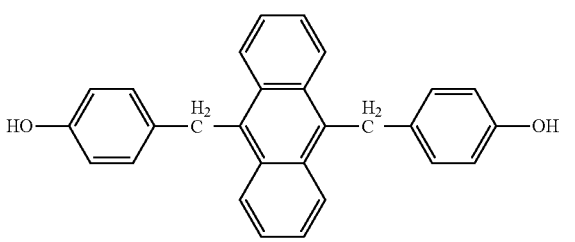
(IS)

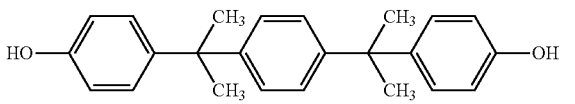
(JS)

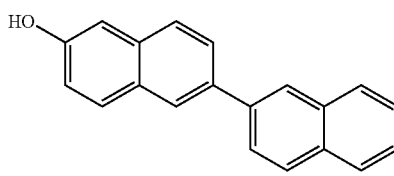
(KS)

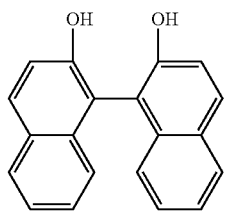
and

In Chemical Formula DS, Y is —$CH_2$—, —$C(CH_3)_2$—, —$C(CF_3)_2$—, —S— or —$SO_2$—.

[Chemical Formulae (A11) to (K11)]

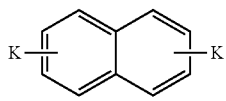
(A11)

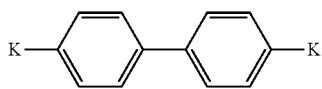
(B11)

(C11) 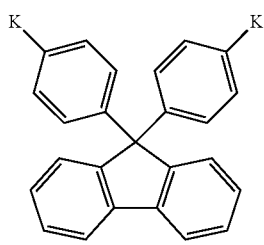

(D11) 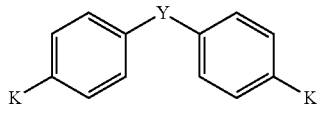

(E11) 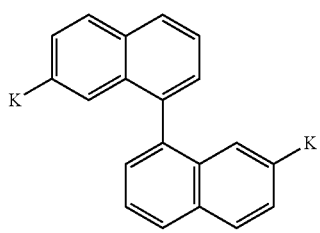

(F11) 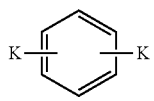

(G11) 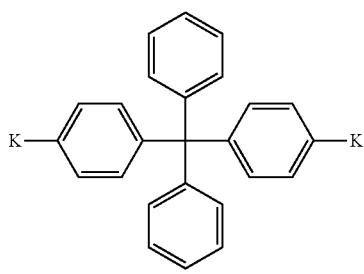

(H11) 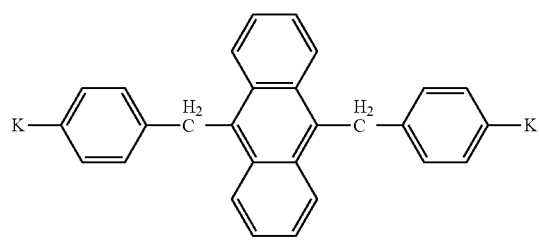

(I11) 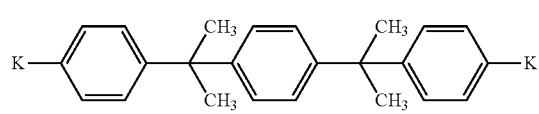

(J11) 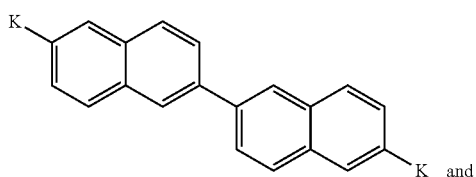

(K11) 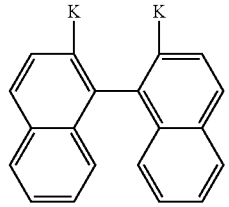

In Chemical Formulae A11 to K11, at least one of K is —O—CH$_2$—CR$_a$=CR$_b$R$_c$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of K is a hydroxyl group, and in Chemical Formula D11 above, Y is —CH$_2$—, —C(CH$_3$)$_2$—, —C(CF$_3$)$_2$—, —S— or —SO$_2$—.

[Chemical Formulae (A12) to (K12)]

(A12) 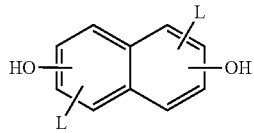

(B12) 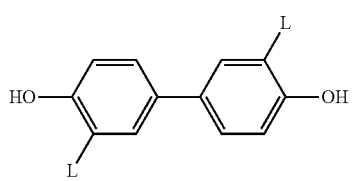

(C12) 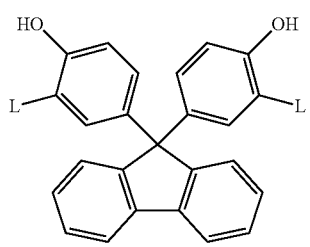

(D12) 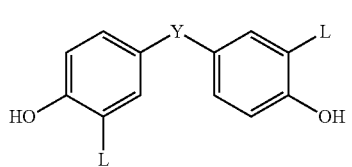

(E12) 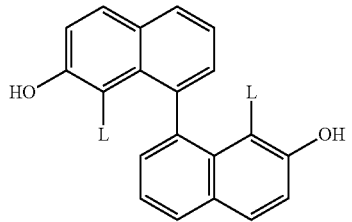

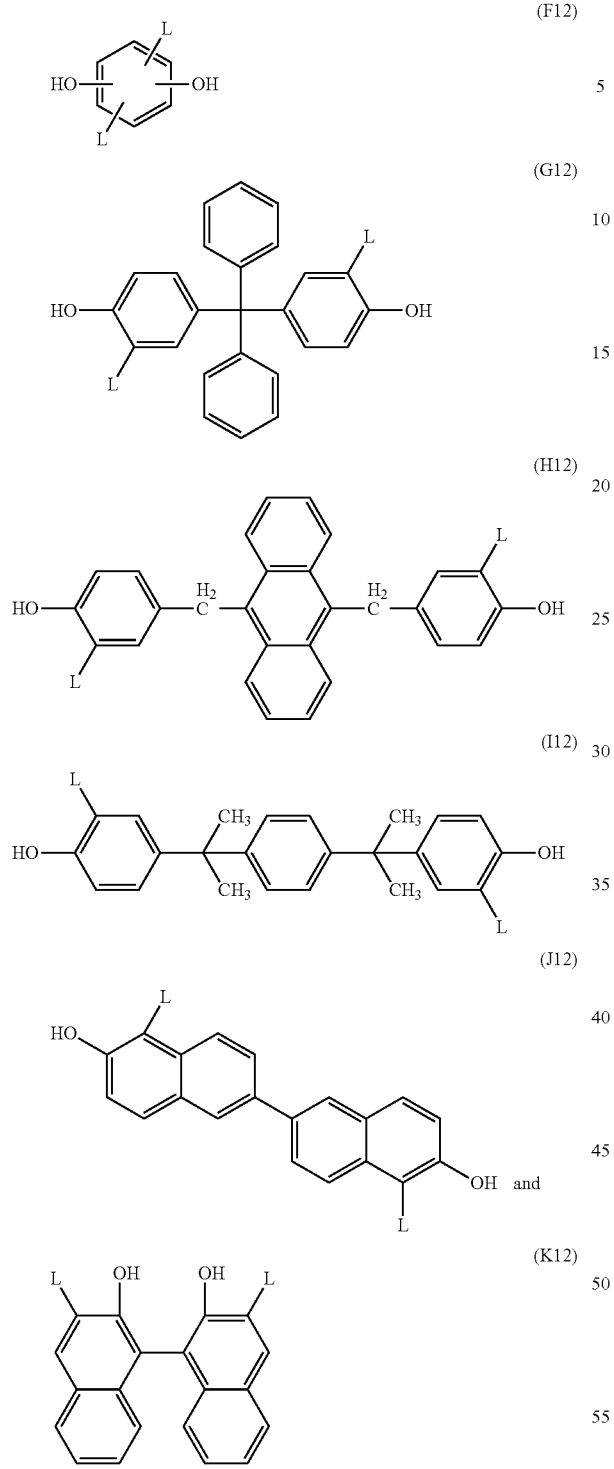

In Chemical Formulae A12 to K12, at least one of L is —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of L is hydrogen, and in Chemical Formula D12 above, Y is —CH$_2$—, —C(CH$_3$)$_2$—, —C(CF$_3$)$_2$—, —S— or —SO$_2$—.

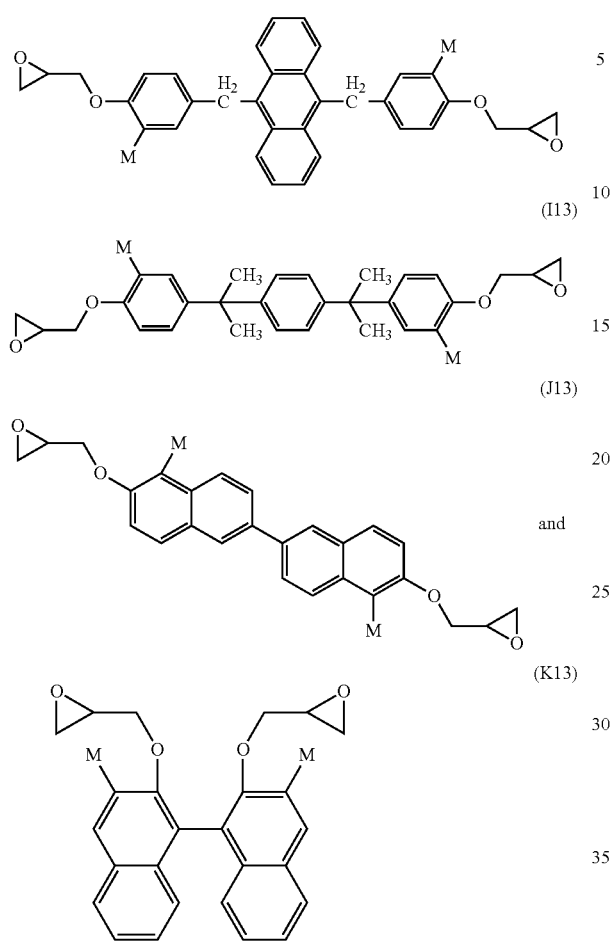
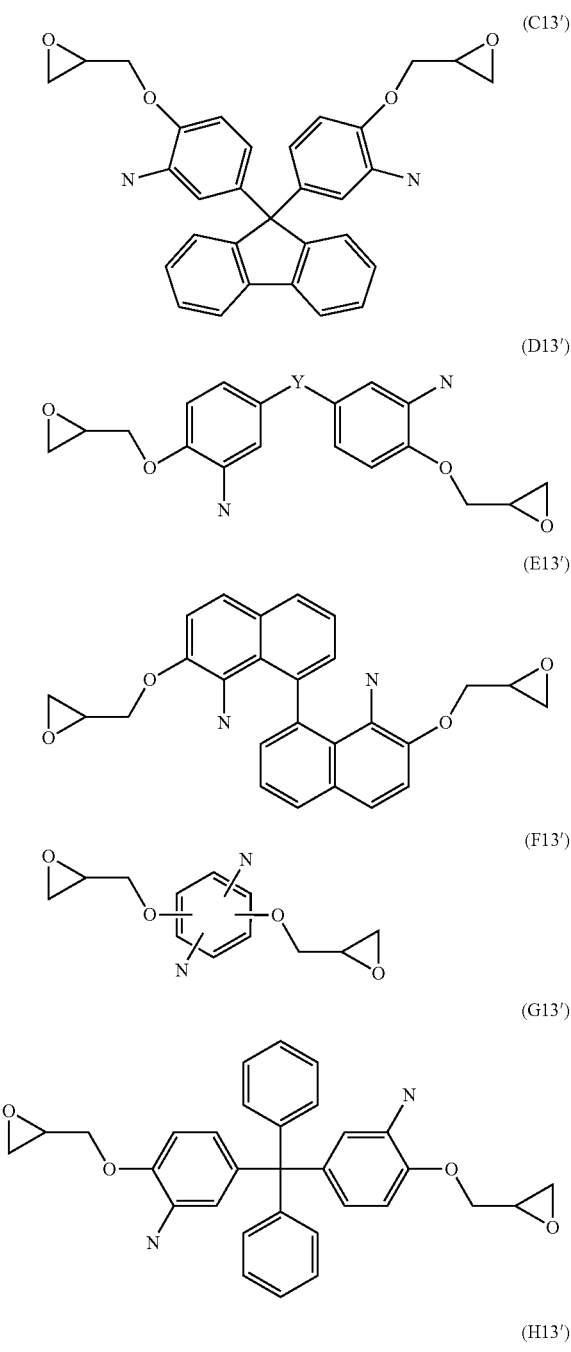

In Chemical Formulae A13 to K13, at least one of M is —CR$_b$R$_c$—CR$_a$═CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, N, O, S, or P heteroatom), and the remainder of M is hydrogen, and in Chemical Formula D13 above, Y is —CH$_2$—, —C(CH$_3$)$_2$—, —C(CF$_3$)$_2$—, —S— or —SO$_2$—.

[Chemical Formulae (A13') to (K13')]

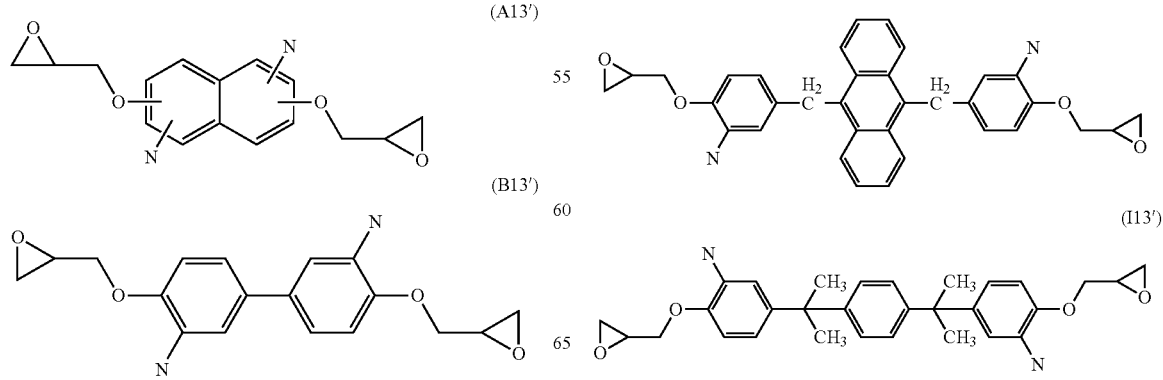

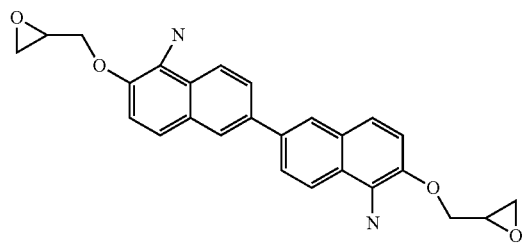
(J13′)

and

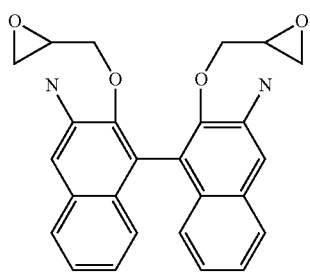
(K13′)

In Chemical Formulae A13′ to K13′, one of N is —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of N is Chemical Formula S3, and in Chemical Formula D13′ above, Y is —CH$_2$—, —C(CH$_3$)$_2$—, —C(CF$_3$)$_2$—, —S— or —SO$_2$—.

[Chemical Formula S3]

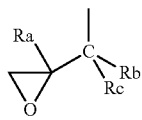

In Chemical Formula S3, each of R$_a$, R$_b$ and R$_c$ is independently H or an alkyl group having 1 to 6 carbon atoms, and the alkyl group may be a linear chain or a branched chain, may be cyclic or acyclic, and may or may not contain an N, O, S or P heteroatom.

[Chemical Formulae (A14) to (K14)]

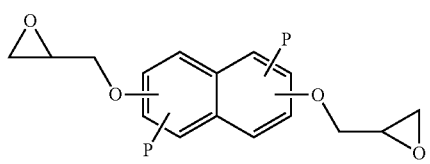
(A14)

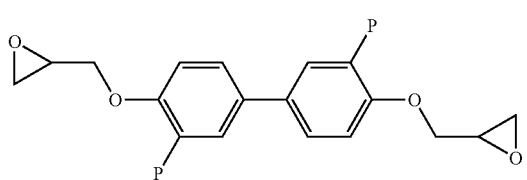
(B14)

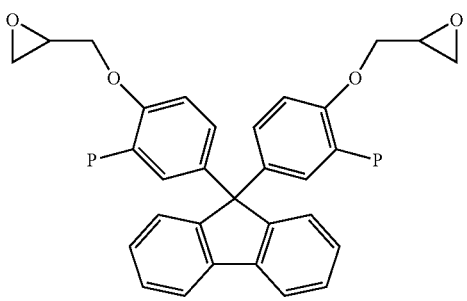
(C14)

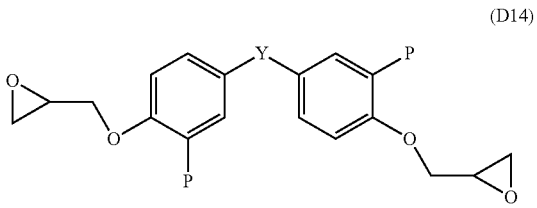
(D14)

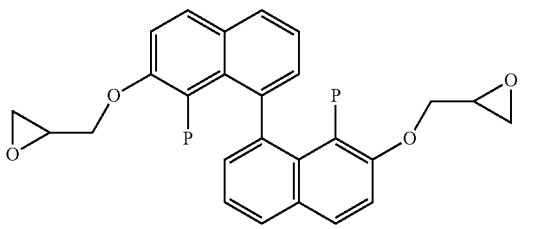
(E14)

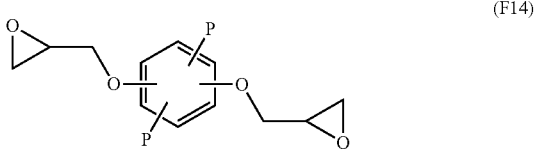
(F14)

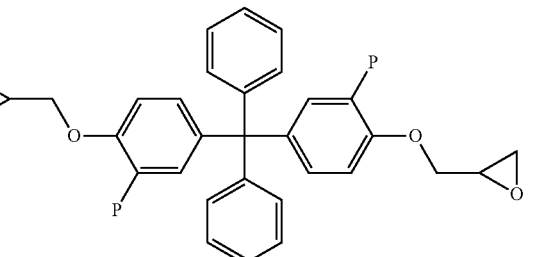
(G14)

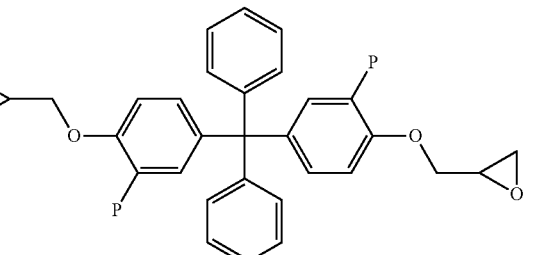
(H14)

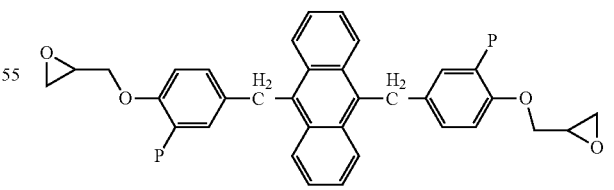
(I14)

-continued (J14)

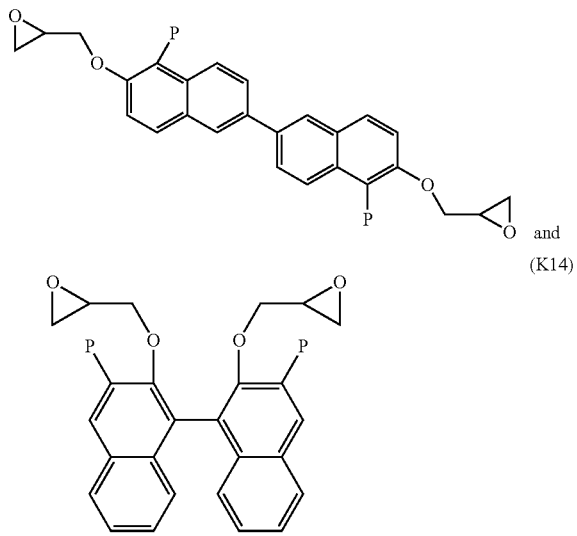
and
(K14)

In Chemical Formulae A14 to K14, at least one of P is Chemical Formula S1, each of the remainder of P is independently selected from the group consisting of the following Chemical Formula S3, hydrogen and —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), and in Chemical Formula D14 above, Y is —$CH_2$—, —$C(CH_3)_2$—, —$C(CF_3)_2$—, —S— or —$SO_2$—.

—$CR_bR_c$—$CHR_a$—$CH_2$—$SiR_1R_2R_3$     [Chemical Formula S1]

In Chemical Formula S1, each of $R_a$, $R_b$ and $R_c$ is independently H or an alkyl group having 1 to 6 carbon atoms, at least one of $R_1$ to $R_3$ is an alkoxy group having 1 to 6 carbon atoms, and the remainder of $R_1$ to $R_3$ is an alkyl group having 1 to 10 carbon atoms, and the alkyl group and the alkoxy group may be a linear chain or a branched chain, may be cyclic or acyclic, and may or may not contain an N, O, S or P heteroatom. The epoxy compound of the Chemical Formula F14 having one of S1, in which all of $R_a$, $R_b$ and $R_c$ are hydrogen, and all of $R_1$ to $R_3$ are the alkoxy group having 1 to 6 carbon atoms is excluded.

[Chemical Formula S3]

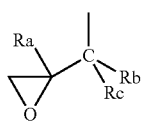

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

[Chemical Formula B1]

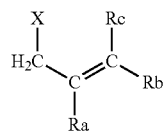

In Chemical Formula B1, X is Cl, Br, I, —O—$SO_2$—$CH_3$, —O—$SO_2$—$CF_3$, or —O—$SO_2$—$C_6H_4$—$CH_3$, each of $R_a$, $R_b$ and $R_c$ is independently H or an alkyl group having 1 to 6 carbon atoms, and the alkyl group may have a linear chain or a branched chain, may be cyclic or acyclic, and may or may not contain an N, O, S, or P heteroatom.

$HSiR_1R_2R_3$     [Chemical Formula B2]

In Chemical Formula B2, at least one of $R_1$ to $R_3$ is an alkoxy group having 1 to 6 carbon atoms, the remainder of $R_1$ to $R_3$ is an alkyl group having 1 to 10 carbon atoms, and the alkyl group and the alkoxy group may have a linear chain or a branched chain, may be cyclic or acyclic, and may or may not contain an N, O, S, or P heteroatom.

According to the thirty-first aspect of the present invention, there is provided a method of preparing an epoxy compound having an alkoxysilyl group of Chemical Formulae (A26) to (J26), comprising:

a $1^{st}$ step of preparing one intermediate product (11) from the following Chemical Formulae (A1) to (J1) by reacting one starting material from the following Chemical Formulae (AS) to (JS) with an allyl compound of the following Chemical Formula B1 in a presence of a base and an optional solvent;

a $2^{nd}$ step of preparing one intermediate product (12) from the following Chemical Formulae (A12) to (J12) by heating one of the intermediate product (11) in a presence of an optional solvent;

a 2-1-th step of preparing one intermediate product (23) from the following Chemical Formulae (A23) to (J23) by reacting one of the intermediate product (12) with the allyl compound of the following Chemical Formula B1 in a presence of a base and an optional solvent;

a 2-2-th step of preparing one intermediate product (24) from the following Chemical Formulae (A24) to (J24) by heating the intermediate product (23) in a presence of an optional solvent;

a $3^{rd}$ step of preparing one intermediate product (25) from the following Chemical Formulae (A25) to (J25) by reacting one of the intermediate product (24) with epichlorohydrin in a presence of a base and an optional solvent;

an optional 3-1-th step of preparing one intermediate product (25') from the following Chemical Formulae (A25') to (J25') by reacting one of intermediate product (25) with a peroxide compound in a presence of an optional base and an optional solvent; and a $4^{th}$ step of reacting one of the intermediate product (25) or one of the intermediate product (25') with an alkoxysilane of the following Chemical Formula B2 in a presence of a metal catalyst and an optional solvent.

[Chemical Formulae (AS) to (JS)]

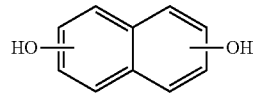
(AS)

-continued
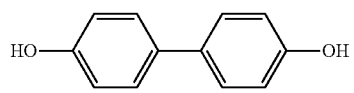 (B12)
 (CS)
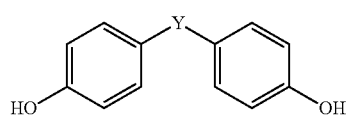 (DS)
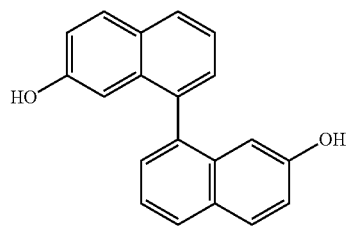 (ES)
 (FS)
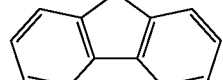 (GS)
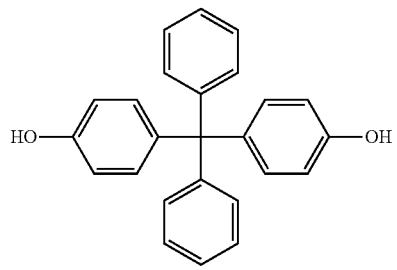 (HS)
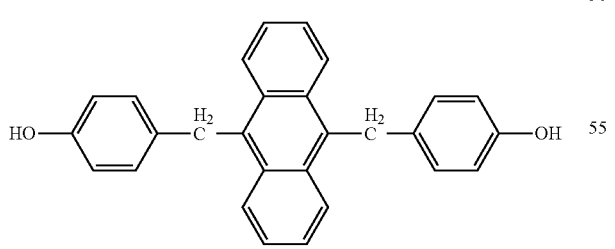 (IS)
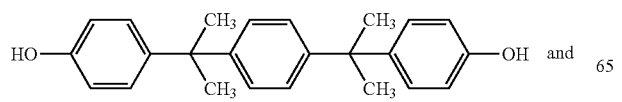 and
-continued
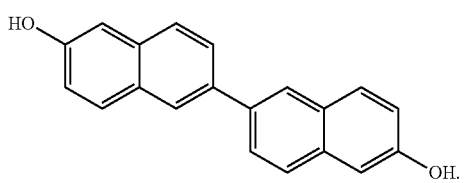 (JS)
In Chemical Formula DS, Y is —CH$_2$—, —C(CH$_3$)$_2$—, —C(CF$_3$)$_2$—, —S— or —SO$_2$—.
[Chemical Formulae (A11) to (J11)]
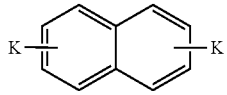 (A11)
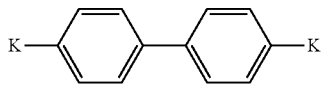 (B11)
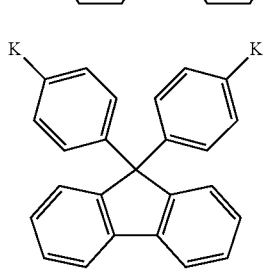 (C11)
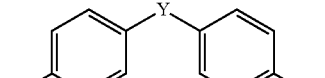 (D11)
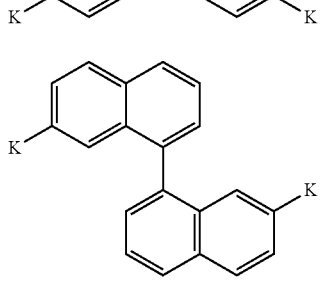 (E11)
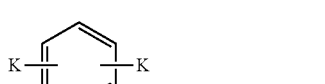 (F11)
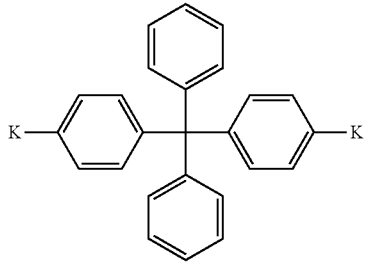 (G11)

-continued

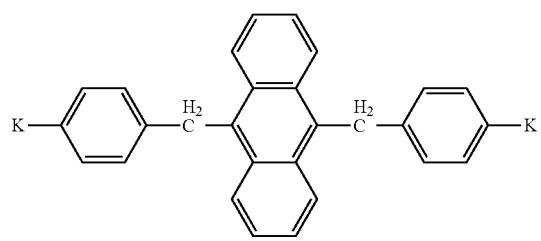
(H11)

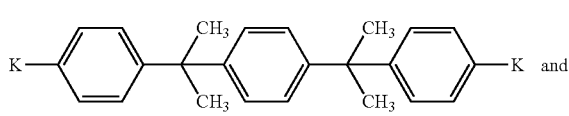
(I11)

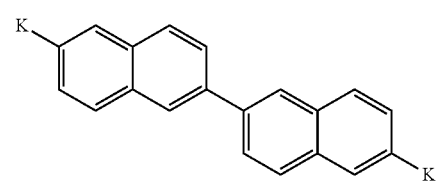
(J11)

In Chemical Formulae A11 to J11, at least one of K is —O—CH$_2$—CR$_a$=CR$_b$R$_c$ (in which each of R$_a$, R$_b$ and R$_c$ is independently H or an alkyl group having 1 to 6 carbon atoms, and the alkyl group may have a linear chain or a branched chain, may be cyclic or acyclic, and may or may not contain an N, O, S, or P heteroatom), and the remainder of K is a hydroxyl group, and in Chemical Formula D11 above, Y is —CH$_2$—, —C(CH$_3$)$_2$—, —C(CF$_3$)$_2$—, —S— or —SO$_2$—.

[Chemical Formulae (A12) to (J12)]

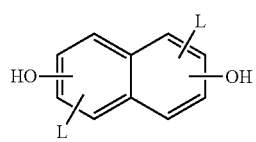
(A12)

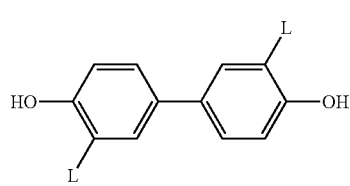
(B12)

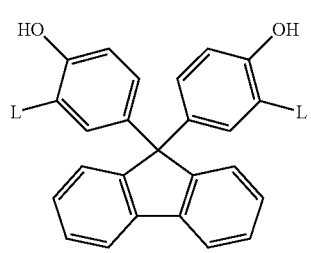
(C12)

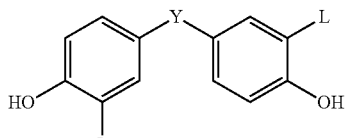
(D12)

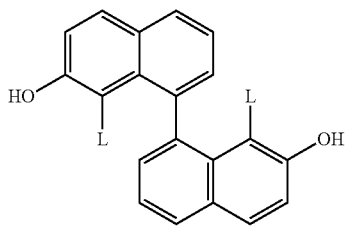
(E12)

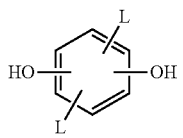
(F12)

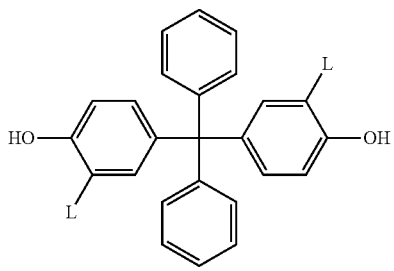
(G12)

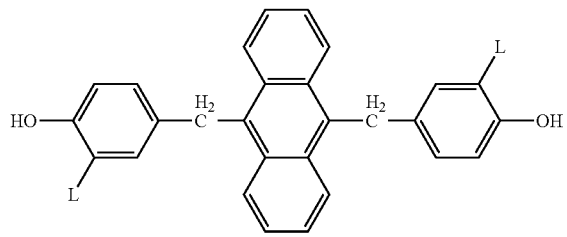
(H12)

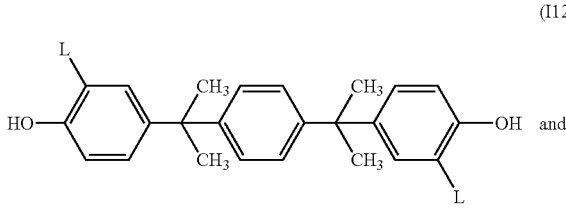
(I12)

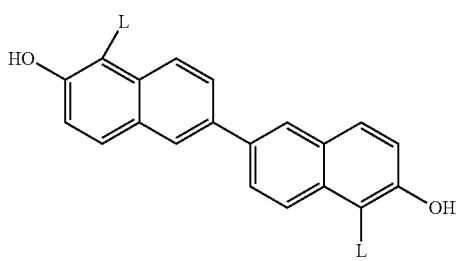
(J12)

In Chemical Formulae A12 to J12, at least one of L is —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of L is hydrogen, and in Chemical Formula D12 above, Y is —CH$_2$—, —C(CH$_3$)$_2$—, —C(CF$_3$)$_2$—, —S— or —SO$_2$—.

[Chemical Formulae (A23) to (J23)]

(A23)
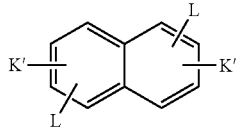

(B23)
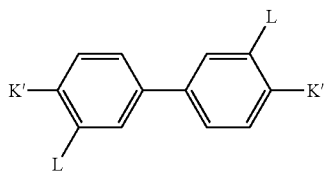

(C23)
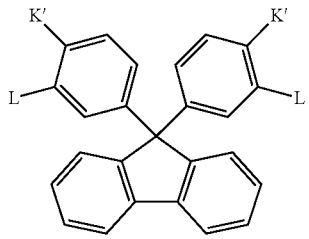

(D23)
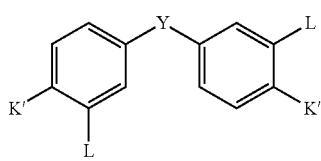

(E23)
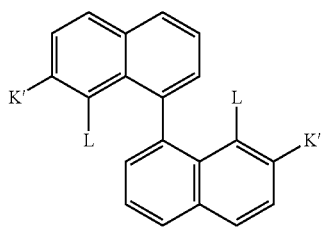

(F23)
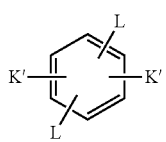

(G23)
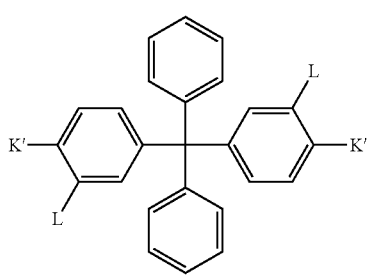

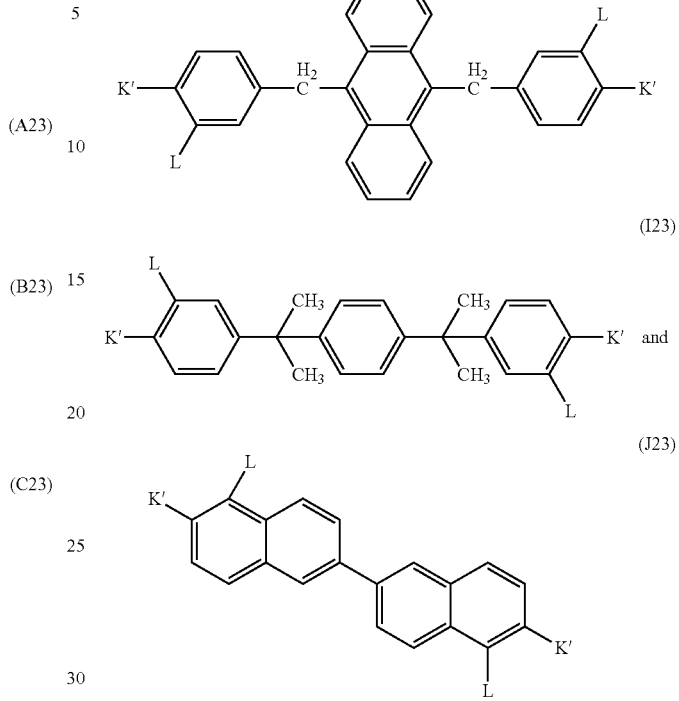

(H23)

(I23)

and (J23)

In Chemical Formulae A23 to J23, at least one of K' is —O—CH$_2$—CR$_a$═CR$_b$R$_c$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of K' is hydrogen, at least one of L is —CR$_b$R$_c$—CR$_a$═CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of L is hydrogen, and in Chemical Formula D23 above, Y is —CH$_2$—, —C(CH$_3$)$_2$—, —C(CF$_3$)$_2$—, —S— or —SO$_2$—.

[Chemical Formulae (A24) to (J24)]

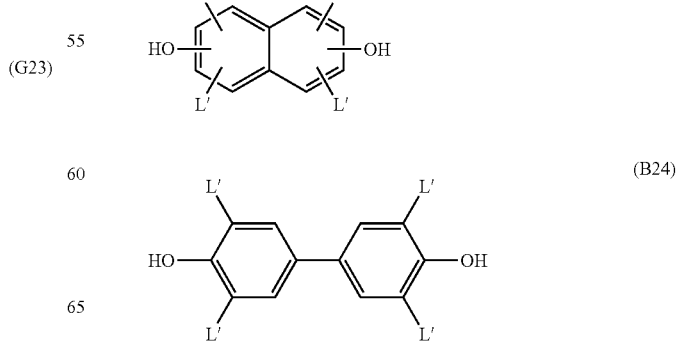

(A24)

(B24)

(C24)

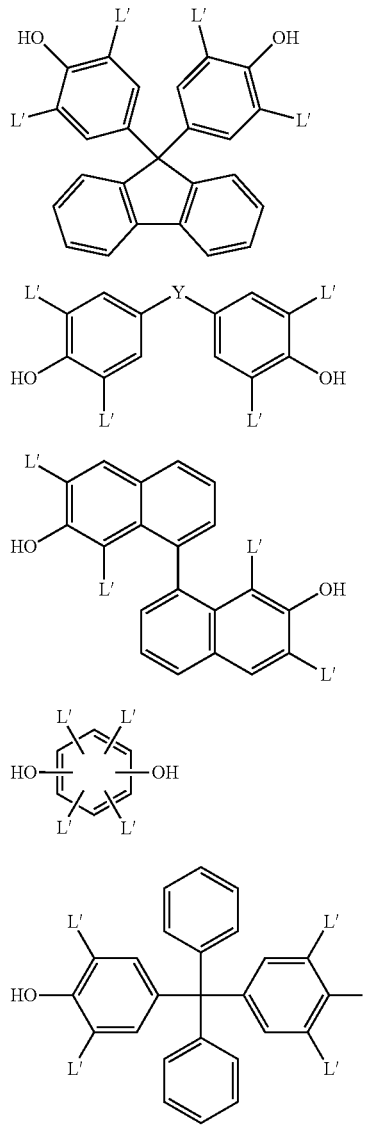

(D24)

(E24)

(F24)

(G24)

(H24)

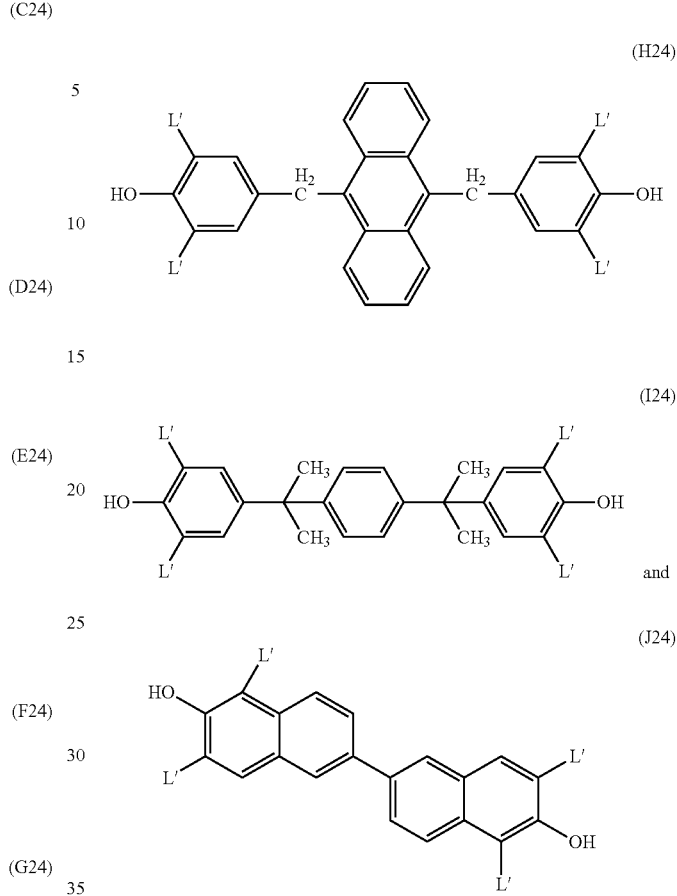

(I24)

(J24)

In Chemical Formulae A24 to J24, at least two of a plurality of L' are —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of the L' is hydrogen, and in Chemical Formula D24 above, Y is —CH$_2$—, —C(CH$_3$)$_2$—, —C(CF$_3$)$_2$—, —S— or —SO$_2$—.

[Chemical Formulae (A25) to (J25)]

(A25)

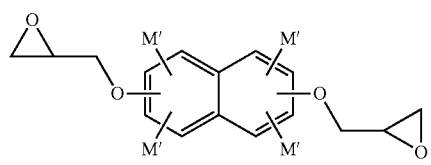

(B25)

(C25)

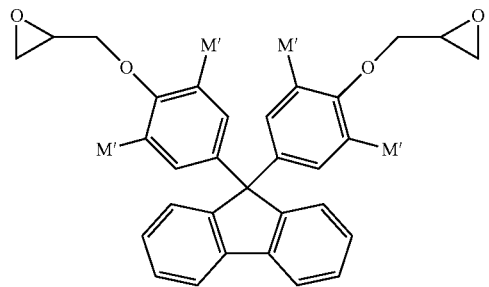

(D25)

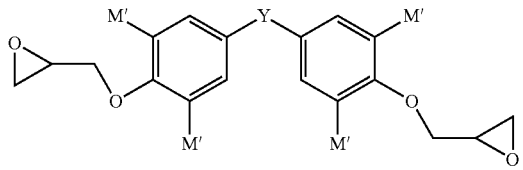

-continued

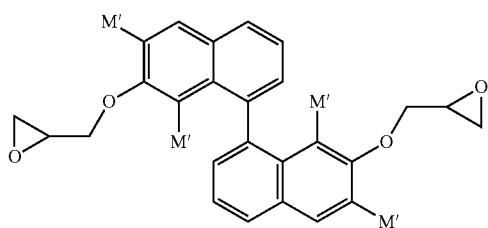 (E25)

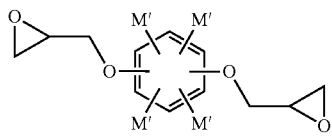 (F25)

(G25)

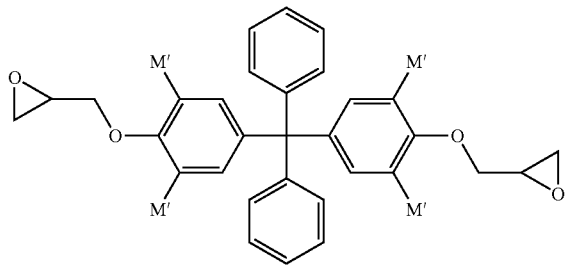

(H25)

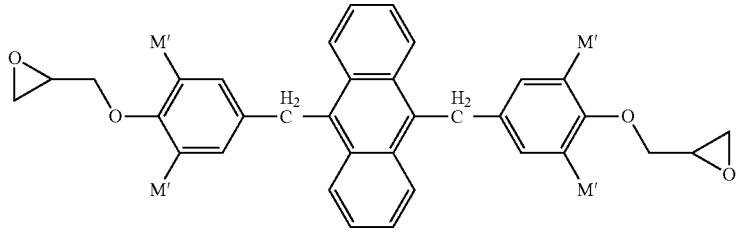

(I25)

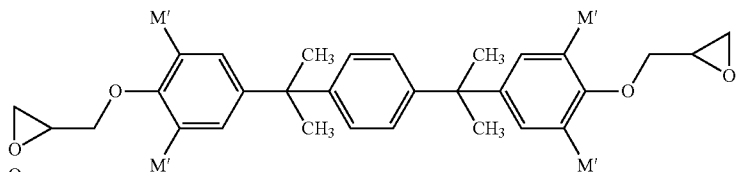

and (J25)

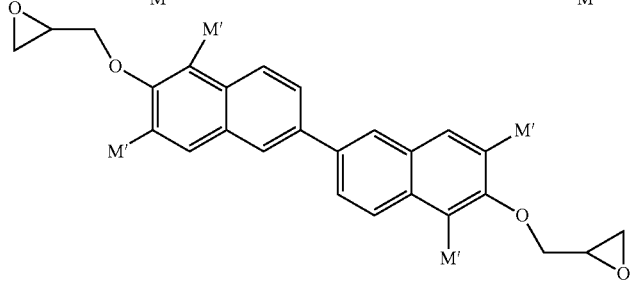

In Chemical Formulae A25 to J25, at least two of a plurality of M' are —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of the M' is hydrogen, and in Chemical Formula D25 above, Y is —$CH_2$—, —$C(CH_3)_2$—, —$C(CF_3)_2$—, —S— or —$SO_2$—.

[Chemical Formulae (A25') to (J25')]

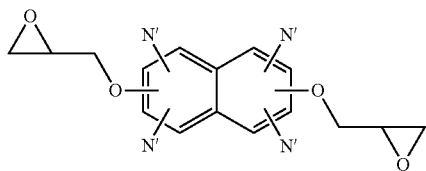 (A25')

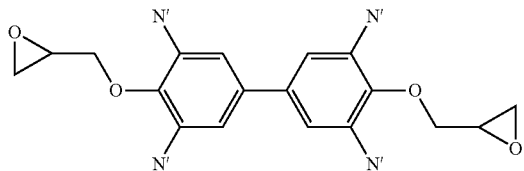 (B25')

-continued
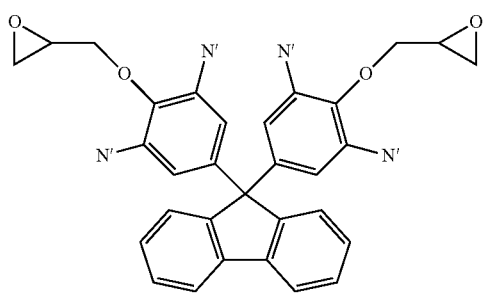
(C25')
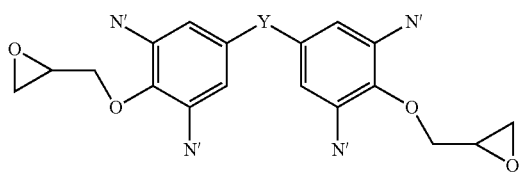
(D25')
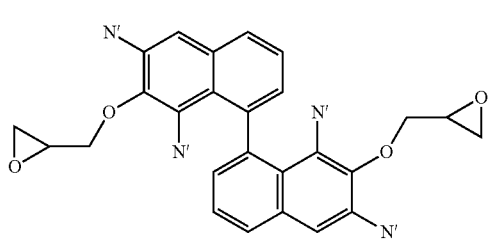
(E25')
(F25')
(G25')
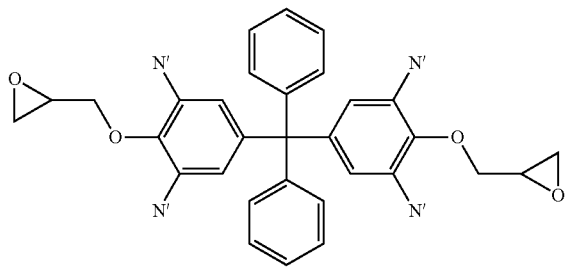
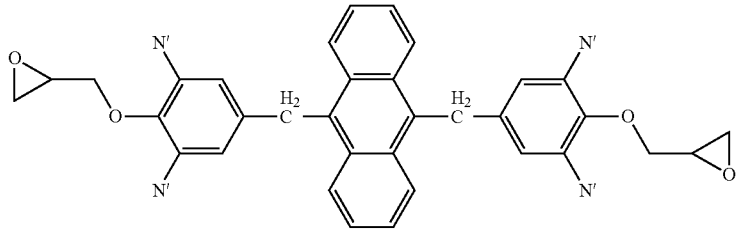
(H25')
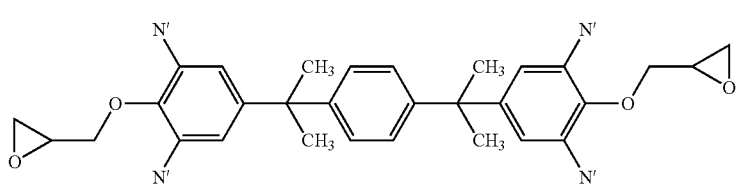
(I25')
and
(J25')
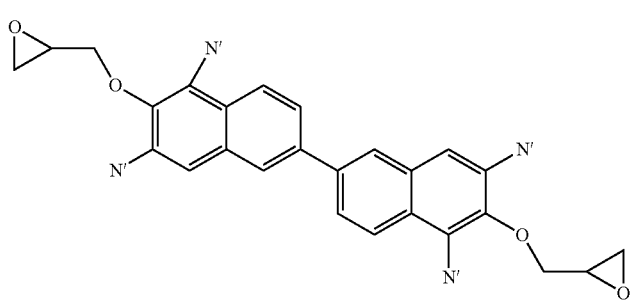
In Chemical Formulae A25' to J25', one to three of a plurality of N' are —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), one to three of the plurality of the N' are the following Chemical Formula S3, and the remainder of the N' is hydrogen, and in Chemical Formula D25' above, Y is —CH$_2$—, —C(CH$_3$)$_2$—, —C(CF$_3$)$_2$—, —S— or —SO$_2$—.
[Chemical Formulae (A26) to (J26)]
(A26)
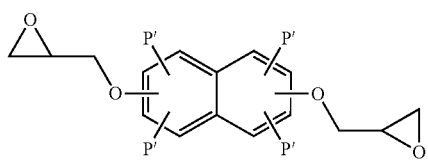
(B26)
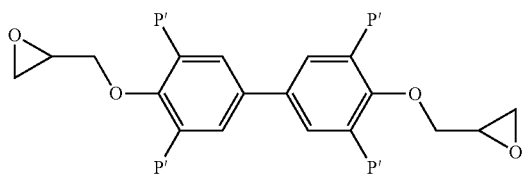
(C26)
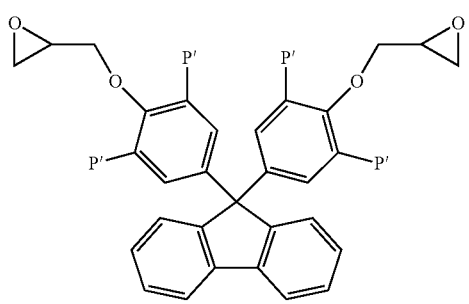
(D26)
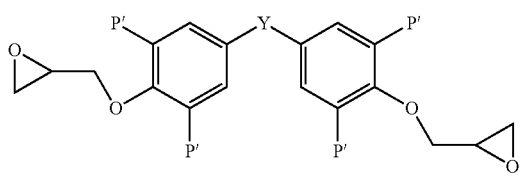
(E26)
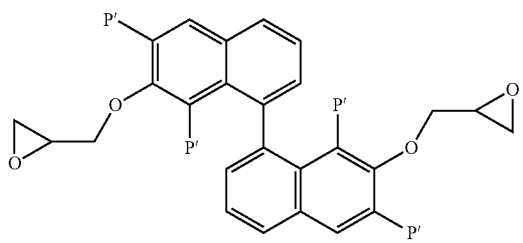
(F26)
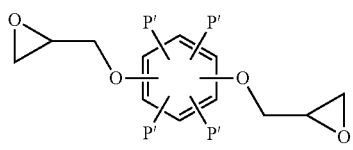
(G26)
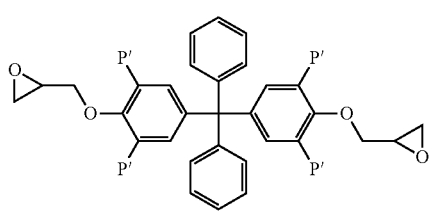
(H26)
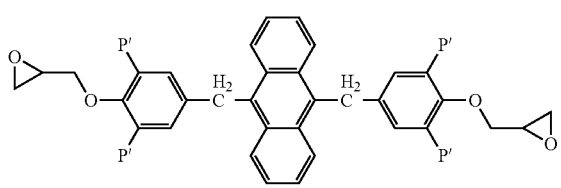
(I26)
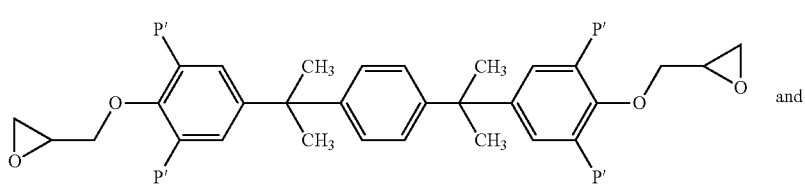
and
(J26)
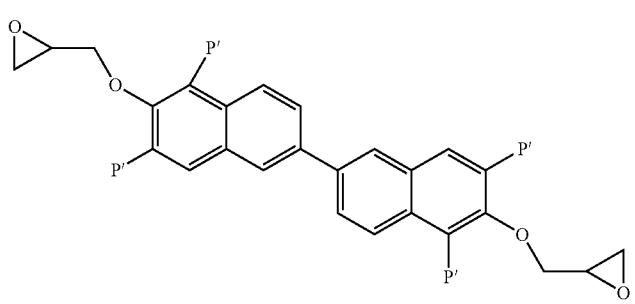

In Chemical Formulae A26 to J26, at least one of P' is the following Chemical Formula S1, each of the remainder of P' is independently selected from the group consisting of the following Chemical Formula S3, hydrogen and —CR$_b$R$_c$—CR$_a$=CH$_2$ (in which each of R$_a$, R$_b$ and R$_c$ is independently H or an alkyl group having 1 to 6 carbon atoms, and the alkyl group may have a linear chain or a branched chain, may be cyclic or acyclic, and may or may not contain an N, O, S, or P heteroatom), and in Chemical Formula D26 above, Y is —CH$_2$—, —C(CH$_3$)$_2$—, —C(CF$_3$)$_2$—, —S— or —SO$_2$—.

—CR$_b$R$_c$—CHR$_a$—CH$_2$—SiR$_1$R$_2$R$_3$    [Chemical Formula S1]

In Chemical Formula S1, each of R$_a$, R$_b$ and R$_c$ is independently H or an alkyl group having 1 to 6 carbon atoms, at least one of R$_1$ to R$_3$ is an alkoxy group having 1 to 6 carbon atoms, and the remainder of R$_1$ to R$_3$ is an alkyl group having 1 to 10 carbon atoms, and the alkyl group and the alkoxy group may be a linear chain or a branched chain, may be cyclic or acyclic, and may or may not contain an N, O, S or P heteroatom. The epoxy compound of Chemical Formula F26 having one of S1, in which all of R$_a$, R$_b$ and R$_c$ are hydrogen, and all of R$_1$ to R$_3$ are the alkoxy group having 1 to 6 carbon atoms is excluded.

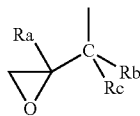

[Chemical Formula S3]

In Chemical Formula S3, each of R$_a$, R$_b$ and R$_c$ is independently H or an alkyl group having 1 to 6 carbon atoms, and the alkyl group may be a linear chain or a branched chain, may be cyclic or acyclic, and may or may not contain an N, O, S or P heteroatom.

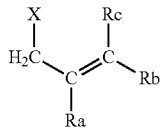

[Chemical Formula B1]

In Chemical Formula B1, X is Cl, Br, I, —O—SO$_2$—CH$_3$, —O—SO$_2$—CF$_3$, or —O—SO$_2$—C$_6$H$_4$—CH$_3$, each of R$_a$, R$_b$ and R$_c$ is independently H or an alkyl group having 1 to 6 carbon atoms, and the alkyl group may have a linear chain or a branched chain, may be cyclic or acyclic, and may or may not contain an N, O, S, or P heteroatom.

HSiR$_1$R$_2$R$_3$    [Chemical Formula B2]

In Chemical Formula B2, at least one of R$_1$ to R$_3$ is an alkoxy group having 1 to 6 carbon atoms, the remainder of R$_1$ to R$_3$ is an alkyl group having 1 to 10 carbon atoms, and the alkyl group and the alkoxy group may have a linear chain or a branched chain, may be cyclic or acyclic, and may or may not contain an N, O, S, or P heteroatom.

According to the thirty-second aspect of the present invention, the method of preparing an epoxy compound having an alkoxysilyl group of the thirtieth or thirty-first aspect, in which the allyl compound of Chemical Formula B1 above is provided as having 0.5 to 10 equivalents of an allyl group, based on 1 equivalent of a hydroxyl group in the starting material in the 1$^{st}$ step, may be provided.

According to the thirty-third aspect of the present invention, the method of preparing an epoxy compound having an alkoxysilyl group of the thirtieth or thirty-first aspect, in which the reaction is conducted at a temperature of room temperature to 100° C. for 1 to 120 hours in the 1$^{st}$ step, may be provided.

According to the thirty-fourth aspect of the present invention, the method of preparing an epoxy compound having an alkoxysilyl group of the thirtieth or thirty-first aspect, in which the base used in the 1$^{st}$ step is at least one selected from the group consisting of KOH, NaOH, K$_2$CO$_3$, Na$_2$CO$_3$, KHCO$_3$, NaHCO$_3$, NaH, triethylamine and diisopropylethylamine, may be provided.

According to the thirty-fifth aspect of the present invention, the method of preparing an epoxy compound having an alkoxysilyl group of the thirtieth or thirty-first aspect, in which the solvent used in the 1$^{st}$ step is at least one selected from the group consisting of acetonitrile, tetrahydrofuran, methyl ethyl ketone, dimethylformamide, dimethyl sulfoxide and methylene chloride, may be provided.

According to the thirty-sixth aspect of the present invention, the method of preparing an epoxy compound having an alkoxysilyl group of the thirtieth or thirty-first aspect, in which the intermediate product (11) is heated to 140° C. to 250° C. for 1 to 200 hours in the 2$^{nd}$ step, may be provided.

According to the thirty-seventh aspect of the present invention, the method of preparing an epoxy compound having an alkoxysilyl group of the thirtieth or thirty-first aspect, in which the solvent in the 2$^{nd}$ step is at least one selected from the group consisting of xylene, 1,2-dichlorobenzene and N,N-diethylaniline, may be provided.

According to the thirty-eighth aspect of the present invention, the method of preparing an epoxy compound having an alkoxysilyl group of the thirty-first aspect, in which the allyl compound of Chemical Formula B1 above is provided as having 0.5 to 10 equivalents of an allyl group, based on 1 equivalent of a hydroxyl group in the intermediate product (12) in the 2-1-th step, may be provided.

According to the thirty-ninth aspect of the present invention, the method of preparing an epoxy compound having an alkoxysilyl group of the thirty-first aspect, in which the reaction in the 2-1-th step is conducted at a temperature of room temperature to 100° C. for 1 to 120 hours, may be provided.

According to the fortieth aspect of the present invention, the method of preparing an epoxy compound having an alkoxysilyl group of the thirty-first aspect, in which the base used in the 2-1-th step is at least one selected from the group consisting of KOH, NaOH, K$_2$CO$_3$, Na$_2$CO$_3$, KHCO$_3$, NaHCO$_3$, NaH, triethylamine and diisopropylethylamine, may be provided.

According to the forty-first aspect of the present invention, the method of preparing an epoxy compound having an alkoxysilyl group of the thirty-first aspect, in which the solvent used in the 2-1-th step is at least one selected from the group consisting of acetonitrile, tetrahydrofuran, methyl ethyl ketone, dimethylformamide, dimethyl sulfoxide and methylene chloride, may be provided.

According to the forty-second aspect of the present invention, the method of preparing an epoxy compound having an alkoxysilyl group of the thirty-first aspect, in which the 2-2-th step is conducted at 140° C. to 250° C. for 1 to 200 hours, may be provided.

According to the forty-third aspect of the present invention, the method of preparing an epoxy compound having an alkoxysilyl group of the thirty-first aspect, in which the solvent in the 2-2-th step is at least one selected from the group consisting of xylene, 1,2-dichlorobenzene and N,N-diethylaniline, may be provided.

According to the forty-fourth aspect of the present invention, the method of preparing an epoxy compound having an alkoxysilyl group of the thirtieth or the thirty-first aspect, in which the epichlorohydrin is provided as having 1 to 10 equivalents of a glycidyl group, based on 1 equivalent of a hydroxyl group in the intermediate product (12) or the intermediate product (24) in the 3rd step, may be provided.

According to the forty-fifth aspect of the present invention, the method of preparing an epoxy compound having an alkoxysilyl group of the thirtieth or the thirty-first aspect, in which the reaction in the $3^{rd}$ step is conducted at a temperature of room temperature to 100° C. for 1 to 120 hours, may be provided.

According to the forty-sixth aspect of the present invention, the method of preparing an epoxy compound having an alkoxysilyl group of the thirtieth or the thirty-first aspect, in which the base used in the $3^{rd}$ step is at least one selected from the group consisting of KOH, NaOH, $K_2CO_3$, $Na_2CO_3$, $KHCO_3$, $NaHCO_3$, NaH, triethylamine and diisopropylethylamine, may be provided.

According to the forty-seventh aspect of the present invention, the method of preparing an epoxy compound having an alkoxysilyl group of the thirtieth or the thirty-first aspect, in which the solvent used in the $3^{rd}$ step is at least one selected from the group consisting of acetonitrile, tetrahydrofuran, methyl ethyl ketone, dimethylformamide, dimethyl sulfoxide and methylene chloride, may be provided.

According to the forty-eighth aspect of the present invention, the method of preparing an epoxy compound having an alkoxysilyl group of the thirtieth or the thirty-first aspect, in which the peroxide compound is provided as having 1 to 10 equivalents of a peroxide group, based on 1 equivalent of an allyl group in the intermediate product (13) or the intermediate product (25) in the 3-1-th step, may be provided.

According to the forty-ninth aspect of the present invention, the method of preparing an epoxy compound having an alkoxysilyl group of the thirtieth or the thirty-first aspect, in which the peroxide compound in the 3-1-th step is at least one selected from the group consisting of meta-chloroperoxybenzoic acid (m-CPBA), $H_2O_2$, and dimethyldioxirane (DMDO), may be provided.

According to the fiftieth aspect of the present invention, the method of preparing an epoxy compound having an alkoxysilyl group of the thirtieth or the thirty-first aspect, in which the reaction in the 3-1-th step is conducted at a temperature of room temperature to 100° C. for 1 to 120 hours, may be provided.

According to the fifty-first aspect of the present invention, the method of preparing an epoxy compound having an alkoxysilyl group of the thirtieth or the thirty-first aspect, in which the solvent used in the 3-1-th step is at least one selected from the group consisting of acetonitrile, tetrahydrofuran, methyl ethyl ketone, dimethylformamide, dimethyl sulfoxide and methylene chloride, may be provided.

According to the fifty-second aspect of the present invention, the method of preparing an epoxy compound having an alkoxysilyl group of the thirtieth or the thirty-first aspect, in which the base used in the 3-1-th step is at least one selected from the group consisting of KOH, NaOH, $K_2CO_3$, $KHCO_3$, NaH, triethylamine and diisopropylethylamine, may be provided.

According to the fifty-third aspect of the present invention, the method of preparing an epoxy compound having an alkoxysilyl group of the thirtieth or the thirty-first aspect, in which the alkoxysilane of Chemical Formula B2 above is provided as being 1 to 5 equivalents, based on 1 equivalent of an allyl group in the intermediate product (15), the intermediate product (15'), the intermediate product (25) or the intermediate product (25') in the 4th step, may be provided.

According to the fifty-fourth aspect of the present invention, the method of preparing an epoxy compound having an alkoxysilyl group of the thirtieth or the thirty-first aspect, in which the reaction in the $4^{th}$ step is conducted at a temperature of room temperature to 120° C. for 1 to 72 hours, may be provided.

According to the fifty-fifth aspect of the present invention, the method of preparing an epoxy compound having an alkoxysilyl group of the thirtieth or the thirty-first aspect, in which the metal catalyst in the $4^{th}$ step is $PtO_2$ or $H_2PtCl_6$, may be provided.

According to the fifty-sixth aspect of the present invention, the method of preparing an epoxy compound having an alkoxysilyl group of the thirtieth or the thirty-first aspect, in which the solvent used in the $4^{th}$ step is at least one selected from the group consisting of toluene, acetonitrile, tetrahydrofuran, methyl ethyl ketone, dimethylformamide, dimethyl sulfoxide and methylene chloride, may be provided.

According to the fifty-seventh aspect of the present invention, there is provided an epoxy composition comprising at least one of an epoxy compound having an alkoxysilyl group selected from the group consisting of the following Chemical Formulae AI to KI.

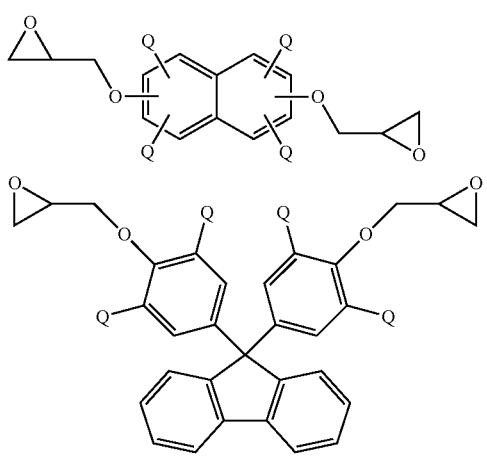
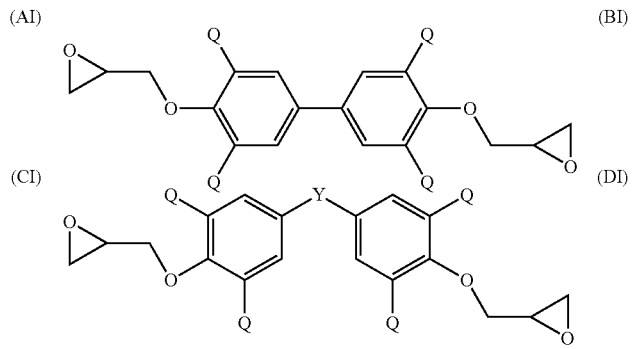

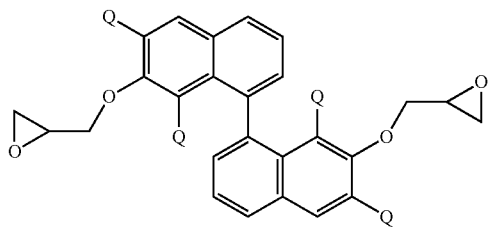
(EI)

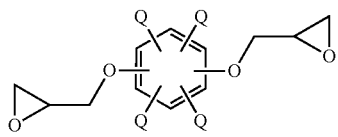
(FI)

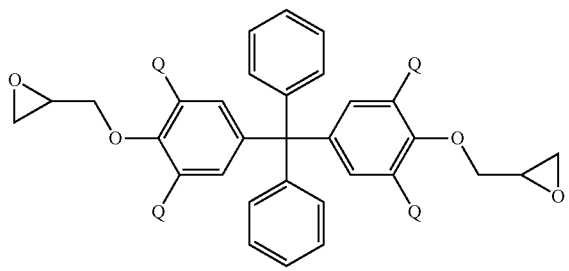
(GI)

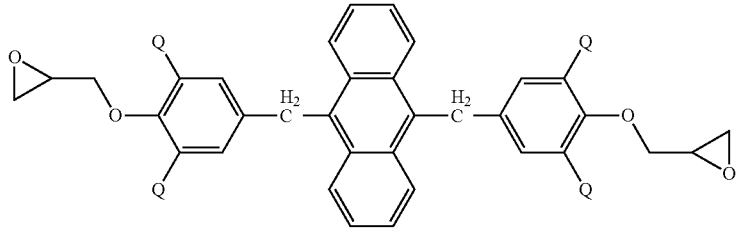
(HI)

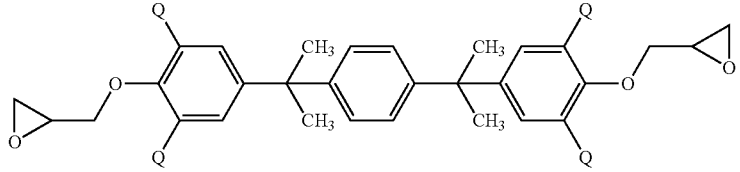
(II)

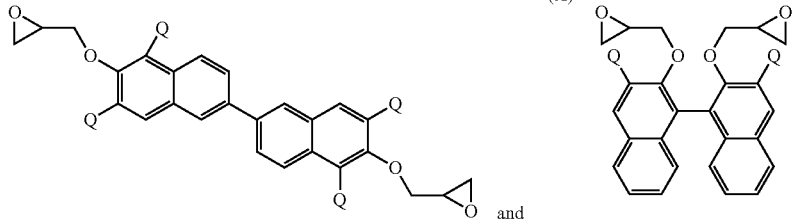
(JI)

(KI)

and

In Chemical Formulae (AI) to (KI), at least one of a plurality of Q is Chemical Formula S1, each of the remainder of the Q is independently selected from the group consisting of the following Chemical Formula S3, hydrogen and —CR$_b$R$_c$—CR$_a$=CH$_2$ (in which each of R$_a$, R$_b$ and R$_c$ is independently H or an alkyl group having 1 to 6 carbon atoms, and the alkyl group may have a linear chain or a branched chain, may be cyclic or acyclic, and may or may not contain an N, O, S, or P heteroatom), and in Chemical Formula DI above, Y is —CH$_2$—, —C(CH$_3$)$_2$—, —C(CF$_3$)$_2$—, —S— or —SO$_2$—.

—CR$_b$R$_c$—CHR$_a$—CH$_2$—SiR$_1$R$_2$R$_2$      [Chemical Formula S1]

In Chemical Formula S1, each of R$_a$, R$_b$ and R$_c$ is independently H or an alkyl group having 1 to 6 carbon atoms, at least one of R$_1$ to R$_3$ is an alkoxy group having 1 to 6 carbon atoms, and the remainder of R$_1$ to R$_3$ is an alkyl group having 1 to 10 carbon atoms, and the alkyl group and the alkoxy group may be a linear chain or a branched chain, may be cyclic or acyclic, and may or may not contain an N, O, S or P heteroatom. The epoxy compound of the Chemical Formula FI having one of S1, in which all of R$_a$, R$_b$ and R$_c$ in Chemical Formula S1 are hydrogen, and all of R$_1$ to R$_3$ in Chemical Formula S1 are the alkoxy group having 1 to 6 carbon atoms is excluded.

[Chemical Formula S3]

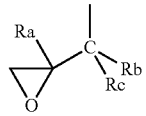

In Chemical Formula S3, each of R$_a$, R$_b$ and R$_c$ is independently H or an alkyl group having 1 to 6 carbon atoms, and the alkyl group may be a linear chain or a branched chain, may be cyclic or acyclic, and may or may not contain an N, O, S or P heteroatom.

According to the fifty-eighth aspect of the present invention, the epoxy composition of the fifty-seventh aspect, further comprising at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound, may be provided.

According to the fifty-ninth aspect of the present invention, the epoxy composition of the fifty-eighth aspect, in which the epoxy compound comprises bisphenol A, bisphenol F, bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol cyclo aliphatic or a novolak unit, as a core structure, may be provided.

According to the sixtieth aspect of the present invention, the epoxy composition of the fifty-ninth aspect, in which the epoxy compound comprises the bisphenol A, the biphenyl, the naphthalene or the fluorene, as the core structure, may be provided.

According to the sixty-first aspect of the present invention, the epoxy composition of any one of the fifty-seventh to sixtieth aspects, in which the epoxy composition comprises 10 to below 100 wt % of the epoxy compound having the alkoxysilyl group and excess of 0 to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on a total amount of the epoxy compound, may be provided.

According to the sixty-second aspect of the present invention, the epoxy composition of any one of the fifty-seventh to sixtieth aspects, in which the epoxy composition comprises 30 to below 100 wt % of the epoxy compound having the alkoxysilyl group and excess of 0 to 70 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on the total amount of the epoxy compound, may be provided.

According to the sixty-third aspect of the present invention, there is provided an epoxy composition comprising at least one epoxy compound having an alkoxysilyl group selected from the group consisting of the following Chemical Formulae AI to KI, and a curing agent.

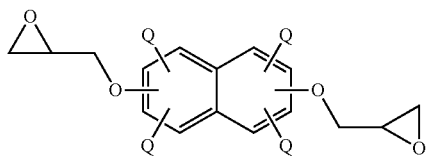
(AI)

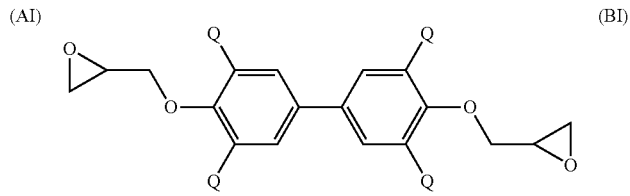
(BI)

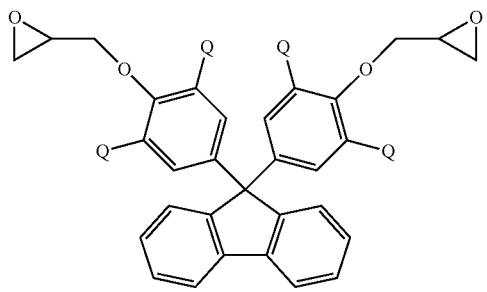
(CI)

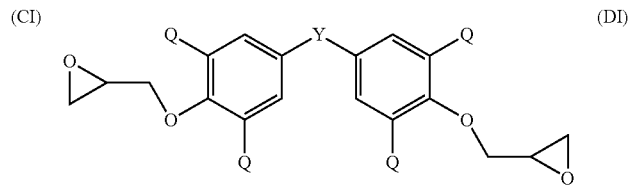
(DI)

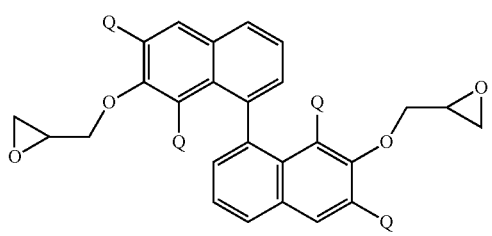
(EI)

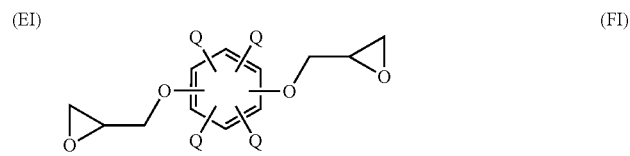
(FI)

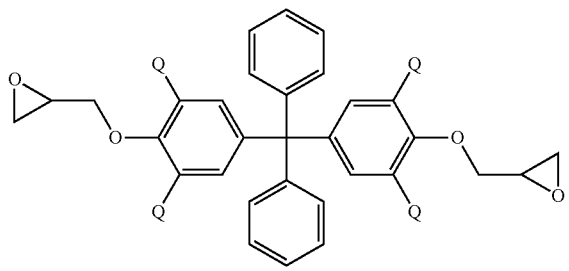
(GI)

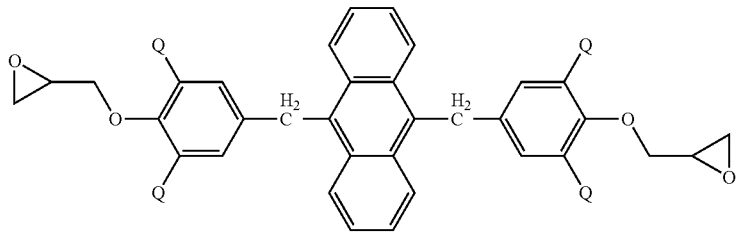
(HI)

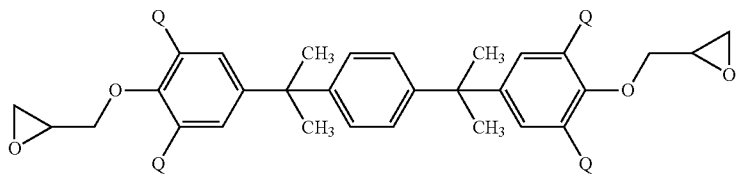
(II)

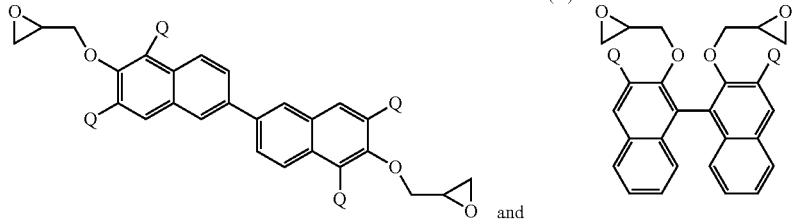
(JI)

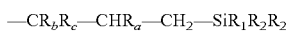
and (KI)

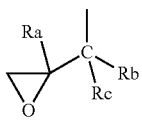

In Chemical Formulae (AI) to (KI), at least one of a plurality of Q is Chemical Formula S1, each of the remainder of the Q is independently selected from the group consisting of the following Chemical Formula S3, hydrogen and —$CR_bR_c$—$CR_a$=$CH_2$ (in which each of $R_a$, $R_b$ and $R_c$ is independently H or an alkyl group having 1 to 6 carbon atoms, and the alkyl group may have a linear chain or a branched chain, may be cyclic or acyclic, and may or may not contain an N, O, S, or P heteroatom), and in Chemical Formula DI above, Y is —$CH_2$—, —$C(CH_3)_2$—, —$C(CF_3)_2$—, —S— or —$SO_2$—.

—$CR_bR_c$—$CHR_a$—$CH_2$—$SiR_1R_2R_2$    [Chemical Formula S1]

In Chemical Formula S1, each of $R_a$, $R_b$ and $R_c$ is independently H or an alkyl group having 1 to 6 carbon atoms, at least one of $R_1$ to $R_3$ is an alkoxy group having 1 to 6 carbon atoms, and the remainder of $R_1$ to $R_3$ is an alkyl group having 1 to 10 carbon atoms, and the alkyl group and the alkoxy group may be a linear chain or a branched chain, may be cyclic or acyclic, and may or may not contain an N, O, S or P heteroatom. The epoxy compound of the Chemical Formula FI having one of Chemical Formula S1, in which all of $R_a$, $R_b$ and $R_c$ in Chemical Formula S1 are hydrogen, and all of $R_1$ to $R_3$ in Chemical Formula S1 are the alkoxy group having 1 to 6 carbon atoms is excluded.

[Chemical Formula S3]

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

According to the sixty-fourth aspect of the present invention, the epoxy composition of the sixty-third aspect, further comprising at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound, may be provided.

According to the sixty-fifth aspect of the present invention, the epoxy composition of the sixty-fourth aspect, comprising bisphenol A, bisphenol F, bisphenol, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol cyclo aliphatic or a novolak unit, as a core structure, may be provided.

According to the sixty-sixth aspect of the present invention, the epoxy composition of the sixty-fifth aspect, comprising the bisphenol A, the biphenyl, the naphthalene or the fluorene, as the core structure, may be provided.

According to the sixty-seventh aspect of the present invention, the epoxy composition of any one of the sixty-third to sixty-sixth aspect, comprising 10 to below 100 wt % of the epoxy compound having an alkoxysilyl group and excess of 0 to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on a total amount of the epoxy compound, may be provided.

According to the sixty-eighth aspect of the present invention, the epoxy composition of any one of the sixty-third to sixty-seventh aspects, comprising 30 to below 100 wt % of the epoxy compound having alkoxysilyl group and excess of 0 to 70 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on the total amount of the epoxy compound, may be provided.

According to the sixty-ninth aspect of the present invention, the epoxy composition of any one of the fifty-seventh to sixty-eighth aspects, further comprising a curing accelerator, may be provided.

According to the seventieth aspect of the present invention, the epoxy composition of any one of the fifty-seventh to sixty-ninth aspects, further comprising at least one filler selected from inorganic particles and fiber, may be provided.

According to the seventy-first aspect of the present invention, the epoxy composition of the seventieth aspect, in which the inorganic particle is at least one selected from the group consisting of metal oxide selected from the group consisting of $SiO_2$, $ZrO_2$, $TiO_2$ and $Al_2O_2$, T-10 type silsesquioxane, ladder type silsesquioxane and cage type silsesquioxane, may be provided.

According to the seventy-second aspect of the present invention, the epoxy composition of the seventieth or seventy-first aspect, in which an amount of the inorganic particles is 5 to 1,000 phr based on the epoxy compound, may be provided.

According to the seventy-third aspect of the present invention, the epoxy composition of the seventieth or seventy-second aspect, in which the amount of the inorganic particles is 100 phr to 900 phr based on the epoxy compound, may be provided.

According to the seventy-fourth aspect of the present invention, the epoxy composition of the seventieth or seventy-third aspect, in which the amount of the inorganic particles is 50 phr to 200 phr based on the epoxy compound, may be provided.

According to the seventy-fifth aspect of the present invention, the epoxy composition of the seventieth aspect, in which the fiber is at least one selected from the group consisting of glass fiber selected from the group consisting of E, T(S), NE, D and quartz glass fiber, and an organic fiber selected from the group consisting of liquid crystal polyester fiber, polyethyleneterephthalate fiber, whole aromatic fiber, polybenzoxazole fiber, nylon fiber, polyethylene naphthalate fiber, polypropylene fiber, polyether sulfone fiber, polyvinylidene fluoride fiber, polyethylene sulfide fiber and polyether ether ketone fiber, may be provided.

According to the seventy-sixth aspect of the present invention, the epoxy composition of the seventy-fifth aspect, in which the fiber is the E glass fiber, may be provided.

According to the seventy-seventh aspect of the present invention, the epoxy composition of the seventy-fifth aspect, in which the fiber is the T glass fiber, may be provided.

According to the seventy-eighth aspect of the present invention, the epoxy composition of any one of the seventieth, seventy-sixth and seventy-seventh aspects, in which an amount of the fiber is 10 to 90 wt % based on a total amount of the epoxy composition, may be provided.

According to the seventy-ninth aspect of the present invention, an electronic material comprising the epoxy composition according to any one of the fifty-seventh to seventy-eighth aspects may be provided.

According to the eightieth aspect of the present invention, a prepreg comprising the epoxy composition according to any one of the fifty-seventh to seventy-eighth aspects may be provided.

According to the eighty-first aspect of the present invention, a laminate comprising a metal layer placed on the prepreg according to the eightieth aspect may be provided.

According to the eighty-second aspect of the present invention, a substrate comprising the epoxy composition according to any one of the fifty-seventh to seventy-eighth aspects may be provided.

According to the eighty-third aspect of the present invention, a film comprising the epoxy composition according to any one of the fifty-seventh to seventy-eighth aspects may be provided.

According to the eighty-fourth aspect of the present invention, a printed circuit board comprising the prepreg according to the eightieth aspect may be provided.

According to the eighty-fifth aspect of the present invention, a semiconductor device comprising a semiconductor element installed on the printed circuit board according to the eighty-fourth aspect may be provided.

According to the eighty-sixth aspect of the present invention, a semiconductor packaging material comprising the epoxy composition according to any one of the fifty-seventh to seventy-eighth aspects may be provided.

According to the eighty-seventh aspect of the present invention, there is provided a semiconductor device comprising the semiconductor packaging material according to the eighty-sixth aspect may be provided.

According to the eighty-eighth aspect of the present invention, a cured product of the epoxy composition according to any one of the fifty-seventh to seventy-eighth aspects may be provided.

According to the eighty-ninth aspect of the present invention, a cured product of the epoxy composition according to any one of the fifty-seventh to seventy-eighth aspects, having a coefficient of thermal expansion of 50 ppm/° C. to 150 ppm/° C. may be provided.

According to the ninetieth aspect of the present invention, a cured product of the epoxy composition according to any one of seventieth to seventy-eighth aspects, having a coefficient of thermal expansion of 15 ppm/° C. or less may be provided.

According to the ninety-first aspect of the present invention, a cured product of the epoxy composition according to any one of seventieth to seventy-eighth aspects, having a glass transition temperature of 100° C. or over, or do not showing glass transition temperature is provided.

Advantageous Effects

The Chemical bonding efficiency between the epoxy compound and a filler may be increased due to the chemical bonding of the alkoxysilyl group in the epoxy compound and the filler in the composite of the novel epoxy composition comprising an novel epoxy compound having an alkoxysilyl group. Due to the increase in chemical bonding efficiency, heat-resistant properties may be improved. That is, the CTE of the epoxy composite may be decreased, and the glass transition temperature may be increased or the glass transition temperature may not be observed (hereinafter, 'Tg-less'). In addition, a cured product comprising the epoxy compound having the alkoxysilyl group in accordance with the present invention may show good flame retardant property through the introduction of the alkoxysilyl group.

Further, when the epoxy composition is applied to a surface of metal substrate, good adhesive property may be exhibited due to the chemical bonding between the functional groups on the metal surface and the alkoxysilyl group. In addition, due to the increase in chemical bonding efficiency of the composition comprising the alkoxysilylated epoxy compound, a silane coupling agent used in common epoxy compositions may not necessarily be included in the composition comprising the alkoxysilylated epoxy compound. The epoxy composition comprising the above epoxy compound may have good curing (including thermal curing and/or photo curing) efficiency, and a cured composite may show good thermal expansion properties such as a low CTE and a high glass transition temperature or Tg-less.

DESCRIPTION OF DRAWINGS

The above and other aspects, features and other advantages of the present invention will be more clearly understood from the following detailed description taken in conjunction with the accompanying drawings, in which.

BEST MODE

Figure 1:
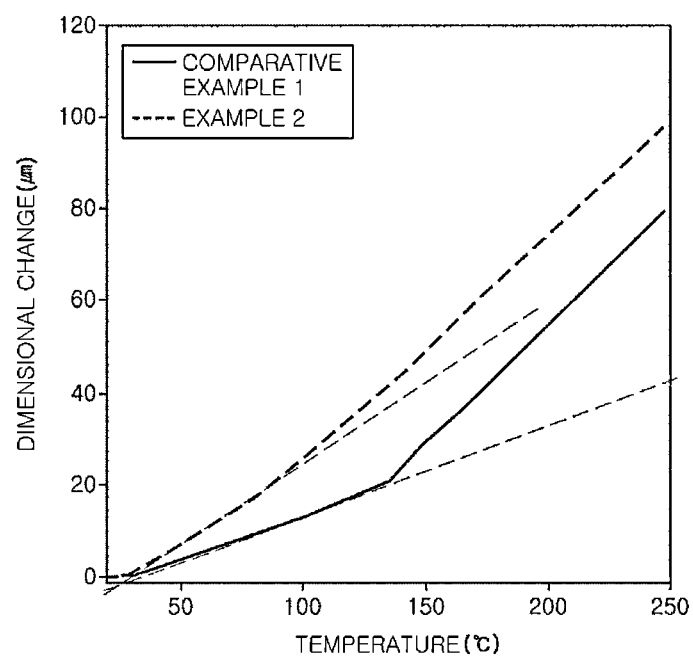
FIG. 1 is a graph illustrating CTE and Tg of Comparative Example 1 and Example 2.

Exemplary embodiments of the present invention will now be described in detail with reference to the accompanying drawings.

The present invention provides a new alkoxysilylated epoxy compound of which a cured composite exhibits improved heat resistant properties, particularly a low CTE and a high Tg or Tg-less and/or a cured product of which exhibits good flame retardant properties, a method of preparing the same, an epoxy composition comprising the same, a cured product of the composition and a use of the composition. In the present invention, the term "composite" refers to a cured product of a composition comprising an epoxy compound and an inorganic material (fiber and/or inorganic particles). In the present invention, the term "cured product" refers to a cured product of a composition comprising an epoxy compound, for example, a composition comprising an epoxy compound; a curing agent; and at least one selected from the group consisting of an optional inorganic material (filler), an optional curing accelerator and other additives. In addition, the term "cured product" is used to comprise "partially cured product" as well.

When forming a composite through curing the epoxy composition comprising the alkoxysilylated epoxy compound in accordance with the present invention, the epoxy group may react with a curing agent to conduct a curing reaction, and the alkoxysilyl group may form an interface bonding with the surface of the filler which is an inorganic material. Thus, very good chemical bonding efficiency in an epoxy composite system may be obtained, and thus, a low CTE and high glass transition temperature increasing effect or Tg-less may be achieved. Therefore, dimensional stability of cured product may be improved. In addition, the cured product comprising the alkoxysilylated epoxy compound according to the present invention may show good flame retardant property.

Further, the epoxy composition comprising the alkoxysilylated epoxy compound according to the present invention may show good curing properties. The curing properties apply to both thermal curing and photo curing.

In addition, when applying the epoxy composition of the present invention on a chemically processed metal film such as a copper film, a chemical bonding may be made with a —OH group or the like at the surface of the metal, which is chemically treated, which leads to good adhesiveness with the metal film.

1. Compounds

In accordance with one aspect of the present invention, an alkoxysilylated epoxy compound comprising at least one substituent of the following Chemical Formula S1 and two epoxy groups at the core of the epoxy compound may be provided. Specifically, the epoxy group may be the substituent in the following Chemical Formula S2.

  [Chemical Formula S1]

In Chemical Formula S1, each of $R_a$, $R_b$ and $R_c$ is independently H or an alkyl group having 1 to 6 carbon atoms, at least one of $R_1$ to $R_3$ is an alkoxy group having 1 to 6 carbon atoms, and the remainder of $R_1$ to $R_3$ is an alkyl group having 1 to 10 carbon atoms, and the alkyl group and the alkoxy group may be a linear chain or a branched chain, may be cyclic or acyclic, and may or may not contain an N, O, S or P heteroatom, and $R_1$ to $R_3$ are preferably ethoxy groups.

[Chemical Formula S2]

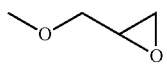

In addition, the alkoxysilylated epoxy compound provided in exemplary embodiments of the present invention may further include a substituent of the following Chemical Formula S3.

[Chemical Formula S3]

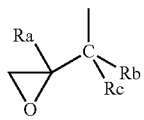

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

The term "core" used in the present application refers to a linear or branched, or cyclic or acyclic, or aromatic or aliphatic hydrocarbon compound comprising at least three substituents, and containing or not containing an N, O, S or P heteroatom.

The term "aromatic compound" used in the present application refers to an aromatic compound defined in the field of chemistry, comprises a hetero aromatic compound, which comprises heteroatoms and an aromatic compound, which does not comprise the heteroatom. The hetero aromatic compound may include heteroatoms of N, O, S or P.

The core may be an aromatic compound. Examples of the aromatic compound may include benzene, naphthalene, biphenyl, fluorene, anthracene, phenanthrene, chrysene, pyrene, annulene, corannulene, coronene, purine, pyrimidine, benzopyrene, dibenzanthracene, or hexahelicene, without limitation, and may include a polycyclic aromatic compound in which one of the above-described compounds make at least one covalent bonding directly or through a linker.

The linker may be —$CR_eR_f$— in which, each of $R_e$ and $R_f$ is independently hydrogen, a halogen atom of F, Cl, Br or I, an alkyl group having 1 to 3 carbon atoms, or a cyclic compound having 4 to 6 carbon atoms), carbonyl (—CO—), ester (—COO—), carbonate (—OCOO—), ethylene (—CH$_2$CH$_2$—), propylene (—CH$_2$CH$_2$CH$_2$—), ether (—O—), amine (—NH—), thioether (—S—) or sulfuryl (—SO$_2$—).

The core may be any one selected from the group consisting of the following Chemical Formulae A' to K'.

[Core structure]

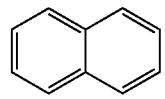
(A')

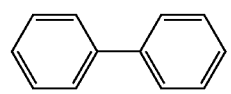
(B')

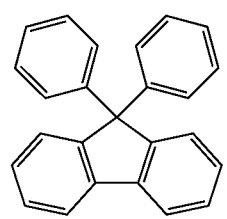
(C')

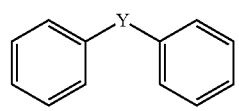
(D')

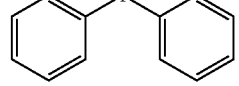
(E')

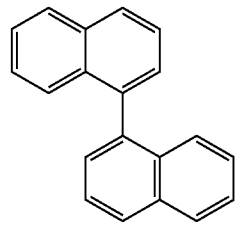
(F')

(G')

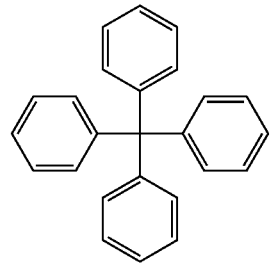
(H')

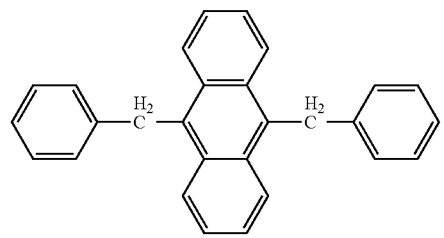
(I')

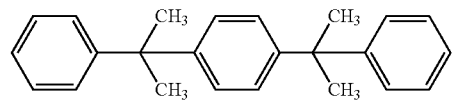

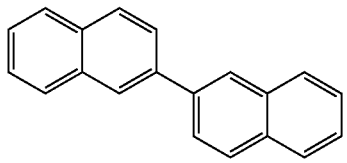
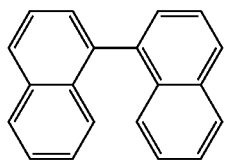
In Chemical Formula D', Y is —CH$_2$—, —C(CH$_3$)$_2$—, —C(CF$_3$)$_2$—, —S— or —SO$_2$—.
The alkoxysilylated epoxy compound of exemplary embodiments of the present invention may particularly include any alkoxysilylated epoxy compound selected from the group consisting of the following Chemical Formulae AI to KI.
[Chemical Formulae AI to KI]
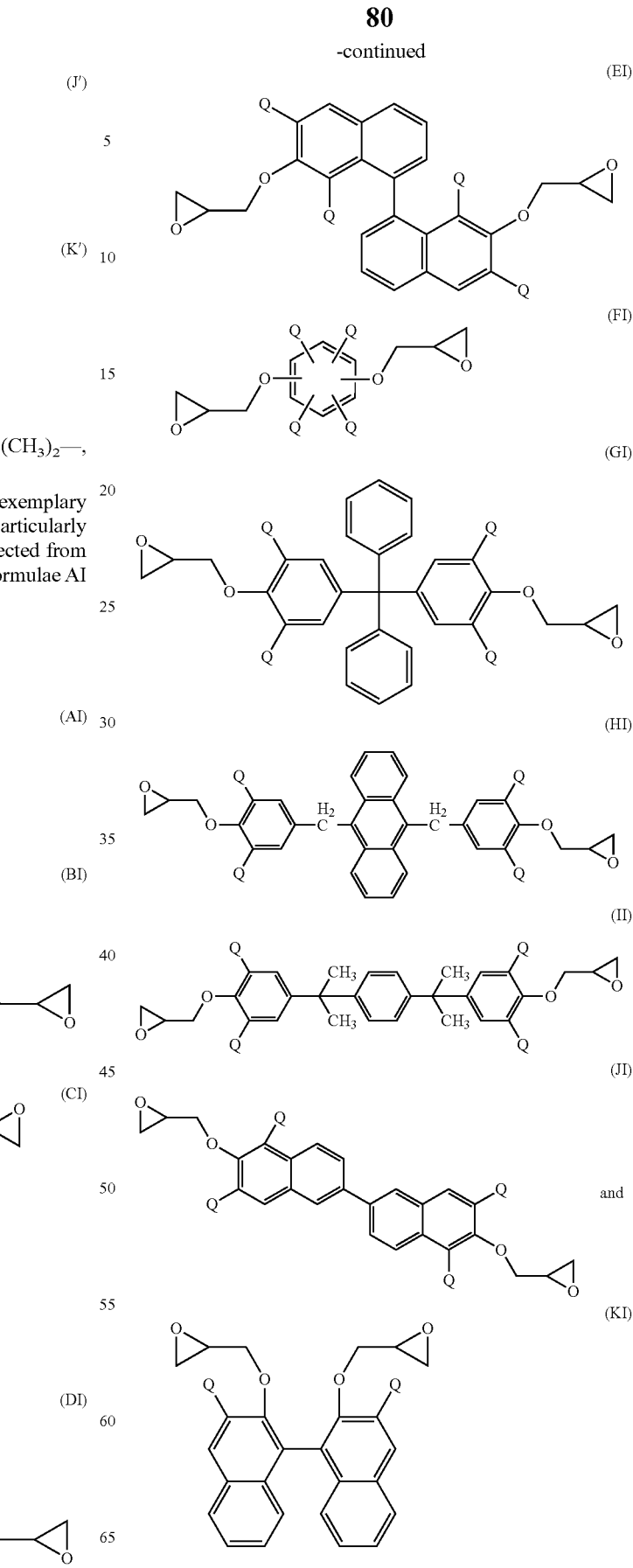

In Chemical Formulae (AI) to (KI), at least one, for example, 1 to 4 of a plurality of Q is Chemical Formula S1, each of the remainder of the plurality of Q is independently selected from the group consisting of the following Chemical Formula S3, hydrogen and —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), and in Chemical Formula DI above, Y is —$CH_2$—, —$C(CH_3)_2$—, —$C(CF_3)_2$—, —S— or —$SO_2$.

   [Chemical Formula S1]

In Chemical Formula S1, each of $R_a$, $R_b$ and $R_c$ is independently H or an alkyl group having 1 to 6 carbon atoms, at least one of $R_1$ to $R_3$ is an alkoxy group having 1 to 6 carbon atoms, and the remainder of $R_1$ to $R_3$ is an alkyl group having 1 to 10 carbon atoms, and the alkyl group and the alkoxy group may be linear chains or branched chains, may be cyclic or acyclic, and may or may not contain an N, O, S or P heteroatom.

The epoxy compound of Chemical Formula F1 having one of Si, in which all of $R_a$, $R_b$ and $R_c$ are hydrogen, and all of $R_1$ to $R_3$ are the alkoxy group having 1 to 6 carbon atoms, is excluded.

Preferably, $R_1$ to $R_3$ may be ethoxy groups.

[Chemical Formula S3]

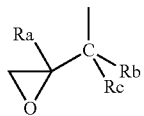

In Chemical Formula S3, each of $R_a$, $R_b$ and $R_c$ is independently H or an alkyl group having 1 to 6 carbon atoms, and the alkyl group may be a linear chain or a branched chain, may be cyclic or acyclic, and may or may not contain an N, O, S or P heteroatom.

In accordance with an exemplary embodiment, the alkoxysilylated epoxy compound may be one selected from the compounds of Chemical Formulae AI to DI above. In addition, in accordance with an exemplary embodiment, the alkoxysilylated epoxy compound may be a compound of Chemical Formula BI or Chemical Formula DI above. In addition, for example, in Chemical Formula DI above, Y may be —$C(CH_3)_2$—.

In accordance with another exemplary embodiment, one of the compounds of Chemical Formulae AI to KI above, for example, one of the compounds of Chemical Formulae AI to DI above, for example, the compound of BI or the compound of DI, for example, the compound of DI, in which Y is —$C(CH_3)_2$—, may additionally include Chemical Formula S3 substituent above, for example, 1 to 3 of the S3 substituent.

The composite comprising the compounds of Chemical Formulae AI to KI may show an increased glass transition temperature or a Tg-less due to the introduction of the alkoxysilyl group. However, the cured product of the compounds of Chemical Formulae AI to KI itself which do not include an inorganic material may show the decreased glass transition temperature through the introduction of a flexible alkoxysilyl group. The decrease of the glass transition temperature of the cured product of the epoxy compound itself which do not include the inorganic material may be dependent on the concentration ratio (equivalent ratio) of the epoxy group to the alkoxysilyl group present in the epoxy compound. Thus, in consideration of the heat-resistant properties of the composite, the increase in the concentration of the alkoxysilyl group in the epoxy compound may be desirable in consideration of the CTE of the cured product of epoxy compound itself. However, the glass transition temperature of the composite may be lowered, reflecting the decrease of the glass transition temperature of the cured product of the epoxy compound itself. In this case, the glass transition temperature of the composite may be increased or a Tg-less composite may be obtained by decreasing the resin content of the composite or by additionally introducing the epoxy group of Chemical Formula S3 above into the epoxy compound.

In accordance with exemplary embodiments of the present invention, particular examples of the alkoxysilylated epoxy compounds may include the compounds illustrated in Chemical Formula M above.

In accordance with exemplary embodiments of the present invention, intermediate products (A11) to (K11), for example, (A11) to (D11), in addition, for example, a compound of Chemical Formula S11 above; intermediate products (A12) to (K12), for example, (A12) to (D12), in addition, for example, a compound of Chemical Formula S12; intermediate products (A13) to (K13), for example, (A13) to (D13), in addition, for example, a compound of Chemical Formula S13 above; intermediate products (A13') to (K13'), for example, (A13') to (D13'), in addition, for example, a compound of Chemical Formula S13' above; intermediate products (A23) to (J23), for example, (A23) to (D23), in addition, for example, a compound of Chemical Formula S23 above; intermediate products (A24) to (J24), for example, (A24) to (D24), in addition, for example, a compound of Chemical Formula S24; intermediate products (A25) to (J25), for example, (A25) to (D25), in addition, for example, a compound of Chemical Formula S25 above; and intermediate products (A25') to (J25'), for example, (A25') to (D25'), in addition, for example, a compound of Chemical Formula S25', may be provided.

In accordance with other exemplary embodiments, an epoxy polymer of Chemical Formulae (AP) to (KP) above, for example, Chemical Formulae (AP) to (DP), for example, Chemical Formula (CP) or (DP), may be provided. In the epoxy polymer of Chemical Formulae (AP) to (KP), repeating unit m may be an integer of 1 to 100, and more preferably, an integer of 1 to 10.

For example, when preparing the alkoxysilylated epoxy compound according to the present invention, that is, when conducting an epoxidation reaction of an aromatic alcohol by using epichlorohydrin, the epoxy group introduced into the reaction product (core) may react with a hydroxyl group in a reactant, which results in producing dimeric and higher molecular ones (an 'epoxy polymer' in this application), in addition to an monomeric epoxy compound. The 'epoxy polymer' in this application may include an oligomer and a polymer.

2. Method of Preparing Epoxy Compounds

In accordance with other exemplary embodiments of the present invention, a method of preparing an alkoxysilylated epoxy compound comprising in the core thereof according to exemplary embodiments, at least one substituent of Chemical Formula S1 and two epoxy groups above, particularly, the epoxy group of Chemical Formula S2 above, and optionally an epoxy group of Chemical Formula S3 above, for example, the alkoxysilylated epoxy compound of Chemical Formulae AI to KI above, for example, Chemical Formulae AI to DI above, for example, Chemical Formulae CI or DI above, for example, the alkoxysilylated epoxy compound of Chemical Formula DI in which Y is —$C(CH_3)_2$— may be provided.

The alkoxysilylated epoxy compound may be prepared by conducting allylation, claisen rearrangement, epoxidation and alkoxysilylation on a starting material, for example, from one of Chemical Formulae (AS) to (KS) above. As clearly understood from the method of preparing the alkoxysilylated epoxy compound in accordance with an example embodiment, when the allylation and the claisen rearrangement are conducted one time, respectively, the alkoxysilylated epoxy compound of Chemical Formulae (A14) to (K14) above may be obtained, and when the allylation and the claisen rearrangement are conducted two times, respectively, the alkoxysilylated epoxy compound of Chemical Formulae (A26) to (J26) above may be obtained. Chemical Formulae (AI) to (KI) above may include the above two cases.

In accordance with an example embodiment, a method of preparing an alkoxysilylated epoxy compound comprising allylation on a starting material of one of the following Chemical Formulae (AS) to (KS) ($1^{st}$ step), claisen rearrangement ($2^{nd}$ step), epoxidation ($3^{rd}$ step), optional and additional epoxidation ($3\text{-}1^{th}$ step), and alkoxysilylation ($4^{th}$ step) may be provided. Hereinafter, the above-described method will be described as Method 1.

In the $1^{st}$ step, through conducting an allylation reaction on a hydroxyl group of a starting material of one of the following Chemical Formulae (AS) to (KS), an intermediate product (11) of one of the following Chemical Formulae (A11) to (K11) may be obtained.

In this case, only one of two hydroxyl groups of the starting materials of (AS) to (KS) may be allylated, or all of the two hydroxyl groups may be allylated. According to the number of hydroxyl group to be allylated in the $1^{st}$ step, the number of functional groups, i.e. the number of alkoxysilyl groups in the final target alkoxysilylated epoxy compound of Chemical Formulae (AI) to (KI) may be determined. Particularly, when one hydroxyl group is allylated, the number of alkoxysilyl group of Chemical Formula S1 in the final target compound may be one. When two hydroxyl groups are allylated, the maximum number of alkoxysilyl group of Chemical Formula S1 in the final target compound may be two, or one alkoxysilyl group of Chemical Formula S1 and one epoxy group of Chemical Formula S3. The number of hydroxyl group to be allylated may be controlled by the equivalent ratio of the reactants.

In the $1^{st}$ step, a reaction of one starting material from Chemical Formulae (AS) to (KS) above and the allyl compound of Chemical Formula B1 may be conducted in the presence of a base and an optional solvent. In this case, the reaction may be conducted by controlling the ally compound of the Chemical Formula B1 to be 0.5 to 10 equivalents, based on 1 equivalent of the hydroxyl group of the starting material.

[Chemical Formulae (AS) to (KS)]-Starting materials

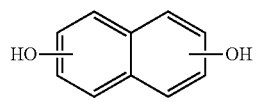

(AS)

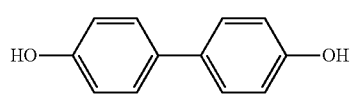

(BS)

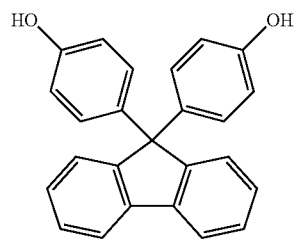

(CS)

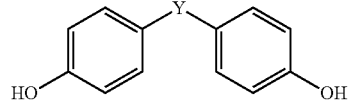

(DS)

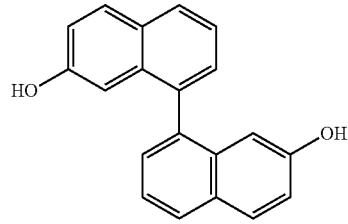

(ES)

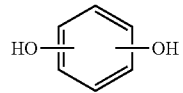

(FS)

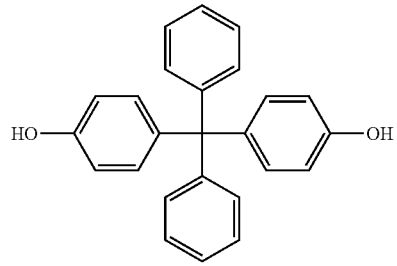

(GS)

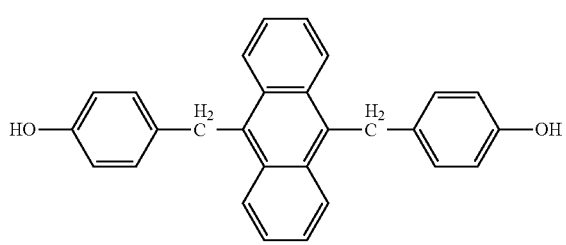

(HS)

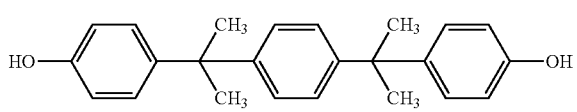

(IS)

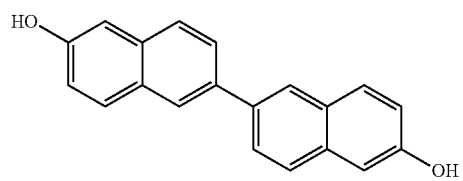

(JS)

and

-continued

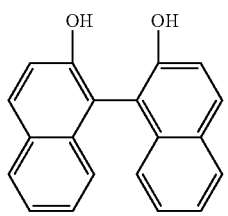
(KS)

In Chemical Formula DS, Y is —CH$_2$—, —C(CH$_3$)$_2$—, —C(CF$_3$)$_2$—, —S— or —SO$_2$—.

[Chemical Formula B1]

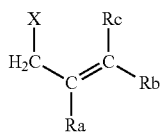

In Chemical Formula B1, X is Cl, Br, I, —O—SO$_2$—CH$_3$, —O—SO$_2$—CF$_3$, or —O—SO$_2$—C$_6$H$_4$—CH$_3$, each of R$_a$, R$_b$ and R$_c$ is independently H or an alkyl group having 1 to 6 carbon atoms, and the alkyl group may have a linear chain or a branched chain, may be cyclic or acyclic, and may or may not contain an N, O, S, or P heteroatom.

The reaction temperature and the reaction time in the 1$^{st}$ step may be changed depending on the kinds of reactants. For example, one of intermediate product (11) from the following Chemical Formulae (A11) to (K11) may be obtained by conducting the a reaction at a temperature of room temperature (for example, from 15° C. to 25° C.) to 100° C. for 1 to 120 hours.

[Chemical Formulae (A11) to (K11)]

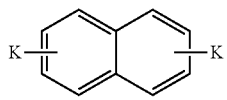
(A11)

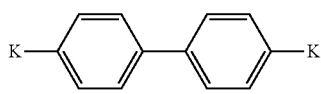
(B11)

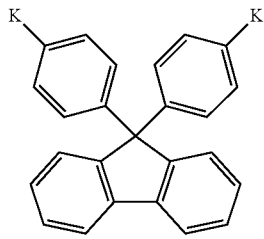
(C11)

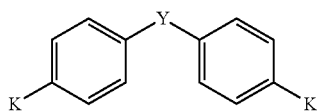
(D11)

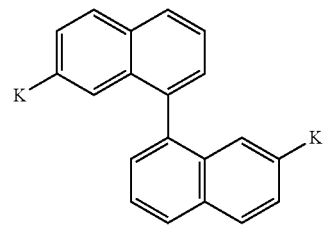
(E11)

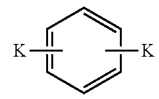
(F11)

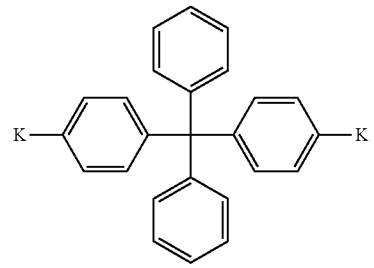
(G11)

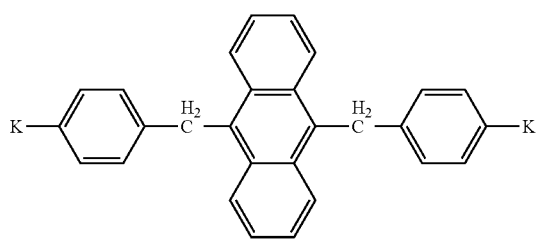
(H11)

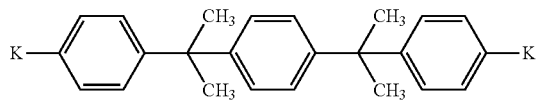
(I11)

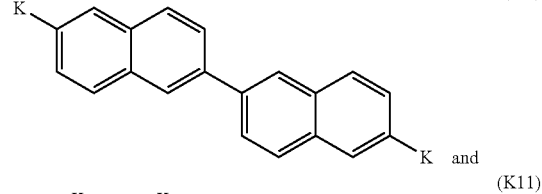
(J11)

and

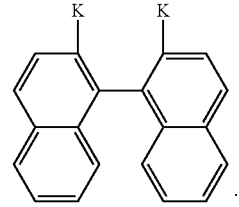
(K11)

In Chemical Formulae A11 to K11, at least one of two of K is —O—CH$_2$—CR$_a$=CR$_b$R$_c$ (in which, each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the remainder of K is a hydroxyl group, and in Chemical Formula D11 above, Y is —CH$_2$—, —C(CH$_3$)$_2$—, —C(CF$_3$)$_2$—, —S— or —SO$_2$—.

Examples of the bases that may be possibly used may include, for example, without limitation, KOH, NaOH, $K_2CO_3$, $Na_2CO_3$, $KHCO_3$, $NaHCO_3$, NaH, triethylamine and diisopropylethylamine. These bases may be used alone or two or more of the bases may be used at the same time. 1 to 5 equivalents of the base with respect to 1 equivalent of the hydroxyl groups of the starting material may be used in consideration of reaction efficiency.

The solvents may be optionally used as occasion demands in the $1^{st}$ step reaction. For example, when the viscosity of the reactants at the reaction temperature is appropriate for conducting the reaction without an additional solvent in the $1^{st}$ step reaction, the solvent may not be necessary. That is, when the viscosity of the reactants is sufficiently low so that the mixing and the stirring of the reactants may be conducted smoothly without the solvent, additional use of the solvent may not be necessary. This state may be easily understood by a person skilled in the art. When the solvent is used, any organic solvents that may easily dissolve the reactants, that do not have any adverse effects, and that may be easily removed after the reaction, may be used without limitation. For example, acetonitrile, tetrahydrofuran (THF), methyl ethyl ketone (MEK), dimethylformamide (DMF), dimethyl sulfoxide (DMSO), methylene chloride (MC), or the like, may be used. These solvents may be used alone or as a mixture of two or more. The amount of the solvent may not be limited to a specific range, and an appropriate amount of the solvent may be used within a range for sufficiently dissolving the reactants and not adversely affecting the reaction. A person skilled in the art may select an appropriate solvent considering the above-mentioned points.

In the $2^{nd}$ step, through heating the intermediate product (11) obtained in the $1^{st}$ step, the intermediate (12) of the following Chemical Formulae (A12) to (K12) may be formed by the claisen rearrangement.

The intermediate product (11) may undergo the claisen rearrangement through heating at from 140° C. to 250° C. for 1 to 20 hours. The reaction in the $2^{nd}$ step may be conducted in the presence of the optional solvent as occasion demands, and xylene, 1,2-dichlorobenzene, N,N-diethylaniline, or the like, may be used as the solvent without limitation.

[Chemical Formulae (A12) to (K12)]

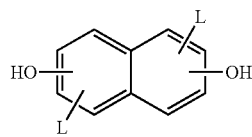

(A12)

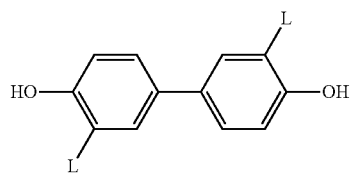

(B12)

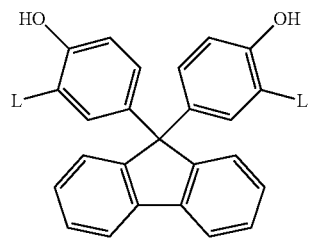

(C12)

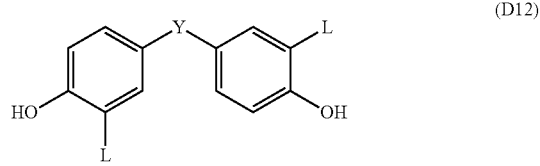

(D12)

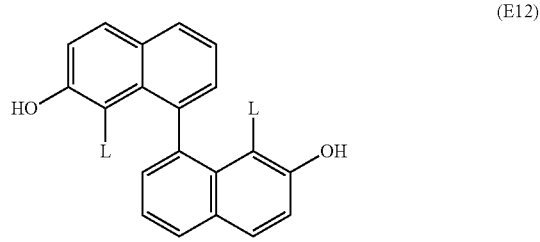

(E12)

(F12)

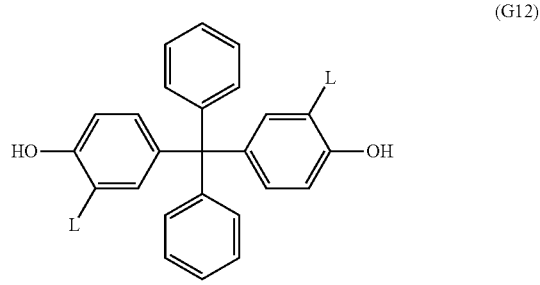

(G12)

(H12)

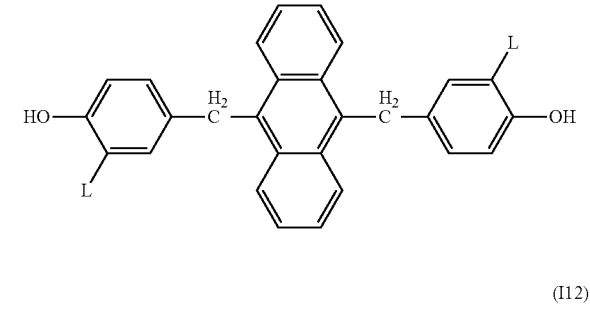

(I12)

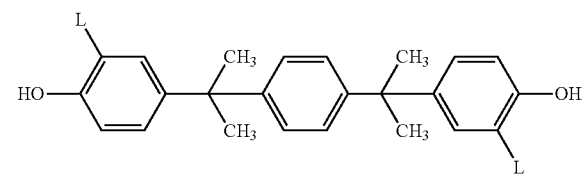

(J12)

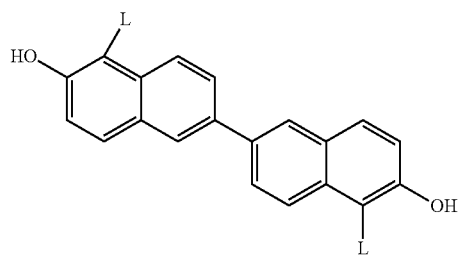

and (K12)

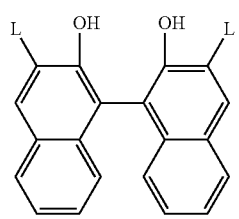

In Chemical Formulae A12 to K12, at least one of L is —CR$_b$R$_c$—CR$_a$=CH$_2$ (in which, each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the remainder of L is hydrogen, and in Chemical Formula D12 above, Y is —CH$_2$—, —C(CH$_3$)$_2$—, —C(CF$_3$)$_2$—, —S— or —SO$_2$—.

In the 3$^{rd}$ step, a hydroxyl group may be epoxidized through the reaction of one intermediate product (12) from Chemical Formulae (A12) to (K12) above with epichlorohydrin to form the intermediate product (13) of Chemical Formulae (A13) to (K13). In this case, a reaction of the intermediate product (12) and the epichlorohydrin may produce the intermediate product (13) by conducting the reaction in the presence of a base and an optional solvent, by using epichlorohydrine, so as to be 1 to 10 equivalents of the epoxy group, based on 1 equivalent of the hydroxyl group of the intermediate product (12). In addition, an excessive amount of the epichlorohydrin may be used instead, without using an optional solvent.

[Chemical Formulae (A13) to (K13)]

(A13)

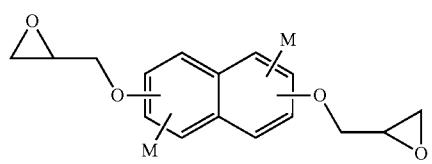

(B13)

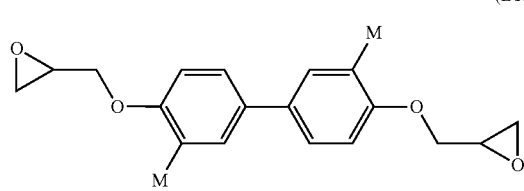

(C13)

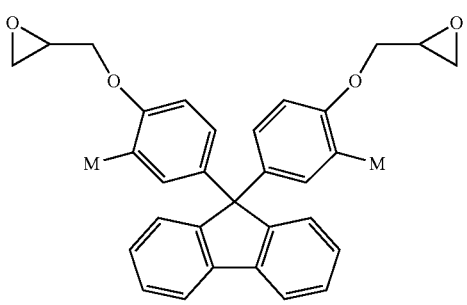

(D13)

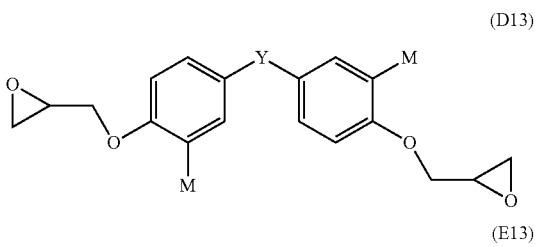

(E13)

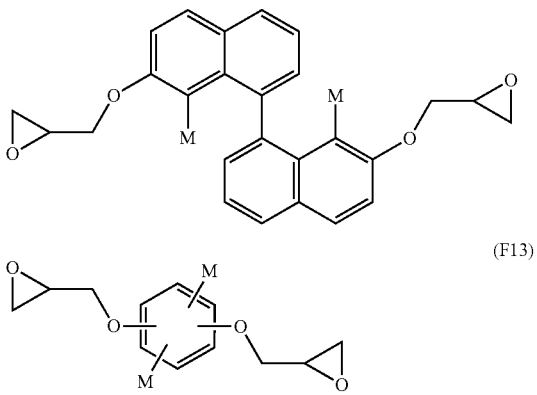

(F13)

(G13)

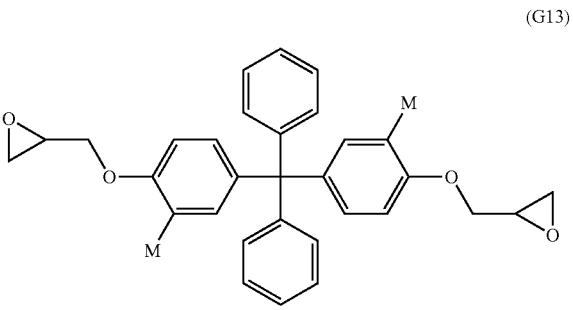

(H13)

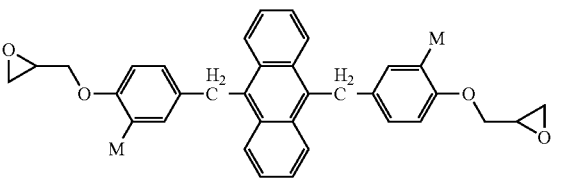

(I13)

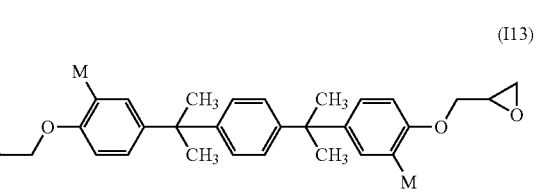

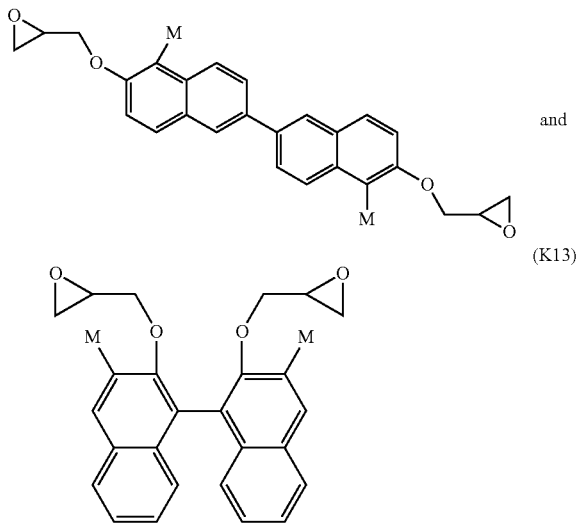

(J13)

and (K13)

In Chemical Formulae A13 to K13, at least one from two of M is —$CR_bR_c$—$CR_a$=$CH_2$ (in which, each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), the remainder of M is hydrogen, and in Chemical Formula D13 above, Y is —$CH_2$—, —$C(CH_3)_2$—, —$C(CF_3)_2$—, —S— or —$SO_2$—.

The reaction temperature and the reaction time in the $3^{rd}$ step may be changed depending on the kinds of reactants. For example, the intermediate product (13) may be produced by conducting a reaction at a temperature of room temperature (for example, from 15° C. to 25° C.) to 100° C. for 1 to 120 hours.

Examples of the bases that may be used may include, without limitation, KOH, NaOH, $K_2CO_3$, $Na_2CO_3$, $KHCO_3$, $NaHCO_3$, NaH, triethylamine and diisopropylethylamine. These bases may be used alone or in combination of two or more. 1 to 5 equivalents of the base with respect to 1 equivalent of the hydroxyl group of the intermediate product (12) may be used in consideration of reaction efficiency.

The solvents may be optionally used as occasion demands in the $3^{rd}$ step reaction. For example, when the viscosity of the reactant at the reaction temperature is appropriate for conducting the reaction without using a additional solvent in the $3^{rd}$ step, the solvent may not be used. That is, when the viscosity of the reactant is sufficiently low so that the mixing and the stirring of the reactants may be conducted smoothly without the solvent, the additional solvent may not be necessary. This state may be easily understood by a person skilled in the art. When the solvent is used, any organic solvents that may easily dissolve the reactants, that do not have any adverse effects, and that may be easily removed after the reaction may be used without limitation. For example, acetonitrile, tetrahydrofuran (THF), methyl ethyl ketone (MEK), dimethylformamide (DMF), dimethyl sulfoxide (DMSO), methylene chloride (MC), or the like, may be used. These solvents may be used alone or in combination of two or more. The amount of the solvent may not be limited to a specific range, and an appropriate amount of the solvent may be used within the range for sufficiently dissolving the reactants and not adversely affecting the reaction. A person skilled in the art may select an appropriate solvent in consideration of the above-mentioned points.

Meanwhile, in the epoxidation process in the $3^{rd}$ step, the reaction illustrated by the following Reaction (1) may be conducted, and an epoxidized intermediate product (13) may be reacted with the hydroxyl group of the intermediate product (12) to produce a dimer and the higher molecular compounds, as illustrated in Chemical Formulae (AP) to (KP) above.

In the following example of Reaction (1), the intermediate product (B13) in which all of the M are —$CH_2$—CH=$CH_2$ is prepared by the epoxidation of the intermediate product (B12).

[Reaction 1]

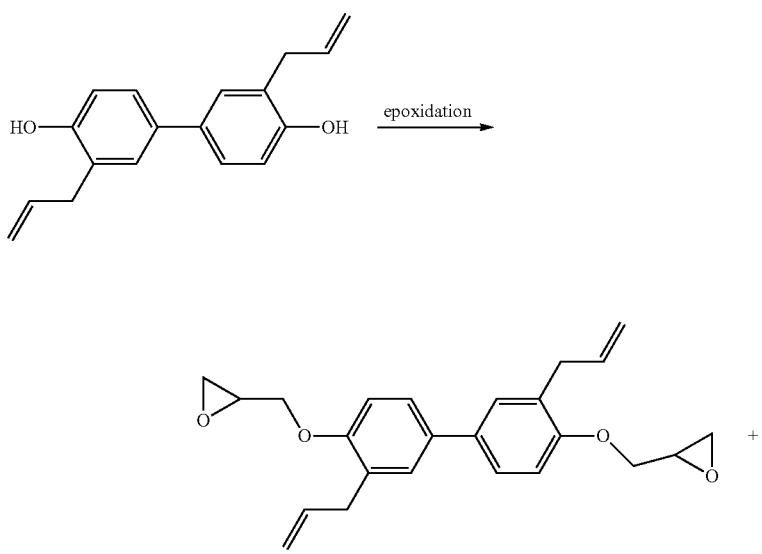

(1)

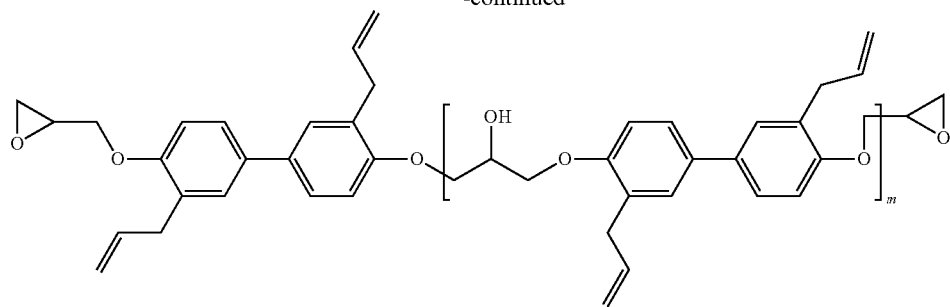

(in which, m is an integer of 1 to 100)

After conducting the $3^{rd}$ step, 3-1-th step in which an allyl group may be optionally epoxidized as occasion demands, may be conducted for an additional epoxidation. In the 3-1-th step, the allyl group of one compound from the intermediate product (13) may be oxidized to conduct the epoxidation to produce one intermediate product (13') from the following Chemical Formulae (A13') to (K13').

In the 3-1-th step, the intermediate product (13) and a peroxide compound may react in the presence of an optional base and an optional solvent. In this case, the intermediate product (13) and the peroxide compound may react with each other so that the peroxide compound is to be 1 to 10 equivalent of peroxide group, based on 1 equivalent of the allyl group of the intermediate product (13).

[Chemical Formulae (A13') to (K13')]

(A13')

(B13')

(C13')

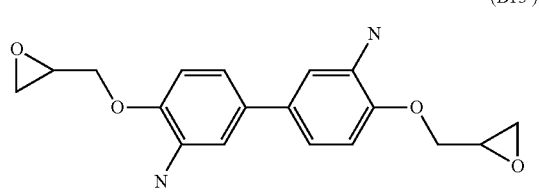

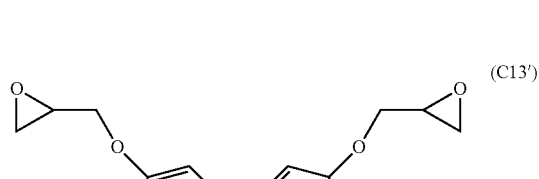

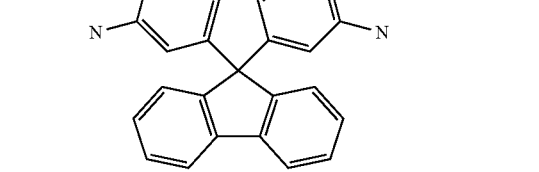

-continued (D13')

(E13')

(F13')

(G13')

(H13')

(I13')

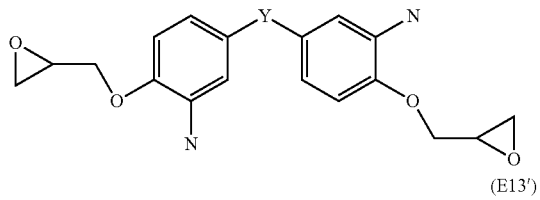

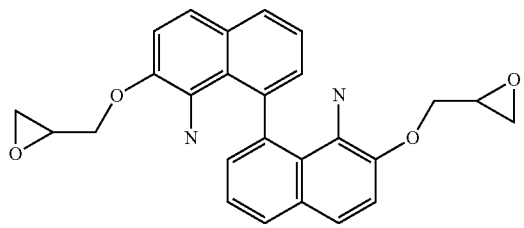

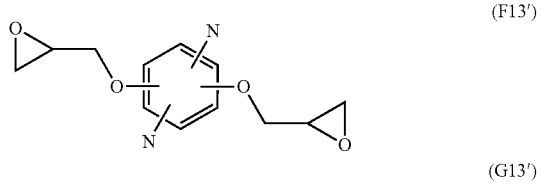

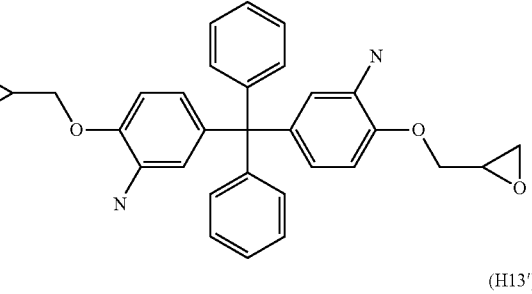

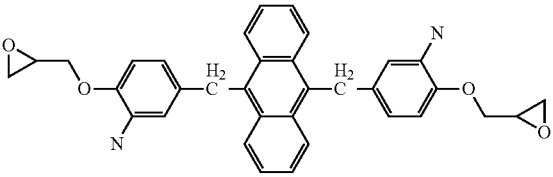

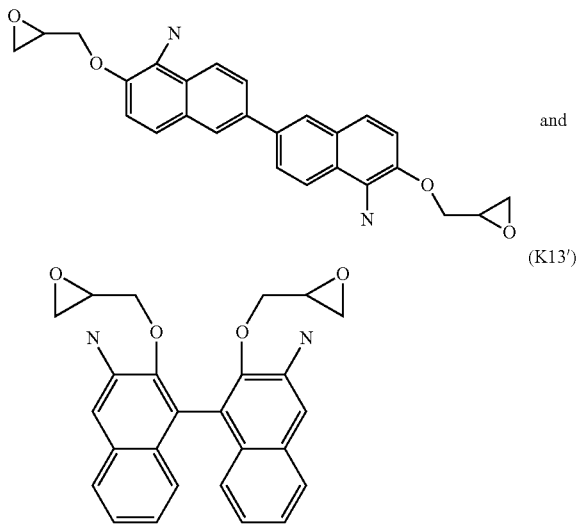

In Chemical Formulae A13' to K13', one of N is —CR$_b$R$_c$—CR$_a$=CH$_2$ (in which, each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the other of N is Chemical Formula S3 above, and in Chemical Formula D13' above, Y is —CH$_2$—, —C(CH$_3$)$_2$—, —C(CF$_3$)$_2$—, —S— or —SO$_2$—.

The reaction temperature and the reaction time in the 3-1-th step may be changed depending on the kinds of reactants, for example, from room temperature (for example, from 15° C. to 25° C.) to 100° C. for 1 to 120 hours.

The peroxide compound may include, for example, without limitation, meta-chloroperoxybenzoic acid (m-CPBA), H$_2$O$_2$, and dimethyldioxirane (DMDO). These peroxide compounds may be used alone or in combination of two or more.

In the 3-1-th step reaction, the base may be optionally used as occasion demands. The base may be used to neutralize an acid ingredient possibly remaining after the reaction depending on the kinds of peroxide compounds used. Examples of the bases that may be used may include, without limitation, KOH, NaOH, K$_2$CO$_3$, KHCO$_3$, NaHCO$_3$, NaH, triethylamine and diisopropylethylamine. These bases may be used alone or in combination of two or more. 0.1 to 5 equivalents of the base with respect to 1 equivalent of the allyl group of the intermediate product (13) may be used in consideration of reaction efficiency.

The solvents may be optionally used as occasion demands in the 3-1-th step reaction. For example, when the viscosity of the reactant at the reaction temperature is appropriate for conducting the reaction without using an additional solvent in the 3-1-th step, the solvent may not be necessary. That is, when the viscosity of the reactants is sufficiently low so that the mixing and the stirring of the reactants may be conducted smoothly without the solvent, the additional use of the solvent may be unnecessary. This state may be easily understood by a person skilled in the art. When the solvent is used, any organic solvents that may easily dissolve the reactants, that do not have any adverse effects, and that may be easily removed after the reaction may be used without limitation. For example, acetonitrile, tetrahydrofuran (THF), methyl ethyl ketone (MEK), dimethylformamide (DMF), dimethyl sulfoxide (DMSO), methylene chloride (MC), or the like, may be used. These solvents may be used alone or in combination of two or more. The amount of the solvent may not be limited to a specific range, and an appropriate amount of the solvent may be used within a range for sufficiently dissolving the reactants and not adversely affecting the reaction. A person skilled in the art may select an appropriate solvent considering the above-mentioned points.

In the 4$^{th}$ step, any one of the intermediate product (13) or any one of the intermediate product (13') when the 3-1-th step is optionally conducted, may react with the alkoxysilane of the following Chemical Formula B2 to conduct the alkoxysilylation of the allyl group of the intermediate product (13) or (13') to produce an alkoxysilylated epoxy compound.

In the 4th step reaction, with respect to the intermediate product (13) or the intermediate product (13'), and the alkoxysilane, the allyl group of the intermediate product (13) or the intermediate product (13') reacts with the alkoxysilane by the stoichiometric ratio. Accordingly, the intermediate product (13) or (13'), and the alkoxysilane of the following Chemical Formula B2 may be used so that the alkoxysilane of Chemical Formula B2 is provided to be 1 to 5 equivalents with respect to 1 equivalent of the allyl group of the intermediate product (13) or the intermediate product (13').

HSiR$_1$R$_2$R$_3$ [Chemical Formula B2]

In Chemical Formula B2, at least one of R$_1$ to R$_3$ is an alkoxy group having 1 to 6 carbon atoms, the remainder of R$_1$ to R$_3$ is an alkyl group having 1 to 10 carbon atoms, the alkyl group and the alkoxy group may have a linear chain or a branched chain, may be cyclic or acyclic, and may or may not contain an N, O, S, or P heteroatom. Preferably, R$_1$ to R$_3$ may be ethoxy groups.

The reaction temperature and the reaction time in the 4th step may be changed depending on the kinds of reactants, for example, from room temperature (for example, from 15° C. to 25° C.) to 120° C. for 1 to 72 hours.

In the 4th step reaction, as the metal catalysts, for example, a platinum catalyst such as PtO$_2$ or chloroplatinic acid (H$_2$PtCl$_6$) may be used without limitation. In consideration of reaction efficiency, 0.01 to 0.05 equivalents of the platinum catalyst may be preferably used with respect to 1 equivalent of the allyl group of the intermediate product (13) or the intermediate product (13').

The solvents may be optionally used as occasion demands in the 4th step reaction. For example, when the viscosity of the reactants at the reaction temperature is appropriate for conducting the reaction without an additional solvent in the 4th step, the solvent may not be necessary. That is, when the viscosity of the reactants is sufficiently low so that the mixing and the stirring of the reactants may be conducted smoothly without the solvent, the additional use of the solvent is not necessary. This state may be easily understood by a person skilled in the art. When the solvent is used, any organic solvents that may easily dissolve the reactants, that do not have any adverse effects, and that may be easily removed after the reaction may be used without limitation. For example, toluene, acetonitrile, tetrahydrofuran (THF), methyl ethyl ketone (MEK), dimethylformamide (DMF), dimethyl sulfoxide (DMSO), methylene chloride (MC), or the like, may be used. These solvents may be used alone or in combination of two or more. The amount of the solvent may not be limited to a specific range, and an appropriate amount of the solvent may be used within a range for sufficiently dissolving the reactants, that do not have any adverse effects to the reaction.

A person skilled in the art may select an appropriate solvent considering the above-mentioned points.

In the 4th step, the allyl group of the intermediate product (13) or the intermediate product (13') may be alkoxysilylated through the reaction of the intermediate product (13) or the intermediate product (13') with the alkoxysilane of Chemical Formula B2 above, to obtain the following Chemical Formulae A14 to K14, for example, A14 to D14, for example, B14 or D14, for example D14 wherein Y is $C(CH_3)_2$.

[Chemical Formulae (A14) to (K14) - Final product (14)]

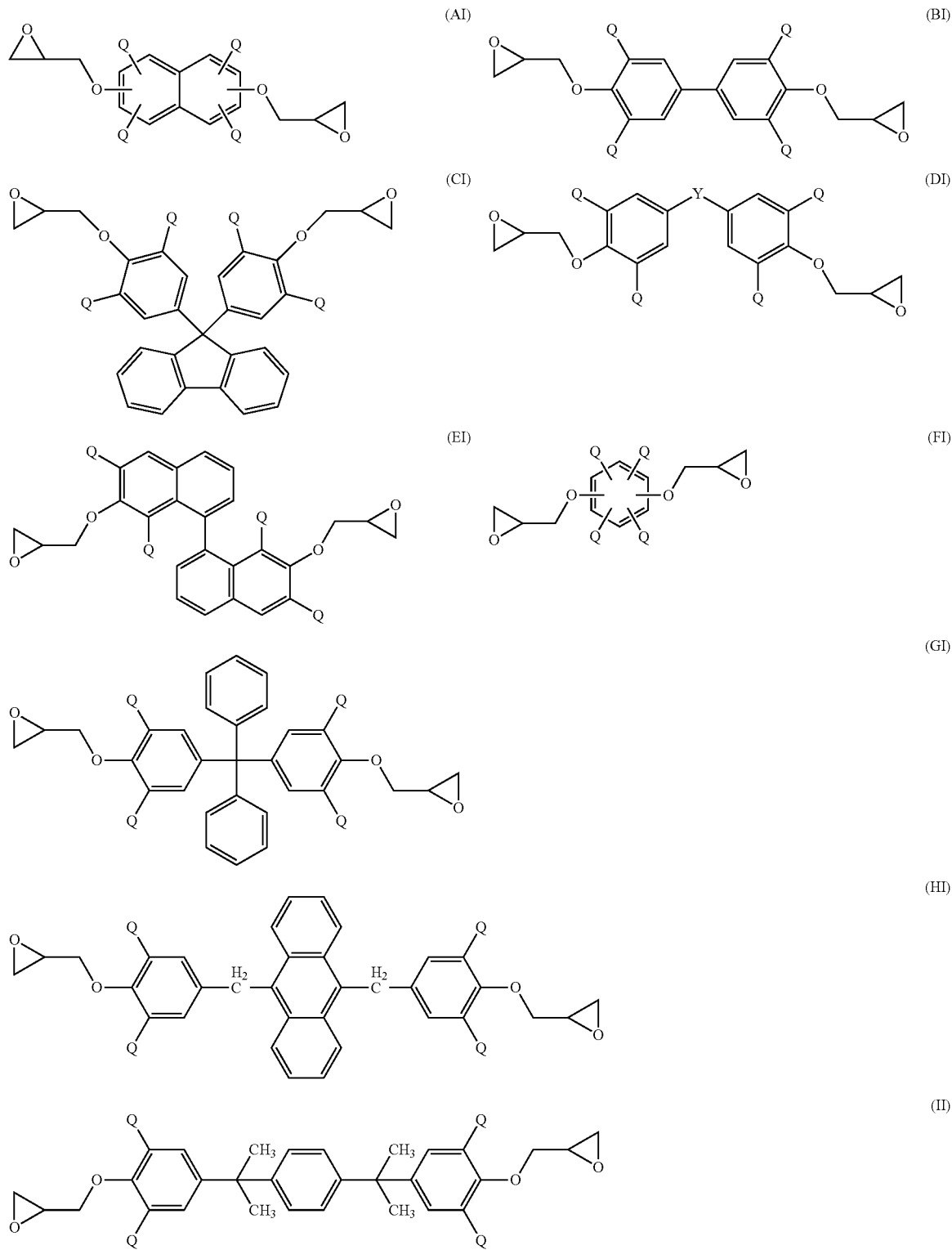

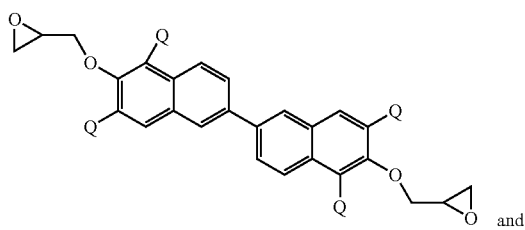
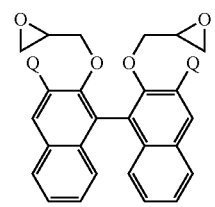

In Chemical Formulae A14 to K14, at least one of P is Chemical Formula S1 above, each of the remainder of P is independently selected from Chemical Formula S3 above, hydrogen and —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), and preferably Chemical Formula S3 above, and in Chemical Formula D14 above, Y is —$CH_2$—, —$C(CH_3)_2$—, —$C(CF_3)_2$—, —S— or —$SO_2$—. The epoxy compound of the Chemical Formula FI having one of S1, in which all of $R_a$, $R_b$ and $R_c$ are hydrogen and all of $R_1$ to $R_3$ are alkoxy groups having 1 to 6 carbon atoms may be excluded.

Exemplary reaction schemes (I) to (III) by above Method 1 are explained as follows. Examples may be explained for D1 when Y is —$C(CH_3)_2$—, which may be a bisphenol A compound. Reaction scheme (I) is an example when only one hydroxyl group is allylated at the allylation process in the 1st step, reaction scheme (II) is an example when all of the two hydroxyl groups are allylated at the allylation process in the 1st step, and reaction scheme (III) is an example when additional epoxidation of the 3-1-th step is conducted.

In D14 in the reaction scheme (I), one of P is —$(CH_2)_3SiR_1R_2R_3$ ($R_1$ to $R_3$ are the same as defined above) and the other of the P is H; in D14 in the reaction scheme (II), all of the P is —$(CH_2)_3SiR_1R_2R_3$ ($R_1$ to $R_3$ are the same as defined above); and in D14 in the reaction scheme (III), one of the P is —$(CH_2)_3SiR_1R_2R_3$ (R1 to R3 are the same as defined above), and the remainder of P is a substituent of Chemical Formula S3.

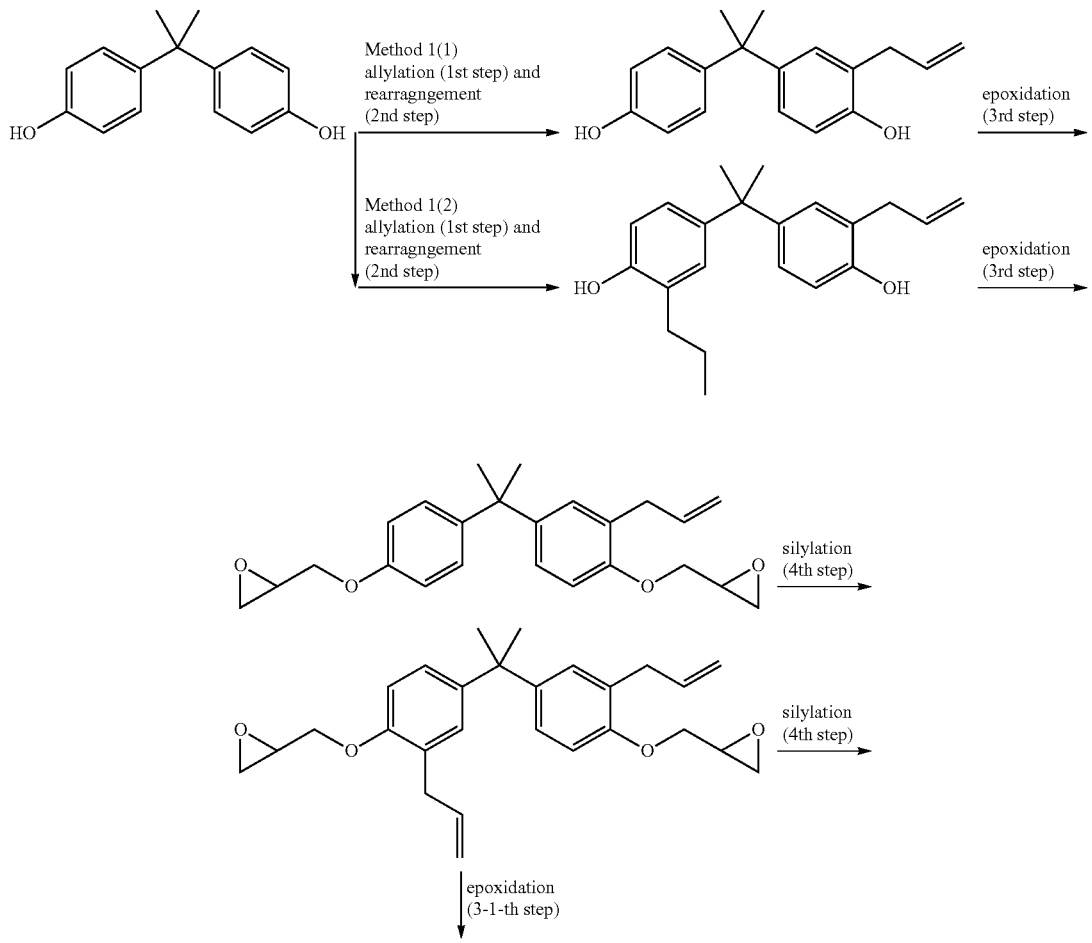

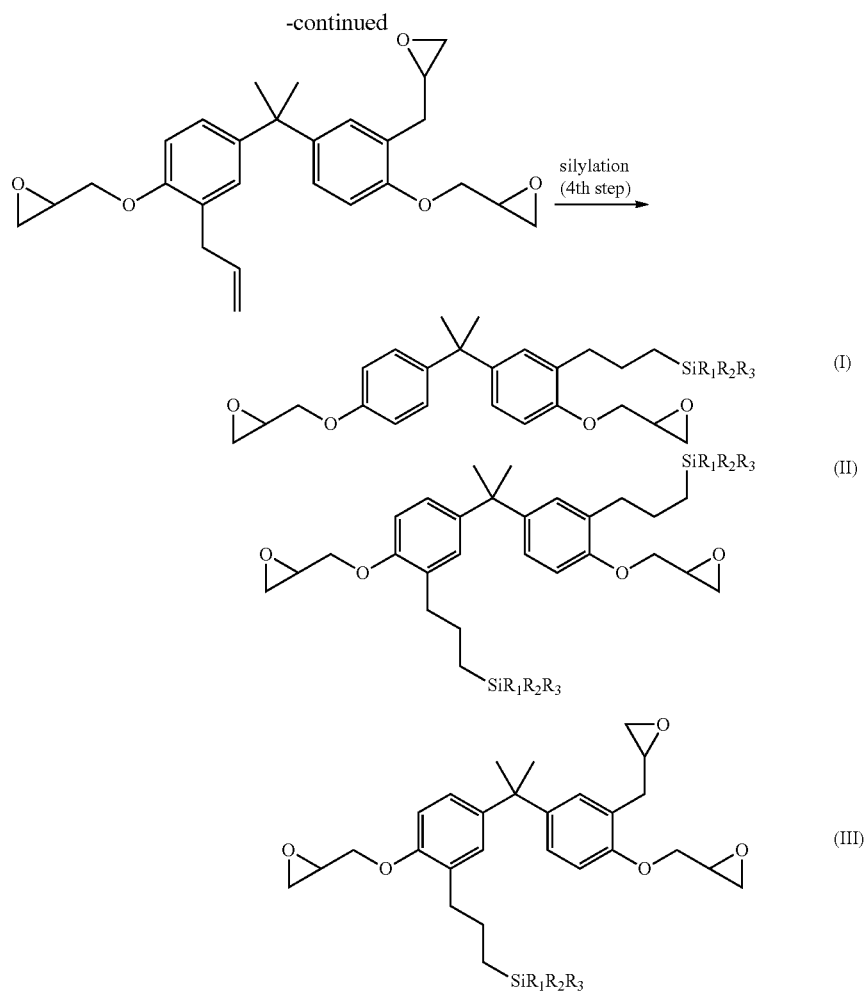

In accordance with other exemplary embodiments of the present invention, a method of preparing an alkoxysilylated epoxy compound of Chemical Formulae (A26) to (J26) (or (AI) to (JI)) comprising allylation on a starting material of one of Chemical Formulae (AS) to (KS) above ($1^{st}$ step), claisen rearrangement ($2^{nd}$ step), allylation (2-1-th step), claisen rearrangement (2-2-th step), epoxidation ($3^{rd}$ step), optional epoxidation (3-1-th step) and alkoxysilylation ($4^{th}$ step) may be provided. Hereinafter, the above-mentioned method will be described as Method 2.

The $1^{st}$ step and the $2^{nd}$ step in Method 2 may be respectively the same as the $1^{st}$ step and the $2^{nd}$ step in the above Method 1. Only Chemical Formula (KS) from the starting materials may not undergo the claisen rearrangement two times due to the structure thereof, and may not be applied in Method 2. As described in the above Method 1, in the $1^{st}$ step, only one or all of the two hydroxyl groups of the starting material may be allylated.

In the 2-1-th step, one intermediate product (23) from the following Chemical Formulae (A23) to (J23) may be obtained through the allylation of the hydroxyl group of one intermediate product (12) from Chemical Formulae (A12) to (J12) above.

In the 2-1-th step, the intermediate product (12) may react with the allyl compound of Chemical Formula B1 above in the presence of a base and an optional solvent. In this case, the allyl compound of Chemical Formula B1 above is provided as having 0.5 to 10 equivalents of an allyl group, based on 1 equivalent of a hydroxyl group in the intermediate product (12).

The 2-1-th step may be the same as the $1^{st}$ step in the above Method 1. Particularly, all of reaction conditions comprising reaction temperature, reaction time, equivalent ratios of reactants, and the kind and the amount of the base and the optional solvent, or the like, may be the same as explained in the $1^{st}$ step in method 1.

[Chemical Formulae (A23) to (J23)]

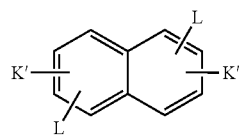

(A23)

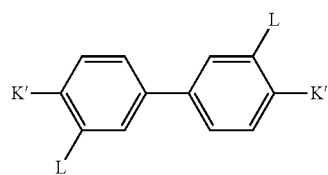

(B23)

(C23)
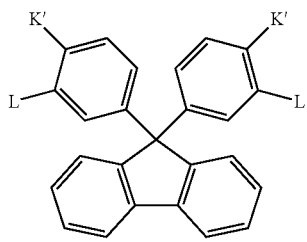

(D23)
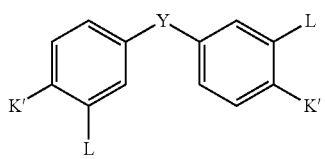

(E23)
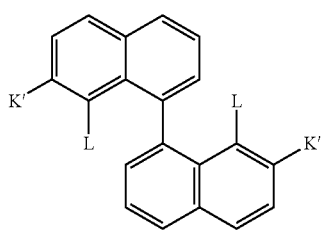

(F23)
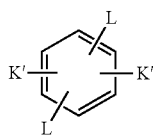

(G23)
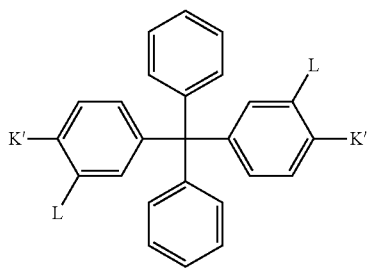

(H23)
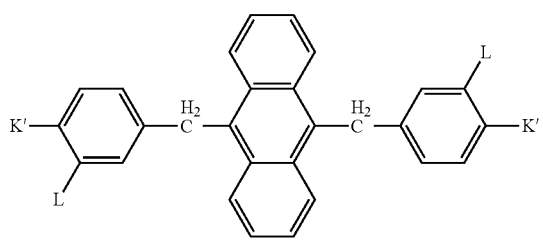

(I23)
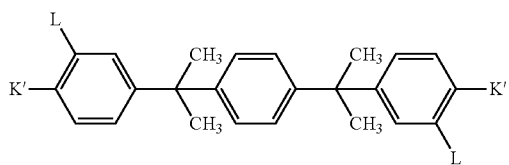

(J23)
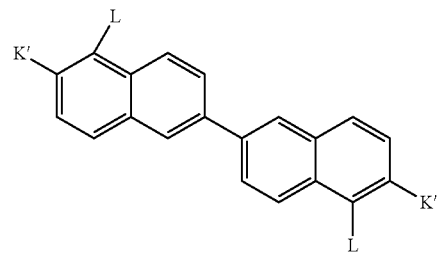

In Chemical Formulae A23 to J23, at least one of K' is —O—CH$_2$—CR$_a$═CR$_b$R$_c$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the remainder of K' is a hydroxyl group, at least one of L is —CR$_b$R$_c$—CR$_a$═CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the remainder of L is hydrogen, and in Chemical Formula D23 above, Y is —CH$_2$—, —C(CH$_3$)$_2$—, —C(CF$_3$)$_2$—, —S— or —SO$_2$—.

In the 2-1-th step, one of the two hydroxyl groups of the intermediate product (12) may be allylated, and all of the two hydroxyl groups may be allylated. According to the number of hydroxyl group to be allylated, the number of alkoxysilyl substituent S1 and/or S3 may be changed in the alkoxysilylated epoxy compound of final target, Chemical Formulae (A26) to (J26) (or Chemical Formulae (AI) to (JI)). In this case, the number of hydroxyl group to be allylated may be changed by controlling the equivalent ratios of the reactants.

In the 2-2-th step, the intermediate product (24) of the following Chemical Formulae (A24) to (J24) may be obtained by the claisen rearrangement by heating the intermediate product (23) obtained in the 2-1-th step. The 2-2-th step may be the same as the 2$^{nd}$ step of the above Method 1.

Particularly, all of reaction conditions comprising reaction temperature, reaction time, equivalent ratios of reactants, and the kind and the amount of the base and the optional solvent, or the like, may be the same as explained in the 2$^{nd}$ step in method 1.

[Chemical Formulae (A24) to (J24)]

(A24)
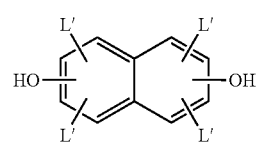

(B24)
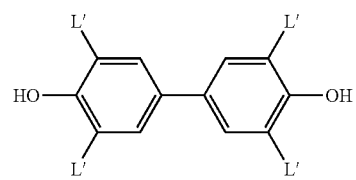

and (C24)

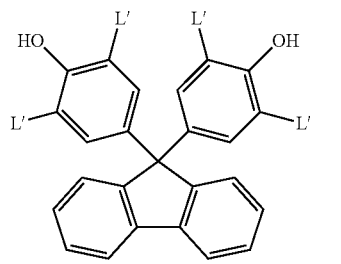

(D24)

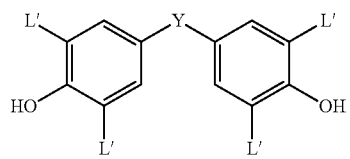

(E24)

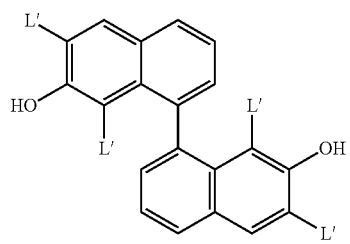

(F24)

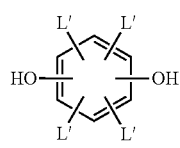

(G24)

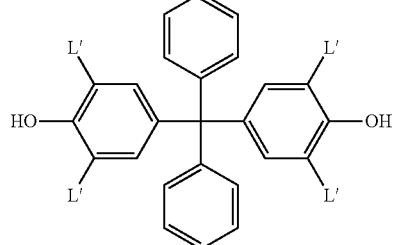

(H24)

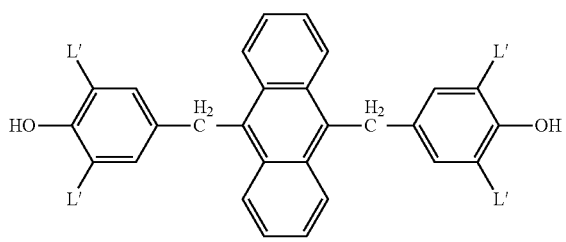

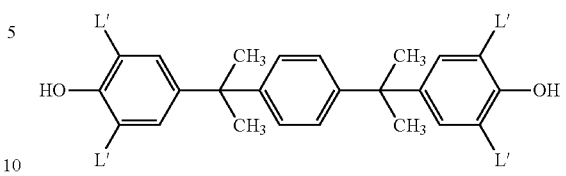

and (I24)

(J24)

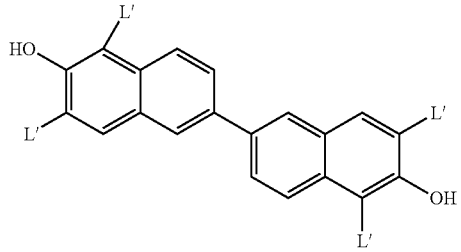

In Chemical Formulae A24 to J24, at least two, and for example, at least three of L' is —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), and the remainder of L' is hydrogen, and in Chemical Formula D24 above, Y is —CH$_2$—, —C(CH$_3$)$_2$—, —C(CF$_3$)$_2$—, —S— or —SO$_2$—.

In the 3$^{rd}$ step, the hydroxyl group of the intermediate product (24) may be epoxidized by the reaction of one of the intermediate product (24) of Chemical Formulae (A24) to (J24) above and epichlorohydrin, to produce the intermediate product (25) of the following Chemical Formulae (A25) to (M25). In this case, the intermediate product (24) may react with the epichlorohydrin to produce the intermediate product (25) in the presence of a base and an optional solvent, in which the epichlorohydrine is used to be 1 to 10 equivalents of the epoxy group, based on 1 equivalent of the hydroxyl group of the intermediate product (24). The 3$^{rd}$ step in Method 2 may be the same as the 3$^{rd}$ step in Method 1. Particularly, all of reaction conditions comprising reaction temperature, reaction time, equivalent ratios of reactants, and the kind and the amount of the base and the optional solvent, or the like, may be the same as explained in the 3$^{rd}$ step in method 1.

[Chemical Formulae (A25) to (J25)]

(A25)

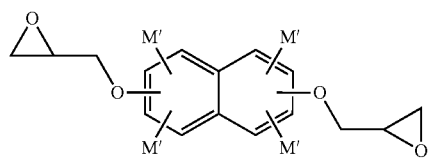

(B25)

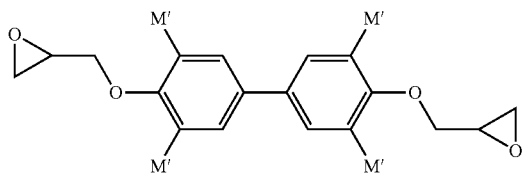

-continued (C25)

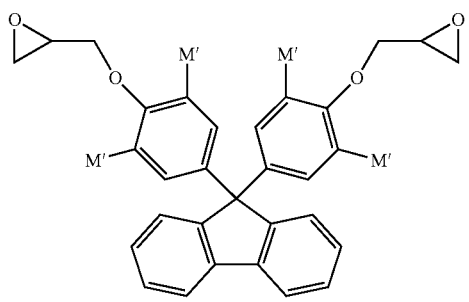

(D25)

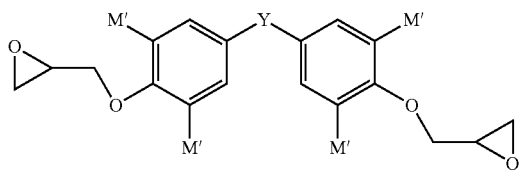

(E25)

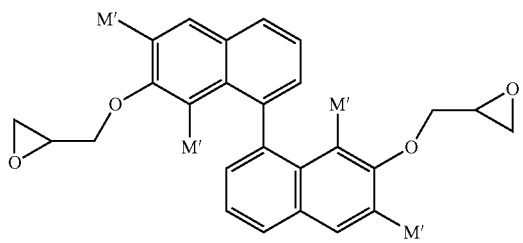

(F25)

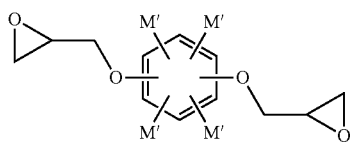

(G25)

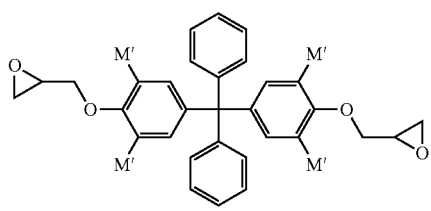

(H25)

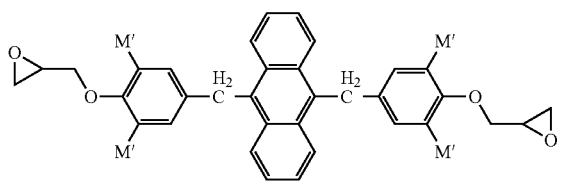

(I25)

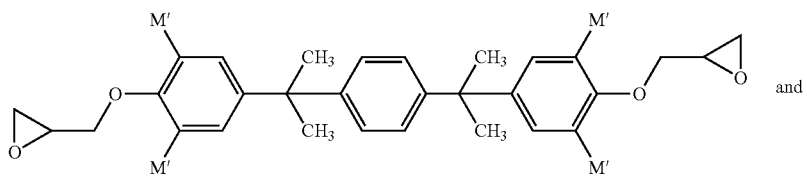

and (J25)

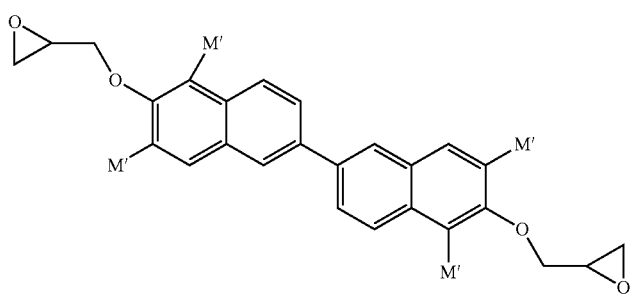

In Chemical Formulae A25 to J25, at least two, for example, at least three of a plurality of M' is —CR$_b$R$_c$—CR$_a$=CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), the remainder of M' is hydrogen, and in Chemical Formula D25 above, Y is —CH$_2$—, —C(CH$_3$)$_2$—, —C(CF$_3$)$_2$—, —S— or —SO$_2$—.

Meanwhile, as described in Method 1, through conducting the epoxidation process in the 3$^{rd}$ step as explained in the following Reaction (2), the epoxidized intermediate product (25) reacts with the hydroxyl group of the reactant, that is, the intermediate product (24) to produce dimer and the higher molecular compounds as illustrated in Chemical Formulae (AP) to (KP) above.

According to the following Reaction (2), the intermediate product (B25) may be produced by the epoxidation of the intermediate product (B24). In the example, all of the M' are —C$_{H2}$—CH=C$_{H2}$ in B25.

[Reaction 2]

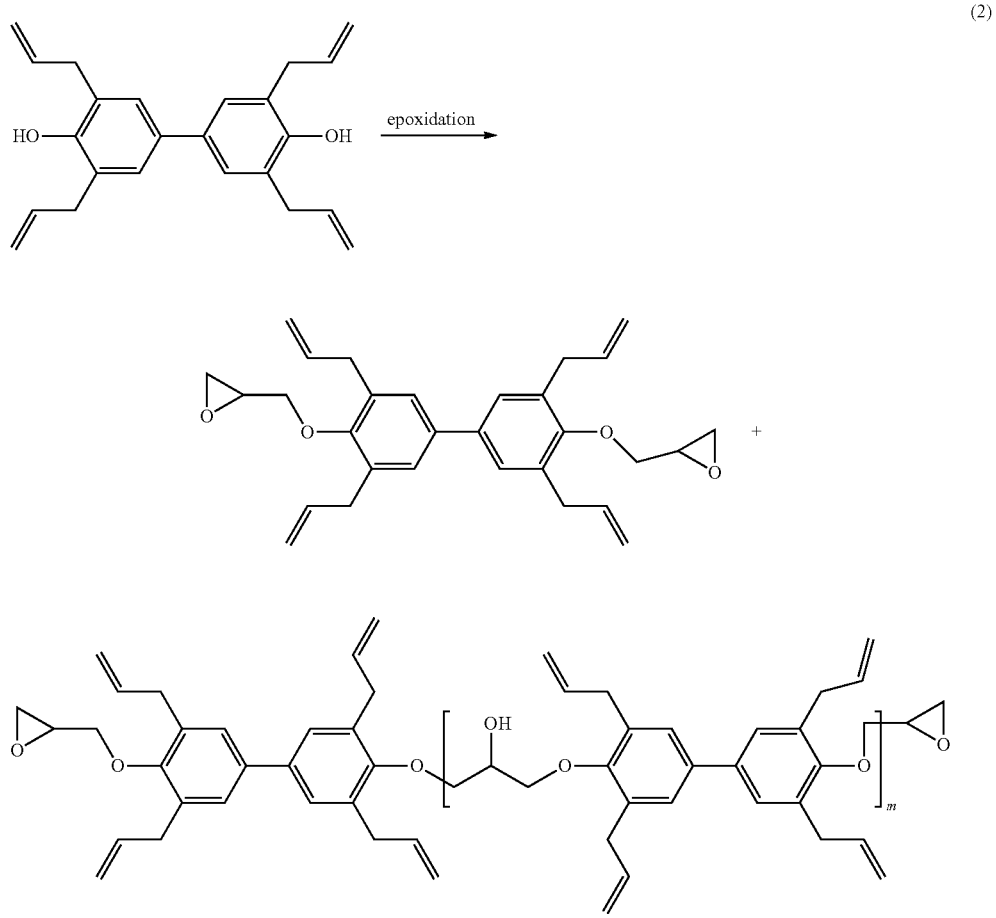

(2)

(in which, m is an integer of 1 to 100)

After conducting the 3$^{rd}$ step, the 3-1-th step of additional epoxidation for epoxidizing the allyl group may be optionally conducted as occasion demands. In the 3-1-th step, the allyl group of one compound from the intermediate product (25) may be oxidized to epoxidize and produce one of the intermediate product (25') from the following intermediate products (A25') to (J25').

In the 3-1-th step, the intermediate product (25) may react with a peroxide compound in the presence of an optional base and an optional solvent. In this case, the intermediate product (25) may react with the peroxide compound so that peroxide compound is to be 1 to 10 equivalents of the peroxide groups, based on 1 equivalent of the allyl group of the intermediate product (25). The 3-1-th step reaction in Method 2 may be the same as the 3-1-th step in Method 1. Particularly, all of reaction conditions comprising reaction temperature, reaction time, equivalent ratios of reactants, and the kind and the amount of the base and the optional solvent, or the like, may be the same as explained in the 3-1-th step in method 1.

[Chemical Formulae (A25') to (J25')]

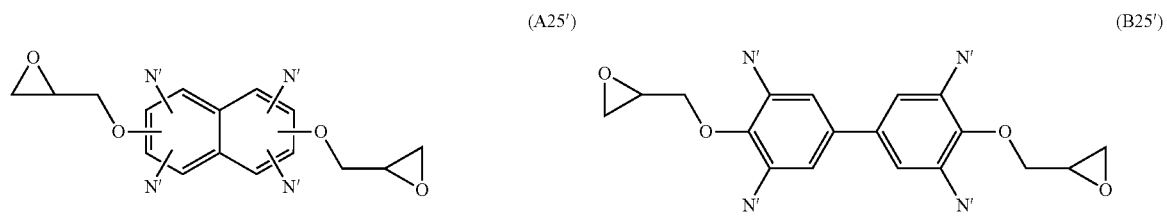

-continued

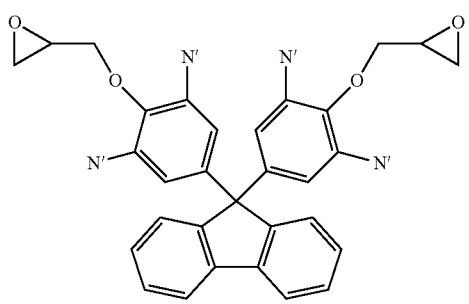 (C25')

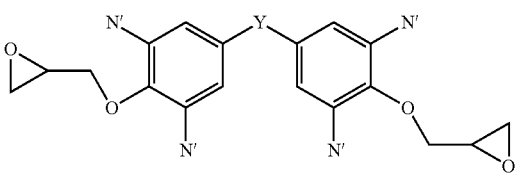 (D25')

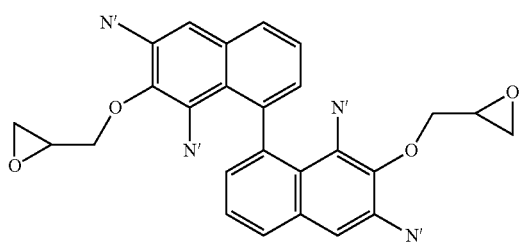 (E25')

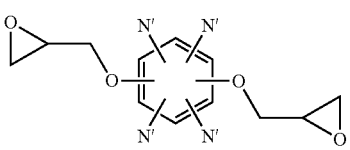 (F25')

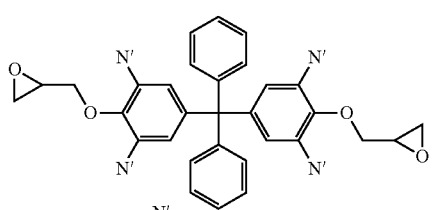 (G25')

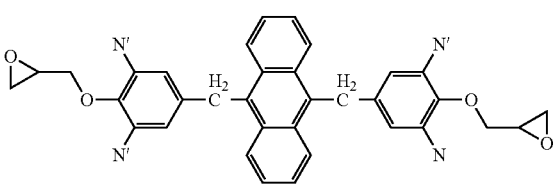 (H25')

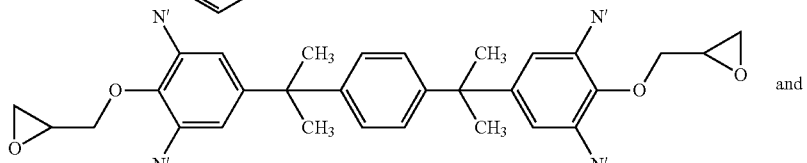 (I25')

and

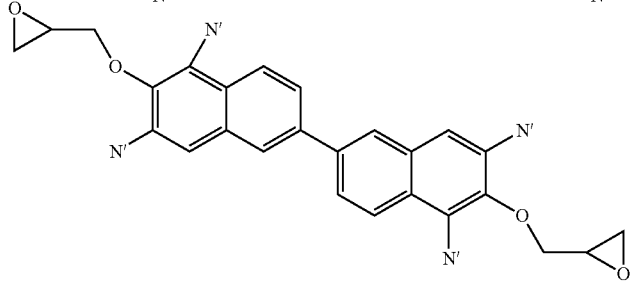 (J25')

In Chemical Formulae A25' to J25', one to three of a plurality of N' are —$CR_bR_c$—$CR_a$=$CH_2$ (in which each of $R_a$, $R_b$ and $R_c$ is independently H or an alkyl group having 1 to 6 carbon atoms, the alkyl group may have a linear chain or a branched chain, may be cyclic or acyclic, and may or may not contain an N, O, S, or P heteroatom), one to three of the N' are Chemical Formula S3 above, and the remainder of N' is hydrogen, and in Chemical Formula D25' above, Y is —$CH_2$—, —$C(CH_3)_2$—, —$C(CF_3)_2$—, —S— or —$SO_2$—.

In the $4^{th}$ step, any one from among the intermediate product (25) or any one of the intermediate product (25') when the 3-1-th step of the optional epoxidation is conducted, may react with the alkoxysilane of Chemical Formula B2 above to produce the alkoxysilylated epoxy compound through conducting the alkoxysilylation of the allyl group of the intermediate product (25) or (25'). In the $4^{th}$ step, the intermediate product (25) or (25') may react with the alkoxysilane of Chemical Formula B2 above in the presence of a metal catalyst and an optional solvent, in which the alkoxysilane of Chemical Formula B2 is used to be 1 to 5 equivalents based on 1 equivalent of the allyl group of the intermediate product (25) or the intermediate product (25'), to produce one target product from the following Chemical Formulae A26 to J26 (or Chemical Formulae AI to JI above). The $4^{th}$ step reaction conditions in Method 2 may be the same as the $4^{th}$ step reaction conditions in Method 1. Particularly, all of reaction conditions comprising reaction temperature, reaction time, equivalent ratios of reactants, and the kind and the amount of the base and the optional solvent, or the like, may be the same as those explained in the $4^{th}$ step in method 1.

[Chemical Formulae (A26) to (J26)]
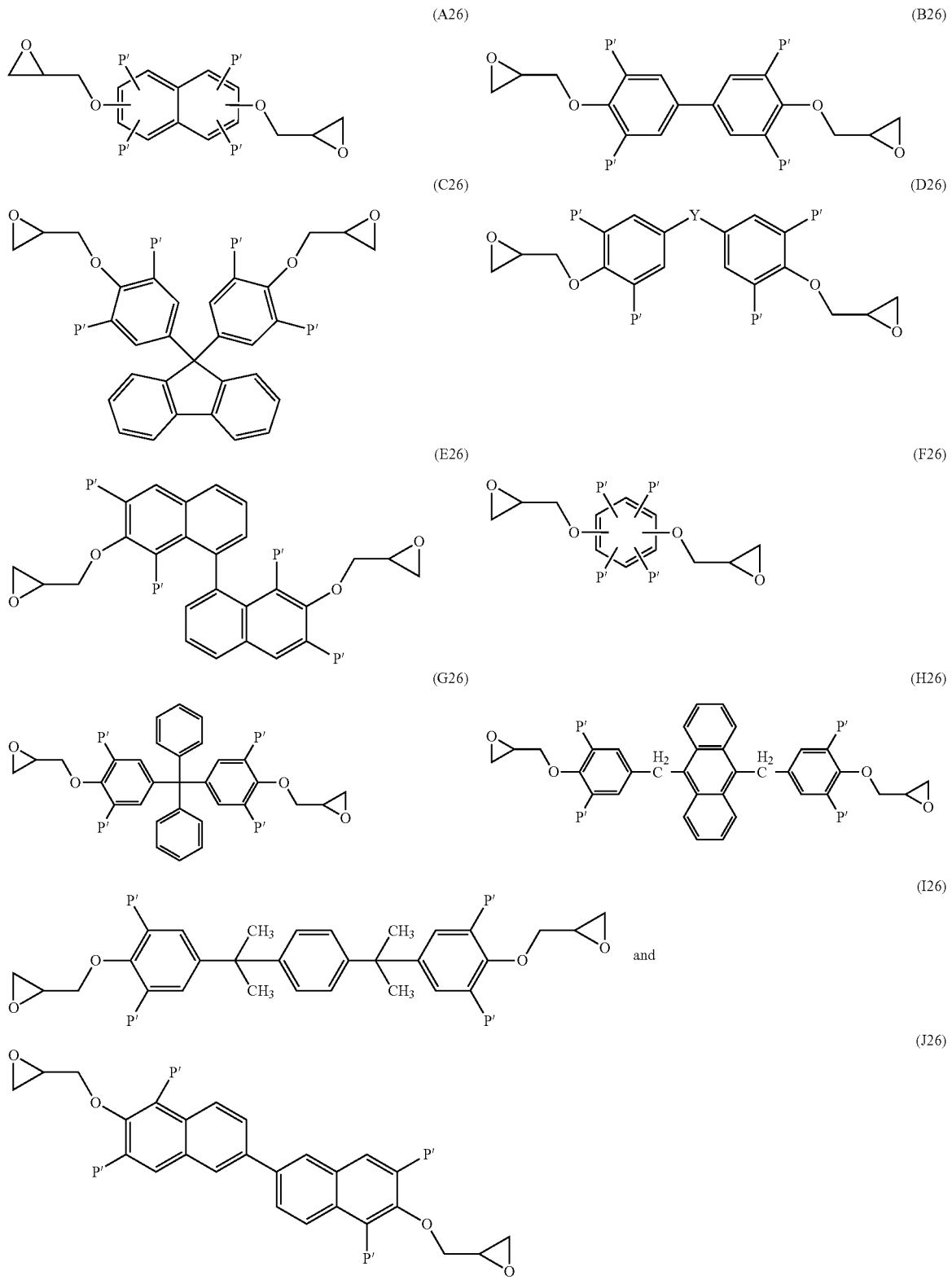
In Chemical Formulae A26 to J26, at least one, for example, 1 to 4 of P' is Chemical Formula S1 above, each of the remainder of P' is independently selected from the group consisting of Chemical Formula S3 above, hydrogen and —CR$_b$R$_c$—CR$_a$═CH$_2$ (in which each of R$_a$, R$_b$ and R$_c$ is independently H or an alkyl group having 1 to 6 carbon atoms, the alkyl group may have a linear chain or a branched chain, may be cyclic or acyclic, and may or may not contain an N, O, S, or P heteroatom), for example, Chemical Formula S3, and S3 may be 1 to 3. In Chemical Formula D26 above, Y is —$CH_2$—, —$C(CH_3)_2$—, —$C(CF_3)_2$—, —S— or —$SO_2$—. Only the epoxy compound of the Chemical Formula FI having one of S1, in which all of $R_a$, $R_b$ and $R_c$ are hydrogen, and all of $R_1$ to $R_3$ are alkoxy groups having 1 to 6 carbon atoms may be excluded.

Exemplary reaction schemes (IV) to (X) according to Method 2 are explained as follows. Bisphenol A of Chemical Formula D1, in which Y is —$C(CH_3)_2$— will be explained. In reaction scheme (IV), two hydroxyl groups may be allylated in the $1^{st}$ step, and one hydroxyl group may be allylated in the 2-1-th step, and in Chemical Formula D26, three of P' are —$(CH_2)_3SiR_1R_2R_3$ ($R_1$ to $R_3$ are as defined above) and one of the P' is hydrogen. In reaction scheme (V), two hydroxyl groups may be allylated in the $1^{st}$ step, one hydroxyl group may be allylated in the 2-1-th step, and one allyl group may be epoxidized at an optional 3-1-th step, and in Chemical Formula D26, two of the P' are —$(CH_2)_3SiR_1R_2R_3$ ($R_1$ to $R_3$ are as defined above), one of the P' is the epoxy group of Chemical Formula S3, and one of the P' is hydrogen. In reaction scheme (VI), two hydroxyl groups may be allylated in the $1^{st}$ step, one hydroxyl group may be allylated in the 2-1-th step, and two allyl groups may be epoxidized in the optional 3-1-th step, and in Chemical Formula D26, one of P' is —$(CH_2)_3SiR_1R_2R_3$ ($R_1$ to $R_3$ are as defined above), two of the P' are the substituents of Chemical Formula S3, and one of the P' is hydrogen. In reaction scheme (VII), two hydroxyl groups may be allylated in the $1^{st}$ step and in the 2-1-th step, respectively, and in Chemical Formula D26, four of the P' are —$(CH_2)_3SiR_1R_2R_3$ ($R_1$ to $R_3$ are as defined above). In reaction scheme (VIII), two hydroxyl groups may be allylated in the $1^{st}$ step and the 2-1-th step, respectively, and one allyl group may be epoxidized in the optional 3-1-th step, and in Chemical Formula D26, three of the P' are —$(CH_2)_3SiR_1R_2R_3$ ($R_1$ to $R_3$ are as defined above), one of the P' is the substituent of Chemical Formula S3. In reaction scheme (IX), two hydroxyl groups may be allylated in the $1^{st}$ step and the 2-1-th step, respectively, and two allyl groups may be epoxidized at an optional 3-1-th step, and in Chemical Formula D26, two of the P' are —$(CH_2)_3SiR_1R_2R_3$ ($R_1$ to $R_3$ are as defined above), two of the P' are the substituents of Chemical Formula S3. In reaction scheme (X), two hydroxyl groups may be allylated in the $1^{st}$ step and the 2-1-th step, respectively, and three allyl groups may be epoxidized in the optional 3-1-th step, and in Chemical Formula D26, one of the P' is —$(CH_2)_3SiR_1R_2R_3$ ($R_1$ to $R_3$ are as defined above), and three of the P' is the substituents of Chemical Formula S3.

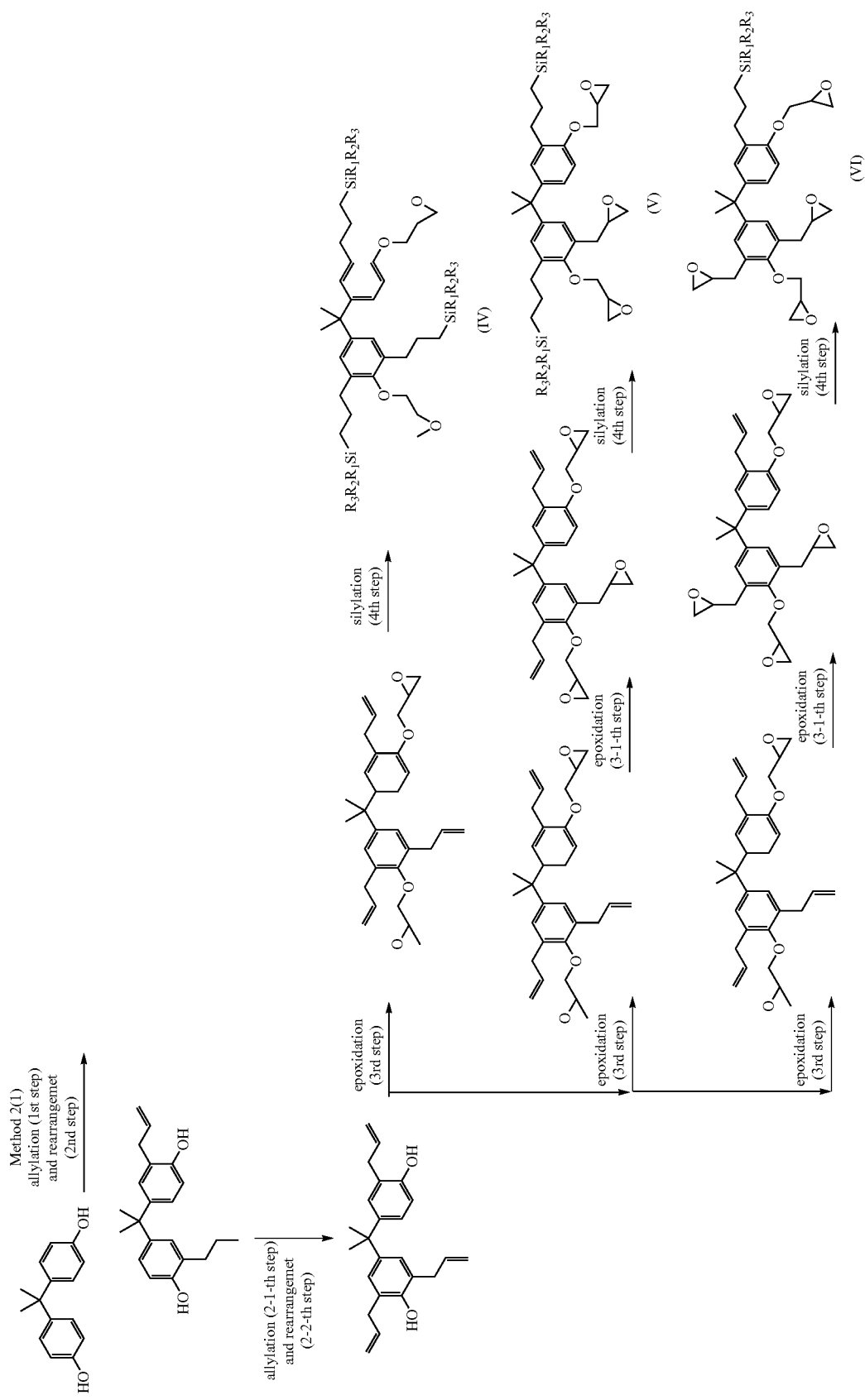

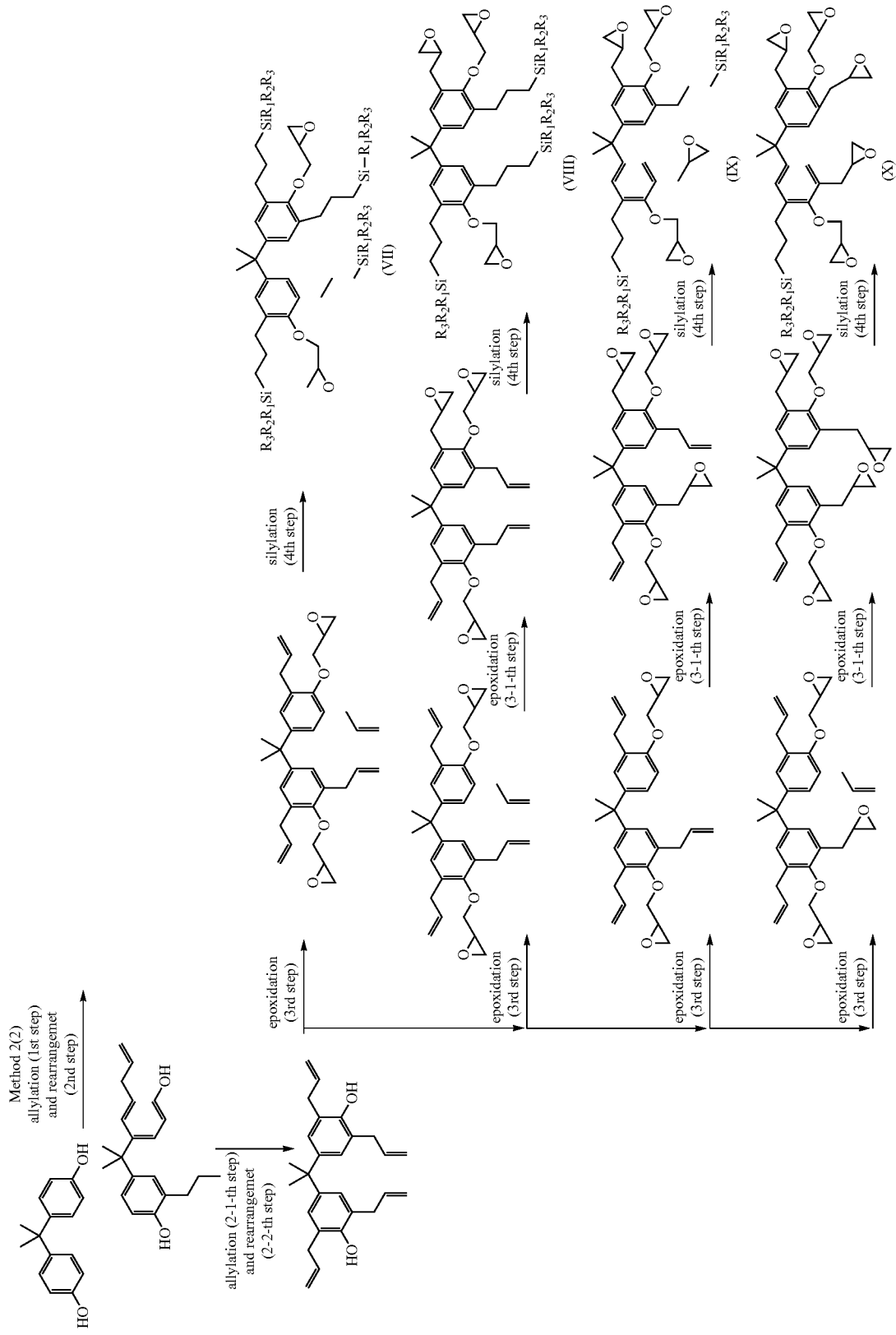

3. Epoxy Composition

In accordance with other exemplary embodiments of the present invention, a composition comprising any alkoxysilylated epoxy compound provided in any embodiments of the present invention may be provided. For example, an epoxy composition comprising an alkoxysilylated epoxy compound having at least one of Chemical Formula S1 substituent above and two epoxy groups, for example, the epoxy group of Chemical Formula S2 above in a core, may be provided. In addition, an epoxy composition comprising an alkoxysilylated epoxy compound having at least one of Chemical Formula S1 substituent above, and two epoxy groups, for example, the epoxy group of Chemical Formula S2 above and additionally the epoxy group of Chemical Formula S3 above, may be provided. Further, an epoxy composition comprising at least one alkoxysilylated epoxy compound selected from the group consisting of Chemical Formulae AI to KI above, for example, Chemical Formulae AI to DI, for example, Chemical Formula CI or DI, and for example, an alkoxysilylated epoxy compound of Chemical Formula DI in which Y is —$C(CH_3)_2$—, may also be provided. Any composition provided in the present invention may be used for an electronic material. In addition, any composition provided in the present invention may be a curable composition and/or a curable composition comprising inorganic materials.

The epoxy composition in accordance with an example embodiment of the present invention may include any epoxy composition of any kinds and/or any mixing ratios commonly known in this technical field only when comprising any alkoxysilylated epoxy compound provided by any embodiments of the present invention. The kind and the mixing ratios of a curing agent, a curing accelerator (catalyst), an inorganic material (filler) (for example, inorganic particles and/or fiber) and other additives may not be limited.

Further, as the epoxy compound in the epoxy composition in accordance with any embodiments of the present invention, an epoxy compound having an alkoxysilyl group provided in any embodiments of the present invention (hereinafter, an 'epoxy compound of the present invention' or an 'alkoxysilylated epoxy compound'), for example, an alkoxysilylated epoxy compound having at least one of Chemical Formula S1 substituent above and two epoxy groups in a core, for example, having the epoxy group of Chemical Formula S2 above; an alkoxysilylated epoxy compound having at least one of Chemical Formula S1 substituent above, and two epoxy groups, for example, the epoxy group of Chemical Formula S2 above and additionally the epoxy group of the above Chemical Formula S3; or at least one alkoxysilylated epoxy compound selected from the group consisting of the above Chemical Formulae AI to KI, for example, at least one alkoxysilylated epoxy compound selected from the group consisting of Chemical Formulae AI to DI, for example, CI or DI, and for example, an alkoxysilylated epoxy compound of Chemical Formula DI in which Y is —$C(CH_3)_2$—, and any epoxy compound known in this technical field (hereinafter, a "common epoxy compound"), may be included.

The common epoxy compound may not be limited to specific compounds, but may be any epoxy compound commonly known in this technical field, for example, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound. In addition, the common epoxy compound may include at least one of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound, having at least one of bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol cyclo aliphatic compound or a novolak unit as a core structure.

Preferably, the common epoxy compound may be at least one of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound, having the bisphenol A, the bisphenol F, the bisphenol S, the biphenyl, the naphthalene, or the fluorene as a core structure.

Any epoxy composition in accordance with an embodiment of the present invention may comprise, without limitation, based on the total amount of an epoxy compound, 1 to 100 wt % of the epoxy compound of the present invention and 0 to 99 wt % of the common epoxy compound; for example, 10 to 100 wt % of the epoxy compound of the present invention and 0 to 90 wt % of the common epoxy compound; for example, 30 to 100 wt % of the epoxy compound of the present invention and 0 to 70 wt % of the common epoxy compound; for example, from 10 to below 100 wt % of the epoxy compound of the present invention and from excess of 0 to 90 wt % of the common epoxy compound; for example, from 30 to below 100 wt % of the epoxy compound of the present invention and from excess of 0 to 70 wt % of the common epoxy compound.

Further, in accordance with other exemplary embodiments of the present invention, a composition comprising any alkoxysilylated epoxy compound provided in any embodiments of the present invention and a curing agent may be provided. In accordance with other exemplary embodiments of the present invention, an epoxy composition comprising an alkoxysilylated epoxy compound having at least one of Chemical Formula S1 substituent above and two epoxy groups, for example, the epoxy group of Chemical Formula S2 above, in a core, and a curing agent may be provided. In addition, an epoxy composition comprising an alkoxysilylated epoxy compound having at least one of Chemical Formula S1 substituent above, and two epoxy groups, for example, the epoxy group of Chemical Formula S2 above and additionally the epoxy group of Chemical Formula S3 above, and a curing agent may be provided. Further, an epoxy composition comprising at least one alkoxysilylated epoxy compound selected from the group consisting of the above Chemical Formulae AI to KI, for example, Chemical Formulae AI to DI, for example, Chemical Formula CI or DI, and for example, an alkoxysilylated epoxy compound of Chemical Formula DI in which Y is —$C(CH_3)_2$—, and a curing agent may also be provided.

Any composition comprising any alkoxysilylated epoxy compound and a curing agent also may comprise any common epoxy compounds as the epoxy compound. In this case, the kind of the common epoxy compounds possibly included, and the mixing ratios of the alkoxysilylated epoxy compound and the common epoxysilyl compound may be the same as described above.

In the composition comprising the alkoxysilylated epoxy compound and the curing agent in accordance with exemplary embodiments of the present invention, any curing agents commonly known as curing agents of an epoxy polymer may be used. For example, an amine-based compounds, a phenol-based compounds, an acid anhydride-based compounds may be used without limitation.

More particularly, an aliphatic amine, an alicyclic amine, an aromatic amine, other amines and a modified amine may be used as the amine-based curing agent without limitation. In addition, an amine compound comprising two or more primary amine groups may be used. Particular examples of the amine curing agents may include at least one aromatic amine selected from the group consisting of 4,4'-dimethylaniline (diamino diphenyl methane, DAM or DDM), diamino diphenyl sulfone (DDS), and m-phenylene diamine, at least one aliphatic amine selected from the group consisting of diethylene triamine (DETA), diethylene tetramine, triethylene tetramine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP), bis(4-amino 3-methylcyclohexyl)methane, and larominc 260, other amines such as dicyanamide (DICY), or the like, and the modified amine such as polyamide-based compound, epoxide-based compound, or the like.

Examples of the phenol-based curing agent may include, without limitation, a phenol novolak resin, a cresol novolak resin, a bisphenol A novolak resin, a xylene novolak resin, a triphenyl novolak resin, a biphenyl novolak resin, a dicyclopentadiene novolak resin, phenol-p-xylene, a naphthalene-based phenol novolak resin, or the like.

Examples of the acid anhydride-based curing agent may include, without limitation, an aliphatic anhydrides such as dodecenyl succinic anhydride (DDSA), poly azelaic poly anhydride, or the like, an alicyclic anhydrides such as hexahydrophthalic anhydride (HHPA), methyl tetrahydrophthalic anhydride (MeTHPA), methylnadic anhydride (MNA), or the like, an aromatic anhydrides such as trimellitic anhydride (TMA), pyromellitic acid dianhydride (PMDA), benzophenonetetracarboxylic dianhydride (BTDA), or the like, and a halogen-based anhydrous compound such as tetrabromophthalic anhydride (TBPA), chlorendic anhydride (HET), or the like.

In general, the crosslinking density of an epoxy composite may be controlled by the extent of reaction of the curing agent with the epoxy group. According to the target crosslinking density, the stoichiometric ratio of the curing agent to epoxy compound may be controlled. For example, when an amine curing agent is used, the stoichimetric ratio of epoxy to amine may be controlled to 0.5 to 2.0, for example, 0.8 to 1.5 in a reaction of the amine curing agent with the epoxy group.

Though the mixing ratio of the curing agent has been explained with respect to the amine-based curing agent, a phenol-based curing agent, an acid anhydride-based curing agent and any curing agents for curing epoxy compounds not separately illustrated in this application but used for curing may be used by appropriately mixing stoichiometric amount according to the chemical reaction of the epoxy functional group and the reactive functional group of the curing agent based on the concentration of the total epoxy group in the epoxy composition according to the desired range of the curing density. The above-described parts are commonly known in this field.

Any photo-curing agent known in this technical field may be used as a cationic photo-curing agent, and an aromatic phosphonium salt, an aromatic iodonium salt, an aromatic sulfonium salt, or the like without limitation. Particularly, diphenyliodonium tetrakis(pentafluorophenyl)borate, diphenyliodonium hexafluorophosphate, diphenyliodonium hexafluoroantimonate, di(4-nonylphenyl)iodonium hexafluorophosphate, triphenylsulfonium hexafluorophosphate, triphenylsulfonium hexafluoroantimonate, triphenylsulfonium tetrakis(pentafluorophenyl)borate, 4,4'-bis[diphenylsulfonio]diphenylsulfide bisphexafluorophosphate, 4,4'-bis[di($\beta$-hydroxyethoxy)phenylsulfonio]diphenylsulfide bishexafluoroantimonate, 4,4'-bis[di($\beta$-hydroxyethoxy)phenylsulfonio]diphenylsulfide bishexafluorophosphate, or the like may be included. The photo-curing agent may be used for example, 0.5 phr (parts per hundred, parts per weight by 100 parts per weight of the epoxy compound) to 20 phr based on the epoxy compound, preferably, 1 phr or more, and more preferably, 1 phr to 5 phr without limitation.

An optional curing accelerator (catalyst) may be additionally included as occasion demands to promote the curing reaction of the alkoxysilylated epoxy compound and the curing agent in any epoxy composition provided in the present invention. Any curing accelerators (catalysts) commonly used for curing an epoxy composition in this art may be used without limitation, for example, imidazoles-based, tertiary amines-based, quaternary ammonium compounds-based, organic acid salts-based, phosphorous compounds-based, Lewis acids, etc. may be used as curing accelerators.

More particularly, for example, the imidazole-based curing accelerator such as 2-methylimidazole (2MZ), 2-undecylimidazole, 2-ethyl-4-methylimidazole (2E4M), 2-phenylimidazole, 1-(2-cyanoethyl)-2-alkyl imidazole, and 2-heptadecylimidazole (2HDI); the tertiary amine-based curing accelerator such as benzyl dimethyl amine (BDMA), trisdimethylaminomethylphenol (DMP-30), and triethylenediamaine; the quaternary ammonium-based curing accelerator such as tetrabutylammoniumbromide, or the like; diazacycloundecene (DBU), or an organic acid salt of DBU; the phosphorous compound-based curing accelerator such as triphenyl phosphine, phosphoric acid ester, or the like, and a Lewis acid such as $BF_3$-monoethylamine ($BF_3$-MEA), may be illustrated without limitation. Latent curing accelerators, which are formed by the microcapsulation and complex salts of accelerators, may also be used. These compounds may be used alone or in combination of two or more according to depending on the curing conditions.

The mixing amount of the curing accelerator may be commonly applied mixing amount in this art without limitation. For example, 0.1 to 10 phr, preferably 0.2 to 5 phr of the curing accelerator based on the epoxy compound may be used. The above-described range of the curing accelerator may be preferably used in consideration of curing reaction accelerating effect and the control of curing reaction rate. Through using the above-described range of the curing accelerator, the curing may be rapidly achieved, and the improvement of working throughput in a packaging process may be expected.

Further, any epoxy composition provided in the present invention, for example, any epoxy composition comprising the alkoxysilylated epoxy compound and at least one selected from the group consisting of a common epoxy compound, a curing agent and a catalyst may additionally include at least one filler of an inorganic material selected from the group consisting of inorganic particles and fiber.

Any inorganic particles known to be used to decrease the coefficient of thermal expansion of a common organic resin may be used. Examples of the inorganic particles may include, without limitation, at least one selected from the group consisting of at least one metal oxide selected from the group consisting of $SiO_2$, $ZrO_2$, $TiO_2$, and $Al_2O_3$, and at least one selected from the group consisting of T-10 type silsesquioxane, ladder type silsesquioxane, and cage type silsesquioxane. The inorganic particles may be used alone or as a mixture of two or more.

The inorganic particles having a particle size of from 0.5 nm to several tens of μm (for example, 100 μm, in addition, for example, 50 to 60 μm) may be used considering the usage of a composite, particularly, the dispersibility of the inorganic particles. Since the dispersibility of the inorganic particle in the epoxy matrix may be different according to the particle size, the inorganic particles having above-mentioned sizes may be preferably used.

In the epoxy composition in accordance with an embodiment of the present invention, the mixing amount of the inorganic particles may be 5 phr to 1,000 phr, for example, 100 phr to 900 phr, in addition, for example, 50 phr to 200 phr based on the amount of the epoxy compound may be used considering the CTE decrease of an epoxy composite and an appropriate viscosity required while applying.

More particularly, in an example embodiment, when the epoxy composition is used as a semiconductor EMC (epoxy molding compound), or the like, the mixing ratio of the inorganic particles may be, for example, 100 to 900 phr, without limitation, based on the amount of the epoxy compound in consideration of the CTE value and material processability. In other exemplary embodiments, when the epoxy composition is used as a semiconductor substrate, the mixing amount of the inorganic particles may be 50 to 200 phr based on the amount of the epoxy compound considering the CTE value and the modulus of the substrate.

Meanwhile, when the fiber is used as the inorganic material, a composite may be obtained by mainly a wetting method of the fiber with the epoxy compound. Thus, the size of the fiber may not be specifically limited. Any kinds and dimensions of the fiber commonly used in this field may be used.

Any commonly used fibers for improving physical properties of common organic resin cured product may be used without limitation. Particularly, a glass fiber, an organic fiber or a mixture thereof may be used. In addition, the term 'glass fiber' used in this application may include a glass fiber fabric, a glass fiber non woven product, or the like, as well as the glass fiber. Examples of the glass fibers may include, without limitation, the glass fiber of E, T(S), NE, D, quartz, or the like, for example, the glass fiber of E or T may be included. The organic fiber may include at least one selected from the group consisting of liquid crystal polyester fiber, polyethyleneterephthalate fiber, wholly aromatic fiber, polybenzoxazole fiber, nylon fiber, polyethylene naphthalate fiber, polypropylene fiber, polyether sulfone fiber, polyvinylidene fluoride fiber, polyethylene sulfide fiber and polyether ether ketone fiber. These fibers may be used alone or in combination of two or more.

When the fiber is used as the filler in the epoxy composition of the present invention, the amount of the fiber may be 10 wt % to 90 wt %, for example, 30 wt % to 70 wt %, in addition, for example, 35 wt % to 65 wt % based on the total weight of the epoxy composition. In the epoxy composition comprising the fiber, the epoxy composition excluding the fiber may be commonly called as a resin content, and in the epoxy composition comprising the fiber, the amount excluding the fiber may be the amount of the resin content. Thus, the amount of the resin content may be 10 wt % to 90 wt %, for example, 30 wt % to 70 wt %, in addition, for example, 35 wt % to 65 wt %. The amount of the fiber within the above-described range may be preferred in consideration of the increase in heat resistance and the processability aspects. The total amount of the epoxy composition means the total weight amounts of all of the constituent components comprising the curing agent, the catalyst, the inorganic material and/or other additives. In addition, as described above, the amount of the resin content may include the amounts of all of the constituent components of the epoxy composition comprising the curing agent, the catalyst and the other additives excluding the fiber.

In the epoxy composition comprising the fiber provided in the present invention may additionally include inorganic particles as occasion demands. In this case, the inorganic particles may be included by 1 to 70 wt % in the resin content by considering the improvement of the physical properties and processability.

In the epoxy composition, other additives such as an organic solvent, a releasing agent, a surface treatment agent, a flame retardant, a plasticizer, bactericides, a leveling agent, a defoaming agent, a colorant, a stabilizer, a coupling agent, a viscosity controlling agent, a diluent, or the like may be mixed to control the physical properties of the epoxy composition within the range of undamaging the physical properties of the epoxy composition as occasion demands.

The epoxy composition provided in accordance with an example embodiment may be used for an electronic material. Particularly, the electronic material may include a prepreg, a laminate of the prepreg and a metal layer, a substrate, a film, a printed circuit board, a packaging material, or the like. In accordance with other exemplary embodiments, a semiconductor device comprising or manufactured by using the electronic material obtained by using the epoxy composition comprising the alkoxysilylated epoxy compound, may be provided. Particularly, the semiconductor device may be a semiconductor device in which a semiconductor element is installed on a printed circuit board manufactured by using the composition comprising the alkoxysilylated epoxy compound of the present invention and/or may be a semiconductor device comprising a semiconductor packaging material.

In accordance with other exemplary embodiments of the present invention, a cured product of the epoxy composition provided in accordance with an example embodiment may be provided. When applying the epoxy composition provided in an example embodiment is practically used, for example, applied as the electronic material, or the like, the cured product of the epoxy composition may be used. In this art, the cured product of the composition comprising the epoxy compound and the filler of the inorganic component may be commonly called as a composite.

The alkoxysilylated epoxy compound provided in above-described exemplary embodiments may show good heat resistance in the composite and/or good flame retardant property in the cured product. Particularly, the composite may show a low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less.

For example, a composite comprising any alkoxysilylated epoxy compound in accordance with exemplary embodiments of the present invention as the epoxy compound, and glass fiber, for example, E-glass fiber as the inorganic material, and having the resin content of 35 wt % to 45 wt % may have a CTE of 15 ppm/° C. or less, for example, 12 ppm/° C. or less. As the number of alkoxysilyl group of Chemical Formula S1 above increases, the CTE of the composite may decrease. For example, a composite comprising an alkoxysilylated epoxy compound having two alkoxysilyl groups in accordance with exemplary embodiments as the epoxy compound, and glass fiber, for example, E-glass fiber as the inorganic material, and having the resin content of 35 wt % to 45 wt % may have a CTE of 10 ppm/° C. or less, for example, 8 ppm/° C. or less. In addition, for example, a composite comprising an alkoxysilylated epoxy compound having two alkoxysilyl groups and a biphenyl core structure in accordance with example embodiments as the epoxy compound, and glass fiber, for example, E-glass fiber as the inorganic material, and having the resin content of 35 wt % to 45 wt % may have a CTE of 10 ppm/° C. or less, for example, 6 ppm/° C. or less.

For example, a composite comprising an alkoxysilylated epoxy compound in accordance with exemplary embodiments as the epoxy compound, and glass fiber, for example, T-glass fiber as the inorganic material, and having the resin content of 35 wt % to 45 wt % may have a CTE of 15 ppm/° C. or less, for example, 10 ppm/° C. or less. As the number of alkoxysilyl groups of Chemical Formula S1 above increases, the CTE of the composite may decrease. For example, a composite comprising an alkoxysilylated epoxy compound having two alkoxysilyl groups in accordance with exemplary embodiments as the epoxy compound, and glass fiber, for example, T-glass fiber as the inorganic material, and having the resin content of 35 wt % to 45 wt % may have a CTE of 6 ppm/° C. or less. In addition, for example, a composite comprising an alkoxysilylated epoxy compound having two alkoxysilyl groups and a naphthalene, biphenyl, cardo, bisphenol core structure in accordance with exemplary embodiments as the epoxy compound, and glass fiber, for example, T-glass fiber as the inorganic material, and having the resin content of 35 wt % to 45 wt % may have a CTE of 4 ppm/° C. or less.

In addition, Tg of the composite (a cured product comprising the inorganic material) according to the present invention may be higher than 100° C., for example, 130° C. or over, in addition, for example, 250° C. or over. Otherwise, the composite may be Tg-less.

Meanwhile, the cured product of the alkoxysilylated epoxy compound itself (a cured product excluding the inorganic material) according to the present invention may have a CTE of 50 ppm/° C. to 150 ppm/° C. For example, when the epoxy compound comprises one alkoxysilyl group, the CTE may be 50 ppm/° C. to 110 ppm/° C. When the epoxy compound comprises two alkoxysilyl groups, the CTE may be 80 ppm/° C. to 150 ppm/° C.

Hereinafter, the present invention will be described in detail referring to exemplary embodiments. The following embodiments may be illustrated as examples, but may not limit the present invention.

Synthetic Example AI-1

Synthesis of Mono-Alkoxysilylated Epoxy Compound Using Dihydroxynaphthalene (1) $1^{st}$ step: Synthesis of 5-(allyloxy)naphthalene-1-ol Into a 1,000 ml two-necked flask equipped with a refluxing condenser, 20.0 g of 1,5-dihydroxynaphthalene (Sigma-Aldrich), 51.81 g of $K_2CO_3$, and 500 ml of acetone were charged and mixed at room temperature. Then, the reaction temperature was set to 80° C., and homogeneous mixture was refluxed (hereinafter, the temperature written during the synthesis represents the set temperature of the refluxing apparatus and was higher than about 10° C. to 15° C. than true reaction temperature of reaction medium). During the refluxing, 13.5 ml of allyl bromide (Sigma-Aldrich) was added in a dropwise manner and allowed to react overnight. After finishing the reaction, the reaction mixture was cooled to room temperature and was filtered using Celite. The solvent was evaporated to obtain a coarse product. A reaction product was extracted from the coarse product using ethyl acetate, washed three times using water, and dried using $MgSO_4$. $MgSO_4$ was filtered off, and solvents were removed by using an evaporator to obtain an intermediate product (11), 5-(allyloxy)naphthalene-1-ol. The reaction scheme in the $1^{st}$ step and the NMR data of the intermediate product (11) thus obtained are as follows.

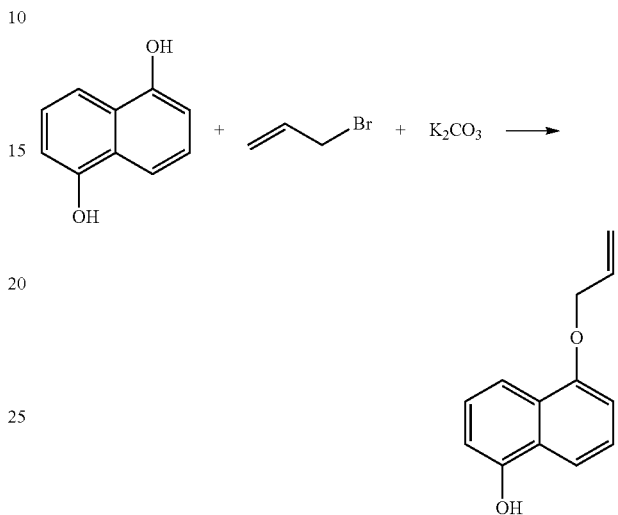

$^{1}$H NMR (400 MHz, $CDCl_3$): δ=4.70 (dt, J=5.2 Hz, 1.6 Hz, 2H), 5.33-5.34 (m, 1H), 5.49-5.53 (m, 2H), 6.12-6.20 (m, 1H), 6.82-6.91 (m, 2H), 7.32-7.43 (m, 2H), 7.72 (d, J=8.8 Hz, 1H), 7.89 (d, J=8.8 Hz, 1H).

(2) $2^{nd}$ step: Synthesis of 2-allylnaphthalene-1,5-diol

Into a 1,000 ml two-necked flask equipped with a refluxing condenser, 10.0 g of the intermediate product (11) obtained in the $1^{st}$ step and 50 ml of 1,2-dichlorobenzene (Sigma-Aldrich) were charged, and mixed at room temperature. The homogenized reaction solution thus obtained was refluxed for 8 hours at 190° C. After finishing the reaction, the reaction mixture was cooled to room temperature, and solvents were removed in a vacuum oven to obtain 2-allylnaphthalene-1,5-diol. The reaction scheme of the $2^{nd}$ step and the NMR data of the intermediate product (12) thus obtained are as follows.

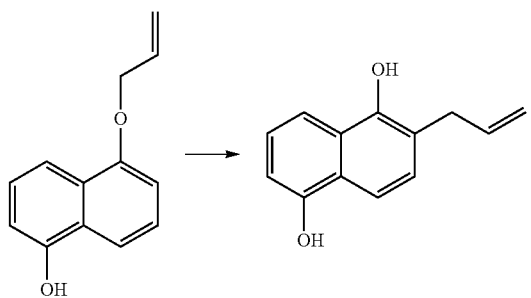

$^{1}$H NMR (400 MHz, $CDCl_3$): δ=3.57 (d, J=5.8 Hz, 2H), 5.09-5.25 (m, 2H), 5.50 (s, 2H), 6.02-6.12 (m, 1H), 6.84 (d, J=8.2 Hz, 1H), 7.19 (d, J=8.5 Hz, 1H), 7.68-7.72 (m, 2H), 7.89 (d, J=8.8 Hz, 1H).

(3) 3$^{rd}$ step: Synthesis of 2,2'-(2-allylnaphthalene-1,5-diyl)bis(oxy)bis(methylene)dioxirane Into a 1,000 ml two-necked flask equipped with a refluxing condenser, 7.0 g of the intermediate product (12) obtained in the 2$^{nd}$ step, 22.75 ml of epichlorohydrin (Sigma-Aldrich), 25.95 g of K$_2$CO$_3$, and 200 ml of acetonitrile were charged and mixed at room temperature. Then, the temperature was increased to 80° C. and the mixture was allowed to react overnight. After finishing the reaction, the reaction mixture was cooled to room temperature and was filtered using Celite. The solvents were evaporated to obtain an intermediate product (13). The reaction scheme of the 3$^{rd}$ step and the NMR data of the intermediate product (13) thus obtained are as follows.

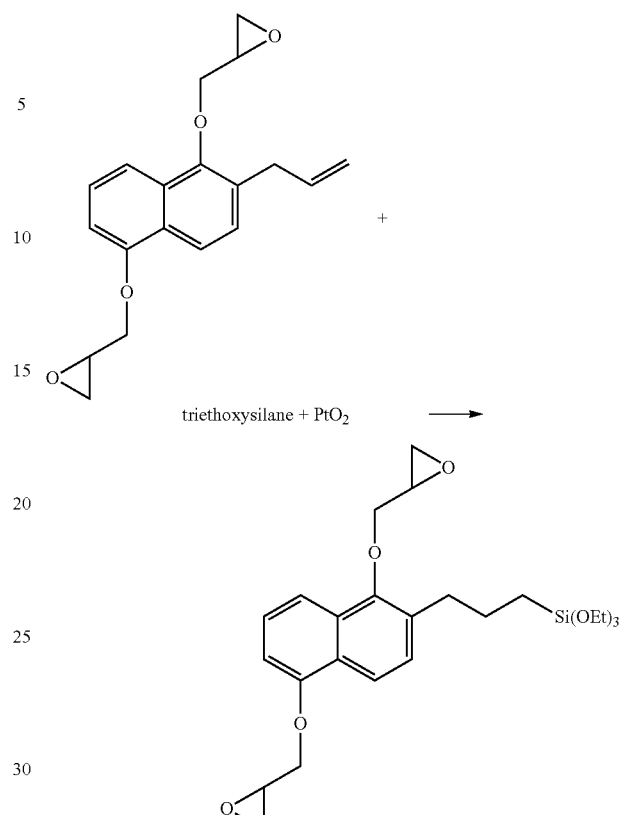

$^1$H NMR (400 MHz, CDCl$_3$): δ=2.76 (dd, J=2.6 Hz, 2H), 2.88 (dd, J=4.2 Hz, 2H), 3.10-3.35 (m, 4H), 3.96 (dd, J=5.4 Hz, 2H), 4.13 (dd, J=3.2 Hz, 2H), 4.96-5.03 (m, 2H), 5.91-6.03 (m, 1H), 6.84 (d, J=8.2 Hz, 1H), 7.19 (d, J=8.5 Hz, 1H), 7.28-7.38 (m, 2H), 7.90 (d, J=8.8 Hz, 1H).

(4) 4$^{th}$ step: Synthesis of (3-(1,5-bis(oxirane-2-ylmethoxy)naphthalene-2-yl)propyl)triethoxysilane Into a 250 ml flask, 10.0 g of the intermediate product (13) obtained in the 3$^{rd}$ step, 6.62 ml of triethoxysilane (Sigma-Aldrich), 58 mg of platinum oxide, and 100 ml of toluene were charged and mixed—homogeneously. The reaction mixture was stirred under argon gas at 85° C. for 24 hours. After finishing the reaction, the coarse product thus obtained was celite filtered, and solvents were removed by using an evaporator to obtain a target product of naphthalene epoxy having an alkoxysilyl group. The reaction scheme of the 4$^{th}$ step and the NMR data of the target product thus obtained are as follows.

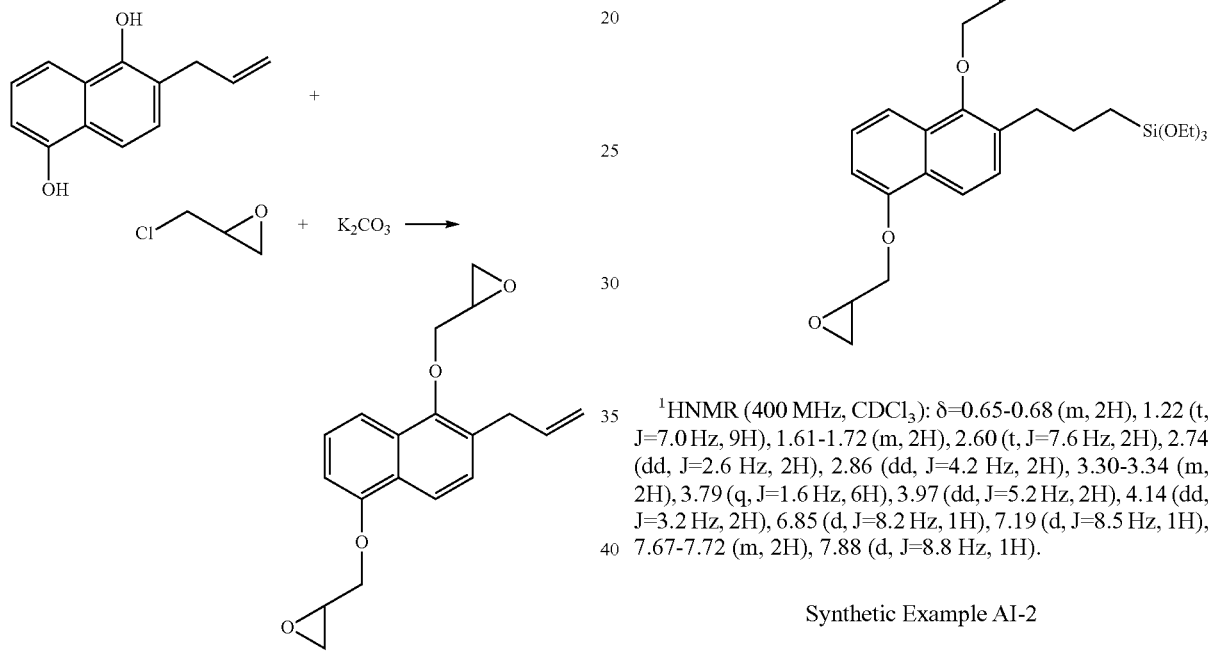

$^1$HNMR (400 MHz, CDCl$_3$): δ=0.65-0.68 (m, 2H), 1.22 (t, J=7.0 Hz, 9H), 1.61-1.72 (m, 2H), 2.60 (t, J=7.6 Hz, 2H), 2.74 (dd, J=2.6 Hz, 2H), 2.86 (dd, J=4.2 Hz, 2H), 3.30-3.34 (m, 2H), 3.79 (q, J=1.6 Hz, 6H), 3.97 (dd, J=5.2 Hz, 2H), 4.14 (dd, J=3.2 Hz, 2H), 6.85 (d, J=8.2 Hz, 1H), 7.19 (d, J=8.5 Hz, 1H), 7.67-7.72 (m, 2H), 7.88 (d, J=8.8 Hz, 1H).

Synthetic Example AI-2

Synthesis of Di-Alkoxysilylated Epoxy Compound Using Dihydroxynaphthalene (1) 1$^{st}$ step: Synthesis of 1,5-bis(allyloxy)naphthalene Into a 1,000 ml two-necked flask equipped with a refluxing condenser, 20.0 g of 1,5-dihydroxynaphthalene (Sigma-Aldrich), 27.0 ml of allyl bromide (Sigma-Aldrich), 103.61 g of K$_2$CO$_3$, and 500 ml of acetone were charged and mixed at room temperature. Then, the reaction temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 1,5-bis(allyloxy)naphthalene. The reaction scheme of the 1$^{st}$ step and the NMR data of the intermediate product (11) thus obtained are as follows.

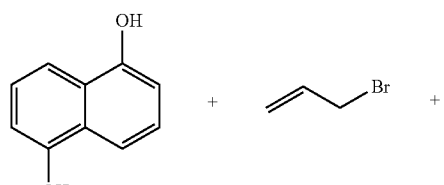

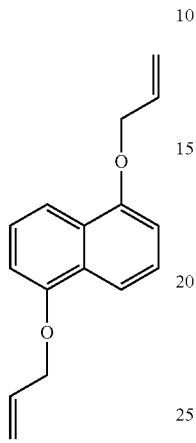

<sup>1</sup>H NMR (400 MHz, CDCl₃): δ=4.70 (dt, J=5.2 Hz, 1.6 Hz, 4H), 5.32-5.34 (m, 2H), 5.49-5.54 (m, 2H), 6.12-6.21 (m, 2H), 6.84 (d, J=8.0 Hz, 2H), 7.35 (dd, J=7.6, 0.8 Hz, 2H), 7.89 (d, J=8.8 Hz, 2H).

(2) 2$^{nd}$ step: Synthesis of 2,6-diallylnaphthalene-1,5-diol

Into a 1,000 ml two-necked flask equipped with a refluxing condenser, 20.0 g of the intermediate product (11) obtained in the 1$^{st}$ step and 100 ml of 1,2-dichlorobenzene (Sigma-Aldrich) were charged, and mixed at room temperature. The homogenized reaction solution thus obtained was refluxed for 8 hours at 190° C. After finishing the reaction, the reaction mixture was cooled to room temperature, and solvent was removed in a vacuum oven to obtain an intermediate product (12), 2,6-diallylnaphthalene-1,5-diol. The reaction scheme of the 2$^{nd}$ step and the NMR data of the intermediate product (12) thus obtained are as follows.

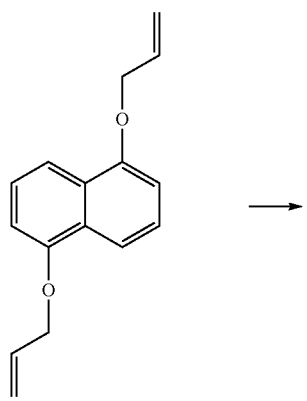

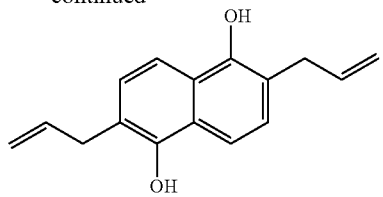

<sup>1</sup>H NMR (400 MHz, CDCl₃): δ=3.57 (dt, J=6.4 Hz, 1.6 Hz, 4H), 5.21-5.27 (m, 4H), 5.50 (s, 2H), 6.02-6.12 (m, 2H), 7.21 (d, J=8.4 Hz, 2H), 7.70 (d, J=8.4 Hz, 2H).

(3) 3$^{rd}$ step: Synthesis of 2,2'-(2,6-diallylnaphthalene-1,5-diyl)bis(oxy)bis(methylene)dioxirane Into a 1,000 ml two-necked flask equipped with a refluxing condenser, 20.0 g of the intermediate product (12) obtained in the 2$^{nd}$ step, 65.07 ml of epichlorohydrin (Sigma-Aldrich), 74.15 g of K₂CO₃, and 300 ml of acetonitrile were charged and mixed at room temperature. Then, the temperature was increased to 80° C. and the mixture was allowed to react overnight. After finishing the reaction, the reaction mixture was cooled to room temperature and was filtered using Celite. The solvent was evaporated to obtain an intermediate product (13). The reaction scheme of the 3$^{rd}$ step and the NMR data of the intermediate product (13) thus obtained are as follows.

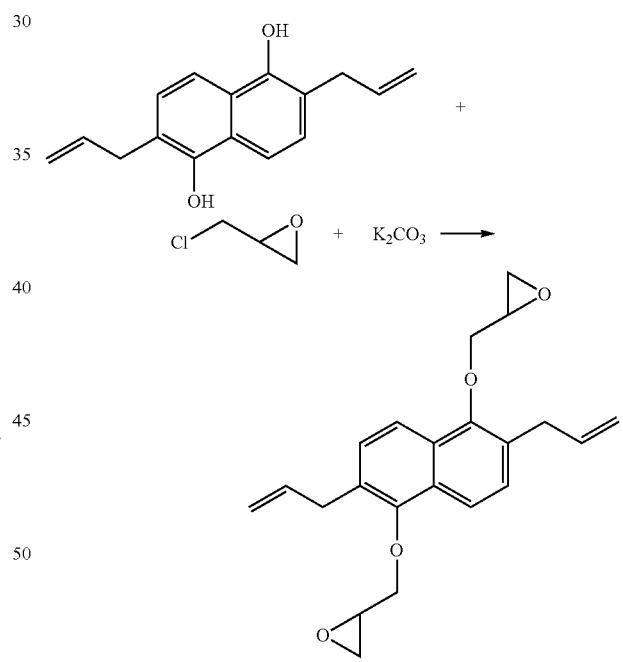

<sup>1</sup>H NMR (400 MHz, CDCl₃): δ=2.77 (dd, J=2.6 Hz, 2H), 2.93 (dd, J=4.4 Hz, 2H), 3.44-3.48 (m, 2H), 3.61 (d, J=6.4 Hz, 4H), 3.91 (dd, J=6.0 Hz, 2H), 4.24 (dd, J=2.8 Hz, 2H), 5.07-5.12 (m, 4H), 5.98-6.08 (m, 2H), 7.34 (d, J=8.4 Hz, 2H), 7.88 (d, J=8.4 Hz, 2H).

(4) 4$^{th}$ step: Synthesis of (3,3'-(1,5-bis(oxirane-2-ylmethoxy)naphthalene-2,6-diyl)bis(propane-3,1-diyl)bis(triethoxysilane)

Into a 500 ml flask, 20.0 g of the intermediate product (13) obtained in the 3$^{rd}$ step, 23.50 ml of triethoxysilane (Sigma- Aldrich), 200 mg of platinum oxide, and 200 ml of toluene were charged, and stirred under argon gas at 85° C. for 24 hours. After finishing the reaction, the coarse product thus obtained was celite filtered, and solvents were removed by using an evaporator to obtain a target product of naphthalene epoxy compound having an alkoxysilyl group. The reaction scheme of the 4$^{th}$ step and the NMR data of the target product thus obtained are as follows.

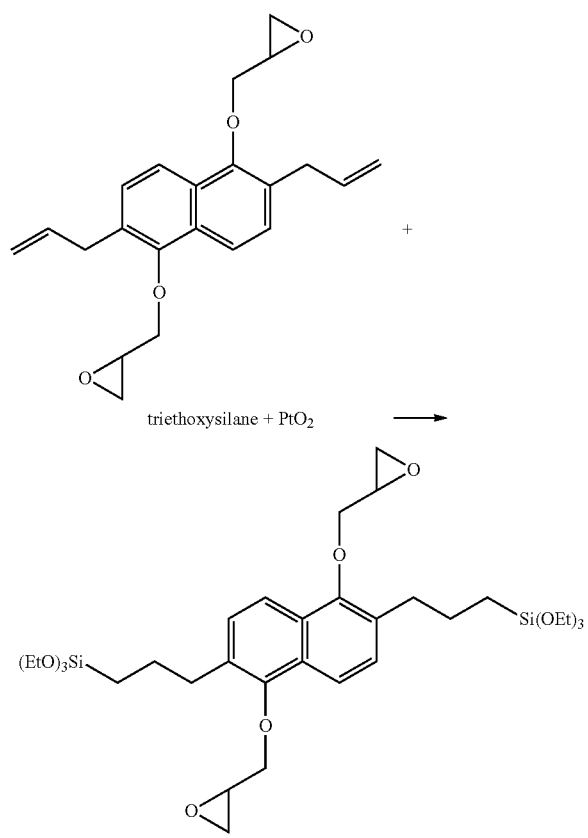

? indicates text missing or illegible when filed $^1$H NMR (400 MHz, CDCl$_3$): δ=0.64-0.69 (m, 4H), 1.20 (t, J=7.0 Hz, 18H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.79 (q, J=1.6 Hz, 12H), 3.97 (dd, J=5.2 Hz, 2H), 4.14 (dd, J=3.2 Hz, 2H), 7.28 (d, J=8.5 Hz, 2H), 7.75 (d, J=8.5 Hz, 2H).

Prediction Example AI-3

Synthesis of Tri-Alkoxysilylated Epoxy Compound Using Dihydroxynaphthalene (1) 1$^{st}$ step: Synthesis of 2,6-bis(allyloxy)naphthalene Into a 1,000 ml two-necked flask equipped with a refluxing condenser, 20.0 g of 2,6-dihydroxynaphthalene (Sigma-Aldrich), 27.0 ml of allyl bromide (Sigma-Aldrich), 103.61 g of K$_2$CO$_3$, and 500 ml of acetone were charged and mixed at room temperature. Then, the reaction temperature was set to 80° C., and the homogeneous mixture thus obtained was refluxed overnight. After finishing the reaction, the reaction mixture was cooled to room temperature and filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 2,6-bis(allyloxy)naphthalene. The reaction scheme in the 1$^{st}$ step is as follows.

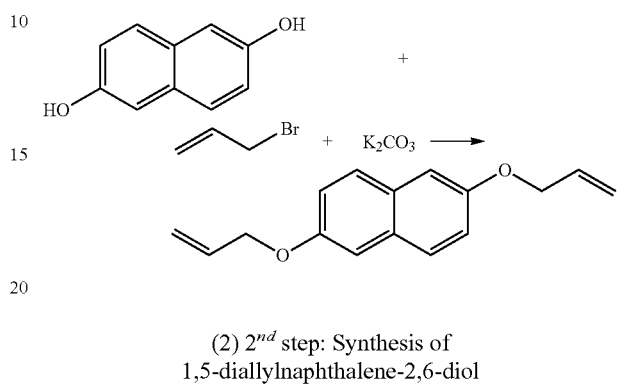

(2) 2$^{nd}$ step: Synthesis of 1,5-diallylnaphthalene-2,6-diol

Into a 1,000 ml two-necked flask equipped with a refluxing condenser, 20.0 g of the intermediate product (11) obtained in the 1$^{st}$ step and 100 ml of 1,2-dichlorobenzene (Sigma-Aldrich) are charged and mixed at room temperature. The homogenized reaction solution thus obtained is refluxed for 8 hours at 190° C. After finishing the reaction, the reaction mixture is cooled to room temperature, and solvents are is removed in a vacuum oven to obtain the intermediate product (12) of 1,5-diallylnaphthalene-2,6-diol. The reaction scheme of the 2$^{nd}$ step is as follows.

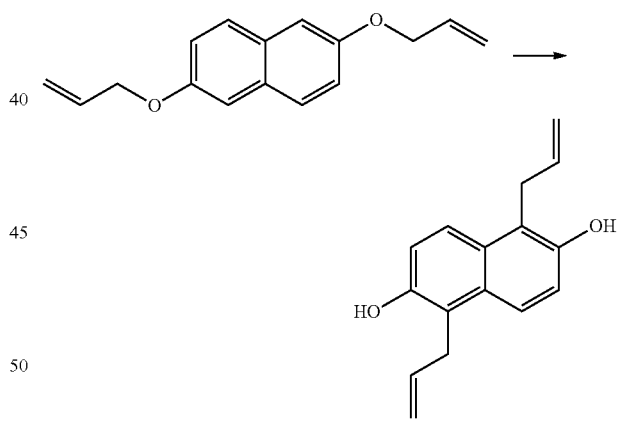

(3) 2-1-th step: Synthesis of 1,5-diallyl-6-(allyloxy)naphthalene-2-ol

Into a 1,000 ml two-necked flask equipped with a refluxing condenser, 20.0 g of the intermediate product (12) obtained in the 2$^{nd}$ step, 29.60 g of K$_2$CO$_3$, and 500 ml of acetone are charged and mixed at room temperature. Then, the temperature is set to 80° C., and the homogeneous mixture thus obtained is refluxed. During the refluxing, 6.78 ml of allyl bromide (Sigma-Aldrich) is added in a dropwise manner and the mixture is allowed to react overnight. After finishing the reaction, the reaction mixture is cooled to room temperature and filtered using Celite. The solvent is evaporated to obtain a coarse product. A target product is extracted from the coarse product using ethyl acetate, washed three times using water, and dried using MgSO$_4$. MgSO$_4$ is filtered off, and solvents are removed by using an evaporator. The product is purified by silica gel chromatography to obtain an intermediate product (23), 1,5-diallyl-6-(allyloxy)naphthalene-2-ol. The reaction scheme of the 2-1-th step is as follows.

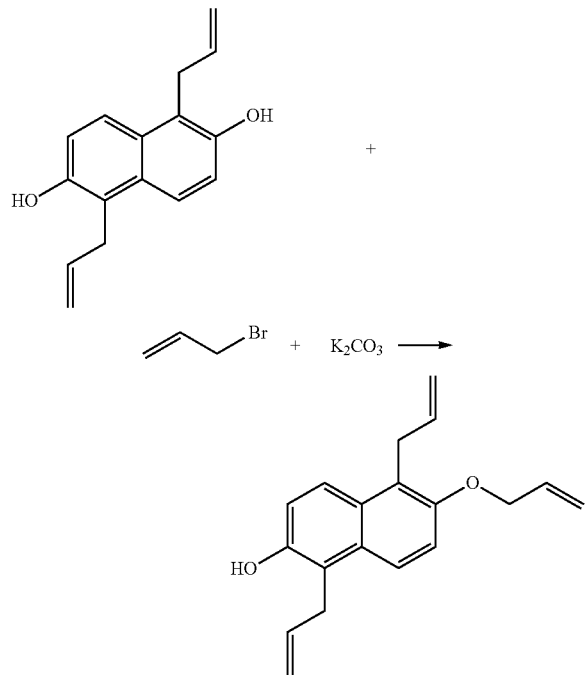

(4) 2-2-th step: Synthesis of 1,3,5-triallylnaphthalene-2,6-diol

Into a 1,000 ml two-necked flask equipped with a refluxing condenser, 20.0 g of the intermediate product (23) obtained in the 2-1-th step and 100 ml of 1,2-dichlorobenzene (Sigma-Aldrich) are charged and mixed at room temperature. The homogenized reaction solution thus obtained is refluxed for 8 hours at 190° C. After finishing the reaction, the reaction mixture is cooled to room temperature, and solvent are is removed in a vacuum oven to obtain an intermediate product (24) of 1,3,5-triallylnaphthalene-2,6-diol. The reaction scheme of the 2-2-th step is as follows.

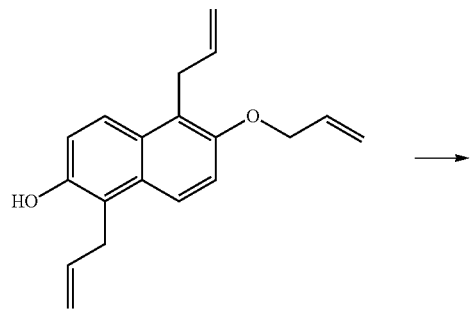

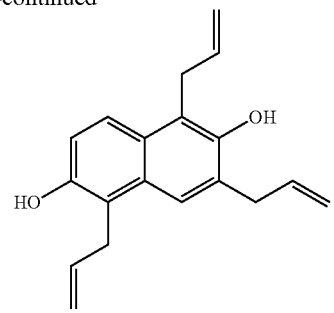

(5) 3$^{rd}$ step: Synthesis of 2,2'-(1,3,5-triallylnaphthalene-2,6-diyl)bis(oxy)bis(methylene)dioxirane Into a 1,000 ml two-necked flask equipped with a refluxing condenser, 20.0 g of the intermediate product (24) obtained in the 2-2-th step, 55.76 ml of epichlorohydrin (Sigma-Aldrich), 64.49 g of K$_2$CO$_3$, and 300 ml of acetonitrile are charged and mixed at room temperature. Then, the temperature is increased to 80° C. and the mixture is allowed to react overnight. After finishing the reaction, the reaction mixture is cooled to room temperature, and filtered using Celite. The solvent is evaporated to obtain an intermediate product (25), 2,2'-(1,3,5-triallylnaphthalene-2,6-diyl)bis(oxy)bis(methylene)dioxirane. The reaction scheme of the 3$^{rd}$ step is as follows.

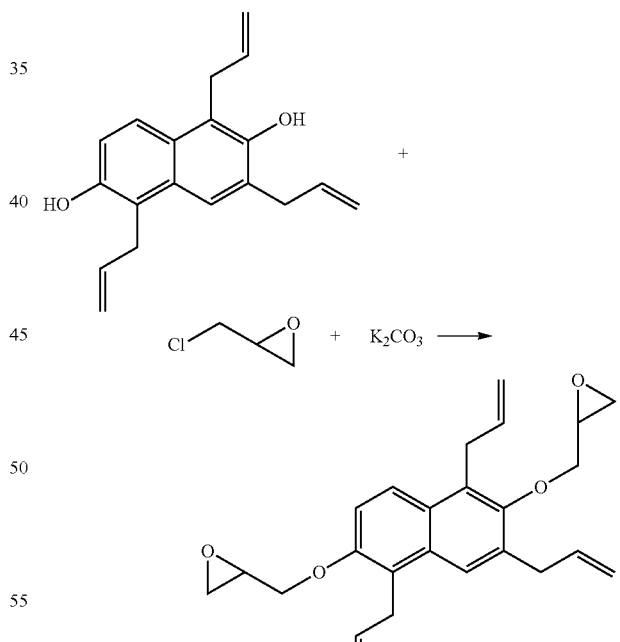

(6) 4$^{th}$ step: Synthesis of (3,3',3''-(2,6-bis(oxirane-2-ylmethoxy)naphthalene-1,3,5-triyl)tris(propane-3,1-diyl)tris(triethoxysilane)

Into a 500 ml flask, 20.0 g of the intermediate product, 2,2'-(1,3,5-triallylnaphthalene-2,6-diyl)bis(oxy)bis(methylene)dioxirane obtained in the 3$^{rd}$ step, 31.06 ml of triethoxysilane (Sigma-Aldrich), 348 mg of platinum oxide, and 200 ml of toluene are charged, and stirred under argon gas at 85° C. for 24 hours. After finishing the reaction, the coarse product thus obtained is celite filtered, and solvent are is removed by using an evaporator to obtain a target product of naphthalene epoxy compound having an alkoxysilyl group. The reaction scheme of the 4$^{th}$ step and the NMR data of the target product thus obtained are as follows.

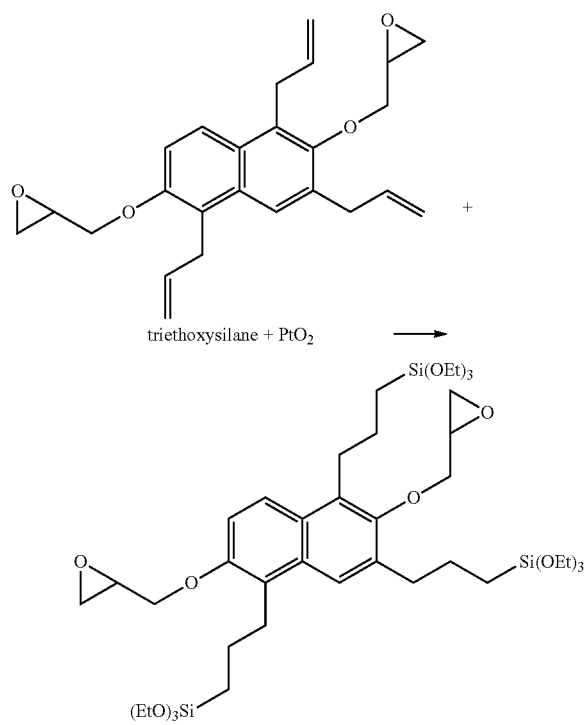

$^1$H NMR (400 MHz, CDCl$_3$): δ=0.65-0.70 (m, 6H), 1.20-1.25 (t, 27H), 1.60-1.70 (m, 6H), 2.60-2.65 (t, 6H), 2.80-2.85 (m, 2H), 2.90-2.95 (m, 2H), 3.40-3.45 (m, 2H), 3.75-3.80 (q, 18H), 4.00-4.05 (m, 2H), 4.30-4.35 (m, 2H), 6.80-7.20 (d, 1H), 7.60-7.65 (s, 1H), 7.65-7.70 (s, 1H).

Prediction Example AI-4

Synthesis of Tetra-Alkoxysilylated Epoxy Compound Using Dihydroxynaphthalene (1) 1$^{st}$ step: Synthesis of 2,6-bis(allyloxy)naphthalene Into a 1,000 ml two-necked flask equipped with a refluxing condenser, 20.0 g of 2,6-dihydroxynaphthalene (Sigma-Aldrich), 27.0 ml of allyl bromide (Sigma-Aldrich), 103.61 g of K$_2$CO$_3$, and 500 ml of acetone are charged and mixed at room temperature. Then, the temperature was set to 80° C., and the homogeneous mixture thus obtained is refluxed overnight. After finishing the reaction, the reaction mixture is cooled to room temperature and filtered using Celite. Organic solvent is evaporated to obtain a coarse product. A target product is extracted from the coarse product using ethyl acetate, washed three times using water, and dried using MgSO$_4$. MgSO$_4$ is filtered off, and solvents are removed by using an evaporator to obtain an intermediate product (11), 2,6-bis(allyloxy) naphthalene. The reaction scheme of the 1$^{st}$ step is as follows.

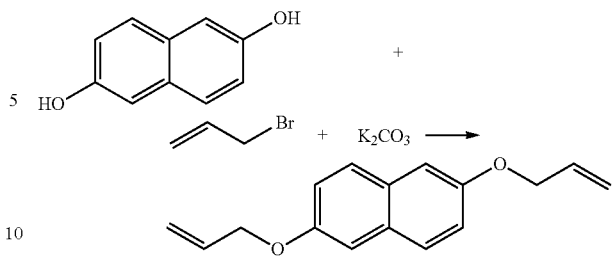

(2) 2$^{nd}$ step: Synthesis of 1,5-diallylnaphthalene-2,6-diol

Into a 1,000 ml two-necked flask equipped with a refluxing condenser, 20.0 g of the intermediate product (11) obtained in the 1$^{st}$ step and 100 ml of 1,2-dichlorobenzene (Sigma-Aldrich) are charged and mixed at room temperature. The homogenized reaction solution thus obtained is refluxed for 8 hours at 190° C. After finishing the reaction, the reaction mixture is cooled to room temperature, and solvent is removed in a vacuum oven to obtain the intermediate product (12), 1,5-diallylnaphthalene-2,6-diol. The reaction scheme of the 2$^{nd}$ step is as follows.

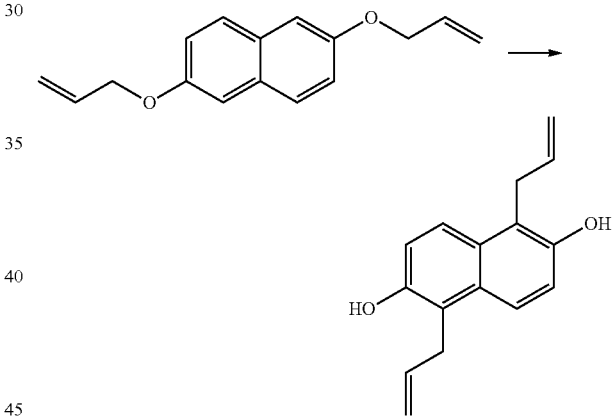

(3) 2-1-th step: Synthesis of 1,5-diallyl-2,6-bis(allyloxy)naphthalene

Into a 1,000 ml two-necked flask equipped with a refluxing condenser, 20.0 g of the intermediate product (12) obtained in the 2$^{nd}$ step, 27.0 ml of allyl bromide (Sigma-Aldrich), 103.61 g of K$_2$CO$_3$, and 500 ml of acetone are charged and mixed at room temperature. Then, the temperature is set to 80° C., and the homogeneous mixture thus obtained is refluxed overnight. After finishing the reaction, the reaction mixture is cooled to room temperature and filtered using Celite. The solvent is evaporated to obtain a coarse product. A target product is extracted from the coarse product using ethyl acetate, washed three times using water, and dried using MgSO$_4$. MgSO$_4$ is filtered off, and solvents are removed by using an evaporator to obtain an intermediate product (23), 1,5-diallyl-2,6-bis(allyloxy)naphthalene. The reaction scheme of the 2-1-th step is as follows.

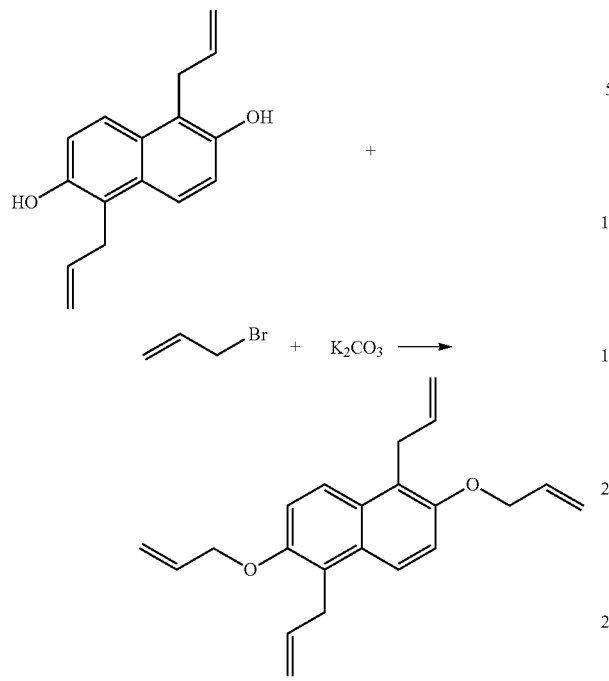

(4) 2-2-th step: Synthesis of
1,3,5,7-tetraallylnaphthalene-2,6-diol

Into a 1,000 ml two-necked flask equipped with a refluxing condenser, 20.0 g of the intermediate product (23) obtained in the 2-1-th step and 100 ml of 1,2-dichlorobenzene (Sigma-Aldrich) are charged, and mixed at room temperature. The homogenized reaction solution thus obtained is refluxed for 8 hours at 190° C. After finishing the reaction, the reaction mixture is cooled to room temperature, and solvent is removed in a vacuum oven to obtain an intermediate product (24) of 1,3,5,7-tetraallylnaphthalene-2,6-diol. The reaction scheme of the 2-2-th step is as follows.

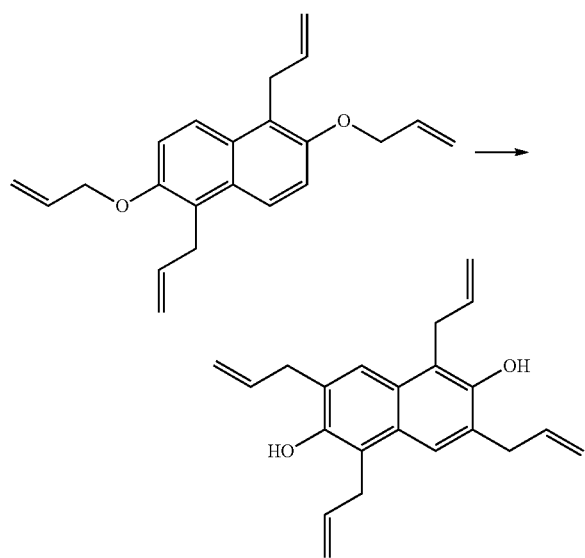

(5) 3$^{rd}$ step: Synthesis of 2,2'-(1,3,5,7-tetraallylnaphthalene-2,6-diyl)bis(oxy)bis(methylene)dioxirane Into a 1,000 ml two-necked flask equipped with a refluxing condenser, 20.0 g of the intermediate product (24) obtained in the 2-2-th step, 55.76 ml of epichlorohydrin (Sigma-Aldrich), 64.49 g of K$_2$CO$_3$, and 300 ml of acetonitrile are charged and mixed at room temperature. Then, the temperature is increased to 80° C. and the mixture is allowed to react overnight. After finishing the reaction, the reaction mixture is cooled to room temperature, and filtered using Celite. The solvent is evaporated to obtain an intermediate product (25), 2,2'-(1,3,5,7-tetraallylnaphthalene-2,6-diyl)bis(oxy)bis(methylene)dioxirane. The reaction scheme of the 3$^{rd}$ step is as follows.

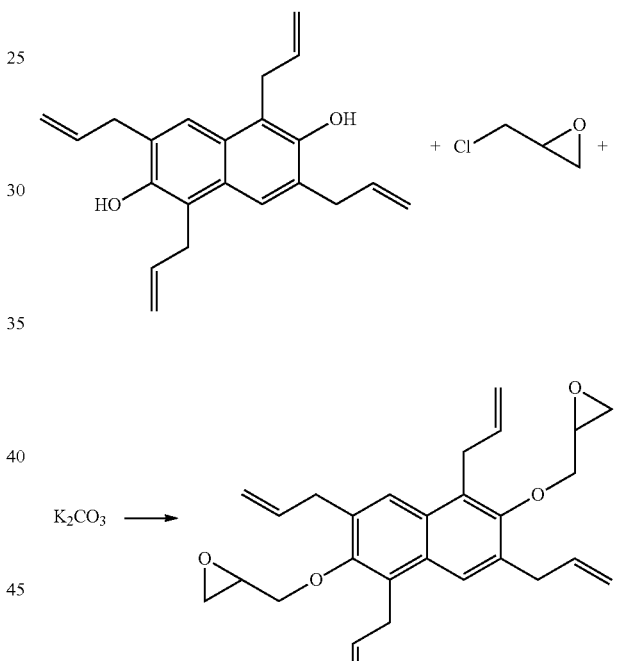

(6) 4$^{th}$ step: Synthesis of (3,3',3'',3'''-(2,6-bis(oxirane-2-ylmethoxy)naphthalene-1,3,5,7-tetrayl)tetrakis(propane-3,1-diyl)tetrakis(triethoxysilane)

Into a 500 ml flask, 20.0 g of the intermediate product (25) obtained in the 3$^{rd}$ step, 31.06 ml of triethoxysilane (Sigma-Aldrich), 348 mg of platinum oxide, and 200 ml of toluene are charged, and stirred under argon gas at 85° C. for 24 hours. After finishing the reaction, the coarse product thus obtained is celite filtered, and solvent is removed by using an evaporator to obtain a target product of naphthalene epoxy compound having an alkoxysilyl group. The reaction scheme of the 4$^{th}$ step and the NMR data of the target product thus obtained are as follows.

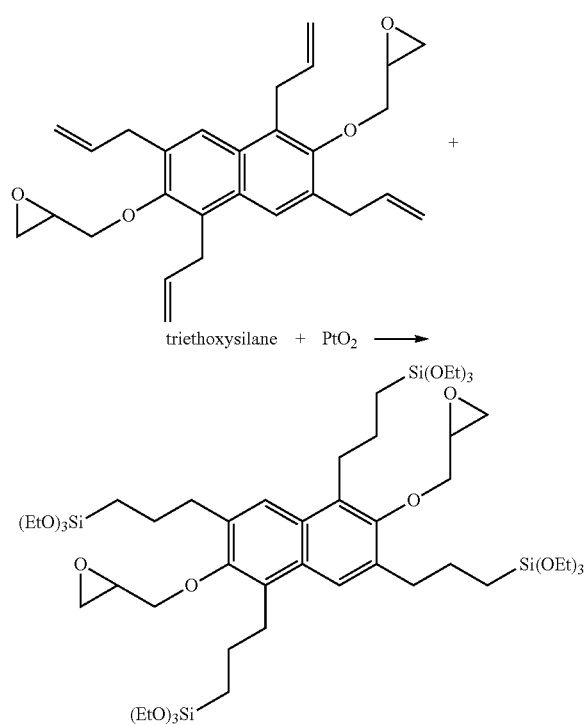

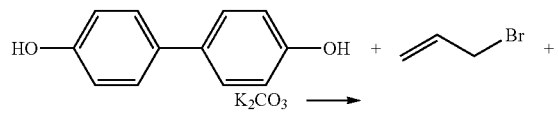

¹H NMR (400 MHz, CDCl₃): δ=0.65-0.70 (m, 8H), 1.20-1.25 (t, 36H), 1.60-1.70 (m, 8H), 2.60-2.65 (t, 8H), 2.80-2.85 (m, 2H), 2.90-2.95 (m, 2H), 3.40-3.45 (m, 2H), 3.75-3.80 (q, 24H), 4.00-4.05 (m, 2H), 4.30-4.35 (m, 2H), 7.60-7.65 (s, 1H), 7.65-7.70 (s, 1H).

Synthetic Example BI-1

Synthesis of Mono-Alkoxysilylated Epoxy Compound Using Dihydroxybiphenyl (1) 1$^{st}$ step: Synthesis of 4-(allylyloxy)biphenyl-4-ol Into a 1,000 ml two-necked flask equipped with a refluxing condenser, 10.0 g of biphenyl-4,4'-diol (Sigma-Aldrich), 22.28 g of K₂CO₃, and 500 ml of acetone were charged and mixed at room temperature. Then, the temperature was set to 80° C., and the homogeneous mixture thus obtained was refluxed. During the refluxing, 5.81 ml of allyl bromide (Sigma-Aldrich) was added in a dropwise manner and allowed to react overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO₄. MgSO₄ was filtered off, and solvents were removed by using an evaporator to obtain an intermediate product (11), 4-(allylyloxy)biphenyl-4-ol. The reaction scheme of the 1$^{st}$ step and the NMR data of the intermediate product (11) thus obtained are as follows.

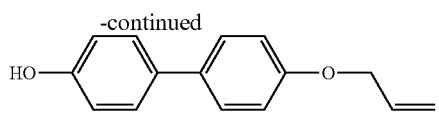

-continued

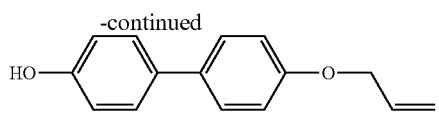

¹H NMR (400 MHz, CDCl₃): δ=4.56 (dt, J=5.2 Hz, 1.6 Hz, 2H), 5.30 (m, 2H), 5.41-5.45 (m, 1H), 6.03-6.12 (m, 1H), 6.86 (d, J=8.2 Hz, 2H), 7.02 (d, J=8.4 Hz, 2H), 7.46 (td, J=3.0, 2.2, 8.8 Hz, 4H).

(2) 2$^{nd}$ step: Synthesis of 3-allylbiphenyl-4,4'-diol

Into a 1,000 ml two-necked flask equipped with a refluxing condenser, 10.0 g of the intermediate product (11) obtained in the 1$^{st}$ step and 50 ml of 1,2-dichlorobenzene (Sigma-Aldrich) were charged, and mixed at room temperature. The homogenized reaction solution thus obtained was refluxed for 72 hours at 190° C. After finishing the reaction, the reaction mixture was cooled to room temperature, and solvent was removed in a vacuum oven to obtain 3-allylbiphenyl-4,4'-diol. The reaction scheme of the 2$^{nd}$ step and the NMR data of the intermediate product (12) thus obtained are as follows.

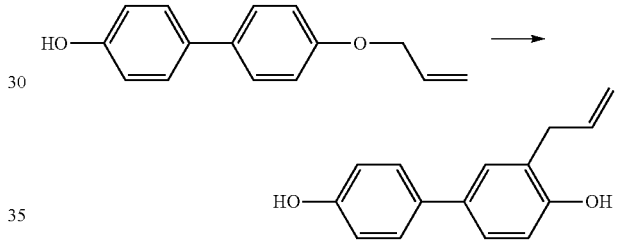

¹H NMR (400 MHz, CDCl₃): δ=3.35 (d, J=6.4 Hz, 2H), 5.08-5.12 (m, 4H), 5.99-6.07 (m, 1H), 6.85-6.90 (m, 3H), 7.30-7.39 (m, 4H).

(3) 3$^{rd}$ step: Synthesis of 2,2'-(3-allylbiphenyl-4,4'-diyl)bis(oxy)bis(methylene)dioxirane Into a 1,000 ml two-necked flask equipped with a refluxing condenser, 10.0 g of the intermediate product (12) obtained in the 2$^{nd}$ step, 30.38 ml of epichlorohydrin (Sigma-Aldrich), 35.13 g of K₂CO₃, and 300 ml of acetonitrile were charged and mixed at room temperature. Then, the temperature was increased to 80° C. and the mixture was allowed to react overnight. After finishing the reaction, the reaction mixture was cooled to room temperature and was filtered using Celite. The solvent was evaporated to obtain an intermediate product (13). The reaction scheme of the 3$^{rd}$ step and the NMR data of the intermediate product (13) thus obtained are as follows.

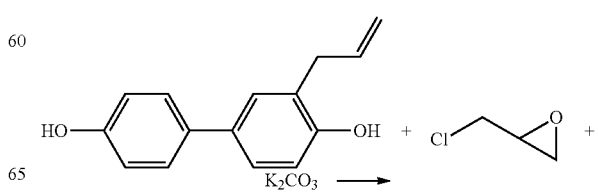

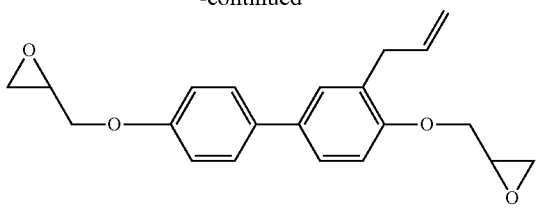

$^1$H NMR (400 MHz, CDCl$_3$): δ=2.75 (dd, J=2.6 Hz, 2H), 2.87 (dd, J=4.2 Hz, 2H), 3.10-3.35 (m, 4H), 3.96 (dd, J=5.4 Hz, 2H), 4.24 (dd, J=3.2 Hz, 2H), 4.97-5.03 (m, 2H), 5.93-6.03 (m, 1H), 6.86-6.95 (m, 3H), 7.31-7.40 (m, 4H).

(4) 4$^{th}$ step: Synthesis of (3-(4,4'-bis(oxirane-2-yl-methoxy)biphenyl-3-yl)propyl)triethoxysilane Into a 250 ml flask, 10.0 g of the intermediate 3rd product (13) obtained in the step, 4.84 ml of triethoxysilane (Sigma-Aldrich), 55 mg of platinum oxide (PtO$_2$), and 100 ml of toluene were charged and mixed homogeneously. The reaction mixture was stirred under argon gas at 85° C. for 24 hours. After finishing the reaction, the coarse product thus obtained was filtered using Celite, and solvent was removed by using an evaporator to obtain a target product of biphenyl epoxy compound having an alkoxysilyl group. The reaction scheme of the 4$^{th}$ step and the NMR data of the target product thus obtained are as follows.

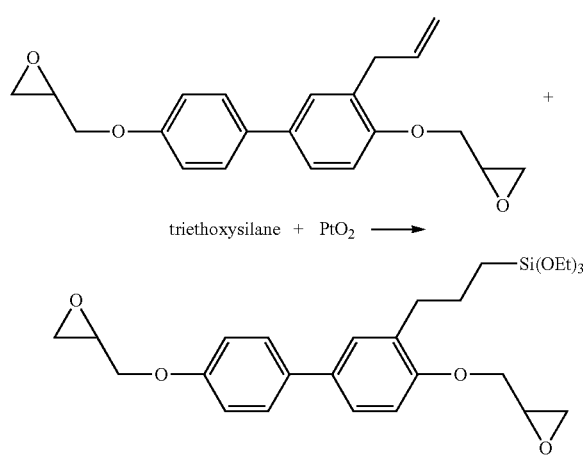

$^1$H NMR (400 MHz, CDCl$_3$): δ=0.64-0.69 (m, 2H), 1.20 (t, J=7.0 Hz, 9H), 1.62-1.72 (m, 2H), 2.61 (t, J=7.6 Hz, 2H), 2.74 (dd, J=2.6 Hz, 2H), 2.86 (dd, J=4.2 Hz, 2H), 3.30-3.34 (m, 2H), 3.79 (q, J=1.6 Hz, 6H), 3.97 (dd, J=5.2 Hz, 2H), 4.14 (dd, J=3.2 Hz, 2H), 6.88-6.97 (m, 3H), 7.30-7.43 (m, 4H).

Synthetic Example BI-2

Synthesis of Di-Alkoxysilylated Epoxy Compound Using Dihydroxybiphenyl (1) 1$^{st}$ step: Synthesis of 4,4'-bis(allylyloxy)biphenyl Into a 1,000 ml two-necked flask equipped with a refluxing condenser, 10.0 g of biphenyl-4,4'-diol (Sigma-Aldrich), 11.61 ml of allyl bromide (Sigma-Aldrich), 44.56 g of K$_2$CO$_3$, and 500 ml of acetone were charged and mixed at room temperature. Then, the temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 4,4'-bis(allylyloxy)biphenyl. The reaction scheme of the 1$^{st}$ step and the NMR data of the intermediate product (11) thus obtained are as follows.

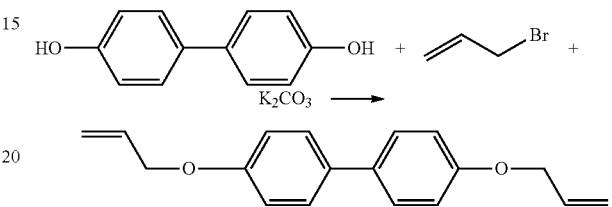

$^1$H NMR (400 MHz, CDCl$_3$): δ=4.56 (dt, J=5.2 Hz, 1.6 Hz, 4H), 5.30-5.33 (m, 2H), 5.41-5.44 (m, 2H), 6.03-6.12 (m, 2H), 6.96 (td, J=3.0, 2.2, 8.8 Hz, 4H), 7.46 (td, J=3.0, 2.2, 8.8 Hz, 4H).

(2) 2$^{nd}$ step: Synthesis of 3,3'-diallylbiphenyl-4,4'-diol

Into a 1,000 ml two-necked flask equipped with a refluxing condenser, 10.0 g of the intermediate product (11) obtained in the 1$^{st}$ step and 100 ml of 1,2-dichlorobenzene (Sigma-Aldrich) were charged and mixed at room temperature. The homogenized reaction solution thus obtained was refluxed for 72 hours at 190° C. After finishing the reaction, the reaction mixture was cooled to room temperature, and solvents were removed in a vacuum oven to obtain an intermediate product (12) of 3,3'-diallylbiphenyl-4,4'-diol. The reaction scheme of the 2$^{nd}$ step and the NMR data of the intermediate product (12) thus obtained are as follows.

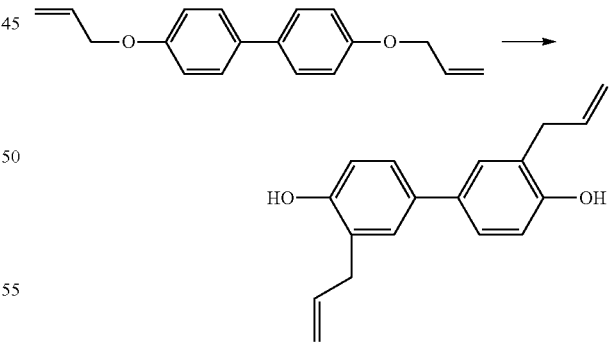

$^1$H NMR (400 MHz, CDCl$_3$): δ=3.35 (d, J=6.4 Hz, 4H), 5.14-5.25 (m, 6H), 6.00-6.10 (m, 2H), 6.84 (dd, J=2.0 Hz, 7.2 Hz, 2H), 7.29 (dd, J=10.6 Hz, 4H).

(3) 3$^{rd}$ step: Synthesis of 2,2'-(3,3'-diallylbiphenyl-4,4'-diyl)bis(oxy)bis(methylene)dioxirane Into a 1,000 ml two-necked flask equipped with a refluxing condenser, 10.0 g of the intermediate product (12) obtained in the 2nd step, 30.38 ml of epichlorohydrin (Sigma-Aldrich), 35.13 g of K₂CO₃, and 300 ml of acetonitrile were charged and mixed at room temperature. Then, the temperature was increased to 80° C. and the mixture was allowed to react overnight. After finishing the reaction, the reaction mixture was cooled to room temperature and was filtered using Celite. The solvent was evaporated to obtain an intermediate product (13). The reaction scheme of the 3rd step and the NMR data of the intermediate product (13) thus obtained are as follows.

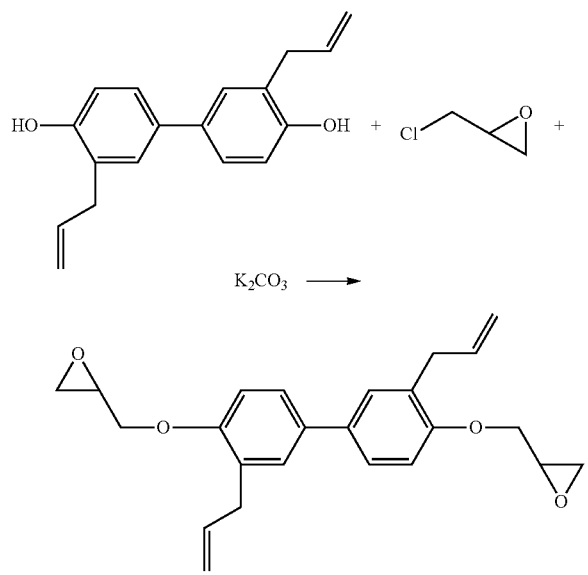

$^1$H NMR (400 MHz, CDCl$_3$): δ=2.75 (dd, J=2.6 Hz, 2H), 2.87 (dd, J=4.2 Hz, 2H), 3.11-3.35 (m, 6H), 3.96 (dd, J=5.4 Hz, 2H), 4.25 (dd, J=3.2 Hz, 2H), 5.03-5.13 (m, 4H), 5.93-6.03 (m, 2H), 6.81 (d, J=7.2 Hz, 2H), 7.34-7.42 (m, 4H).

(4) 4$^{th}$ step: Synthesis of (3,3'-(4,4'-bis(oxirane-2-ylmethoxy)biphenyl-3,3'-diyl)bis(propane-3,1-diyl) bis(triethoxysilane)

Into a 500 ml flask, 10.0 g of the intermediate product (13) obtained in the 3$^{rd}$, 9.67 ml of triethoxysilane (Sigma-Aldrich), 109 mg of platinum oxide, and 200 ml of toluene were charged and stirred under argon gas at 85° C. for 24 hours. After finishing the reaction, the coarse product thus obtained was filtered using Celite, and solvent was removed by using an evaporator to obtain a target product of biphenyl epoxy compound having an alkoxysilyl group. The reaction scheme of the 4$^{th}$ step and the NMR data of the target product thus obtained are as follows.

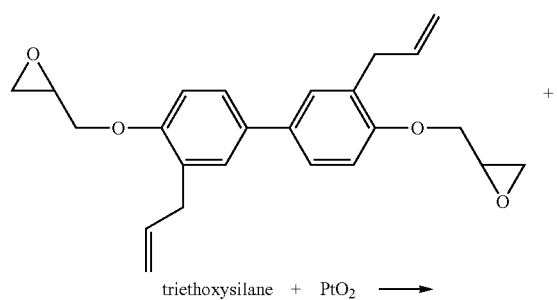

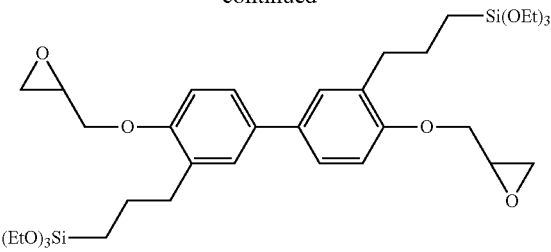

$^1$H NMR (400 MHz, CDCl$_3$): δ=0.64-0.69 (m, 4H), 1.20 (t, J=7.0 Hz, 18H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.79 (q, J=1.6 Hz, 12H), 3.97 (dd, J=5.2 Hz, 2H), 4.14 (dd, J=3.2 Hz, 2H), 6.85 (d, J=7.2 Hz, 2H), 7.32-7.42 (m, 4H).

Prediction Example BI-3

Synthesis of Tri-Alkoxysilylated Epoxy Compound Using Dihydroxybiphenyl (1) 1$^{st}$ step: Synthesis of 4,4'-bis(allylyloxy)biphenyl Into a 1,000 ml two-necked flask equipped with a refluxing condenser, 10.0 g of biphenyl-4,4'-diol (Sigma-Aldrich), 11.61 ml of allyl bromide (Sigma-Aldrich), 44.56 g of K₂CO₃, and 500 ml of acetone were charged and mixed at room temperature. Then, the temperature was set to 80° C., and the homogeneous mixture was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO₄. MgSO₄ was filtered off, and solvents were removed by using an evaporator to obtain an intermediate product (11), 4,4'-bis (allylyloxy)biphenyl. The reaction scheme of the 1$^{st}$ step and the NMR data of the intermediate product (11) are as follows.

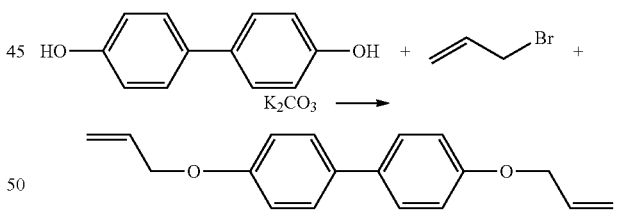

$^1$H NMR (400 MHz, CDCl$_3$): δ=4.56 (dt, J=5.2 Hz, 1.6 Hz, 4H), 5.30-5.33 (m, 2H), 5.41-5.44 (m, 2H), 6.03-6.12 (m, 2H), 6.96 (td, J=3.0, 2.2, 8.8 Hz, 4H), 7.46 (td, J=3.0, 2.2, 8.8 Hz, 4H).

(2) 2$^{nd}$ step: Synthesis of 3,3'-diallylbiphenyl-4,4'-diol

Into a 1,000 ml two-necked flask equipped with a refluxing condenser, 10.0 g of the intermediate product (11) obtained in the 1$^{st}$ step and 100 ml of 1,2-dichlorobenzene (Sigma-Aldrich) were charged and mixed at room temperature. The homogenized reaction solution thus obtained was refluxed for 72 hours at 190° C. After finishing the reaction, the reaction mixture was cooled to room temperature, and solvent was removed in a vacuum oven to obtain an intermediate product (12) of 3,3'-diallylbiphenyl-4,4'-diol. The reaction scheme of the 2$^{nd}$ step and the NMR data of the intermediate product (12) are as follows.

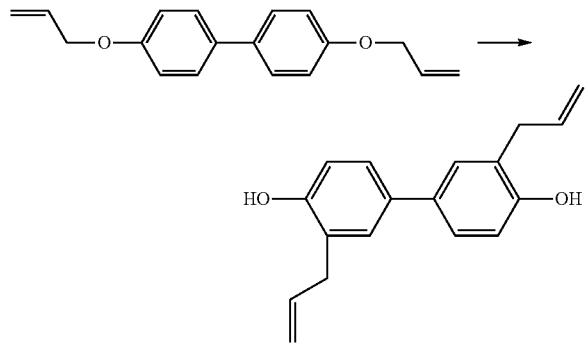

$^1$H NMR (400 MHz, CDCl$_3$): δ=3.35 (d, J=6.4 Hz, 4H), 5.14-5.25 (m, 6H), 6.00-6.10 (m, 2H), 6.84 (dd, J=2.0 Hz, 7.2 Hz, 2H), 7.29 (dd, J=10.6 Hz, 4H).

(3) 2-1-th step: Synthesis of 3,3'-diallyl-4'-(allyloxy)biphenyl-4-ol

Into a 1,000 ml two-necked flask equipped with a refluxing condenser, 20.0 g of the intermediate product (12) obtained in the 2$^{nd}$ step, 26.71 g of K$_2$CO$_3$, and 500 ml of acetone are charged and mixed at room temperature. Then, the temperature is set to 80° C., and the homogeneous mixture thus obtained is refluxed. During the refluxing, 6.12 ml of allyl bromide (Sigma-Aldrich) is added in a dropwise manner, and the mixture is allowed to react overnight. After finishing the reaction, the reaction mixture is cooled to room temperature and is filtered using Celite. The solvent is evaporated to obtain a coarse product. A target product is extracted from the coarse product using ethyl acetate, washed three times using water, and dried using MgSO$_4$. MgSO$_4$ is filtered off, and solvents are removed by using an evaporator. The product is purified by silica gel chromatography to obtain an intermediate product (23), 3,3'-diallyl-4'-(allyloxy)biphenyl-4-ol. The reaction scheme of the 2-1-th step is as follows.

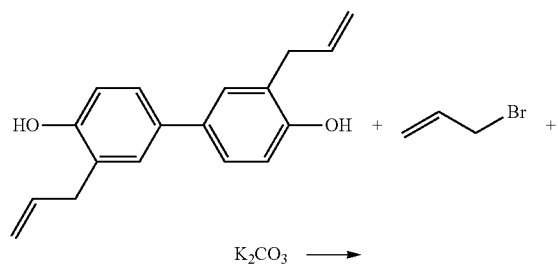

(4) 2-2-th step: Synthesis of 3,3',5-triallylbiphenyl-4,4'-diol

Into a 1,000 ml two-necked flask equipped with a refluxing condenser, 20.0 g of the intermediate product (23) obtained in the 2-1-th step and 100 ml of 1,2-dichlorobenzene (Sigma-Aldrich) are charged, and mixed at room temperature. The homogenized reaction solution thus obtained is refluxed for 8 hours at 190° C. After finishing the reaction, the reaction mixture is cooled to room temperature, and solvent is removed in a vacuum oven to obtain the intermediate product (24), 3,3',5-triallylbiphenyl-4,4'-diol. The reaction scheme of the 2-2-th step is as follows.

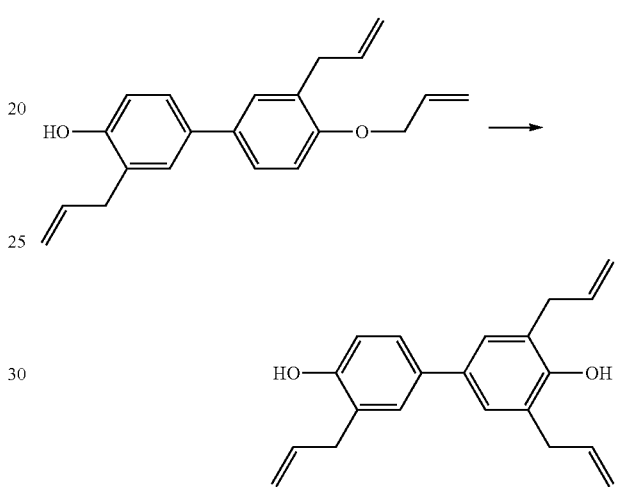

(5) 3$^{rd}$ step: Synthesis of 2,2'-(3,3',5-triallylbiphenyl-4,4'-diyl)bis(oxy)bis(methylene)dioxirane Into a 1,000 ml two-necked flask equipped with a refluxing condenser, 20.0 g of the intermediate product (24) obtained in the 2-2-th step, 50.31 ml of epichlorohydrin (Sigma-Aldrich), 58.18 g of K$_2$CO$_3$, and 300 ml of acetonitrile are charged and mixed at room temperature. Then, the temperature is increased to 80° C. and the mixture is allowed to react overnight. After finishing the reaction, the reaction mixture is cooled to room temperature and is filtered using Celite. The solvent is evaporated to obtain an intermediate product (25), 2,2'-(3,3',5-triallylbiphenyl-4,4'-diyl)bis(oxy)bis(methylene)dioxirane. The reaction scheme of the 3$^{rd}$ step is as follows.

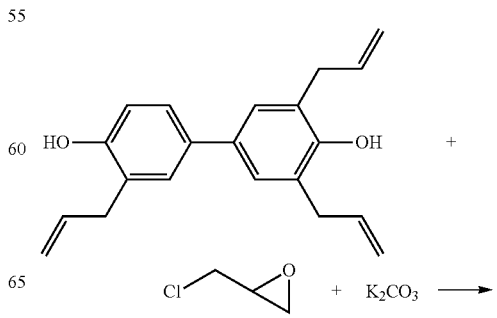

-continued

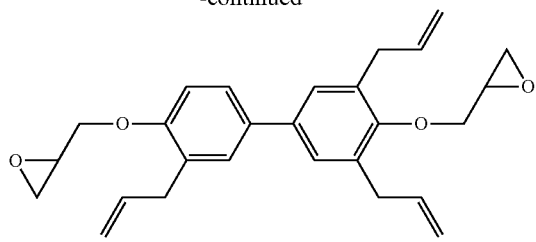

(6) 4^(th) step: Synthesis of (3,3',3''-(2,6-bis(oxirane-2-ylmethoxy)naphthalene-1,3,5-triyl)tris(propane-3,1-diyl))tris(triethoxysilane)

Into a 500 ml flask, 20.0 g of the intermediate product (23) obtained in the 3^(rd) step, 29.13 ml of triethoxysilane (Sigma-Aldrich), 326 mg of platinum oxide, and 200 ml of toluene are charged, and stirred under argon gas at 85° C. for 24 hours. After finishing the reaction, the coarse product thus obtained is filtered using Celite, and solvent is removed by using an evaporator to obtain a target product of biphenyl epoxy compound having an alkoxysilyl group. The reaction scheme of the 4^(th) step and the NMR data of the target product thus obtained are as follows.

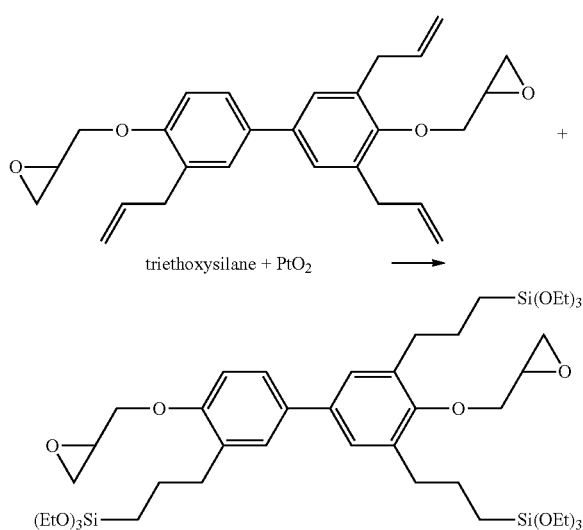

$^1$H NMR (400 MHz, CDCl$_3$): δ=0.60-0.70 (m, 6H), 1.20-1.25 (t, 27H), 1.60-1.70 (m, 6H), 2.50-2.70 (t, 6H), 2.70-2.80 (m, 2H), 2.80-2.90 (m, 2H), 3.30-3.40 (m, 2H), 3.70-4.00 (m, 20H), 4.10-4.20 (m, 2H), 6.90-7.50 (m, 5H).

Prediction Example BI-4

Synthesis of Tetra-Alkoxysilylated Epoxy Compound Using Dihydroxybiphenyl (1) 1^(st) step: Synthesis of 4,4'-bis(allylyloxy)biphenyl Into a 1,000 ml two-necked flask equipped with a refluxing condenser, 10.0 g of biphenyl-4,4'-diol (Sigma-Aldrich), 11.61 ml of allyl bromide (Sigma-Aldrich), 44.56 g of K$_2$CO$_3$, and 500 ml of acetone were charged and mixed at room temperature. Then, the temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 4,4'-bis(allylyloxy)biphenyl. The reaction scheme of the 1^(st) step and the NMR data of the intermediate product (11) were as follows.

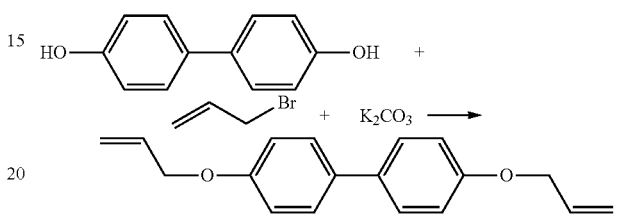

$^1$H NMR (400 MHz, CDCl$_3$): δ=4.56 (dt, J=5.2 Hz, 1.6 Hz, 4H), 5.30-5.33 (m, 2H), 5.41-5.44 (m, 2H), 6.03-6.12 (m, 2H), 6.96 (td, J=3.0, 2.2, 8.8 Hz, 4H), 7.46 (td, J=3.0, 2.2, 8.8 Hz, 4H).

(2) 2^(nd) step: Synthesis of 3,3'-diallylbiphenyl-4,4'-diol

Into a 1,000 ml two-necked flask equipped with a refluxing condenser, 10.0 g of the intermediate product (11) obtained in the 1^(st) step and 100 ml of 1,2-dichlorobenzene (Sigma-Aldrich) were charged and mixed at room temperature. The homogenized reaction solution thus obtained was refluxed for 72 hours at 190° C. After finishing the reaction, the reaction mixture was cooled to room temperature, and solvent was removed in a vacuum oven to obtain an intermediate product (12) of 3,3'-diallylbiphenyl-4,4'-diol. The reaction scheme of the 2^(nd) step and the NMR data of the intermediate product (12) were as follows.

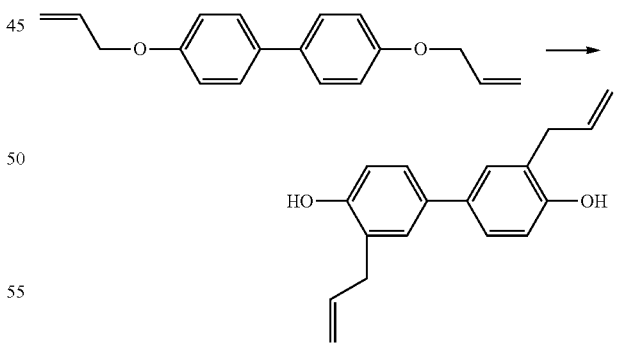

$^1$H NMR (400 MHz, CDCl$_3$): δ=3.35 (d, J=6.4 Hz, 4H), 5.14-5.25 (m, 6H), 6.00-6.10 (m, 2H), 6.84 (dd, J=2.0 Hz, 7.2 Hz, 2H), 7.29 (dd, J=10.6 Hz, 4H).

(3) 2-1-th step: Synthesis of 3,3'-diallyl-4,4'-bis(allyloxy)biphenyl

Into a 1,000 ml two-necked flask equipped with a refluxing condenser, 20.0 g of the intermediate product (12) obtained in the 2$^{nd}$ step, 24.40 ml of allyl bromide (Sigma-Aldrich), 93.47 g of K$_2$CO$_3$, and 500 ml of acetone are charged and mixed at room temperature. Then, the homogeneous mixture thus obtained is refluxed overnight at 80° C. After finishing the reaction, the reaction mixture is cooled to room temperature and is filtered using Celite. The solvent is evaporated to obtain a coarse product. A target product is extracted from the coarse product using ethyl acetate, washed three times using water, and dried using MgSO$_4$. MgSO$_4$ is filtered off, and solvents are removed by using an evaporator to obtain an intermediate product (23), 3,3'-diallyl-4,4'-bis(allyloxy)biphenyl. The reaction scheme of the 2-1-th step is as follows.

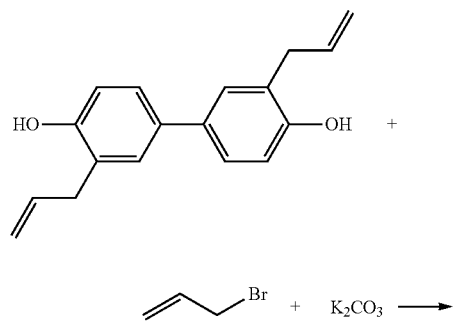

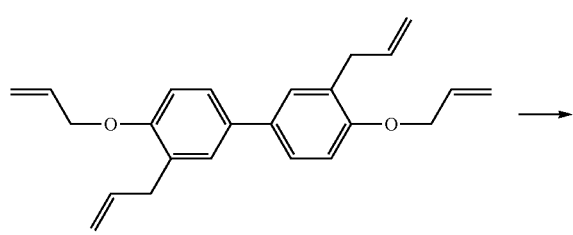

(4) 2-2-th step: Synthesis of 3,3',5,5'-tetraallylbiphenyl-4,4'-diol

Into a 1,000 ml two-necked flask equipped with a refluxing condenser, 20.0 g of the intermediate product (23) obtained in the 2-1-th step and 100 ml of 1,2-dichlorobenzene (Sigma-Aldrich) are charged and mixed at room temperature. The homogenized reaction solution thus obtained is refluxed for 8 hours at 190° C. After finishing the reaction, the reaction mixture is cooled to room temperature, and solvent is removed in a vacuum oven to obtain the intermediate product (24), 3,3',5,5'-tetraallylbiphenyl-4,4'-diol. The reaction scheme of the 2-2-th step is as follows.

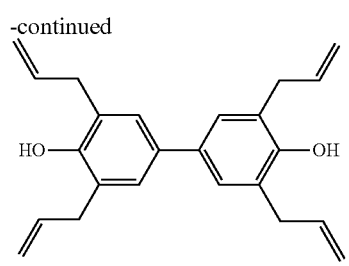

(5) 3$^{rd}$ step: Synthesis of 2,2'-(3,3',5,5'-tetraallylbiphenyl-4,4'-diyl)bis(oxy)bis(methylene)dioxirane Into a 1,000 ml two-necked flask equipped with a refluxing condenser, 20.0 g of the intermediate product (24) obtained in the 2-2-th step, 55.76 ml of epichlorohydrin (Sigma-Aldrich), 64.49 g of K$_2$CO$_3$, and 300 ml of acetonitrile are charged and mixed at room temperature. Then, the temperature is increased to 80° C. and the mixture is allowed to react overnight. After finishing the reaction, the reaction mixture is cooled to room temperature and is filtered using Celite. The solvent is evaporated to obtain an intermediate product (25), 2,2'-(3,3',5,5'-tetraallylbiphenyl-4,4'-diyl)bis(oxy)bis(methylene)dioxirane. The reaction scheme of the 3$^{rd}$ step is as follows.

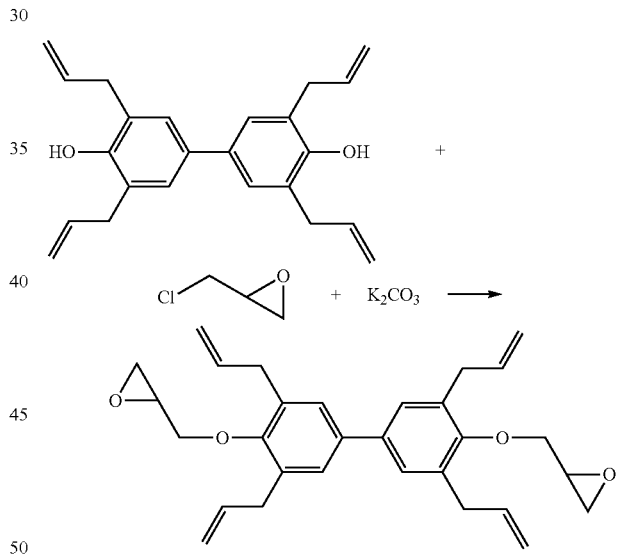

(6) 4$^{th}$ step: Synthesis of (3,3',3",3'"-(4,4'-bis(oxirane-2-ylmethoxy)biphenyl-3,3',5,5'-tetrayl)tetrakis(propane-3,1-diyl)tetrakis(triethoxysilane)

Into a 500 ml flask, 20.0 g of the intermediate product (25) obtained in the 3$^{rd}$ step, 29.29 ml of triethoxysilane (Sigma-Aldrich), 328 mg of platinum oxide, and 200 ml of toluene are charged, and stirred under argon gas at 85° C. for 24 hours. After finishing the reaction, the coarse product thus obtained is filtered using Celite, and solvent is removed by using an evaporator to obtain a target product of biphenyl epoxy compound having an alkoxysilyl group. The reaction scheme of the 4$^{th}$ step and the NMR data of the target product thus obtained are as follows.

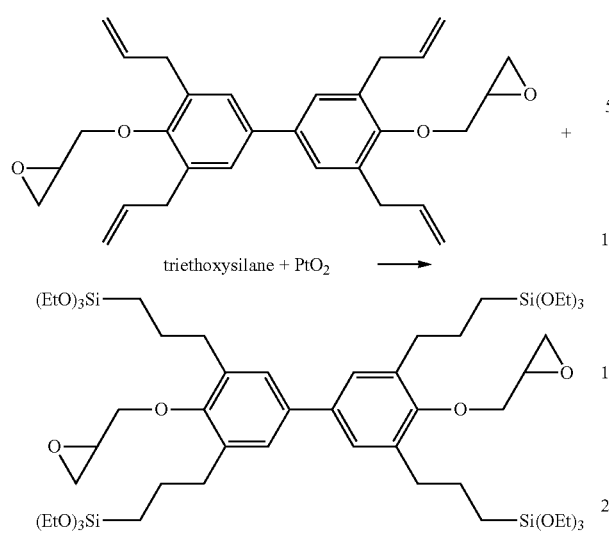

¹H NMR (400 MHz, CDCl₃): δ=0.60-0.70 (m, 8H), 1.20-1.25 (t, 36H), 1.60-1.70 (m, 8H), 2.50-2.70 (t, 8H), 2.70-2.80 (m, 2H), 2.80-2.90 (m, 2H), 3.30-3.40 (m, 2H), 3.70-4.00 (m, 26H), 4.10-4.20 (m, 2H), 7.30-7.50 (s, 4H).

Synthetic Example CI-1

Synthesis of Mono-Alkoxysilylated Epoxy Compound Using Fluorene (1) 1$^{st}$ step: Synthesis of 4-(9-(4-(allyloxy)phenyl)-9H-fluorene-9-yl)phenol Into a 1,000 ml two-necked flask equipped with a refluxing condenser, 10.0 g of 4,4'-(9H-fluorene-9,9-diyl)diphenol (Sigma-Aldrich), 11.84 g of K₂CO₃, and 500 ml of acetone were charged and mixed at room temperature. Then, the reaction temperature was set to 80° C., and the homogeneous mixture thus obtained was refluxed. During the refluxing, 3.08 ml of allyl bromide (Sigma-Aldrich) was added in a dropwise manner and was allowed to react overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO₄. MgSO₄ was filtered off, and solvents were removed by using an evaporator to obtain an intermediate product (11). The reaction scheme of the 1$^{st}$ step and the NMR data of the intermediate product (11) thus obtained are as follows.

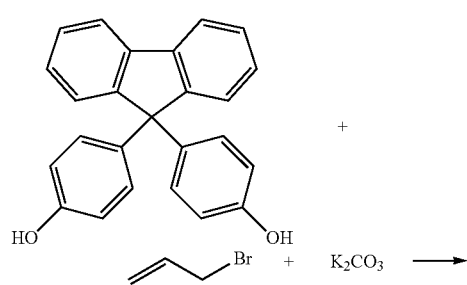

¹H NMR (400 MHz, CDCl₃): δ=4.46 (dt, J=5.2, 1.6 Hz, 2H), 5.20-5.25 (m, 2H), 5.35-5.38 (m, 1H), 5.98-6.06 (m, 1H), 6.72-6.76 (m, 4H), 7.06-7.11 (m, 4H), 7.24-7.39 (m, 6H), 7.70-7.79 (m, 2H).

(2) 2$^{nd}$ step: Synthesis of 2-allyl-4-(9-(4-hydroxyphenyl)-9H-fluorene-9-yl)phenol Into a 1,000 ml two-necked flask equipped with a refluxing condenser, 10.0 g of the intermediate product (11) obtained in the 1$^{st}$ step and 50 ml of 1,2-dichlorobenzene (Sigma-Aldrich) were charged and mixed at room temperature. The homogenized reaction solution thus obtained was refluxed for 96 hours at 190° C. After finishing the reaction, the reaction mixture was cooled to room temperature, and the solvent was removed in a vacuum oven to obtain 2-allyl-4-(9-(4-hydroxyphenyl)-9H-fluorene-9-yl)phenol. The reaction scheme of the 2$^{nd}$ step and the NMR data of the intermediate product (12) thus obtained are as follows.

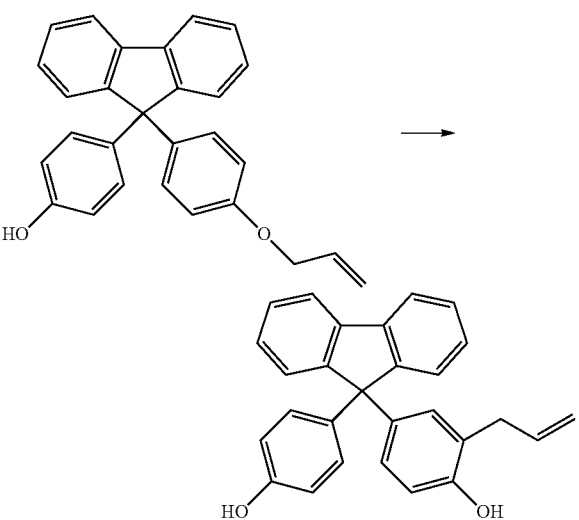

¹H NMR (400 MHz, CDCl₃): δ=3.28 (d, J=6.0 Hz, 2H), 5.04-5.10 (m, 2H), 5.21 (br.s, 2H), 5.87-5.97 (m, 1H), 6.71-6.75 (m, 3H), 7.05-7.11 (m, 4H), 7.24-7.39 (m, 6H), 7.70-7.78 (m, 2H).

(3) 3$^{rd}$ step: Synthesis of 2-((2-allyl-4-(9-(4-(oxirane-2-ylmethoxy)phenyl)-9H-fluorene-9-yl)phenoxy)methyl)oxirane Into a 1,000 ml two-necked flask equipped with a refluxing condenser, 10.0 g of the intermediate product (12) obtained in the 2$^{nd}$ step, 18.16 ml of epichlorohydrin (Sigma-Aldrich), 21.00 g of K$_2$CO$_3$, and 200 ml of acetonitrile were charged and mixed at room temperature. Then, the temperature was increased to 80° C. and the mixture was allowed to react overnight. After finishing the reaction, the reaction mixture was cooled to room temperature, and was filtered using Celite. The solvent was evaporated to obtain an intermediate product (13). The reaction scheme of the 3$^{rd}$ step and the NMR data of the intermediate product (13) thus obtained are as follows.

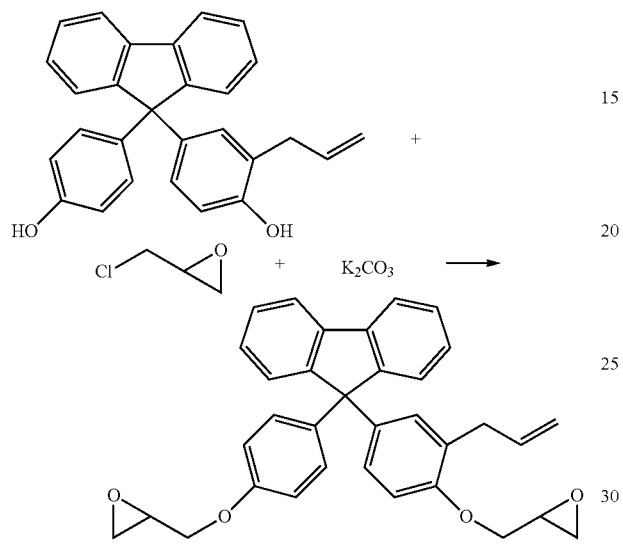

$^1$H NMR (400 MHz, CDCl$_3$): δ=2.77 (dd, J=2.6 Hz, 2H), 2.87 (dd, J=4.2 Hz, 2H), 3.10-3.36 (m, 4H), 3.98 (dd, J=5.4 Hz, 2H), 4.14 (dd, J=3.2 Hz, 2H), 4.97-5.04 (m, 2H), 5.92-6.03 (m, 1H), 6.75-6.85 (m, 3H), 7.01-7.12 (m, 4H), 7.24-7.39 (m, 6H), 7.70-7.78 (m, 2H).

(4) 4$^{th}$ step: Synthesis of triethoxy(3-(2-(oxirane-2-ylmethoxy)-5-(9-(4-(oxirane-2-ylmethoxy)phenyl)-9H-fluorene-9-yl)phenyl)propyl)silane Into a 250 ml flask, 10.0 g of the intermediate product (13) obtained in the 3$^{rd}$ step, 3.74 ml of triethoxysilane (Sigma-Aldrich), 41 mg of platinum oxide, and 100 ml of toluene were charged, mixed homogeneously and stirred under argon gas at 85° C. for 72 hours. After finishing the reaction, the coarse product thus obtained was filtered using Celite, and solvent was removed by using an evaporator to obtain the target product of fluorene epoxy having an alkoxysilyl group. The reaction scheme of the 4$^{th}$ step and the NMR data of the target product thus obtained are as follows.

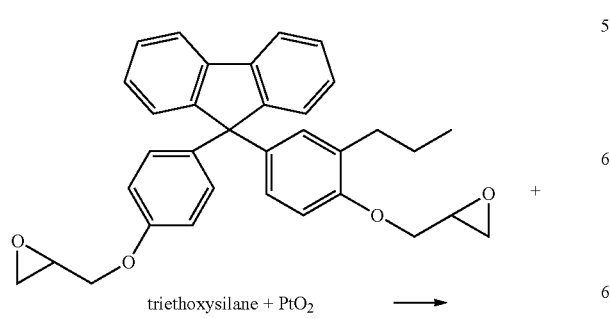

triethoxysilane + PtO$_2$ →

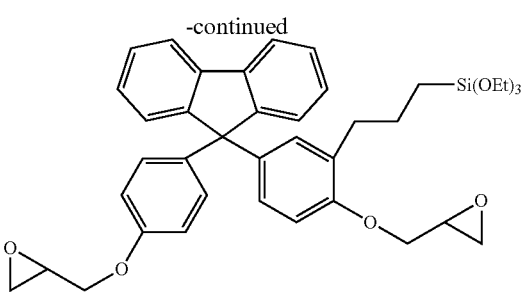

$^1$H NMR (400 MHz, CDCl$_3$): δ=0.64-0.69 (m, 2H), 1.21 (t, J=7.0 Hz, 9H), 1.62-1.74 (m, 2H), 2.64 (t, J=7.6 Hz, 2H), 2.74 (dd, J=2.6 Hz, 2H), 2.87 (dd, J=4.2 Hz, 2H), 3.29-3.34 (m, 2H), 3.79 (q, J=1.6 Hz, 6H), 3.97 (dd, J=5.2 Hz, 2H), 4.14 (dd, J=3.2 Hz, 2H), 6.81-6.87 (m, 3H), 6.96-7.07 (m, 4H), 7.24-7.39 (m, 6H), 7.70-7.78 (m, 2H).

Synthetic Example CI-2

Synthesis of Di-Alkoxysilylated Epoxy Compound Using Fluorene (1) 1$^{st}$ step: Synthesis of 9,9-bis(4-(allyloxy)phenyl)-9H-fluorene Into a 1,000 ml two-necked flask equipped with a refluxing condenser, 10.0 g of 4,4'-(9H-fluorene-9,9-diyl)diphenol (Sigma-Aldrich), 6.17 ml of allyl bromide (Sigma-Aldrich), 23.68 g of K$_2$CO$_3$, and 500 ml of acetone were charged and mixed at room temperature. Then, the reaction temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11) of 9,9-bis(4-(allyloxy)phenyl)-9H-fluorene. The reaction scheme of the 1$^{st}$ step and the NMR data of the intermediate product (11) thus obtained are as follows.

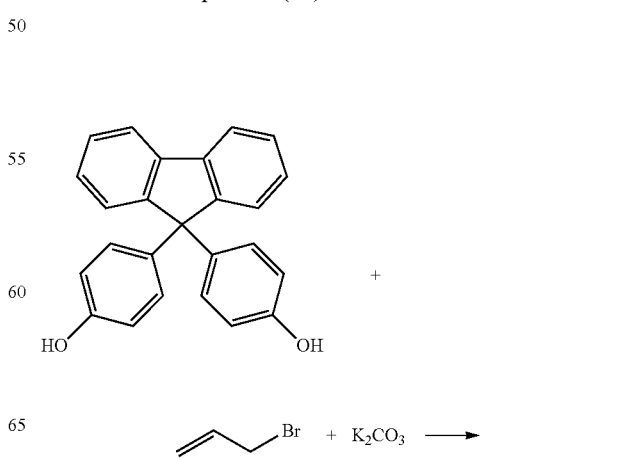

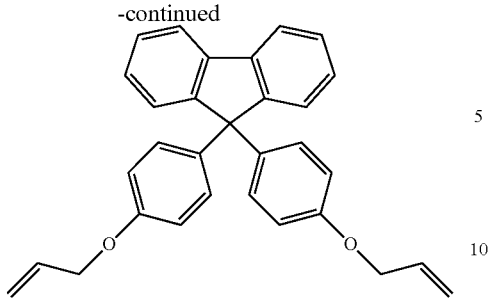

¹H NMR (400 MHz, CDCl₃): δ=4.46 (td, J=1.4, 2.4 Hz, 4H), 5.25 (qd, J=1.6, 1.2, 10.4 Hz, 2H), 5.35-5.38 (m, 2H), 5.97-6.06 (m, 2H), 6.75 (td, J=3.2, 2.0, 8.8 Hz, 4H), 7.10 (td, J=3.2, 2.0, 8.8 Hz, 4H), 7.23-7.39 (m, 6H), 7.70-7.79 (m, 2H).

(2) 2$^{nd}$ step: Synthesis of 4,4'-(9H-fluorene-9,9-diyl)bis(2-allylphenol)

Into a 1,000 ml two-necked flask equipped with a refluxing condenser, 10.0 g of the intermediate product (11) obtained in the 1$^{st}$ step and 100 ml of 1,2-dichlorobenzene (Sigma-Aldrich) were charged and mixed at room temperature. The homogenized reaction solution thus obtained was refluxed for 96 hours at 190° C. After finishing the reaction, the reaction mixture was cooled to room temperature, and solvent was removed in a vacuum oven to obtain the intermediate product (12) of 4,4'-(9H-fluorene-9,9-diyl)bis(2-allylphenol). The reaction scheme of the 2$^{nd}$ step and the NMR data of the intermediate product (12) thus obtained are as follows.

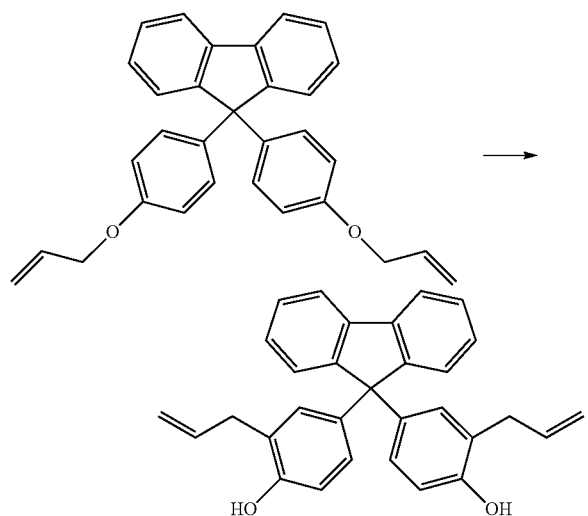

¹H NMR (400 MHz, CDCl₃): δ=3.28 (d, J=6.0 Hz, 4H), 5.04-5.09 (m, 4H), 5.21 (s, 2H), 5.87-5.97 (m, 2H), 6.62 (d, J=8.4 Hz, 2H), 6.88 (dd, J=2.4, 6.0 Hz, 2H), 6.96 (d, J=2.4 Hz, 2H), 7.22-7.36 (m, 6H), 7.74 (d, J=7.2 Hz, 2H).

(3) 3$^{rd}$ step: Synthesis of 2,2'-(4,4'-(9H-fluorene-9,9-diyl)bis(2-allyl-4,1-phenylene))bis(oxy)bis(methylene)dioxirane Into a 1,000 ml two-necked flask equipped with a refluxing condenser, 10.0 g of the intermediate product (12) obtained in the 2$^{nd}$ step, 18.16 ml of epichlorohydrin (Sigma-Aldrich), 21.00 g of K₂CO₃, and 300 ml of acetonitrile were charged and mixed at room temperature. Then, the temperature was increased to 80° C. and the mixture was allowed to react overnight. After finishing the reaction, the reaction mixture was cooled to room temperature and was filtered using Celite. The solvent was evaporated to obtain an intermediate product (13). The reaction scheme of the 3$^{rd}$ step and the NMR data of the intermediate product (13) thus obtained are as follows.

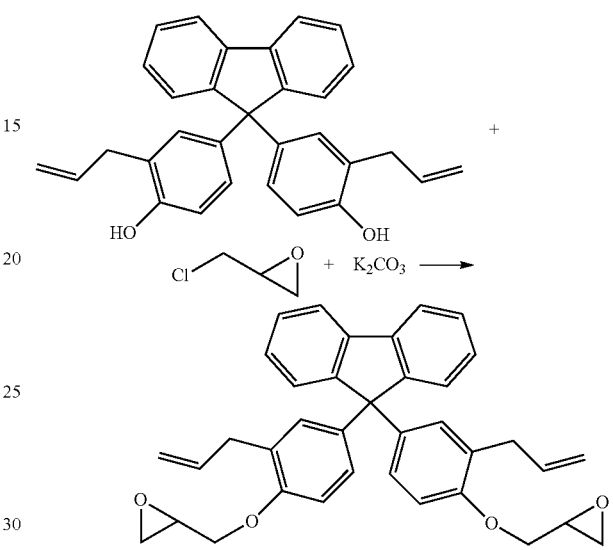

¹H NMR (400 MHz, CDCl₃): δ=2.75 (dd, J=2.6 Hz, 2H), 2.87 (dd, J=4.2 Hz, 2H), 3.11-3.35 (m, 6H), 3.96 (dd, J=5.4 Hz, 2H), 4.12 (dd, J=3.2 Hz, 2H), 4.97-5.03 (m, 4H), 5.93-6.03 (m, 2H), 6.69 (d, J=8.4 Hz, 2H), 6.80-6.83 (m, 2H), 7.05 (s, 2H), 7.22-7.36 (m, 6H), 7.74 (d, J=7.2 Hz, 2H).

(4) 4$^{th}$ step: Synthesis of (3,3'-(5,5'-(9H-fluorene-9,9-diyl)bis(2-(oxirane-2-ylmethoxy)-5,1-phenylene))bis(propane-3,1-diyl))-bis(triethoxysilane)

Into a 500 ml flask, 10.0 g of the intermediate product (13) obtained in the 3$^{rd}$ step, 7.48 ml of triethoxysilane (Sigma-Aldrich), 84 mg of platinum oxide, and 200 ml of toluene were charged and stirred under argon gas at 85° C. for 72 hours. After finishing the reaction, the coarse product thus obtained was filtered using Celite. The solvent was removed by using an evaporator to obtain a target product. The reaction scheme of the 4$^{th}$ step and the NMR data of the target product thus obtained are as follows.

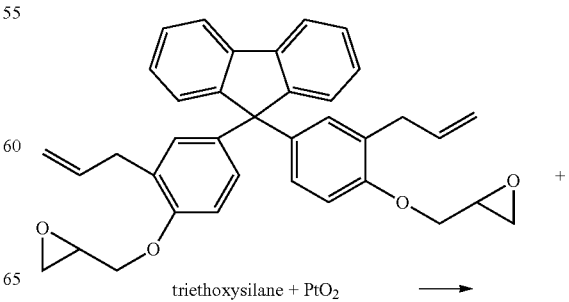

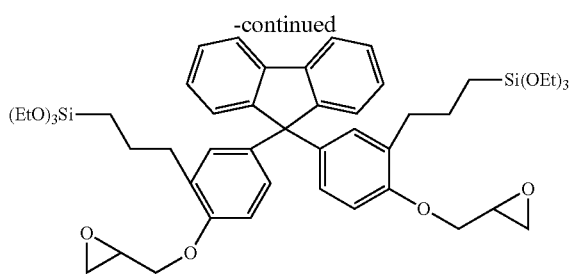

$^1$H NMR (400 MHz, CDCl$_3$): δ=0.66-0.70 (m, 4H), 1.20 (t, J=7.0 Hz, 18H), 1.63-1.71 (m, 4H), 2.61 (t, J=7.6 Hz, 4H), 2.75 (dd, J=2.6 Hz, 2H), 2.86 (dd, J=4.2 Hz, 2H), 3.30-3.35 (m, 2H), 3.79 (q, J=1.6 Hz, 12H), 3.96 (dd, J=5.2 Hz, 2H), 4.14 (dd, J=3.2 Hz, 2H), 6.69 (d, J=8.4 Hz, 2H), 6.80-6.83 (m, 2H), 7.03 (s, 2H), 7.21-7.36 (m, 6H), 7.73 (d, J=7.2 Hz, 2H).

Prediction Example CI-3

Synthesis of Tri-Alkoxysilylated Epoxy Compound Using Dihydroxyfluorene (1) 1$^{st}$ step: Synthesis of 9,9-bis(4-(allyloxy)phenyl)-9H-fluorene Into a 1,000 ml two-necked flask equipped with a refluxing condenser, 10.0 g of 4,4'-(9H-fluorene-9,9-diyl)diphenol (Sigma-Aldrich), 6.17 ml of allyl bromide (Sigma-Aldrich), 23.68 g of K$_2$CO$_3$, and 500 ml of acetone were charged and mixed at room temperature. Then, the temperature was set to 80° C., and the homogeneous mixture thus obtained was refluxed overnight. After finishing the reaction, the reaction mixture was cooled to room temperature and was filtered using Celite. Organic solvent was evaporated to obtain a coarse product. A target product was extracted from the coarse product using ethyl acetate, washed three times using water, and dried using MgSO$_4$. MgSO$_4$ was filtered off, and solvent was removed by using an evaporator to obtain an intermediate product (11), 9,9-bis(4-(allyloxy)phenyl)-9H-fluorene. The reaction scheme in the 1$^{st}$ step and the NMR data of the intermediate product (11) are as follows.

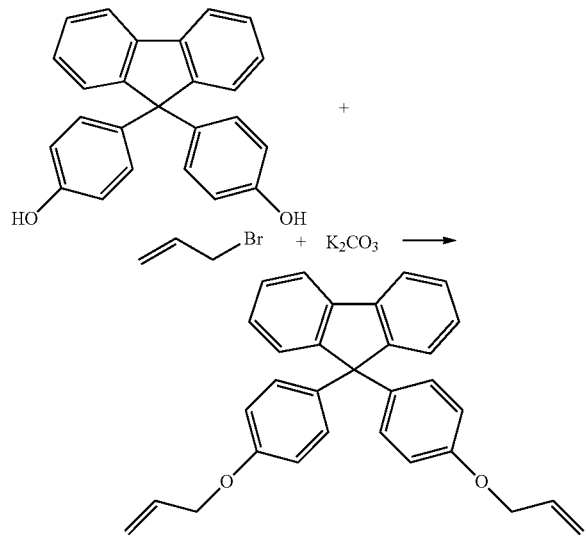

$^1$H NMR (400 MHz, CDCl$_3$): δ=4.46 (td, J=1.4, 2.4 Hz, 4H), 5.25 (qd, J=1.6, 1.2, 10.4 Hz, 2H), 5.35-5.38 (m, 2H), 5.97-6.06 (m, 2H), 6.75 (td, J=3.2, 2.0, 8.8 Hz, 4H), 7.10 (td, J=3.2, 2.0, 8.8 Hz, 4H), 7.23-7.39 (m, 6H), 7.70-7.79 (m, 2H).

(2) 2$^{nd}$ step: Synthesis of 4,4'-(9H-fluorene-9,9-diyl) bis(2-allylphenol)

Into a 1,000 ml two-necked flask equipped with a refluxing condenser, 10.0 g of the intermediate product (11) obtained in the 1$^{st}$ step and 100 ml of 1,2-dichlorobenzene (Sigma-Aldrich) were charged and mixed at room temperature. The homogenized reaction solution thus obtained was refluxed for 96 hours. After finishing the refluxing reaction, the reaction mixture was cooled to room temperature, and solvent was removed in a vacuum oven to obtain an intermediate product (12) of 4,4'-(9H-fluorene-9,9-diyl)bis(2-allylphenol). The reaction scheme of the 2$^{nd}$ step and the NMR data of the intermediate product (12) are as follows.

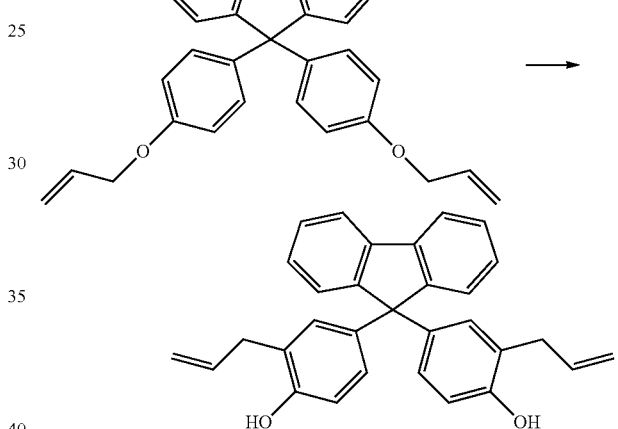

$^1$H NMR (400 MHz, CDCl$_3$): δ=3.28 (d, J=6.0 Hz, 4H), 5.04-5.09 (m, 4H), 5.21 (s, 2H), 5.87-5.97 (m, 2H), 6.62 (d, J=8.4 Hz, 2H), 6.88 (dd, J=2.4, 6.0 Hz, 2H), 6.96 (d, J=2.4 Hz, 2H), 7.22-7.36 (m, 6H), 7.74 (d, J=7.2 Hz, 2H).

(3) 2-1-th step: Synthesis of 2-allyl-4-(9-(3-allyl-4-(allyloxy)phenyl)-9H-fluorene-9-yl)phenol Into a 1,000 ml two-necked flask equipped with a refluxing condenser, 20.0 g of the intermediate product (12) obtained in the 2$^{nd}$ step, 16.52 g of K$_2$CO$_3$, and 500 ml of acetone are charged and mixed at room temperature. Then, the temperature is set to 190° C., and the homogeneous mixture thus obtained is refluxed. During the refluxing, 3.79 ml of allyl bromide (Sigma-Aldrich) is added in a dropwise manner, and is allowed to react overnight. After finishing the reaction, the reaction mixture is cooled to room temperature and is filtered using Celite. The solvent is evaporated to obtain a coarse product. Target product is extracted from the coarse product using ethyl acetate, washed three times using water, and dried using MgSO$_4$. MgSO$_4$ is filtered off, and solvents are removed by using an evaporator. The product is purified by silica gel column chromatography to obtain an intermediate product (23), 2-allyl-4-(9-(3-allyl-4-(allyloxy)phenyl)-9H-fluorene-9-yl)phenol. The reaction scheme in the 2-1-th step is as follows.

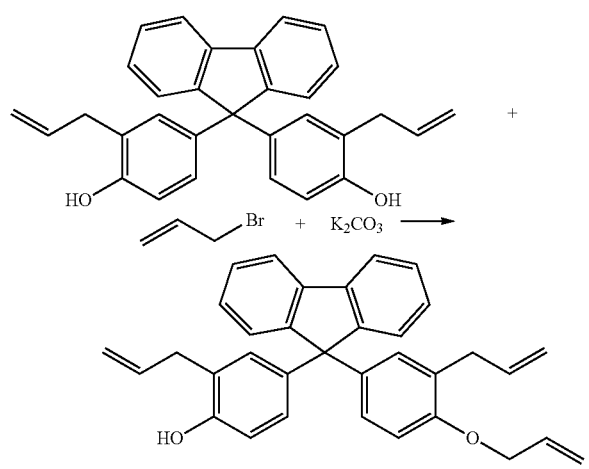

(4) 2-2-th step: Synthesis of 2,6-diallyl-4-(9-(3-allyl-4-hydroxyphenyl)-9H-fluorene-9-yl)phenol Into a 1,000 ml two-necked flask equipped with a refluxing condenser, 20.0 g of the intermediate product (23) obtained in the 2-1-th step and 100 ml of 1,2-dichlorobenzene (Sigma-Aldrich) are charged and mixed at room temperature. The homogenized reaction solution thus obtained is refluxed for 8 hours. After finishing the reaction, the reaction mixture is cooled to room temperature, and solvent is removed in a vacuum oven to obtain an intermediate product (24). The reaction scheme of the 2-2-th step is as follows.

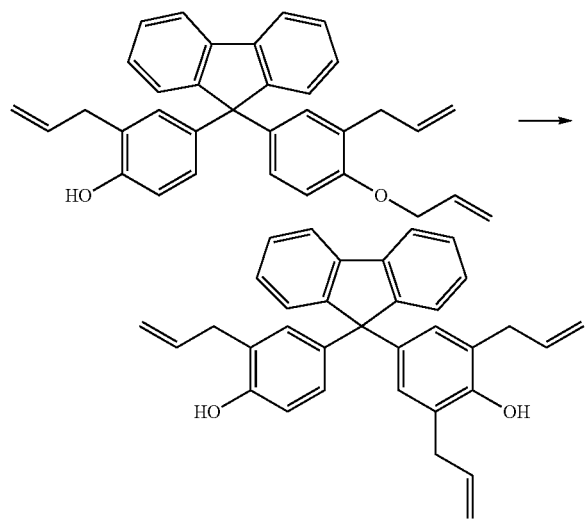

(5) $3^{rd}$ step: Synthesis of 2-((2-allyl-4-(9-(3,5-diallyl-4-(oxirane-2-ylmethoxy)phenyl)-9H-fluorene-9-yl)phenoxy)methyl)oxirane Into a 1,000 ml two-necked flask equipped with a refluxing condenser, 20.0 g of the intermediate product (24) obtained in the 2-2-th step, 32.76 ml of epichlorohydrin (Sigma-Aldrich), 37.88 g of $K_2CO_3$, and 300 ml of acetonitrile are charged and mixed at room temperature. Then, the temperature is increased to 80° C. and the mixture is allowed to react overnight. After finishing the reaction, the reaction mixture is cooled to room temperature and is filtered using Celite. The solvent is evaporated to obtain an intermediate product (25), 2-((2-allyl-4-(9-(3,5-diallyl-4-(oxirane-2-ylmethoxy)phenyl)-9H-fluorene-9-yl)phenoxy)methyl)oxirane. The reaction scheme of the $3^{rd}$ step is as follows.

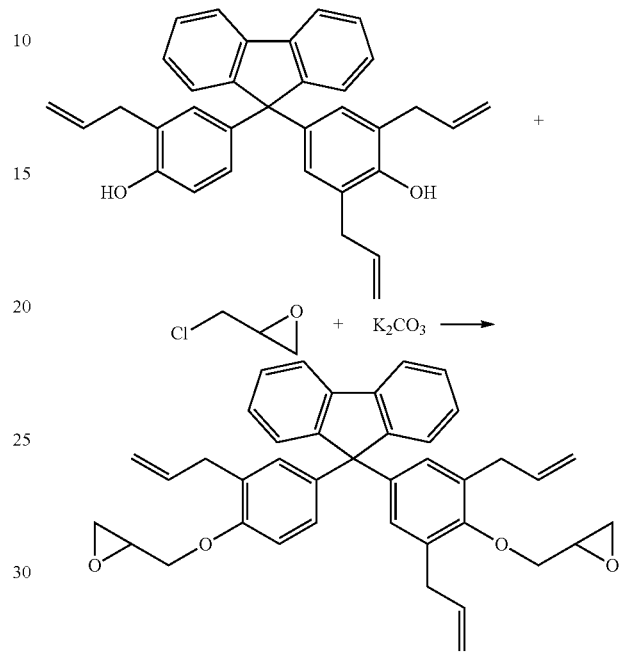

(6) $4^{th}$ step: Synthesis of (2,2'-(2-(oxirane-2-ylmethoxy)-5-(9-(4-(oxirane-2-ylmethoxy)-3-(2-(triethoxysilyl)ethyl)phenyl)-9H-fluorene-9-yl)-1,3-phenylene)bis(ethane-2,1-diyl))bis(triethoxysilane)

Into a 500 ml flask, 20.0 g of the intermediate product (25) obtained in the $3^{rd}$ step, 29.13 ml of triethoxysilane (Sigma-Aldrich), 326 mg of platinum oxide, and 200 ml of toluene are charged and stirred under argon gas at 85° C. for 24 hours. After finishing the reaction, the coarse product thus obtained is filtered using Celite, and solvent is removed by using an evaporator to obtain a target product of a fluorene epoxy compound having an alkoxysilyl group. The reaction scheme of the $4^{th}$ step and the NMR data of the target product thus obtained are as follows.

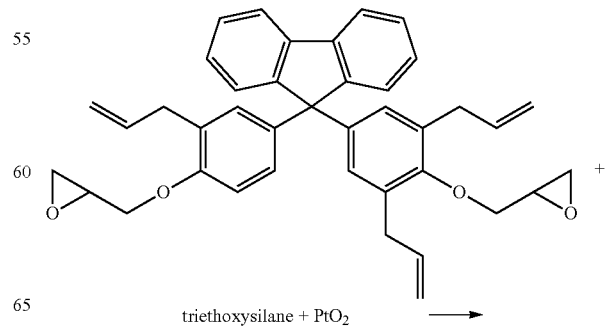

triethoxysilane + $PtO_2$ →

-continued

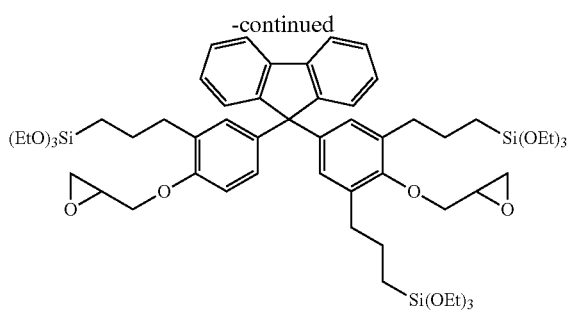

¹H NMR (400 MHz, CDCl₃): δ=0.60-0.70 (m, 6H), 1.20-1.25 (t, 27H), 1.60-1.70 (m, 6H), 2.50-2.70 (t, 6H), 2.70-2.80 (m, 2H), 2.80-2.90 (m, 2H), 3.30-3.40 (m, 2H), 3.70-4.00 (m, 20H), 4.10-4.20 (m, 2H), 6.70-7.00 (m, 5H), 7.20-7.40 (m, 6H), 7.70-7.90 (d, 2H).

Prediction Example CI-4

Synthesis of Tetra-Alkoxysilylated Epoxy Compound Using Dihydroxyfluorene (1) 1$^{st}$ step: Synthesis of 9,9-bis(4-(allyloxy)phenyl)-9H-fluorene Into a 1,000 ml two-necked flask equipped with a refluxing condenser, 10.0 g of 4,4'-(9H-fluorene-9,9-diyl)diphenol (Sigma-Aldrich), 6.17 ml of allyl bromide (Sigma-Aldrich), 23.68 g of K₂CO₃, and 500 ml of acetone were charged and mixed at room temperature. Then, the temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO₄. MgSO₄ was filtered off, and solvents were removed by using an evaporator to obtain an intermediate product (11), 9,9-bis(4-(allyloxy)phenyl)-9H-fluorene. The reaction scheme in the 1$^{st}$ step and the NMR data of the intermediate product (11) are as follows.

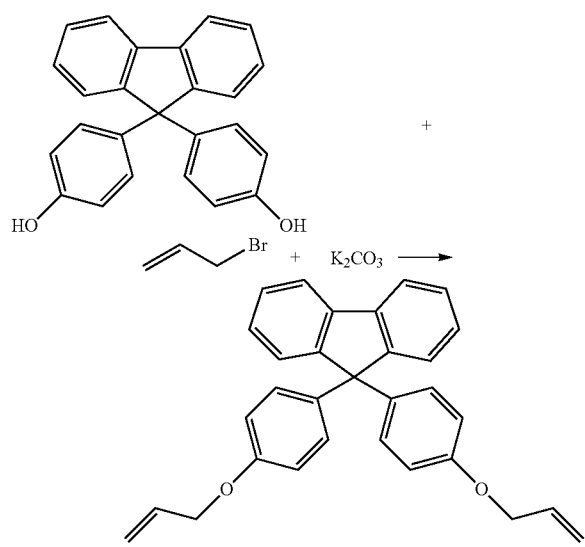

¹H NMR (400 MHz, CDCl₃): δ=4.46 (td, J=1.4, 2.4 Hz, 4H), 5.25 (qd, J=1.6, 1.2, 10.4 Hz, 2H), 5.35-5.38 (m, 2H), 5.97-6.06 (m, 2H), 6.75 (td, J=3.2, 2.0, 8.8 Hz, 4H), 7.10 (td, J=3.2, 2.0, 8.8 Hz, 4H), 7.23-7.39 (m, 6H), 7.70-7.79 (m, 2H).

(2) 2$^{nd}$ step: Synthesis of 4,4'-(9H-fluorene-9,9-diyl)bis(2-allylphenol)

Into a 1,000 ml two-necked flask equipped with a refluxing condenser, 10.0 g of 9,9-bis(4-(allyloxy)phenyl)-9H-fluorene obtained in the 1$^{st}$ step and 100 ml of 1,2-dichlorobenzene (Sigma-Aldrich) were charged and mixed at room temperature. The homogenized reaction solution thus obtained was refluxed for 96 hours at 190° C. After finishing the reaction, the mixture was cooled to room temperature, and solvent was removed in a vacuum oven to obtain an intermediate product (12) of 4,4'-(9H-fluorene-9,9-diyl)bis(2-allylphenol). The reaction scheme of the 2$^{nd}$ step and the NMR data of the intermediate product (12) are as follows.

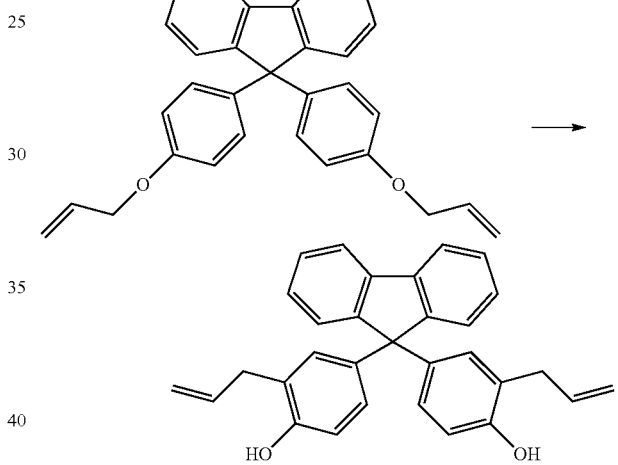

¹H NMR (400 MHz, CDCl₃): δ=3.28 (d, J=6.0 Hz, 4H), 5.04-5.09 (m, 4H), 5.21 (s, 2H), 5.87-5.97 (m, 2H), 6.62 (d, J=8.4 Hz, 2H), 6.88 (dd, J=2.4, 6.0 Hz, 2H), 6.96 (d, J=2.4 Hz, 2H), 7.22-7.36 (m, 6H), 7.74 (d, J=7.2 Hz, 2H).

(3) 2-1-th step: Synthesis of 9,9-bis(3-allyl-4-(allyloxy)phenyl)-9H-fluorene

Into a 1,000 ml two-necked flask equipped with a refluxing condenser, 20.0 g of the intermediate product (12) obtained in the 2$^{nd}$ step, 15.09 ml of allyl bromide (Sigma-Aldrich), 57.82 g of K₂CO₃, and 500 ml of acetone are charged and mixed at room temperature. Then, the temperature of a refluxing apparatus is set to 80° C., and the mixture is allowed to react overnight. After finishing the reaction, the reaction mixture is cooled to room temperature and is filtered using Celite. The solvent is evaporated to obtain a coarse product. A target product is extracted from the coarse product using ethyl acetate, washed three times using water, and dried using MgSO₄. MgSO₄ is filtered off, and solvents are removed by using an evaporator to obtain an intermediate product (23), 9,9-bis(3-allyl-4-(allyloxy)phenyl)-9H-fluorene. The reaction scheme of the 2-1-th step is as follows.

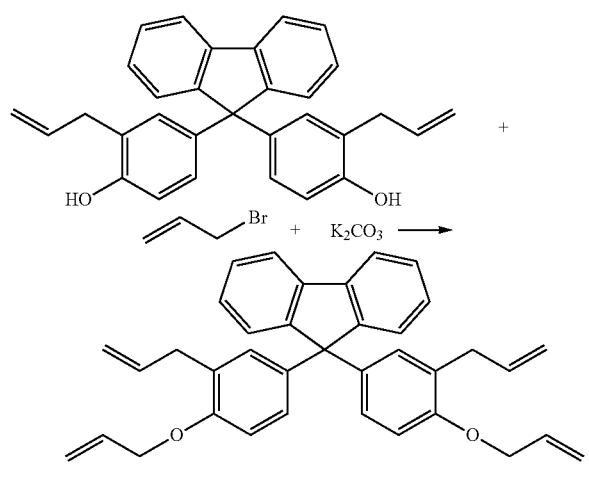

(4) 2-2-th step: Synthesis of 4,4'-(9H-fluorene-9,9-diyl)bis(2,6-diallylphenol)

Into a 1,000 ml two-necked flask equipped with a refluxing condenser, 20.0 g of the intermediate product (23) obtained in the 2-1-th step and 100 ml of 1,2-dichlorobenzene (Sigma-Aldrich) are charged and mixed at room temperature. The homogenized reaction solution thus obtained is refluxed for 8 hours at 190° C. After finishing the reaction, the reaction mixture is cooled to room temperature, and solvent is removed in a vacuum oven to obtain an intermediate product (24), 4,4'-(9H-fluorene-9,9-diyl)bis(2,6-diallylphenol). The reaction scheme of the 2-2-th step is as follows.

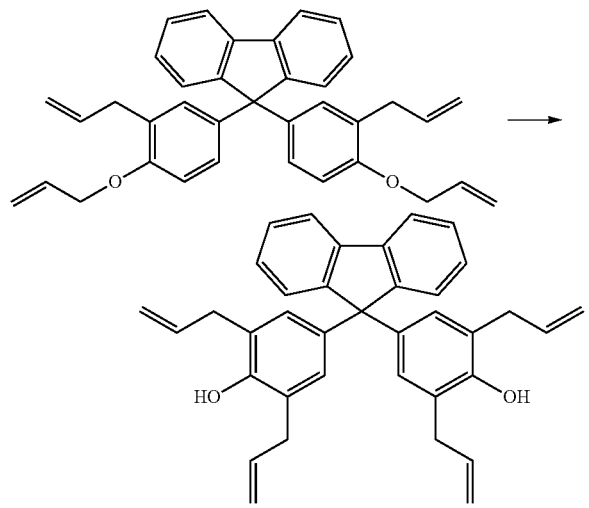

(5) $3^{rd}$ step: Synthesis of 2,2'-(4,4'-(9H-fluorene-9,9-diyl)bis(2,6-diallyl-4,1-phenylene)bis(oxy)bis(methylene)dioxirane Into a 1,000 ml two-necked flask equipped with a refluxing condenser, 20.0 g of the intermediate product (24) obtained in the 2-2-th step, 37.84 ml of epichlorohydrin (Sigma-Aldrich), 43.76 g of $K_2CO_3$, and 300 ml of acetonitrile are charged and mixed at room temperature. Then, the temperature is increased to 80° C. and the mixture is allowed to react overnight. After finishing the reaction, the reaction mixture is cooled to room temperature and filtered using Celite. The solvent is evaporated to obtain an intermediate product (25), 2,2'-(4,4'-(9H-fluorene-9,9-diyl)bis(2,6-diallyl-4,1-phenylene)bis(oxy)bis(methylene)dioxirane. The reaction scheme of the $3^{rd}$ step is as follows.

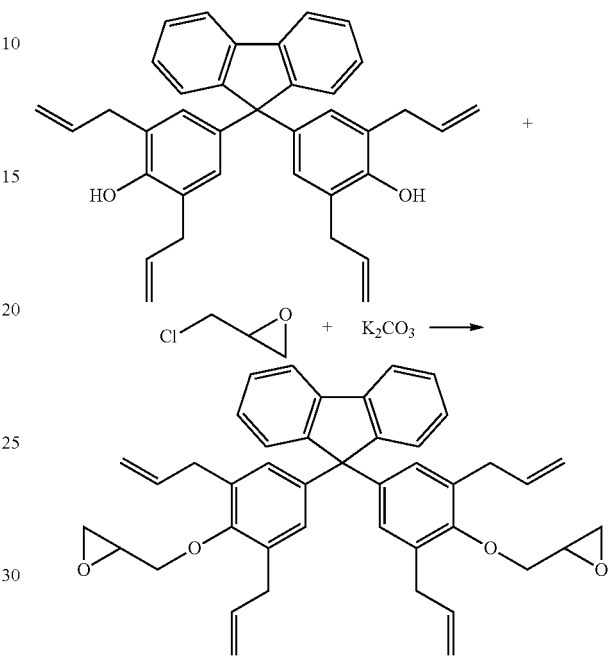

(6) $4^{th}$ step: Synthesis of 3,3',3'',3'''-(5,5'-(9H-fluorene-9,9-diyl)bis(2-(oxirane-2-ylmethoxy)benzene-5,3,1-triyl))tetrakis propane-3,1-diyl))tetrakis(triethoxysilane)

Into a 500 ml flask, 20.0 g of the intermediate product (25) obtained in the $3^{rd}$ step, 21.57 ml of triethoxysilane (Sigma-Aldrich), 241 mg of platinum oxide, and 200 ml of toluene are charged and stirred under argon gas at 85° C. for 24 hours. After finishing the reaction, the coarse product thus obtained is filtered using Celite, and solvent is removed by using an evaporator to obtain a target product of a fluorene epoxy compound having an alkoxysilyl group. The reaction scheme of the $4^{th}$ step and the NMR data of the target product thus obtained are as follows.

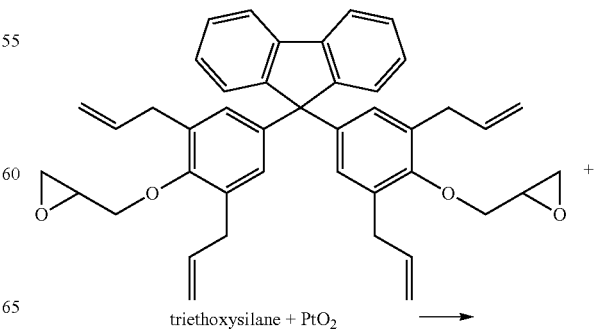

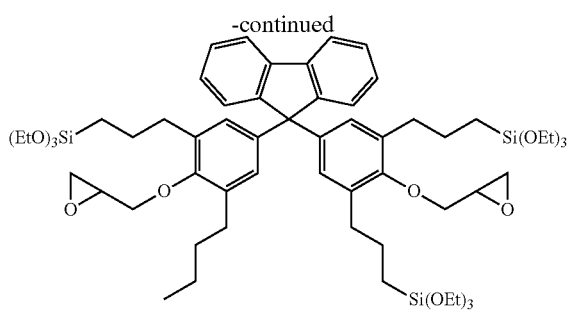

$^1$H NMR (400 MHz, CDCl$_3$): δ=0.60-0.70 (m, 8H), 1.20-1.25 (t, 36H), 1.60-1.70 (m, 8H), 2.50-2.70 (t, 8H), 2.70-2.80 (m, 2H), 2.80-2.90 (m, 2H), 3.30-3.40 (m, 2H), 3.70-4.00 (m, 26H), 4.10-4.20 (m, 2H), 6.70-7.00 (s, 4H), 7.20-7.40 (m, 6H), 7.70-7.90 (d, 2H).

Synthetic Example DI-1

Synthesis of Mono-Alkoxysilylated Epoxy Compound Using Bisphenol A (1) 1$^{st}$ step: Synthesis of 4-(2-(4-(allyloxy)phenyl)propane-2-yl)phenol Into a 1,000 ml two-necked flask equipped with a refluxing condenser, 20.0 g of bisphenol A (sigma-Aldrich), 36.35 g of K$_2$CO$_3$, and 500 ml of acetone were charged and mixed at room temperature. Then, the reaction temperature was set to 80° C., and the homogeneous mixture thus obtained was refluxed. During the refluxing, 8.33 ml of allyl bromide (Sigma-Aldrich) was added in a dropwise manner and allowed to react overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 4-(2-(4-(allyloxy)phenyl)propane-2-yl)phenol. The reaction scheme of the 1$^{st}$ step and the NMR data of the intermediate product (11) thus obtained are as follows.

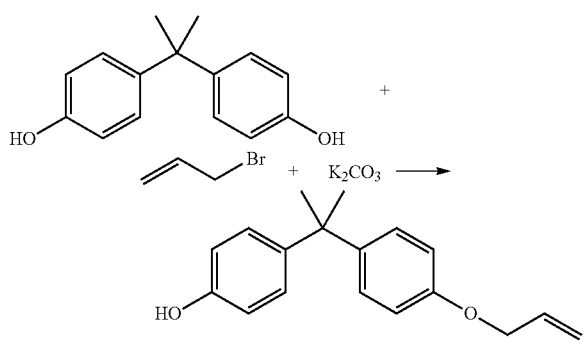

$^1$H NMR (400 MHz, CDCl$_3$): δ=1.60 (s, 6H), 4.87 (s, 1H), 4.60 (d, J=5.2 Hz, 2H), 5.33 (dd, J=1.4 Hz, 1H), 5.44 (dd, J=1.6 Hz, 1H), 6.05-6.15 (m, 1H), 6.47 (d, J=8.2 Hz, 2H), 6.70 (d, J=8.4 Hz, 2H), 7.28 (d, J=10.8 Hz, 4H).

(2) 2$^{nd}$ step: Synthesis of 2-allyl-4-(2-(4-hydroxyphenyl)propane-2-yl)phenol Into a 1,000 ml two-necked flask equipped with a refluxing condenser, 8.0 g of the intermediate product (11) obtained in the 1$^{st}$ step and 250 ml of 1,2-dichlorobenzene (Sigma-Aldrich) were charged and mixed at room temperature. The homogenized reaction solution thus obtained was refluxed for 8 hours at 190° C. After finishing the reaction, the reaction mixture was cooled to room temperature, and solvent was removed in a vacuum oven to obtain an intermediate product (12), 2-allyl-4-(2-(4-hydroxyphenyl)propane-2-yl)phenol. The reaction scheme of the 2$^{nd}$ step and the NMR data of the intermediate product (12) thus obtained are as follows.

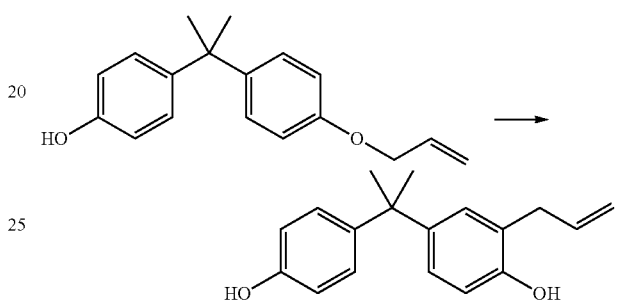

$^1$H NMR (400 MHz, CDCl$_3$): δ=1.60 (s, 6H), 3.36 (d, J=6.4 Hz, 2H), 4.86 (br.s, 2H), 5.08-5.12 (m, 2H), 5.92-6.03 (m, 1H), 6.76 (m, 3H), 6.94 (m, 4H).

(3) 3$^{rd}$ step: Synthesis of 2-((2-allyl-4-(2-(4-(oxirane-2-ylmethoxy)phenyl)propane-2-yl)phenoxy)methyl)oxirane Into a 500 ml two-necked flask equipped with a refluxing condenser, 7.0 g of the intermediate product (12) obtained in the 2$^{nd}$ step, 19.35 ml of epichlorohydrin (Sigma-Aldrich), 21.64 g of K$_2$CO$_3$, and 200 ml of acetonitrile were charged and mixed at room temperature. Then, the temperature was increased to 80° C. and the mixture was allowed to react overnight. After finishing the reaction, the reaction mixture was cooled to room temperature and was filtered using Celite. The solvent was evaporated to obtain an intermediate product (13), 2-((2-allyl-4-(2-(4-(oxirane-2-ylmethoxy)phenyl)propane-2-yl)phenoxy)methyl)oxirane. The reaction scheme of the 3$^{rd}$ step and the NMR data of the intermediate product (13) thus obtained are as follows.

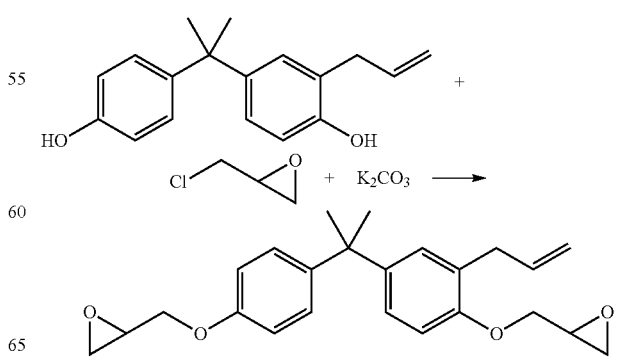

$^1$H NMR (400 MHz, CDCl$_3$): δ=1.60 (s, 6H), 2.76 (dd, J=2.6 Hz, 2H), 2.87 (dd, J=4.2 Hz, 2H), 3.30-3.36 (m, 4H), 3.95-3.98 (m, 2H), 4.17-4.20 (m, 2H), 4.97-5.03 (m, 2H), 5.93-5.98 (m, 1H), 6.72 (m, 3H), 6.96-7.01 (m, 4H).

(4) 4$^{th}$ step: Synthesis of triethoxy(3-(2-(oxirane-2-ylmethoxy)-5-(2-(4-(oxirane-2-ylmethoxy)phenyl) propane-2-yl)phenyl)propyl)silane Into a 250 ml flask, 10.0 g of the intermediate product (13) obtained in the step, 5.95 ml of triethoxysilane (Sigma-Aldrich), 100 mg of platinum oxide, and 100 ml of toluene were charged, mixed homogeneously and stirred under argon gas at 85° C. for 24 hours. After finishing the reaction, the coarse product thus obtained was filtered using Celite, and solvent was removed by using an evaporator to obtain a target product of a bisphenol A epoxy compound having an alkoxysilyl group. The reaction scheme of the 4$^{th}$ step and the NMR data of the target product thus obtained are as follows.

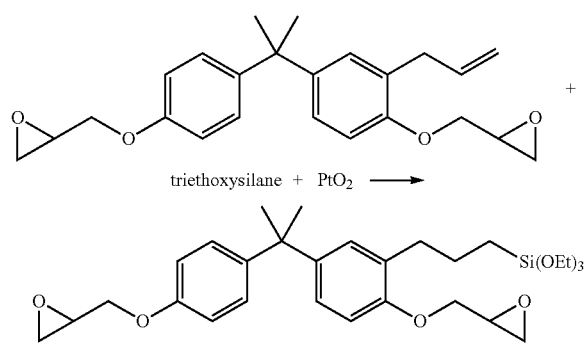

$^1$H NMR (400 MHz, CDCl$_3$): δ=0.65-0.70 (m, 2H), 1.23 (t, J=7.0 Hz, 9H), 1.61 (s, 6H), 1.60-1.71 (m, 2H), 2.62 (t, J=7.6 Hz, 2H), 2.74 (dd, J=2.6 Hz, 2H), 2.86 (dd, J=4.2 Hz, 2H), 3.30-3.34 (m, 2H), 3.80 (q, 1.6 Hz, 6H), 3.98 (dd, J=5.2 Hz, 2H), 4.13 (dd, J=3.2 Hz, 2H), 6.72 (m, 3H), 6.96-7.03 (m, 4H).

Synthetic Example DI-2

Synthesis of Di-Alkoxysilylated Epoxy Compound Using Bisphenol A (1) 1$^{st}$ step: Synthesis of 4,4'-(propane-2,2-diyl)bis(allyloxybenzene)

Into a 1,000 ml two-necked flask equipped with a refluxing condenser, 20.0 g of bisphenol A (Sigma-Aldrich), 18.94 ml of allyl bromide (Sigma-Aldrich), 72.69 g of K$_2$CO$_3$, and 500 ml of acetone were charged and mixed at room temperature. Then, the temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 4,4'-(propane-2,2-diyl)bis(allyloxybenzene). The reaction scheme in the 1$^{st}$ step and the NMR data of the intermediate product (11) thus obtained are as follows.

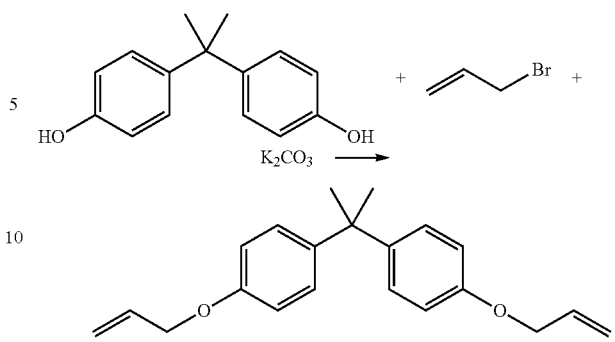

$^1$H NMR (400 MHz, CDCl$_3$): δ=1.60 (s, 6H), 4.61 (d, J=5.2 Hz, 4H), 5.31 (dd, J=1.4 Hz, 2H), 5.45 (dd, J=1.6 Hz, 2H), 6.06-6.15 (m, 2H), 6.69 (d, J=8.4 Hz, 4H), 7.28 (d, J=10.8 Hz, 4H).

(2) 2$^{nd}$ step: Synthesis of 4,4'-(propane-2,2-diyl)bis (2-allylphenol)

Into a 1,000 ml two-necked flask equipped with a refluxing condenser, 20.0 g of the intermediate product (11) obtained in the 1$^{st}$ step and 250 ml of 1,2-dichlorobenzene (Sigma-Aldrich) were charged and mixed at room temperature. The homogenized reaction solution thus obtained was refluxed for 8 hours at 190° C. After finishing the reaction, the reaction mixture was cooled to room temperature, and solvent was removed in a vacuum oven to obtain an intermediate product (12), 2,2'-diallyl bisphenol A. The reaction scheme of the 2$^{nd}$ step and the NMR data of the intermediate product (12) thus obtained are as follows.

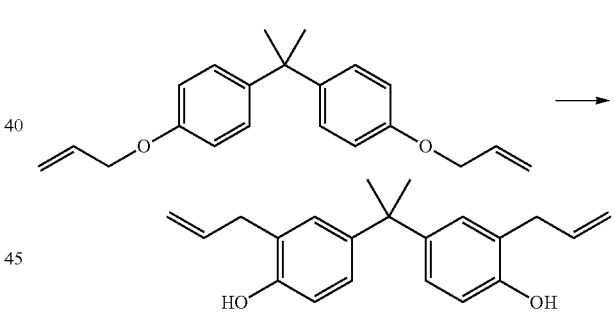

$^1$H NMR (400 MHz, CDCl$_3$): δ=1.60 (s, 6H), 3.35 (d, J=6.4 Hz, 4H), 4.86 (s, 2H), 5.08-5.12 (m, 4H), 5.93-6.03 (m, 2H), 6.75 (d, J=8.4 Hz, 2H), 6.94 (dd, J=10.6 Hz, 4H).

(3) 3$^{rd}$ step: Synthesis of 2,2'-(4,4'-(propane-2,2-diyl) bis(2-allyl-4,1-phenylene))bis(oxy)bis(methylene) dioxirane Into a 1,000 ml two-necked flask equipped with a refluxing condenser, 29.0 g of the intermediate product (12) obtained in the 2$^{nd}$ step, 73.54 ml of epichlorohydrin (Sigma-Aldrich), 85.67 g of K$_2$CO$_3$, and 300 ml of acetonitrile were charged and mixed at room temperature. Then, the temperature was increased to 80° C. and the mixture was allowed to react overnight. After finishing the reaction, the reaction mixture was cooled to room temperature and was filtered using Celite. The solvent was evaporated to obtain an intermediate product (13). The reaction scheme of the 3$^{rd}$ step and the NMR data of the intermediate product (13) thus obtained are as follows.

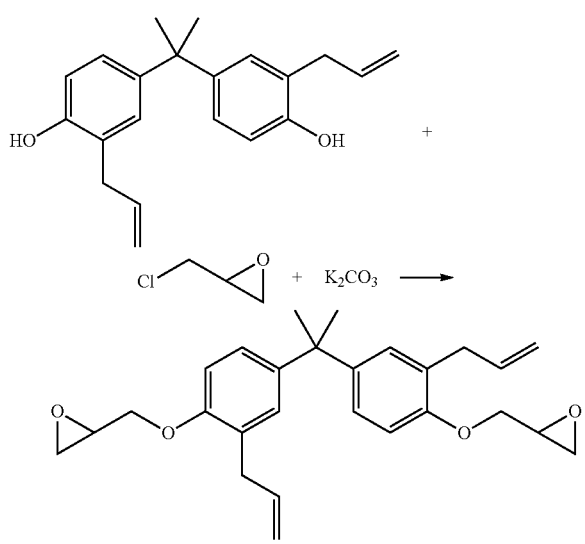

¹H NMR (400 MHz, CDCl₃): δ=1.61 (s, 6H), 2.75 (dd, J=2.6 Hz, 2H), 2.87 (dd, J=4.2 Hz, 2H), 3.32-3.36 (m, 6H), 3.94-3.98 (m, 2H), 4.16-4.20 (m, 2H), 4.97-5.03 (m, 4H), 5.93-5.98 (m, 2H), 6.71 (d, J=8.4 Hz, 2H), 6.97-7.00 (m, 4H).

(4) 4ᵗʰ step: Synthesis of (3,3'-(5,5'-(propane-2,2-diyl)bis(2-(oxirane-2-ylmethoxy)-5,1-phenylene)bis(propane-3,1-diyl))bis(triethoxysilane)

Into a 500 ml flask, 26.25 g of the intermediate 3rd product (13) obtained in the step, 25.35 ml of triethoxysilane (Sigma-Aldrich), 250 mg of platinum oxide, and 200 ml of toluene were charged, mixed homogeneously and stirred under argon gas at 85° C. for 24 hours. After finishing the reaction, the coarse product thus obtained was filtered using Celite, and solvent was removed by using an evaporator to obtain a target product of a bisphenol A epoxy compound having an alkoxysilyl group. The reaction scheme of the 4ᵗʰ step and the NMR data of the target product thus obtained are as follows.

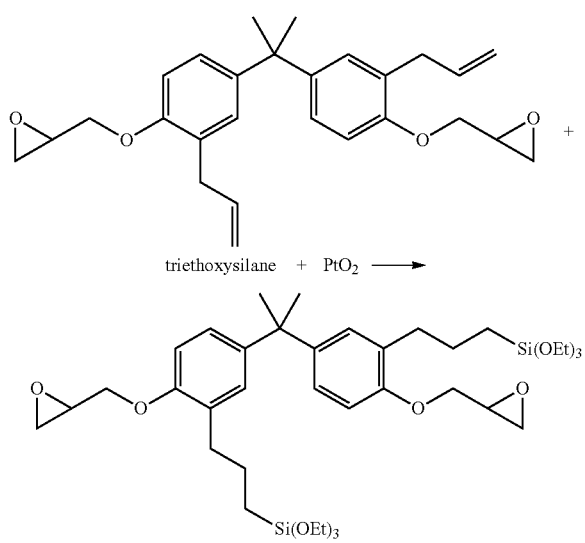

¹H NMR (400 MHz, CDCl₃): δ=0.64-0.69 (m, 4H), 1.22 (t, J=7.0 Hz, 18H), 1.60 (s, 6H), 1.62-1.72 (m, 4H), 2.61 (t, J=7.6 Hz, 4H), 2.74 (dd, J=2.6 Hz, 2H), 2.86 (dd, J=4.2 Hz, 2H), 3.30-3.34 (m, 2H), 3.79 (q, 1.6 Hz, 12H), 3.97 (dd, J=5.2 Hz, 2H), 4.14 (dd, J=3.2 Hz, 2H), 6.70 (d, J=7.6 Hz, 2H), 6.94 (dd, J=2.8 Hz, 2H), 6.99 (d, J=7.6 Hz, 2H).

Synthetic Example DI-2-1

Synthesis of Mono-Alkoxysilylated Epoxy Compound Using Bisphenol a (1) 3-1-th step: 2-((2-allyl-4-(2-(4-(oxirane-2-ylmethoxy)-3-(oxirane-2-ylmethoxy)phenyl)propane-2-yl)phenoxy)-methyl)oxirane Into a 500 ml flask, 15.0 g of 2,2'-(4,4'-(propane-2,2-diyl)bis(2-allyl-4,1-phenylene))bis(oxy)bis(methylene)dioxirane obtained in the 3ʳᵈ step of Synthetic Example D-2, 10.39 g of 77 mol % of 3-chloroperoxybenzoic acid, and 300 ml of methylene chloride were charged and stirred at room temperature for 18 hours. Then, the reaction was worked up by using an aqueous solution of sodium thiosulfate pentahydrate, and product was extracted with ethyl acetate, was washed using 1N aqueous sodium hydroxide solution and brine, and was dried using MgSO₄. After MgSO₄ was filtered off and solvent was removed, it was purified by using a silica column to obtain an intermediate product (13'), 2-((2-allyl-4-(2-(4-(oxirane-2-ylmethoxy)-3-(oxirane-2-ylmethoxy)phenyl)propane-2-yl)phenoxy)-methyl)oxirane. The reaction scheme of the 3-1-th step and the NMR data of the final product thus obtained are as follows.

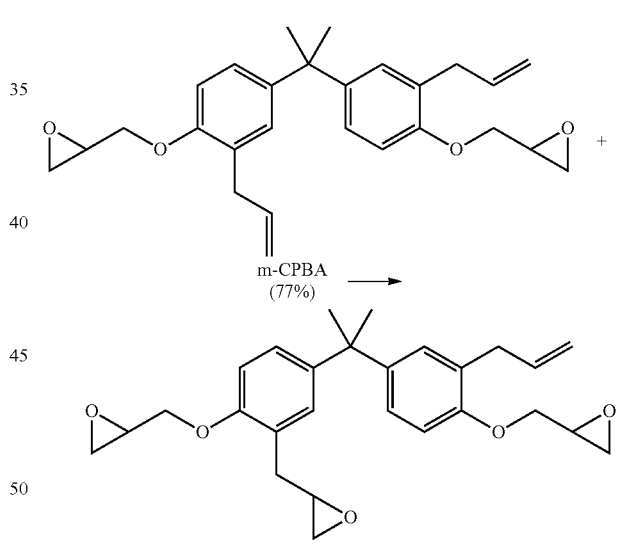

¹H NMR (400 MHz, CDCl₃): δ1.60 (s, 6H), 2.53-2.57 (m, 1H), 2.73-2.81 (m, 5H), 2.89-2.92 (m, 3H), 3.16-3.18 (m, 1H), 3.31-3.35 (m, 3H), 3.90-3.97 (m, 2H), 4.22-4.25 (m, 2H), 4.97-5.04 (m, 2H), 5.93-5.97 (m, 1H), 6.66-6.82 (m, 2H), 6.73-6.75 (m, 2H), 7.03-7.05 (m, 2H).

(2) 4ᵗʰ step: Synthesis of triethoxy(3-(2-(oxirane-2-ylmethoxy)-5-(2-(4-(oxirane-2-ylmethoxy)-3-(oxirane-2-ylmethoxy)phenyl)-propane-2-yl)phenyl)propyl)silane Into a 250 ml flask, 10.0 g of the intermediate product (13') obtained in the 3-1-th step, 5.01 ml of triethoxysilane (Sigma-Aldrich), 100 mg of platinum oxide, and 100 ml of toluene were charged, mixed homogeneously and stirred under argon gas at 85° C. for 24 hours. After finishing the reaction, the product thus obtained was filtered using Celite, and solvent was removed by using an evaporator to obtain a target product of a bisphenol A epoxy compound having an alkoxysilyl group. The reaction scheme of the 4th step and the NMR data of the target product thus obtained are as follows.

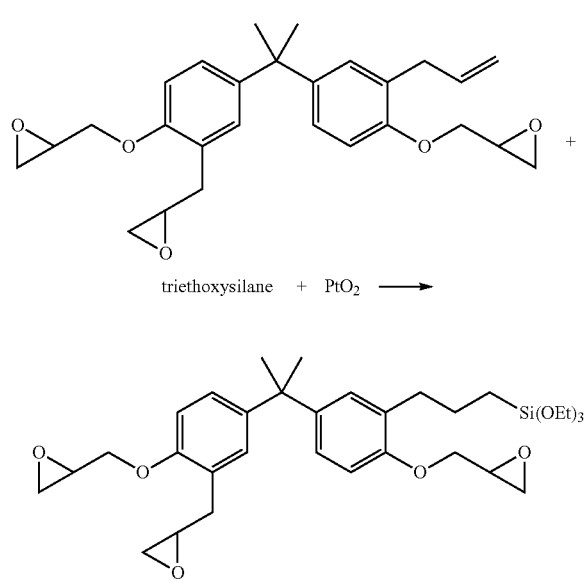

$^1$H NMR (400 MHz, CDCl$_3$): δ=0.64-0.69 (m, 2H), 1.20 (t, J=7.0 Hz, 9H), 1.60 (s, 6H), 1.62-1.72 (m, 2H), 2.53-2.57 (m, 1H), 2.61 (t, J=7.6 Hz, 2H), 2.73-2.81 (m, 5H), 2.89-2.92 (m, 3H), 3.16-3.18 (m, 1H), 3.35-3.37 (m, 1H), 3.79 (q, 1.6 Hz, 6H), 3.90-3.97 (m, 2H), 4.22-4.25 (m, 2H), 6.66-6.82 (m, 2H), 6.73-6.75 (m, 2H), 7.03-7.05 (m, 2H).

Prediction Example DI-3

Synthesis of Tri-Alkoxysilylated Epoxy Compound Using Bisphenol A (1) 1$^{st}$ step: Synthesis of 4,4'-(propane-2,2-diyl)bis(allyloxybenzene)

Into a 1,000 ml two-necked flask equipped with a refluxing condenser, 20.0 g of bisphenol A (Sigma-Aldrich), 18.94 ml of allyl bromide (Sigma-Aldrich), 72.69 g of K$_2$CO$_3$, and 500 ml of acetone were charged and mixed at room temperature. Then, the reaction temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 4,4'-(propane-2,2-diyl)bis(allyloxybenzene). The reaction scheme in the 1$^{st}$ step and the NMR data of the intermediate product (11) are as follows.

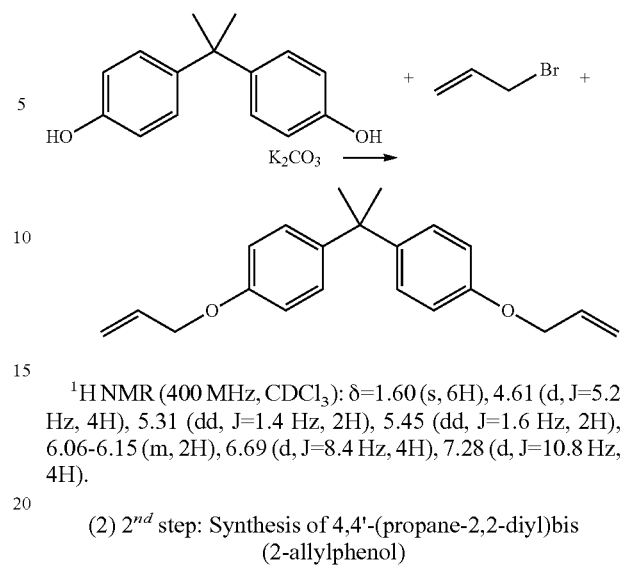

$^1$H NMR (400 MHz, CDCl$_3$): δ=1.60 (s, 6H), 4.61 (d, J=5.2 Hz, 4H), 5.31 (dd, J=1.4 Hz, 2H), 5.45 (dd, J=1.6 Hz, 2H), 6.06-6.15 (m, 2H), 6.69 (d, J=8.4 Hz, 4H), 7.28 (d, J=10.8 Hz, 4H).

(2) 2$^{nd}$ step: Synthesis of 4,4'-(propane-2,2-diyl)bis(2-allylphenol)

Into a 1,000 ml two-necked flask equipped with a refluxing condenser, 20.0 g of the intermediate product (11) obtained in the 1$^{st}$ step and 250 ml of 1,2-dichlorobenzene (Sigma-Aldrich) were charged and mixed at room temperature. The homogenized reaction solution thus obtained was refluxed for 8 hours at 190° C. After finishing the refluxing reaction, the reaction mixture was cooled to room temperature, and solvent was removed in a vacuum oven to obtain an intermediate product (12) of 4,4'-(propane-2,2-diyl)bis(2-allylphenol). The reaction scheme of the 2$^{nd}$ step and the NMR data of the intermediate product (12) are as follows.

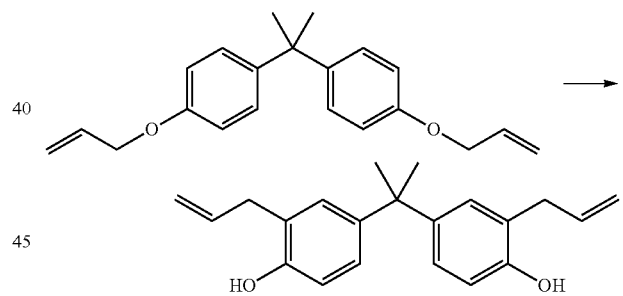

$^1$H NMR (400 MHz, CDCl$_3$): δ=1.60 (s, 6H), 3.35 (d, J=6.4 Hz, 4H), 4.86 (s, 2H), 5.08-5.12 (m, 4H), 5.93-6.03 (m, 2H), 6.75 (d, J=8.4 Hz, 2H), 6.94 (dd, J=10.6 Hz, 4H).

(3) 2-1-th step: Synthesis of 2-allyl-4-(2-(3-allyl-4-(allyloxy)phenyl)propane-2-yl)phenol Into a 1,000 ml two-necked flask equipped with a refluxing condenser, 20.0 g of the intermediate product (12) obtained in the 2$^{nd}$ step, 23.07 g of K$_2$CO$_3$, and 500 ml of acetone are charged and mixed at room temperature. Then, the temperature is set to 80° C., and the homogeneous mixture thus obtained is refluxed. During the refluxing, 5.29 ml of allyl bromide (Sigma-Aldrich) is added in a dropwise manner, and is allowed to react overnight. After finishing the reaction, the reaction mixture is cooled to room temperature and is filtered using Celite. The solvent is evaporated to obtain a coarse product. A target product is extracted from the coarse product using ethyl acetate, washed three times using water, and dried using MgSO$_4$. MgSO$_4$ is filtered off, and solvents are removed by using an evaporator. The product is purified by silica gel column chromatography to obtain an intermediate product (23), 2-allyl-4-(2-(3-allyl-4-(allyloxy)phenyl)propane-2-yl)phenol. The reaction scheme of the 2-1-th step is as follows.

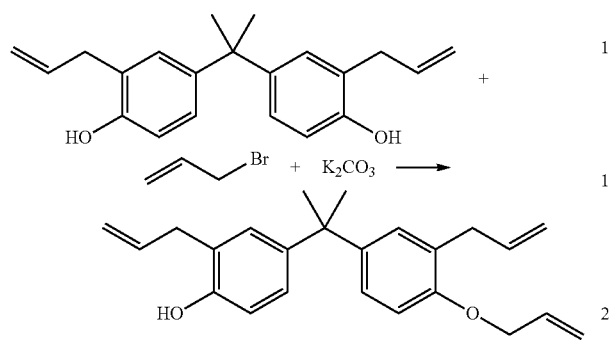

(4) 2-2-th step: Synthesis of 2,6-diallyl-4-(2-(3-allyl-4-hydroxyphenyl)propane-2-yl)phenol Into a 1,000 ml two-necked flask equipped with a refluxing condenser, 20.0 g of the intermediate product (23) obtained in the 2-1-th step and 100 ml of 1,2-dichlorobenzene (Sigma-Aldrich) are charged and mixed at room temperature. The homogenized reaction solution thus obtained is refluxed for 8 hours at 190° C. After finishing the reaction, the reaction mixture is cooled to room temperature, and solvent is removed in a vacuum oven to obtain an intermediate product (24), 2,6-diallyl-4-(2-(3-allyl-4-hydroxyphenyl)propane-2-yl)phenol. The reaction scheme of the 2-2-th step is as follows.

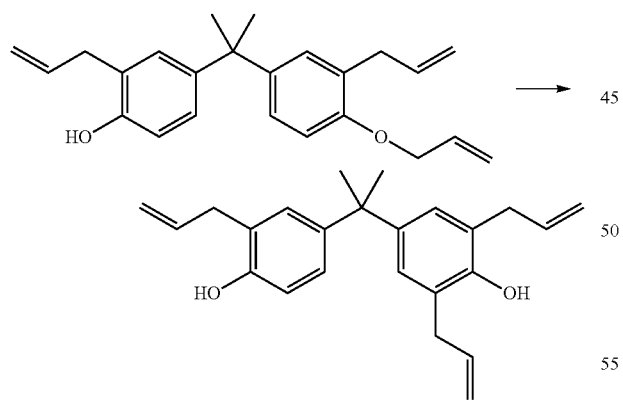

(5) 3$^{rd}$ step: Synthesis of 2-((2-allyl-4-(2-(3,5-diallyl-4-(oxirane-2-ylmethoxy)phenyl)propane-2-yl)phenoxy)methyl)oxirane Into a 1,000 ml two-necked flask equipped with a refluxing condenser, 20.0 g of the intermediate product (24) obtained in the 2-2-th step, 44.24 ml of epichlorohydrin (Sigma-Aldrich), 51.16 g of K$_2$CO$_3$, and 300 ml of acetonitrile are charged and mixed at room temperature. Then, the temperature is increased to 80° C. and the mixture is allowed to react overnight. After finishing the reaction, the reaction mixture is cooled to room temperature, and is filtered though a pad of Celite. The solvent is evaporated to obtain an intermediate product (25), 2-((2-allyl-4-(2-(3,5-diallyl-4-(oxirane-2-yl-methoxy)phenyl) propane-2-yl)phenoxy)methyl)oxirane. The reaction scheme of the 3$^{rd}$ step is as follows.

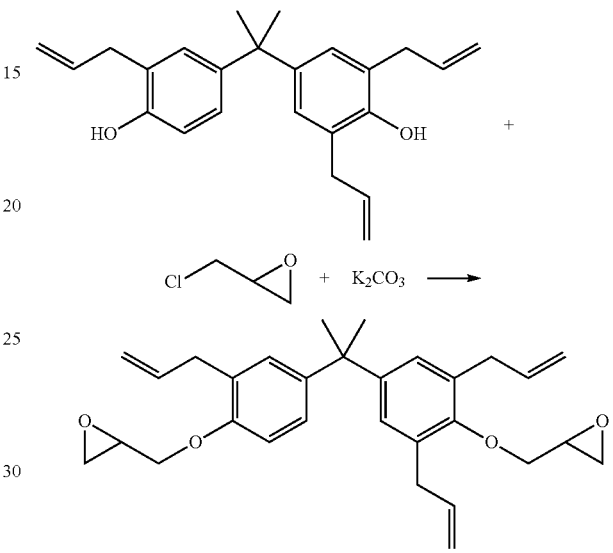

(6) 4$^{th}$ step: Synthesis of (3,3'-(2-(oxirane-2-yl-methoxy)-5-(2-(4-(oxirane-2-ylmethoxy)-3-(2-(tri-ethoxysilyl)propyl)phenyl)propane-2-yl)-1,3-phenylene)bis(propane-3,1-diyl))bis(triethoxysilane)

Into a 500 ml flask, 20.0 g of the intermediate product (25) obtained in the 3$^{rd}$ step, 26.47 ml of triethoxysilane (Sigma-Aldrich), 296 mg of platinum oxide, and 200 ml of toluene are charged and stirred under argon gas at 85° C. for 24 hours. After finishing the reaction, the coarse product thus obtained is filtered using Celite, and solvent is removed by using an evaporator to obtain a target product of a bisphenol A epoxy compound having an alkoxysilyl group. The reaction scheme of the 4$^{th}$ step and the NMR data of the target product thus obtained are as follows.

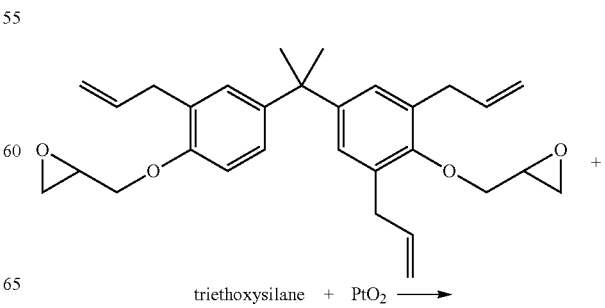

-continued

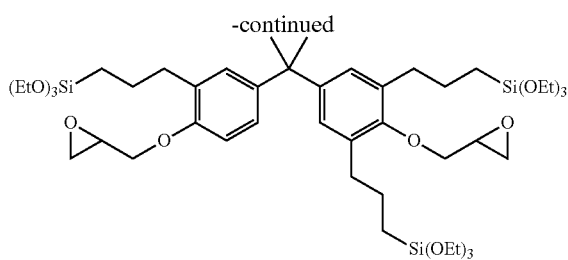

$^1$H NMR (400 MHz, CDCl$_3$): δ=0.60-0.70 (m, 6H), 1.20-1.25 (t, 27H), 1.60-1.80 (m, 12H), 2.50-2.70 (t, 6H), 2.70-2.80 (m, 2H), 2.80-2.90 (m, 2H), 3.30-3.40 (m, 2H), 3.70-4.00 (m, 20H), 4.10-4.20 (m, 2H), 6.80-7.10 (m, 5H).

Prediction Example DI-4

Synthesis of Tetra-Alkoxysilylated Epoxy Compound Using Bisphenol a (1) 1$^{st}$ step: Synthesis of 4,4'-(propane-2,2-diyl)bis(allyloxybenzene)

Into a 1,000 ml two-necked flask equipped with a refluxing condenser, 20.0 g of bisphenol A (Sigma-Aldrich), 18.94 ml of allyl bromide (Sigma-Aldrich), 72.69 g of K$_2$CO$_3$, and 500 ml of acetone were charged and mixed at room temperature. Then, the reaction temperature was set to 80° C., and the homogeneous mixture thus obtained was refluxed overnight. After finishing the reaction, the reaction mixture was cooled to room temperature and was filtered using Celite. The solvent was evaporated to obtain a coarse product. A target product was extracted from the coarse product using ethyl acetate, washed three times using water, and dried using MgSO$_4$. MgSO$_4$ was filtered off, and solvents were removed by using an evaporator to obtain an intermediate product (11), 4,4'-(propane-2,2-diyl)bis(allyloxybenzene). The reaction scheme of the 1$^{st}$ step and the NMR data of the intermediate product (11) are as follows.

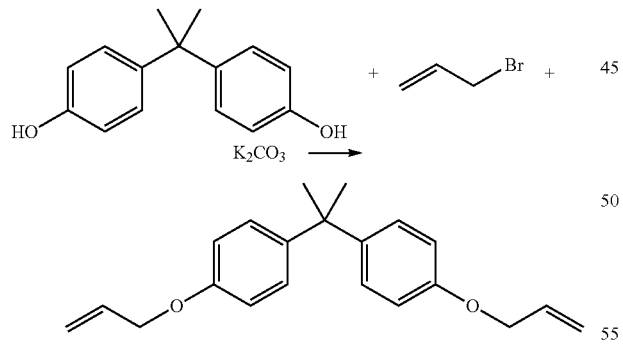

$^1$H NMR (400 MHz, CDCl$_3$): δ=1.60 (s, 6H), 4.61 (d, J=5.2 Hz, 4H), 5.31 (dd, J=1.4 Hz, 2H), 5.45 (dd, J=1.6 Hz, 2H), 6.06-6.15 (m, 2H), 6.69 (d, J=8.4 Hz, 4H), 7.28 (d, J=10.8 Hz, 4H).

(2) 2$^{nd}$ step: Synthesis of 4,4'-(propane-2,2-diyl)bis(2-allylphenol)

Into a 1,000 ml two-necked flask equipped with a refluxing condenser, 20.0 g of the intermediate product (11) obtained in the 1$^{st}$ step and 250 ml of 1,2-dichlorobenzene (Sigma-Aldrich) were charged and mixed at room temperature. The homogenized reaction solution thus obtained was refluxed for 8 hours at 190° C. After finishing the refluxing reaction, the reaction mixture was cooled to room temperature, and solvent was removed in a vacuum oven to obtain an intermediate product (12) of 4,4'-(propane-2,2-diyl)bis(2-allylphenol). The reaction scheme of the 2$^{nd}$ step and the NMR data of the intermediate product (12) are as follows.

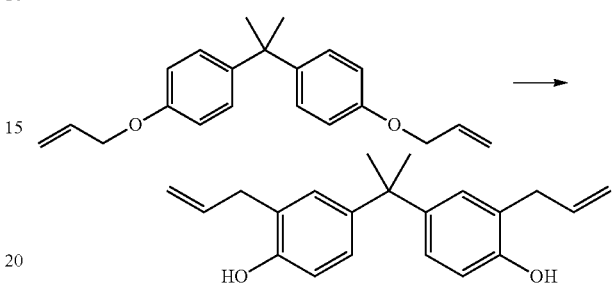

$^1$H NMR (400 MHz, CDCl$_3$): δ=1.60 (s, 6H), 3.35 (d, J=6.4 Hz, 4H), 4.86 (s, 2H), 5.08-5.12 (m, 4H), 5.93-6.03 (m, 2H), 6.75 (d, J=8.4 Hz, 2H), 6.94 (dd, J=10.6 Hz, 4H).

(3) 2-1-th step: Synthesis of 4,4'-(propane-2,2-diyl)bis(2-allyl-1-(allyloxy)benzene)

Into a 1,000 ml two-necked flask equipped with a refluxing condenser, 20.0 g of the intermediate product (12) obtained in the 2$^{nd}$ step, 21.07 ml of allyl bromide (Sigma-Aldrich), 83.31 g of K$_2$CO$_3$, and 500 ml of acetone are charged and mixed at room temperature. Then, the temperature of a refluxing apparatus is set to 80° C. and the homogeneous mixture thus obtained is refluxed. After finishing the reaction, the reaction mixture is cooled to room temperature and is filtered using Celite. The solvent is evaporated to obtain a coarse product. A target product is extracted from the coarse product using ethyl acetate, washed three times using water, and dried using MgSO$_4$. MgSO$_4$ is filtered off, and solvents are removed by using an evaporator to obtain an intermediate product (23), 4,4'-(propane-2,2-diyl)bis(2-allyl-1-(allyloxy)benzene). The reaction scheme of the 2-1-th step is as follows.

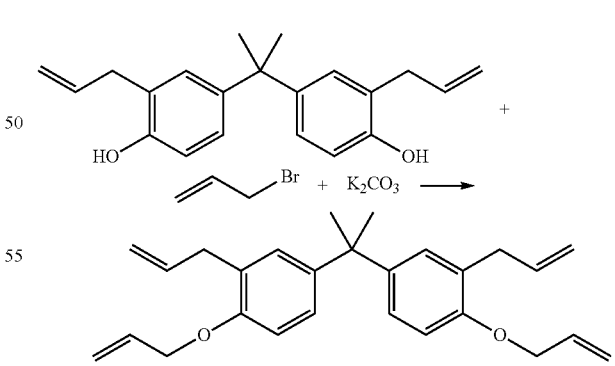

(4) 2-2-th step: Synthesis of 4,4'-(propane-2,2-diyl)bis(2,6-diallylphenol)

Into a 1,000 ml two-necked flask equipped with a refluxing condenser, 20.0 g of the intermediate product (23) obtained in the 2-1-th step and 100 ml of 1,2-dichlorobenzene (Sigma- Aldrich) are charged and mixed at room temperature. The homogenized reaction solution thus obtained is refluxed for 8 hours at 190° C. After finishing the reaction, the reaction mixture is cooled to room temperature, and solvent is removed in a vacuum oven to obtain an intermediate product (24), 4,4'-(propane-2,2-diyl)bis(2,6-diallylphenol). The reaction scheme of the 2-2-th step is as follows.

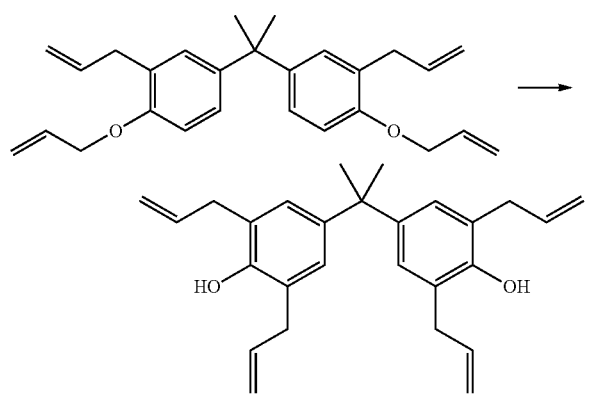

(5) 3$^{rd}$ step: Synthesis of 2,2'-(4,4'-(propane-2,2-diyl) bis(2,6-diallyl-4,1-phenylene)bis(oxy)bis(methylene) dioxirane Into a 1,000 ml two-necked flask equipped with a refluxing condenser, 20.0 g of the intermediate product (24) obtained in the 2-2-th step, 49.71 ml of epichlorohydrin (Sigma-Aldrich), 57.68 g of K$_2$CO$_3$, and 300 ml of acetonitrile are charged and mixed at room temperature. Then, the temperature is increased to 80° C. and the mixture is allowed to react overnight. After finishing the reaction, the reaction mixture is cooled to room temperature, and is filtered using Celite. The solvent is evaporated to obtain an intermediate product (25), 2,2'-(4,4'-(propane-2,2-diyl)bis(2,6-diallyl-4,1-phenylene) bis(oxy)bis(methylene)dioxirane. The reaction scheme of the 3$^{rd}$ step is as follows.

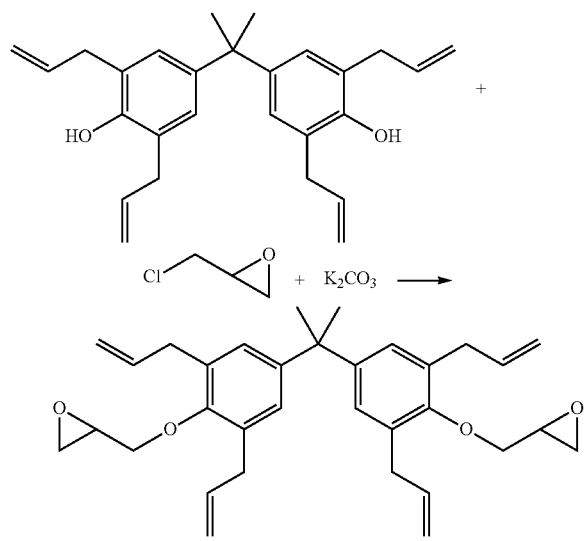

(6) 4$^{th}$ step: Synthesis of (3,3',3'',3'''-(5,5'-(propane-2,2-diyl)bis(2-(oxirane-2-ylmethoxy)benzene-5,3,1-triyl)tetrakis(propane-3,1-diyl))tetrakis(triethoxysilane)

Into a 500 ml flask, 20.0 g of the intermediate product (25) obtained in the 3$^{rd}$ step, 26.83 ml of triethoxysilane (Sigma-Aldrich), 300 mg of platinum oxide, and 200 ml of toluene are charged and stirred under argon gas at 85° C. for 24 hours. After finishing the reaction, the coarse product thus obtained is filtered using Celite, and solvent is removed by using an evaporator to obtain a target product of a bisphenol A epoxy compound having an alkoxysilyl group. The reaction scheme of the 4$^{th}$ step and the NMR data of the target product thus obtained are as follows.

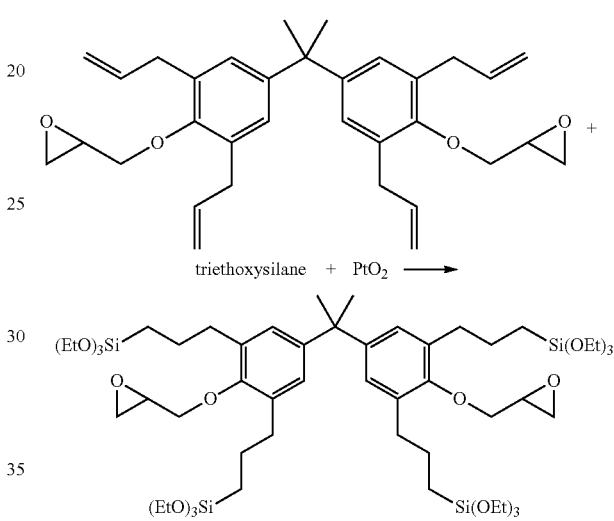

$^1$H NMR (400 MHz, CDCl$_3$): δ=0.60-0.70 (m, 8H), 1.20-1.25 (t, 36H), 1.60-1.80 (m, 14H), 2.50-2.70 (t, 8H), 2.70-2.80 (m, 2H), 2.80-2.90 (m, 2H), 3.30-3.40 (m, 2H), 3.70-4.00 (m, 26H), 4.10-4.20 (m, 2H), 6.80-7.10 (s, 4H).

Evaluation of Physical Properties: Manufacturing of Cured Product and Evaluation of Heat-Resistance 1. Preparation of Epoxy Cured Product An epoxy compound, a phenol-based curing agent (HF-1M™ (Meiwa Plastic Industries, Ltd., 107 g/eq.)) and triphenyl phosphine (Aldrich) as a curing accelerator were dissolved in methyl ethyl ketone, the following the formulation illustrated in the following Table 1. The solid content of the mixture was 40 wt %(the solid content represents the proportion of non-volatile materials contained in a solution). Then, the mixture was put in a vacuum oven at 100° C. to remove solvent, and was then cured in a hot press (which is preheated to 120° C.) at 120° C. for 2 hours, at 180° C. for 2 hours, and at 200° C. to 260° C. for 2 hours.

2. Preparation of Composite (Cured Product) Comprising Exoxy Compound and Glass Fiber An epoxy compound, a phenol-based curing agent (HF-1M™ (Meiwa Plastic Industries, Ltd., 107 g/eq.)) and triphenyl phosphine (Aldrich) as a curing accelerator were dissolved in methyl ethyl ketone, the following the formulation illustrated in the following Table 2. The solid content of the mixture was 40 wt %. Into the mixture thus obtained, a glass fiber (fiber glass fabric of Nittobo Co., E-glass 2116 or T-glass 2116) was impregnated to manufacture a glass fiber composite comprising the epoxy compound. Then, the composite was inserted in a vacuum oven at 100° C. to remove solvent, and was cured in a hot press (which is preheated to 120° C.), at 120° C. for 2 hours, at 180° C. for 2 hours, and at 200° C. to 260° C. for 2 hours to manufacture a glass fiber composite film. The resin content of the glass fiber composite film was controlled by the applied pressure of the press and the viscosity of the resin, which is described in the following Table 2.

3. Preparation of Composite (Cured Product) Comprising Epoxy Compound, Glass Fiber and Silica An epoxy compound, and a silica slurry (solid content 70 wt % in 2-methoxyethanol average size of 1 μm) were dissolved in methyl ethyl ketone, the following the formulation illustrated in the following Table 2. The solid content of the mixture was 40 wt %. The mixture thus obtained was mixed at the rate of 1,500 rpm for 1 hour, and a phenol-based curing agent (HF-1M™ (Meiwa Plastic Industries, Ltd., 107 g/eq.)) was added and additional mixing was conducted for 50 minutes. And then, triphenyl phosphine (Aldrich) was finally added as a curing accelerator and mixed for 10 minutes further to obtain the final epoxy mixture. Into the mixture thus obtained, a glass fiber (fiber glass fabric of Nittobo Co., E-glass 2116 or T-glass 2116) was impregnated to manufacture a glass fiber composite comprising the epoxy compound. Then, the composite was inserted in a vacuum oven at 100° C. to remove the solvent, and was cured in a hot press (which is preheated to 120° C.) at 120° C. for 2 hours, at 180° C. for 2 hours, and at 200° C. to 260° C. for 2 hours to manufacture a glass fiber composite film. The resin content of the glass fiber composite film was controlled by the applied pressure of the press and the viscosity of the resin, which is described in the following Table 2.

4. Evaluation of Physical Properties (1) Evaluation of Heat-Resistant Properties The dimensional changes of the cured products obtained in the Examples and Comparative Examples in Table 1 and Table 2 were evaluated as a function of temperature by using a Thermo-mechanical analyzer (Film/fiber mode, Force 0.1 N) and are illustrated in the following Tables. The samples of the cured products of epoxy compound with the size of 5×5×3 (mm$^3$) and the composite films with the size of 4×16×0.1 (mm$^3$) were prepared.

TABLE 1

| | | Epoxy cured product | | | | |
|---|---|---|---|---|---|---|
| | Epoxy compound | Epoxy composition | | | heat resistance | |
| No. | (Synthetic Example No.) | Epoxy (g) | Curing agent(g) | Curing accelerator (g) | CTE (ppm/° C.) | Tg (° C.) |
| Example 1 | AI-1 | 5.0 | 2.245 | 0.035 | 75 | 140 |
| Example 2 | AI-2 | 5.0 | 1.57 | 0.03 | 127 | 130 |
| Example 3 | BI-1 | 5.0 | 2.219 | 0.05 | 80 | 150 |
| Example 4 | BI-2 | 5.0 | 1.54 | 0.05 | 104 | 120 |
| Example 5 | CI-1 | 5.0 | 1.499 | 0.025 | 76 | 170 |
| Example 6 | CI-2 | 5.0 | 1.27 | 0.03 | 99 | 160 |
| Example 7 | DI-1 | 5.0 | 2.09 | 0.10 | 88 | 135 |
| Example 8 | DI-2 | 5.0 | 1.40 | 0.05 | 130 | 100 |
| Example 9 | DI-2 | 5.0 | 1.86 | 0.05 | 116 | 100 |
| Example 10 | DI-2-1 | 5.0 | 2.67 | 0.05 | 84 | 150 |
| Comparative Example 1 | Naphthalene epoxy[1] | 5.0 | 3.74 | 0.05 | 64 | 145 |
| Comparative Example 2 | Biphenyl epoxy[2] | 5.0 | 3.59 | 0.05 | 71 | 160 |
| Comparative Example 3 | Cardo epoxy[3] | 5.0 | 1.04 | 0.05 | 65 | 170 |
| Comparative Example 4 | Bisphenol epoxy[4] (difunctional) | 5.0 | 2.05 | 0.05 | 74 | 130 |
| Comparative Example 5 | Bisphenol epoxy[5] (tetra-functional) | 5.0 | 4.58 | 0.05 | Crack after post-curing | |

TABLE 2

| | | | Epoxy composite | | | | | | |
|---|---|---|---|---|---|---|---|---|---|
| | | | Epoxy composition | | | | | heat resistance | |
| Example No. | Epoxy compound | Glass fiber type | Epoxy (g) | Curing agent (g) | Curing accelerator (g) | Silica (g) | Resin content (wt %) | CTE (ppm/° C.) | Tg (° C.) |
| 11 | AI-1 | E-glass | 5.0 | 2.245 | 0.035 | 1.82 | 40 | 10 | Tg-less |
| 12 | AI-2 | E-glass | 5.00 | 1.57 | 0.03 | 0.00 | 41 | 8.03 | 135 |
| 13 | AI-2 | E-glass | 5.0 | 1.57 | 0.03 | 1.65 | 40 | 7.48 | Tg-less |
| 14 | AI-2 | T-glass | 5.0 | 1.57 | 0.03 | 0.00 | 39 | 4.005 | 135 |
| 15 | AI-2 | T-glass | 5.0 | 1.57 | 0.03 | 1.65 | 40 | 3.686 | Tg-less |
| 16 | BI-1 | E-glass | 5.0 | 2.129 | 0.05 | 1.79 | 40 | 9 | Tg-less |
| 17 | BI-2 | E-glass | 5.0 | 1.54 | 0.05 | 0.00 | 35 | 5.17 | 150 |

TABLE 2-continued

| | | | | | | | | | |
|---|---|---|---|---|---|---|---|---|---|
| 18 | BI-2 | E-glass | 5.0 | 1.54 | 0.05 | 1.65 | 40 | 4.44 | Tg-less |
| 19 | CI-1 | E-glass | 5.0 | 1.499 | 0.025 | 1.66 | 38 | 10 | Tg-less |
| 20 | CI-2 | E-glass | 5.0 | 1.27 | 0.03 | 0.00 | 40 | 7.24 | Tg-less |
| 21 | DI-1 | E-glass | 5.0 | 2.09 | 0.10 | 0.00 | 35 | 10.32 | Tg-less |
| 22 | DI-1 | E-glass | 5.0 | 2.09 | 0.08 | 1.80 | 43 | 12.09 | 170 |
| 23 | DI-2 | E-glass | 5.0 | 1.86 | 0.05 | 0.00 | 36 | 6.96 | 140 |
| 24 | DI-2 | E-glass | 5.0 | 1.68 | 0.05 | 0.50 | 36 | 6.77 | Tg-less |
| 25 | DI-2 | E-glass | 5.0 | 1.78 | 0.05 | 0.00 | 39 | 8.06 | 140 |
| 26 | DI-2 | E-glass | 5.0 | 1.42 | 0.05 | 0.00 | 45 | 8.40 | 125 |
| 27 | DI-2 | E-glass | 5.0 | 1.68 | 0.50 | 0.50 | 45 | 7.99 | Tg-less |
| 28 | DI-2 | T-glass | 5.0 | 1.86 | 0.05 | 0.00 | 35 | 4.529 | 140 |
| 29 | DI-2 | T-glass | 5.0 | 1.86 | 0.05 | 2.96 | 38 | 5.105 | 120 |
| 30 | DI-2-1 | E-glass | 5.0 | 2.67 | 0.02 | 0.00 | 38 | 10.37 | 180 |
| 31 | DI-2-1 | E-glass | 5.0 | 3.06 | 0.04 | 2.14 | 40 | 8.00 | Tg-less |

| Comparative Example No. | Epoxy compound | Glass fiber type | Epoxy ratio Epoxy (g) | Curing agent (g) | Curing-accelerator (g) | Silica (g) | Resin content (wt %) | Heat resistance CTE (ppm/° C.) | Tg (° C.) |
|---|---|---|---|---|---|---|---|---|---|
| 6 | Naphthalene epoxy[1] | E-glass | 5.0 | 3.74 | 0.05 | 0.00 | 45 | 14 | 160 |
| 7 | Biphenyl epoxy[2] | E-glass | 5.00 | 3.59 | 0.05 | 0.00 | 38 | 14 | 160 |
| 8 | Cardo epoxy[3] | E-glass | 5.0 | 1.04 | 0.05 | 0.00 | 42 | 17 | 170 |
| 9 | Bisphenol A epoxy[4] (difunctional) | E-glass | 5.0 | 2.05 | 0.05 | 0.00 | 37 | 14 | 130 |
| 10 | Bisphenol A epoxy[4] (difunctional) | E-glass | 5.0 | 2.05 | 0.05 | 0.00 | 42 | 16 | 120 |
| 11 | Bisphenol A epoxy[4] (difunctional) | E-glass | 5.0 | 2.05 | 0.05 | 0.50 | 45 | 15 | 120 |
| 12 | Bisphenol A epoxy[5] (tetrafunctional) | E-glass | 5.0 | 4.58 | 0.05 | 0.00 | 40 | 12.58 | 223 |
| 13 | Bisphenol A epoxy[5] (tetrafunctional) | E-glass | 5.0 | 4.58 | 0.05 | 0.00 | 45 | 15 | 218 |

Note:
The common epoxy compounds used in the above Tables 1 and 2 are as follows.
[1] naphthalene epoxy

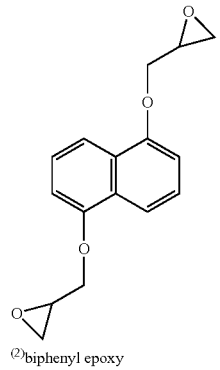

[2] biphenyl epoxy

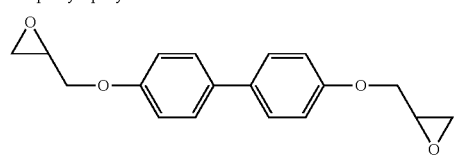

TABLE 2-continued (3) cardo epoxy

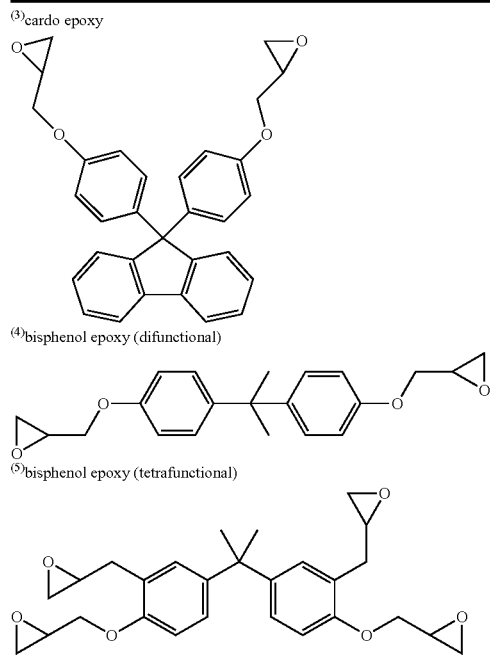

(4) bisphenol epoxy (difunctional)

(5) bisphenol epoxy (tetrafunctional)

As illustrated in the above Tables 1 and 2, and in FIG. 1, the cured product of the alkoxysilylated epoxy compound itself of Chemical Formula AI having the naphthalene core according to the present invention (Example 2) may show an increased CTE and a decreased Tg when compared with that of the epoxy compound having the same naphthalene core structure without the alkoxysilyl group (Comparative Example 1).

Figure 2:
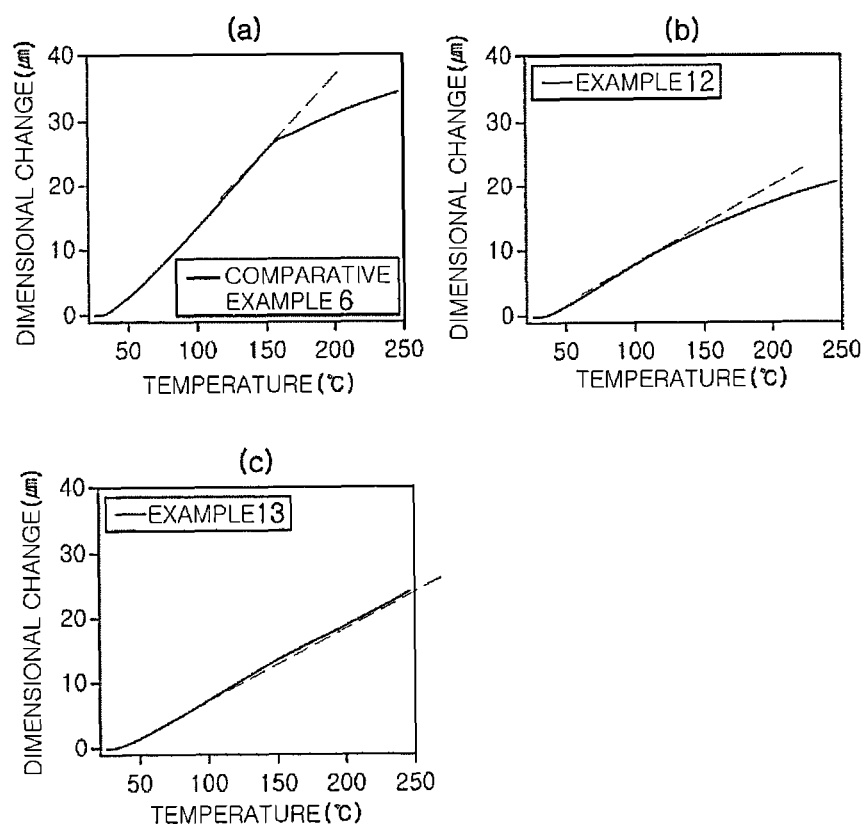
FIGS. 2(a), 2(b) and 2(c) are graphs illustrating CTE of Comparative Example 6 (FIG. 2(a)), Example 12 (FIG. 2(b)) and Example 13 (FIG. 2(c))
Figure 3:
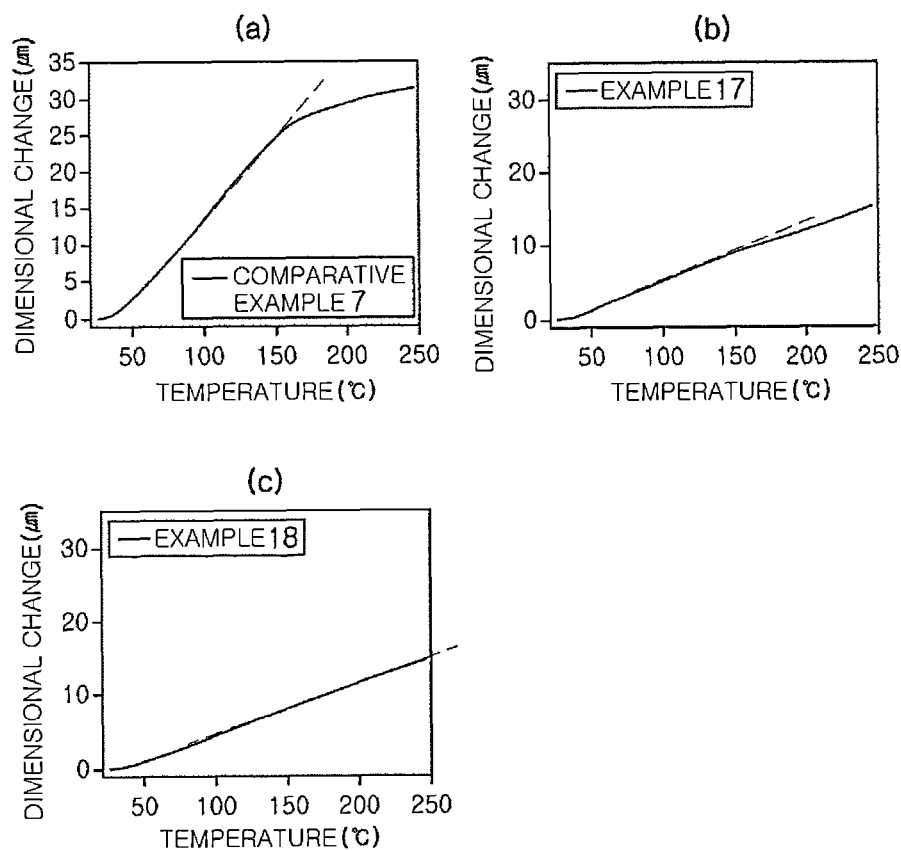
FIGS. 3(a), 3(b) and 3(c) are graphs illustrating CTE of Comparative Example 7 (FIG. 3(a)), Example 17 (FIG. 3(b)) and Example 18 (FIG. 3(c))
Figure 4:
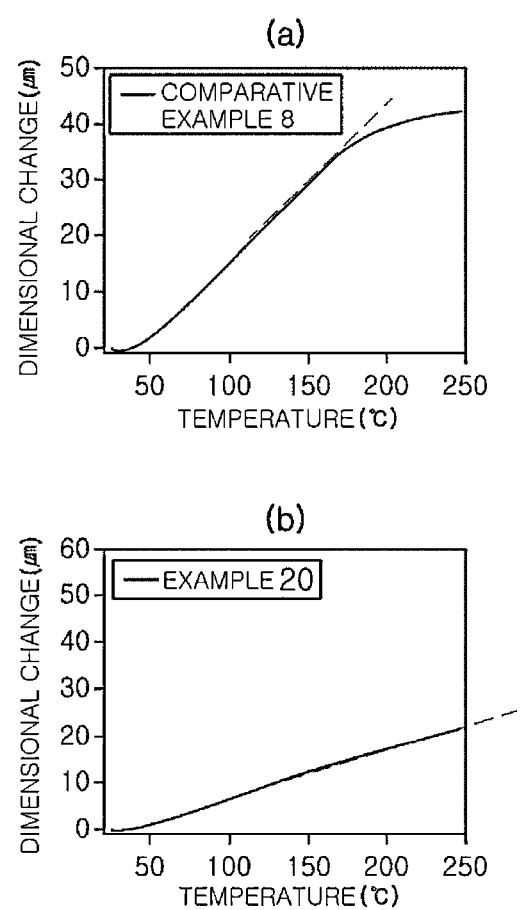
FIGS. 4(a) and 4(b) are graphs illustrating CTE of Comparative Example 8 (FIG. 4(a)) and Example 20 (FIG. 4(b))
Figure 5:
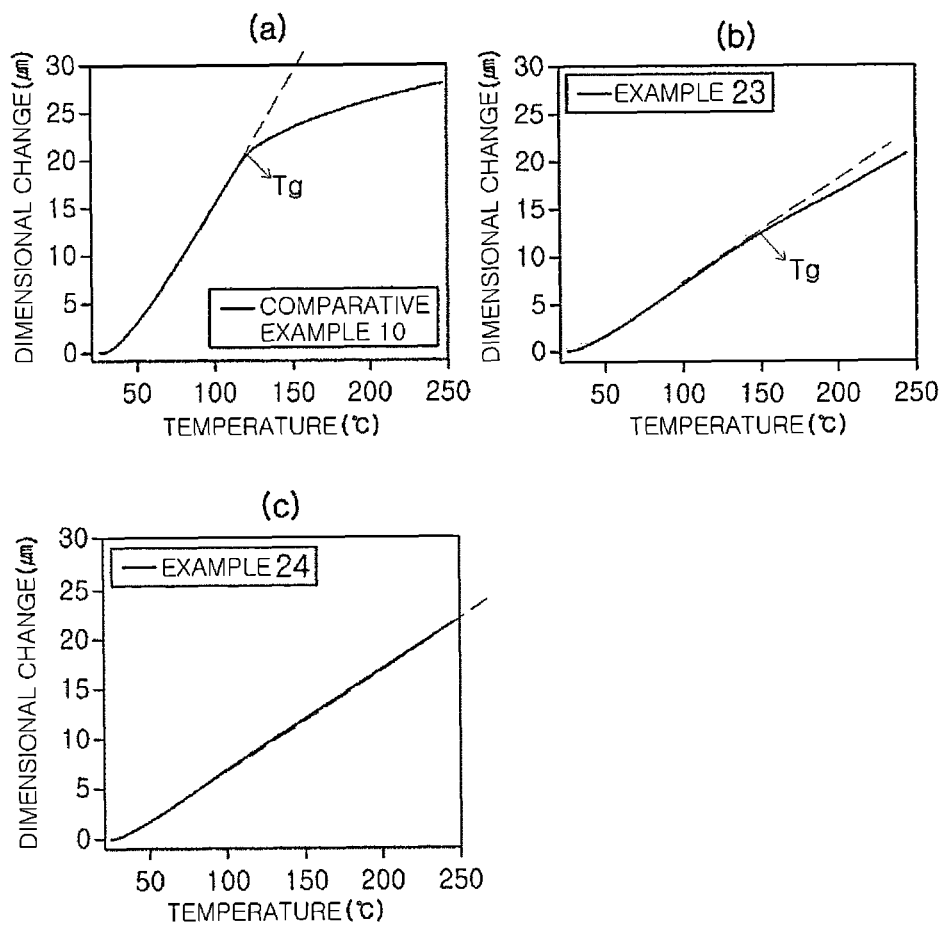
FIGS. 5(a), 5(b) and 5(c) are graphs illustrating CTE of Comparative Example 10 (FIG. 5(a)), Example 23 (FIG. 5(b)) and Example 24 (FIG. 5(c))

However, the CTE values of the Glass fiber composites of the alkoxysilylated naphthalene-type epoxy compound of Chemical Formula AI (Examples 11 to 15) was 7 to 10 ppm/° C. (Examples 12 and 13, E-glass) or about 4 ppm/° C. (Examples 14 and 15, T-glass), which are very low when compared with the CTE=14 ppm/° C. of the composite of the naphthalene epoxy compound without the alkoxysilyl group (Comparative Example 6). Particularly for naphthalene-type epoxy compound, as illustrated in FIG. 2, the CTE values of the composites of Example 12 and Example 13 were decreased when compared with that of Comparative Example 6. For example, for the biphenyl-type epoxy compound, as illustrated in FIG. 3, the CTE values of the composites of Example 17 and Example 18 were decreased when compared with that of Comparative Example 7. For example, for the cardo (fluorene)-type epoxy compound, as illustrated in FIG. 4, the CTE value of the composite of Example 20 was decreased when compared with that of Comparative Example 8. For example, for the bisphenol A-type epoxy compound, as illustrated in FIG. 5, the CTE values of the composites of Example 23 and Example 24 were decreased when compared with that of Comparative Example 10.

Figure 6:
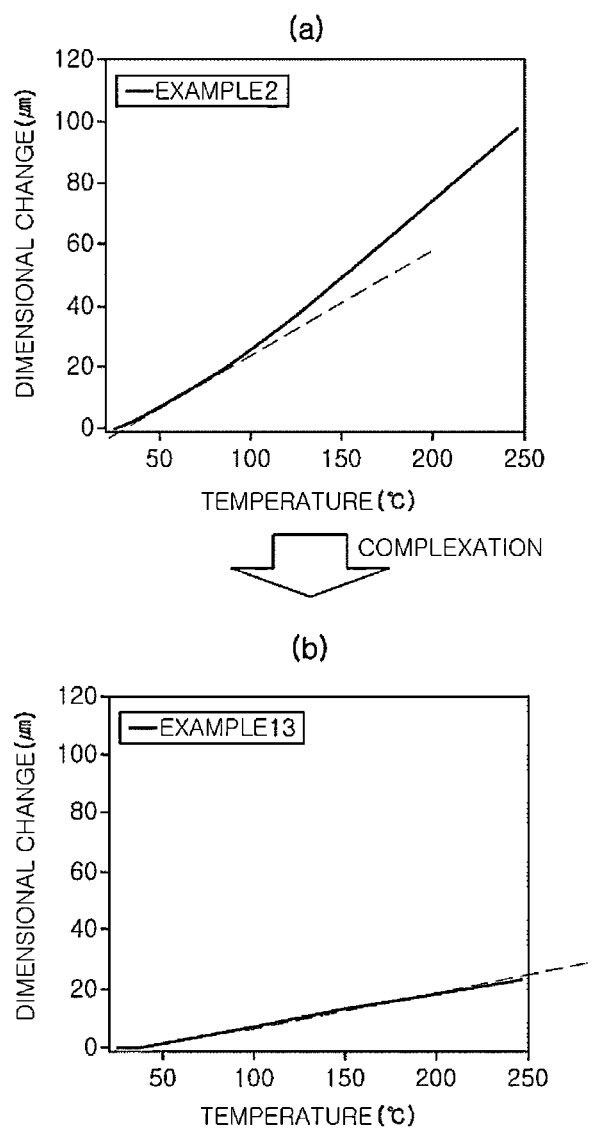
FIGS. 6(a) and 6(b) are graphs illustrating Tg of Example 2 (FIG. 6(a)) and Example 13 (FIG. 6(b))
Figure 7:
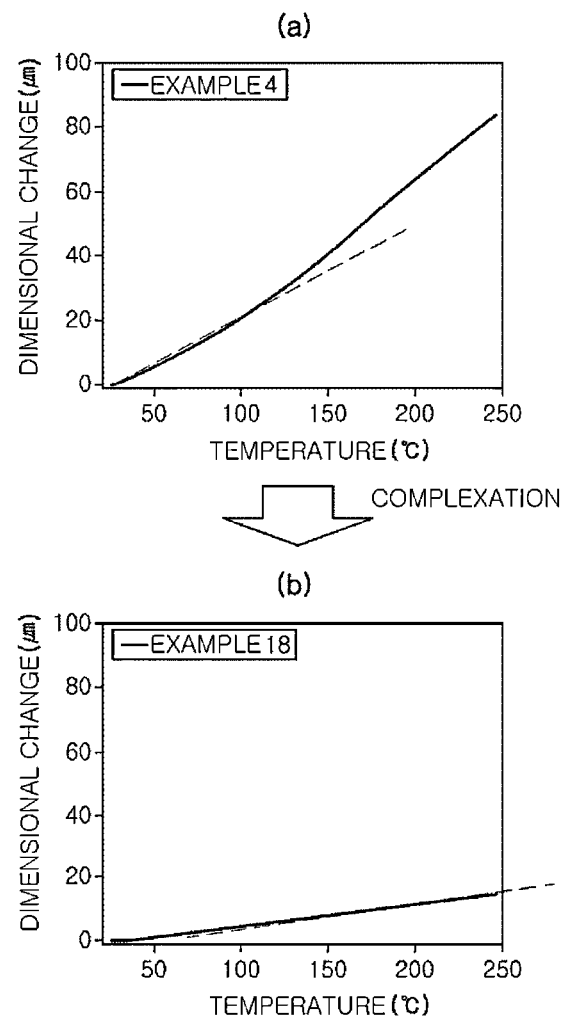
FIGS. 7(a) and 7(b) are graphs illustrating Tg of Example 4 (FIG. 7(a)) and Example 18 (FIG. 7(b))
Figure 8:
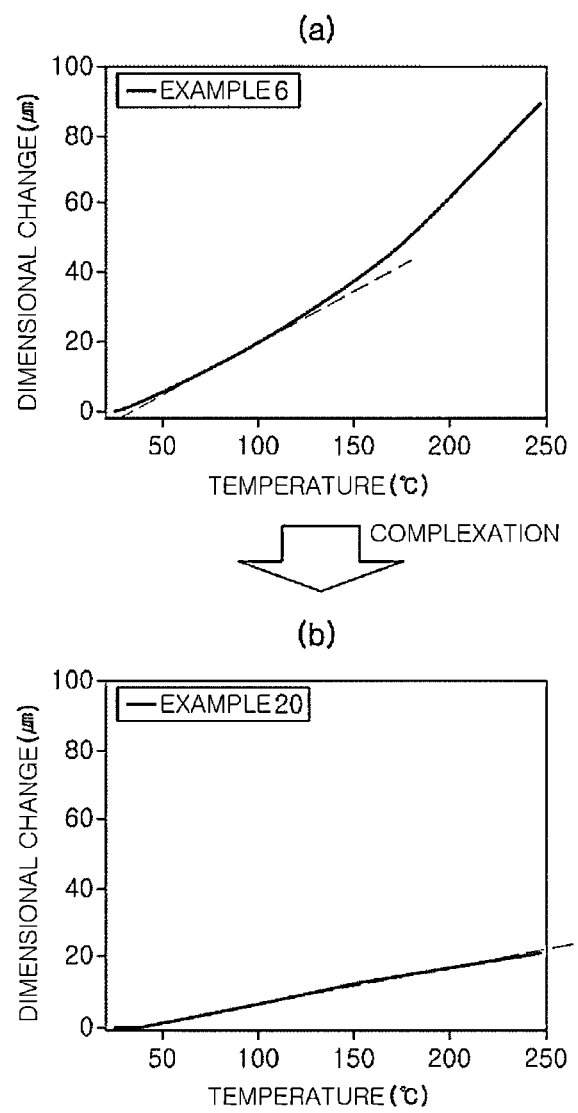
FIGS. 8(a) and 8(b) are graphs illustrating Tg of Example 6 (FIG. 8(a)) and Example 20 (FIG. 8(b))
Figure 9:
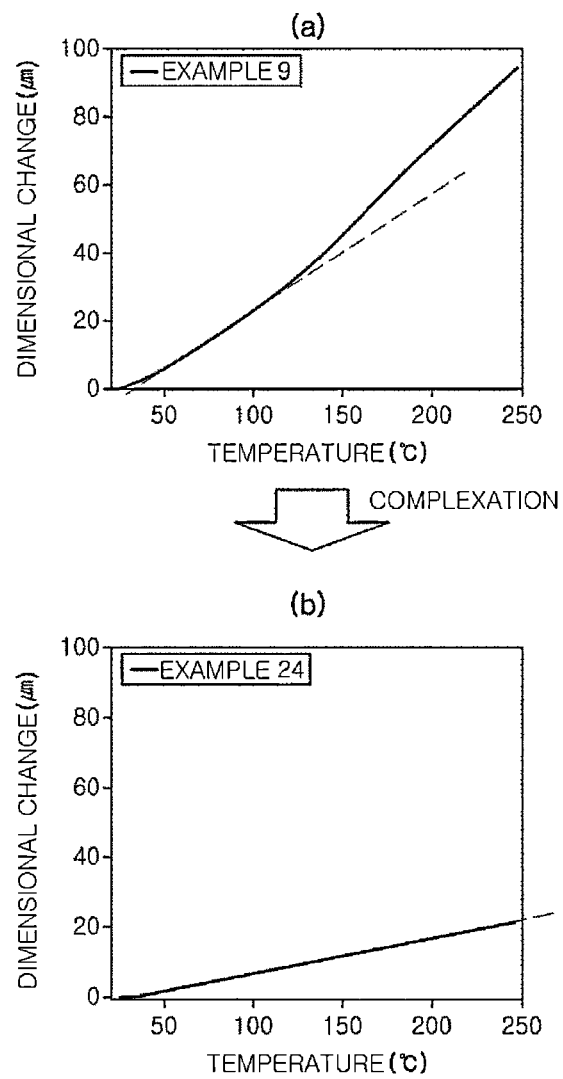
FIGS. 9(a) and 9(b) are graphs illustrating Tg of Example 9 (FIG. 9(a)) and Example 24 (FIG. 9(b))

In addition, the Tg of the composite of the alkoxysilylated epoxy compound according to the present invention may be increased when compared with that of cured product of expoxy compound itself. Tg-less may be observed by appropriately controlling the formulation, for example, through adding a small amount of silica. For example, the naphthalene-type epoxy compound, as illustrated in FIG. 6, shows Tg-less in the composite of Example 13, which is different from the epoxy cured product of Example 2. For example, the biphenyl-type epoxy compound, as illustrated in FIG. 7, shows Tg-less in the composite of Example 18, which is different from epoxy cured product of Example 4. For example, the cardo (fluorene)-type epoxy compound, as illustrated in FIG. 8, shows Tg-less in the composite of Example 20, which is different from epoxy cured product of Example 6. For example, the bisphenol A-type epoxy compound, as illustrated in FIG. 9, shows Tg-less in the composite of Example 24, which is different from the epoxy cured product of Example 9.

As described above, the resin cured product of the alkoxysilylated epoxy compound according to the present invention shows an increased CTE and a decreased Tg when compared with the resin cured product of the epoxy compound without the alkoxysilyl group. However, on the contrary, the composite of the alkoxysilylated epoxy compound according to the present invention shows a decreased CTE when compared with the composite of the epoxy compound without the alkoxysilyl group. In addition, the composite of the alkoxysilylated epoxy compound according to the present invention shows higher Tg or Tg-less when compared with that of epoxy compound without the alkoxysilyl group through proper control of the formulation.

The decreased CTE and the increased Tg or the Tg-less properties in the alkoxysilylated epoxy composite may be obtained due to the improvement of the chemical bonding properties of the epoxy compound with the filler in the composite. From the above-described properties, the improved chemical bonding properties of the epoxy compound and the filler in the composite may be confirmed.

Figure 10:
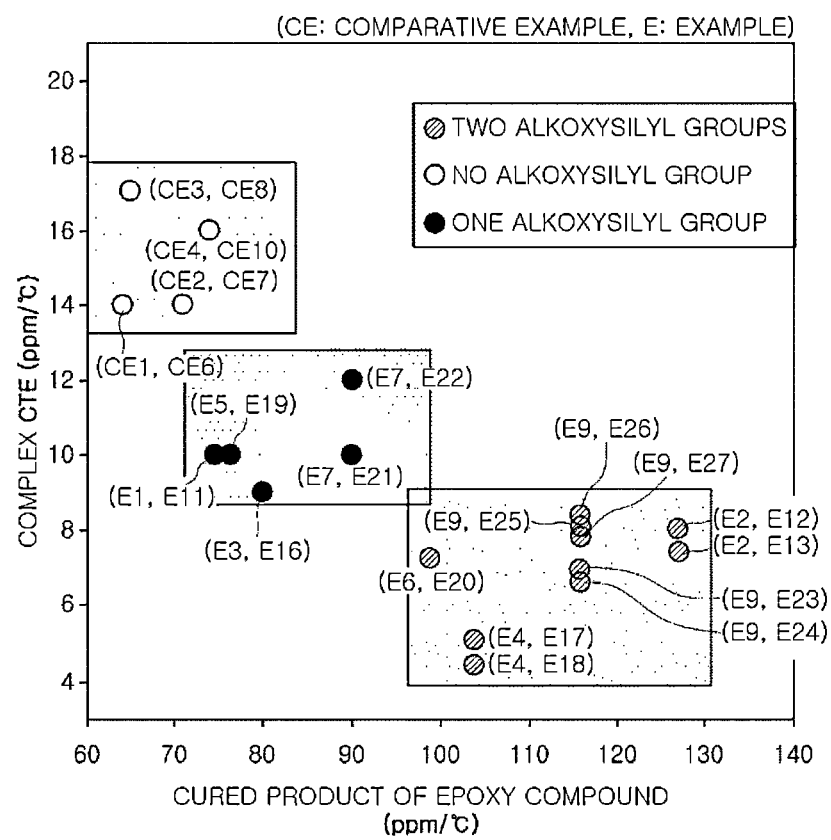
FIG. 10 is a graph illustrating CTE relationships between cured epoxy resins (cured products of epoxy compound) and composites at various numbers of alkoxysilyl groups.
Figure 11:
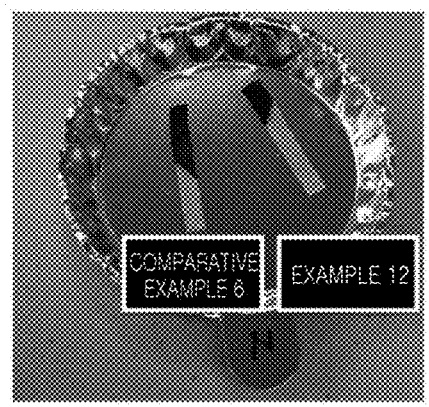
FIG. 11 is a photograph illustrating states of the cured epoxy resins after combustion according to Example 12 and Comparative Example 6.
Figure 12:
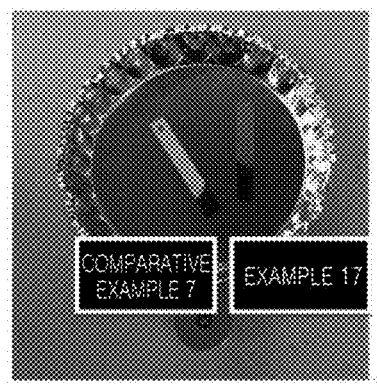
FIG. 12 is a photograph illustrating states of the cured epoxy resins after combustion according to Example 17 and Comparative Example 7.
Figure 13:
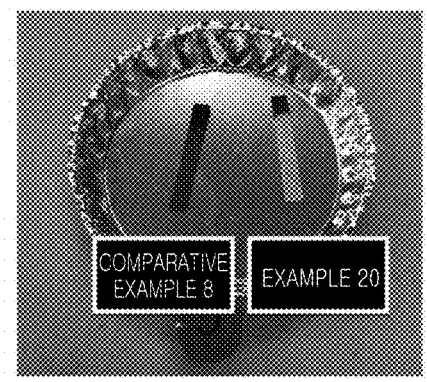
FIG. 13 is a photograph illustrating states of the cured epoxy resins after combustion according to Example 20 and Comparative Example 8.
Figure 14:
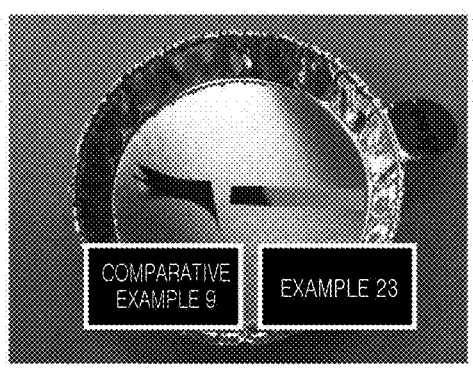
FIG. 14 is a photograph illustrating states of the cured epoxy resins after combustion according to Example 23 and Comparative Example 9.

In addition, the variation of CTE values of cured product of epoxy compound and composite systems with the number of alkoxysilyl groups in the epoxy compound is illustrated in FIG. 10. As illustrated in FIG. 10, the CTE of the cured product of the alkoxysilylated epoxy compound according to the present invention is higher than the CTE of that of the epoxy compound without the alkoxysilyl group. However, the CTE of the composite of the alkoxysilylated epoxy compound according to the present invention is significantly lower than that of the epoxy compound without the alkoxysilyl group. This tendency may increase as the number of alkoxysilyl groups in the epoxy compound increases.

(2) Evaluation of Flame Retardant Properties

Strips of the composites of Examples 12, 17, 20 and 23, and Comparative Examples 6, 7, 8 and 9 in Table 2 were ignited, and photographs of the burned strips are illustrated in FIGS. 11 to 14. As illustrated in FIGS. 11 to 14, all of the strips of the composites of Examples 12, 17, 20 and 23, which are the composites of the epoxy compounds of the present invention, were extinguished spontaneously within 1 to 2 seconds. Some of the strips of the composites of Comparative Examples 6, 7, 8 and 9, without the alkoxysilyl group were also eventually extinguished. However, the time necessary for extinguishing flame of the Comparative Example was longer when compared with that of alkoxysilylated epoxy compound having the same core according to the present invention. The bisphenol epoxy cured product according to Comparative Example 4 was completely burned.

As described above, a cured product comprising an alkoxysilylated epoxy compound according to the present invention has been confirmed to show good flame retardant properties.

While the present invention has been shown and described in connection with the exemplary embodiments, it will be apparent to those skilled in the art that modifications and variations can be made without departing from the spirit and scope of the invention as defined by the appended claims.

The invention claimed is:

1. An epoxy compound having an alkoxysilyl group comprising at least one substituent of the following Chemical Formula S1, two epoxy groups of the following Chemical Formula S2, and a substituent of Chemical Formula S3 at a core selected from the group consisting of the following Chemical Formulae A' to K':

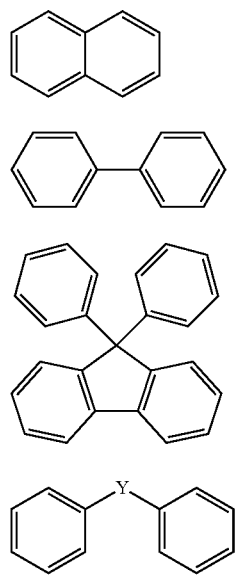

-continued

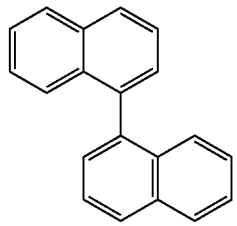

(E')

(F')

(G')

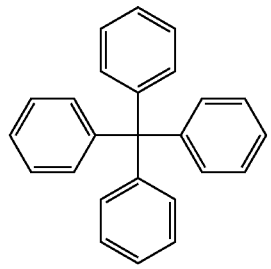

(H')

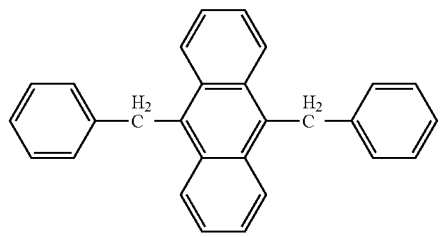

(I')

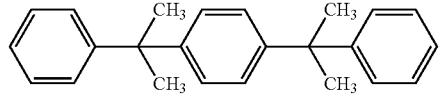

(J')

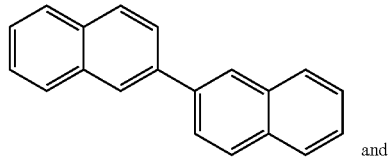

and (K')

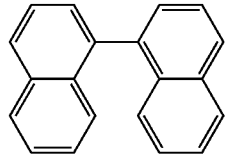

in Chemical Formula D', Y is —CH$_2$—, —C(CH$_3$)$_2$—, —C(CF$_3$)$_2$—, —S— or —SO$_2$—;

—CR$_b$R$_c$—CHR$_a$—CH$_2$—SiR$_1$R$_2$R$_3$   [Chemical Formula S1]

in Chemical Formula S1, each of R$_a$, R$_b$ and R$_c$ is independently H or an alkyl group having 1 to 6 carbon atoms, at least one of $R_1$ to $R_3$ is an alkoxy group having 1 to 6 carbon atoms, and a remainder of $R_1$ to $R_3$ is an alkyl group having 1 to 10 carbon atoms, and the alkyl group and the alkoxy group may be a linear chain or a branched chain

[Chemical Formula S3]

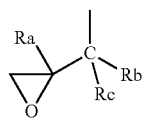

[Chemical Formula S2]

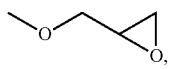

in Chemical Formula S3, each of $R_a$, $R_b$ and $R_c$ is independently H or an alkyl group having 1 to 6 carbon atoms, and the alkyl group may be a linear chain or a branched chain.

2. An epoxy polymer having an alkoxysilyl group which is at least one selected from the group consisting of the following Chemical Formulae AP to KP:

[Chemical Formula AP]

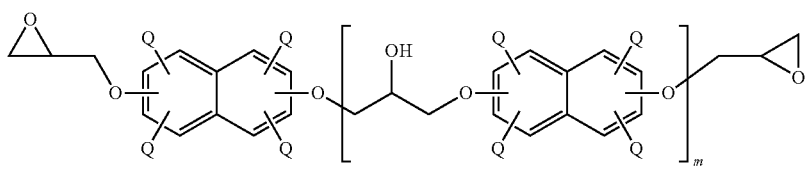

[Chemical Formula BP]

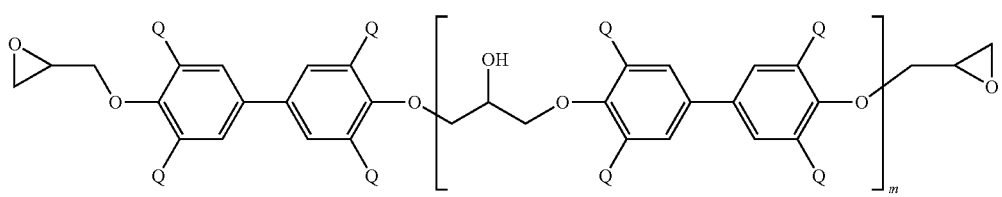

[Chemical Formula CP]

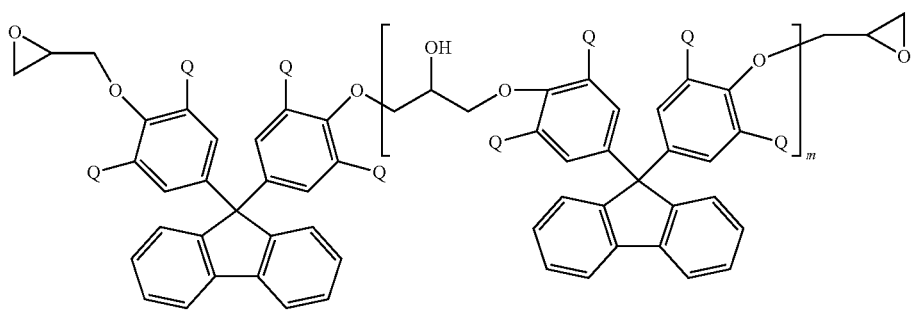

[Chemical Formula DP]

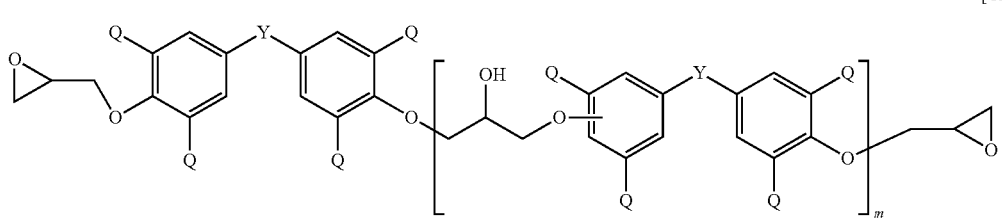

[Chemical Formula EP]

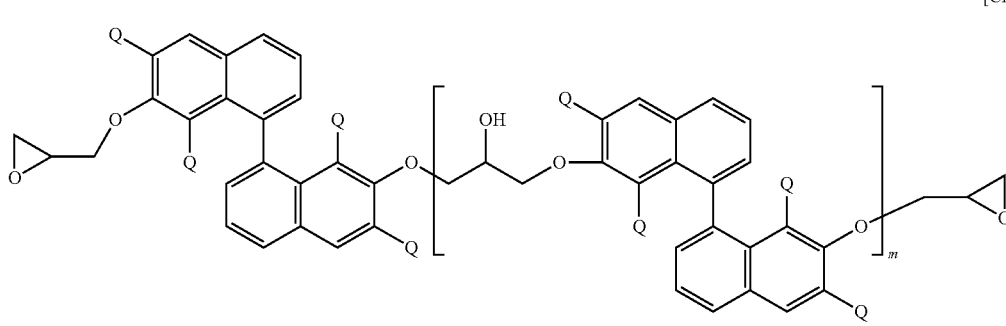

-continued
[Chemical Formula FP]
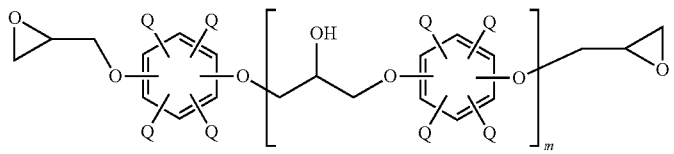
[Chemical Formula GP]
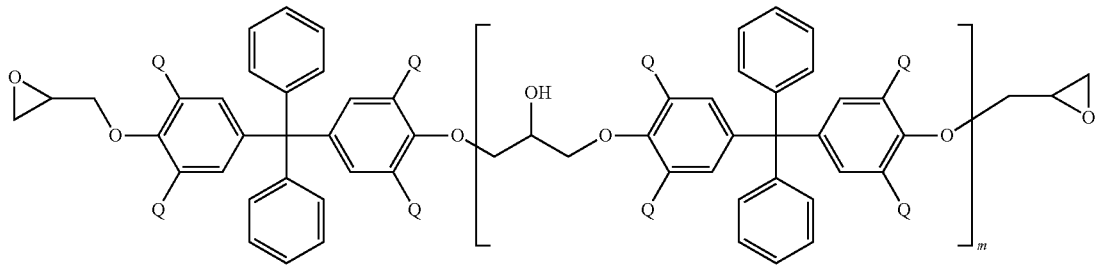
[Chemical Formula HP]
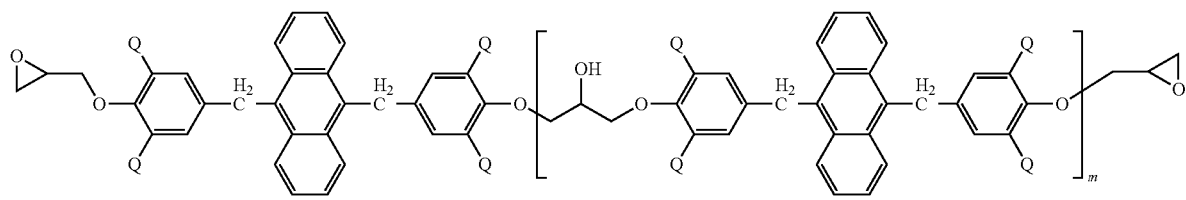
[Chemical Formula IP]
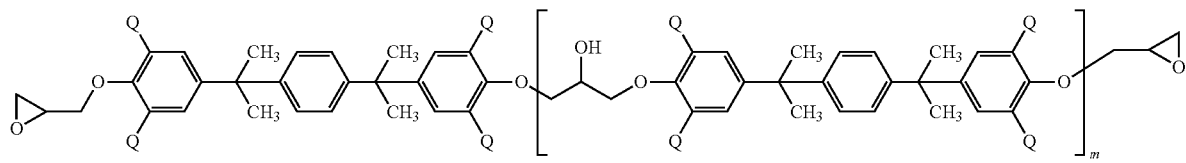
[Chemical Formula JP]
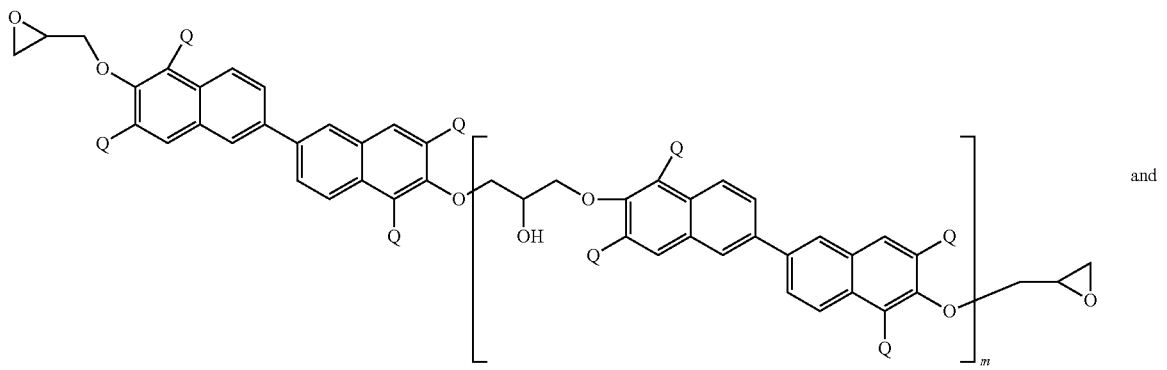
and
[Chemical Formula KP]
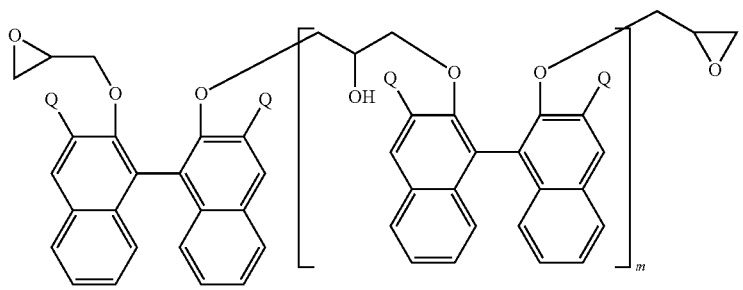

in Chemical Formulae AP to KP, at least one of a plurality of Q is Chemical Formula S1, each of the remainder of Q is independently selected from the group consisting of the following Chemical Formula S3, hydrogen and —CRbRc-CRa=CH2 (in which each of Ra, Rb and Rc is independently H or an alkyl group having 1 to 6 carbon atoms, the alkyl group may have a linear chain or a branched chain), m is an integer of 1 to 100, and in Chemical Formula DP above, Y is —CH2-, —C(CH3)2-, —C(CF3)2-, —S— or —SO2-,

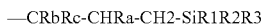   [Chemical Formula S1]

in Chemical Formula S1, each of Ra, Rb and Rc is independently H or an alkyl group having 1 to 6 carbon atoms, at least one of R1 to R3 is an alkoxy group having 1 to 6 carbon atoms, and a remainder of R1 to R3 is an alkyl group having 1 to 10 carbon atoms, and the alkyl group and the alkoxy group may be a linear chain or a branched chain,

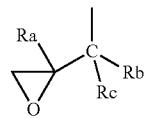   [Chemical Formula S3]

in Chemical Formula S3, each of $R_a$, $R_b$ and $R_c$ is independently H or an alkyl group having 1 to 6 carbon atoms, and the alkyl group may be a linear chain or a branched chain.

3. An epoxy compound having an alkoxysilyl group, wherein the epoxy compound having the alkoxysilyl group is at least one selected from the group consisting of the following Chemical Formulae AI to KI:

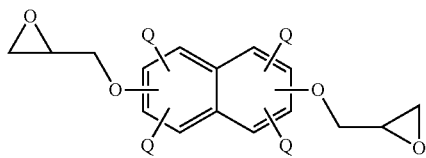 (AI)

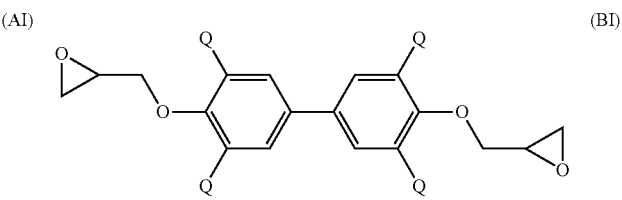 (BI)

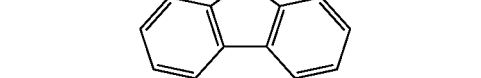 (CI)

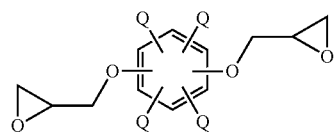 (DI)

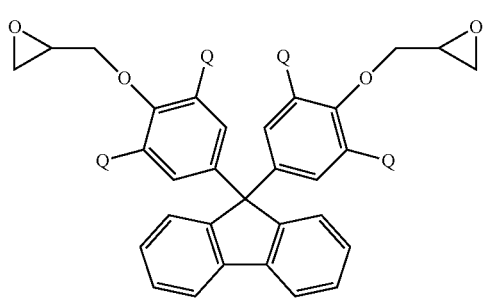 (EI)

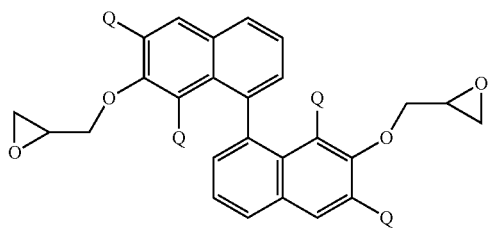 (FI)

(GI)

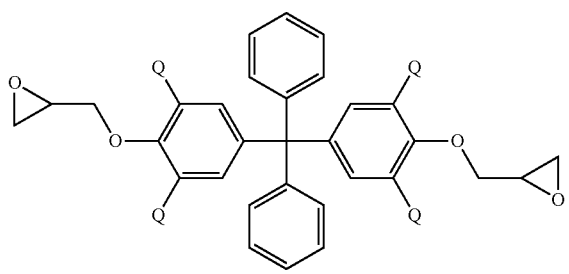

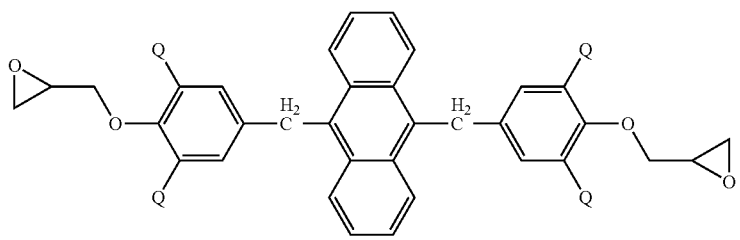
(HI)

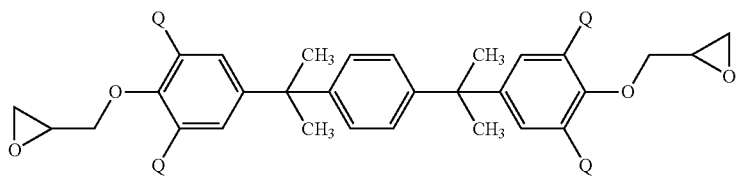
(II)

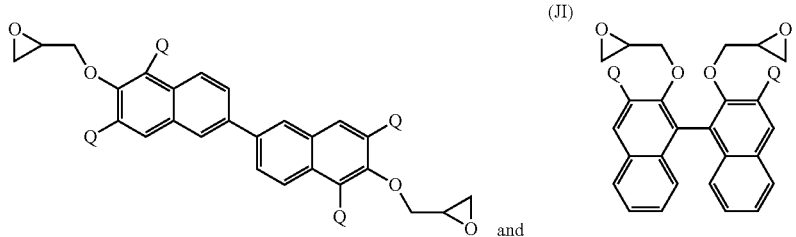
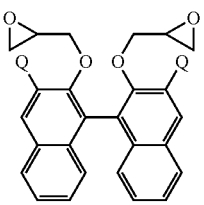
(JI) (KI)

and in Chemical Formulae AI to KI, at least one of a plurality of Q is Chemical Formula S1, at least one of the plurality of Q is Chemical Formula S3, and each of the remainder of Q is independently selected from the group consisting of Chemical Formula S3, hydrogen and —CR$_b$R$_c$—CHR$_a$=CH$_2$ (each of R$_a$, R$_b$ and R$_c$ is independently H or an alkyl group having 1 to 6 carbon atoms, and the alkyl group may be a linear chain or a branched chain), and in Chemical Formula DI, Y is —CH$_2$—, —C(CH$_3$)$_2$—, —C(CF$_3$)$_2$—, —S— or —SO$_2$—, —CR$_b$R$_c$—CHR$_a$—CH$_2$—SiR$_1$R$_2$R$_3$    [Chemical Formula S1]

in Chemical Formula S1, each of R$_a$, R$_b$ and R$_c$ is independently H or an alkyl group having 1 to 6 carbon atoms, at least one of R$_1$ to R$_3$ is an alkoxy group having 1 to 6 carbon atoms, and a remainder of R$_1$ to R$_3$ is an alkyl group having 1 to 10 carbon atoms:

[Chemical Formula S3]

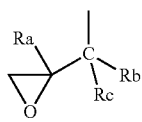

in Chemical Formula S3, each of R$_a$, R$_b$ and R$_c$ is independently H or an alkyl group having 1 to 6 carbon atoms.

4. A composite material including the epoxy composition of claim 3 and an inorganic material.

5. A cured product of the epoxy composition of claim 3.

6. The cured product of claim 5, wherein the cured product has a coefficient of thermal expansion of 15 ppm/° C. or less.

7. The cured product of claim 5, wherein the cured product has a coefficient of thermal expansion of 50 ppm/° C. to 150 ppm/° C.

8. The cured product of claim 5, wherein the cured product does not show a glass transition temperature.

9. The cured product of claim 5, wherein a glass transition temperature of the cured product is greater than 100° C.

10. The cured product of claim 5, wherein the cured product is included in an electronic packaging material.

11. The cured product of claim 5, wherein the cured product is included in a prepreg.

12. The cured product of claim 11, wherein the prepreg is included in a printed circuit board.

13. The cured product of claim 5, wherein the cured product is included in a semiconductor packaging material.

* * * * *